(12) United States Patent
Coit et al.

(10) Patent No.: US 8,119,145 B2
(45) Date of Patent: *Feb. 21, 2012

(54) METHODS FOR PRODUCING NOROVIRUS VLPS

(75) Inventors: Doris Coit, Petaluma, CA (US); Michael Houghton, Danville, CA (US); Colin McCoin, Castro Valley, CA (US); Angelica Medina-Selby, San Francisco, CA (US); Michael Vajdy, Orinda, CA (US)

(73) Assignee: Novartis Vaccines & Diagnostics, Inc., Emeryville, CA (US)

( * ) Notice: Subject to any disclaimer, the term of this patent is extended or adjusted under 35 U.S.C. 154(b) by 110 days.

This patent is subject to a terminal disclaimer.

(21) Appl. No.: 12/383,419

(22) Filed: Mar. 24, 2009

(65) Prior Publication Data
US 2011/0014652 A1 Jan. 20, 2011

Related U.S. Application Data

(63) Continuation of application No. 11/603,913, filed on Nov. 22, 2006, now Pat. No. 7,527,801.

(60) Provisional application No. 60/739,217, filed on Nov. 22, 2005.

(51) Int. Cl.
| | |
|---|---|
| *A01N 63/04* | (2006.01) |
| *A61K 39/38* | (2006.01) |
| *A61K 39/12* | (2006.01) |
| *A61K 39/125* | (2006.01) |
| *C12P 21/04* | (2006.01) |
| *C12N 5/02* | (2006.01) |
| *C12N 15/74* | (2006.01) |

(52) U.S. Cl. ............... 424/216.1; 424/184.1; 424/199.1; 424/204.1; 424/93.51; 435/483; 435/325; 435/70.1

(58) Field of Classification Search ........................ None
See application file for complete search history.

(56) References Cited

U.S. PATENT DOCUMENTS

| | | | |
|---|---|---|---|
| 6,551,820 B1 | 4/2003 | Mason et al. | |
| 6,572,862 B1 * | 6/2003 | Estes et al. | ................. 424/204.1 |
| 2003/0124517 A1 * | 7/2003 | Pichuantes | ........................ 435/5 |
| 2003/0129588 A1 | 7/2003 | Estes et al. | |
| 2005/0152911 A1 | 7/2005 | Hardy | |

FOREIGN PATENT DOCUMENTS

| | | |
|---|---|---|
| JP | 2002020399 A | 1/2002 |
| WO | WO 93/03769 A1 | 3/1993 |
| WO | WO 94/05700 A2 | 3/1994 |
| WO | WO 2005/030806 A2 | 4/2005 |
| WO | WO 2005/032457 A2 | 4/2005 |

OTHER PUBLICATIONS

Asanka, et al., "Replication and Packaging of Norwalk Virus RNA in Cultured Mammalian Cell," *PNAS* 102:10327-10332 (2005).

Belliot, et al., "In Vitro Proteolytic Processing of the MD145 Norovirus ORF1 Nonstructural Polyprotein Yeilds Stable Precursors and Products Similar to Those Detected in Calicivirus-Infected Cells," *J Virol* 77:10957-10974 (2003).

Chakravarty, et al., "Evolutionary Trace Residues in Novoviruses: Importance in Receptor Binding, Antigenicity, Virion Assembly, and Strain Diversity," *J Virol* 79:554-568 (2005).

Chang, et al., "Bile Acids Are Essential for Porcine Enteric Calicivirus Replication in Association With Down-Regulation of Signal Transducer and Activator of Transcription 1," *PNAS* 101:8733-8738 (2004).

Chen, et al., "Inter- and Intragenus Structural Variations in Caliciviruses and Their Functional Implications," *J Virol* 78:6469-6479 (2004).

Fankhauser, et al., "Molecular Epidemiology of 'Norwalk-Like Viruses' in Outbreaks of Gastroenteritis in the United States," *J Infect Dis* 178:1571-1578 (1998).

Fankhauser, et al., "Epidemiologic and Molecular Trends of 'Norwalk-Like Viruses' Associated With Outbreaks of Gastroenteritis in the United States," *J Inf Dis* 186:1-7 (2002).

Farkas, et al., "Genetic Diversity Anong Sapoviruses,"*Arch Virol* 149:1309-1323 (2004).

Glass, et al., "Two Nonoverlapping Domains on the Norwalk Virus Open Reading Frame 3(ORF3) Protein Are Involved in the Formation of the Phosphorylated 35K Protein and in ORF3-Capsid Protein Interactions," *J Virol* 77(6):3569-3577 (2003).

Green, et al., "Expression and Self-Assembly of Recombinant Capsid Protein From the Antigenetically Distinct Hawaii Human Calicicirus," *J Clin Microbiol* 35:1909-1914 (1997).

Harrington, et al., Systemic, Mucosal, and Heterotypic Immune Induction in Mice Inoculated With Venezuelan Wquine Encephalitis Replicons Expressing Norwalk Virus-Like Particles, *J Virol* 76(2):730-742 (2002).

Harrington, et al., "Norovirus Capture With Histo-Blood Group Antigens Reveals Novel Virus-Ligand Interactions,"*J Virol* 78:3035-3045 (2004).

(Continued)

*Primary Examiner* — Benjamin P Blumel
(74) *Attorney, Agent, or Firm* — Regina Bautista; Helen Lee

(57) ABSTRACT

Immunogenic compositions that elicit immune responses against Norovirus and Sapovirus antigens are described. In particular, the invention relates to polynucleotides encoding one or more capsid proteins or other immunogenic viral polypeptides from one or more strains of Norovirus and/or Sapovirus, coexpression of such immunogenic viral polypeptides with adjuvants, and methods of using the polynucleotides in applications including immunization and production of immunogenic viral polypeptides and viral-like particles (VLPs). Methods for producing Norovirus- or Sapovirus-derived multiple epitope fusion antigens or polyproteins and immunogenic compositions comprising one or more immunogenic polypeptides, polynucleotides, VLPs, and/or adjuvants are also described. The immunogenic compositions of the invention may also contain antigens other than Norovirus or Sapovirus antigens, including antigens that can be used in immunization against pathogens that cause diarrheal diseases, such as antigens derived from rotavirus.

8 Claims, 38 Drawing Sheets

OTHER PUBLICATIONS

Hutson, et al., "Norwalk Virus-Like Particle Hemagglutination by Binding to H Histo-Blood Group Antigens," *J Virol* 77:405-415 (2003).

Jiang, et al., "Sapporo-Like Human Caliciviruses Are Genetically and Antigenetically Diverse," *Arch Virol* 142:1813-1827 (1997).

Jiang, et al., "Sequence and Genomic Organization of Norwalk Virus," *Virology* 195:51-61 (1993).

Johnson, et al., "Multiple-Challenge Study of Host Susceptability to Norwalk Gastroenteritis in US Adults," *J Inf Dis* 161:18-21 (1990).

Lindesmith, et al., "Human Susceptibility and Resistance to Norwalk Virus Infection," *Nat Med* 9:548-533 (2003).

Lindesmith, et al., "Cellular and Humoral Immunity Following Snow Maontain Virus Challenge," *J Virol* 79:2900-2909 (2005).

Nicollier-Jamot, et al., "Recombinant Virus-Like Particles of a Norovirus (Genogroup II Strain) Administered Intranasally and Orally With Mucosal Adjuvants LT and LT(R192G) in BALB/C Mice Induce Specific Humoral and Cellular Th1/Th2-Like Immune Responses," *Vaccine* 22:1079-1086 (2004).

Oka, et al., "Proteolytic Processing of Sapovirus ORF1 Polyprotein," *J Virol* 79:7283-7290 (2005).

Schuffenecker, et al., "Genetic Classification of Sapporo-Like Viruses," *Arch Virol* 146(11):2115-2132 (2001).

Subekti, et al., "Experimental Infection of Macaca Nemestrina With Toronto Narwalk-Like Virus of Epidemic Viral Gastoenteris," *J Med Virol* 66:400-406 (2002).

Taube, et al., "Generation of Recombinant Norovirus-Like Particles (VLP) in the Human Endothelial Kidney Cell Line 293T," *Arch Virol* 150:1425-1431 (2005).

* cited by examiner

Figure 1A

```
Alignment of Sequences:
 1: GenBank Accession No. M87661 (orf2 and orf3, length 2294)
 2: SEQ ID NO:2 (Modified orf2 and orf3, length 2319)

0  ................  [ATGATGGCGTCTAAGGACGCTACATCAAGCGTGATGGCGCTAGTGGCGCTGGTCAGTTGTACCGGAG
   0  aagcttacaaaacaaaatg [ATGATGGCGTCTAAGGACGCTACATCAAGCGTGATGGCGCTAGTGGCGCTGGTCAGTTGTACCGGAG 69  GTTAATGCTTCTGACCCTCTTGCAATGGA] t [CCTGTAGCAGGTTCTTCGACAGCAGTCGGCGACTGCTGGACAAGTTAATCCTATTGA
  88  GTTAATGCTTCTGACCCTCTTGCAATGGA] c [CCTGTAGCAGGTTCTTCGACAGCAGTCGGCGACTGCTGGACAAGTTAATCCTATTGA 155  TCCCTGGATAAT] t [AATAATTTTGTGCAAGCCCCCCAAGTGAATTACTATTTCCCAAATAATAACCCCGTGATGTTTTGTTTG
 174  TCCCTGGATAAT] c [AATAATTTTGTGCAAGCCCCCCAAGTGAATTACTATTTCCCAAATAATAACCCCGTGATGTTTTGTTTG 241  ATTTGAGTTTGGGTCCCATCTTAATCCTTTCTTGCTCCATCTATCACAAATGTATAATGTTGGGTTGGTAACATGAGAGTCAGGATTA
 260  ATTTGAGTTTGGGTCCCATCTTAATCCTTTCTTGCTCCATCTATCACAAATGTATAATGTTGGGTTGGTAACATGAGAGTCAGGATTA 331  TG] cta [GCTGGTAATGCCTTTACTGCGGGGAAGATAATAGTTTCCTGCATACCCCCTGGTTTTGTTCACATAATCTTACTATAGCA
 350  TG] ttg [GCTGGTAATGCCTTTACTGCGGGGAAGATAATAGTTTCCTGCATACCCCCTGGTTTTGTTCACATAATCTTACTATAGCA 417  CAAGCAACTCTCTTTCCACATGATTGCTGTAGGACTCTAGACTGTTAGGAGACTCTAGACCCCCATTGAGGTGCCTTTGAAGATGTTAGGAATGTTCTCTTT
 436  CAAGCAACTCTCTTTCCACATGATTGCTGTAGGACTCTAGACTGTTAGGAGACTCTAGACCCCCATTGAGGTGCCTTTGAAGATGTTAGGAATGTTCTCTTT 507  CATAATAATGATAGAAATCAACAACAAACCATGCGCCTTGTGTGCACCCCTGTGTACACCCCCCTCCGCACTGGTTCCTCCTACGGTGGAGCAGAAAACCAGGCCC
 526  CATAATAATGATAGAAATCAACAACAAACCATGCGCCTTGTGTGCACCCCTGTGTACACCCCCCTCCGCACTGGTTCCTCCTACGGTGGAGCAGAAAACCAGGCCC 597  GTAGTTGCAGGGCGAGTTATGACTTGCCCCAGTCCTGATTTTAATTTCTTGTTTTGTTTTTAGTCCCTCCCCAATCAGTAGTATCGGCATTCCCCAGACAATGTC
 616  GTAGTTGCAGGGCGAGTTATGACTTGCCCCAGTCCTGATTTTAATTTCTTGTTTTGTTTTTAGTCCCTCCCCAATCAGTAGTATCGGCATTCCCCAGACAATGTC 687  TTCACACTCCCAAATCTGCCATTGAGTTCTGTCTAACTCACGTGCCCCTCCCCAATCAGTAGTATCGGCATTCCCCAGACAATGTC
 706  TTCACACTCCCAAATCTGCCATTGAGTTCTGTCTAACTCACGTGCCCCTCCCCAATCAGTAGTATCGGCATTCCCCAGACAATGTC 777  CAGAGTGTGCAGTTGCCAAAATGGTCGGTGTACTCTGGATGGCCACCACCCAGTTTCATTGTCACATGTTGCCAAGATA
 796  CAGAGTGTGCAGTTGCCAAAATGGTCGGTGTACTCTGGATGGCCACCACCCAGTTTCATTGTCACATGTTGCCAAGATA
```

Figure 1B

```
 867  AGAGGGACCTCCAATGGCACTGTAATCAACCTTACTGAATTGGATGGCACACCCTTTCACCCTTTTGAGGGCCCTGCCCCCATTGGGTTT
 886  AGAGGGACCTCCAATGGCACTGTAATCAACCTTACTGAATTGGATGGCACACCCTTTCACCCTTTTGAGGGCCCTGCCCCCATTGGGTTT

957  CCAGACCCTCGGTGGTTGTGATTGGCATAT] c [AATATGACACAGTTTGGCCATTCTAGCCAGACCCAGTATGATGTAGACACCACCCC
 976  CCAGACCCTCGGTGGTTGTGATTGGCATAT] t [AATATGACACAGTTTGGCCATTCTAGCCAGACCCAGTATGATGTAGACACCACCCC

1043  TGACACTTTTGTCCCCCATCTGGTTCAATTCAGGCAAATGGCATTGGCAGTGGTAATTATGTTGGTGTTCTTAGCTGGATTTCCC] c
1062  TGACACTTTTGTCCCCCATCTGGTTCAATTCAGGCAAATGGCATTGGCAGTGGTAATTATGTTGGTGTTCTTAGCTGGATTTCCC] a

1131  [CCATCACACCCGTCTGGCTCCCAAGTTGACCTTTGGAAGATCCCAATTATGGGTCAAGTATTACGGAGGCAACACATCTAGCCCTT
1150  [CCATCACACCCGTCTGGCTCCCAAGTTGACCTTTGGAAGATCCCAATTATGGGTCAAGTATTACGGAGGCAACACATCTAGCCCTT

1219  CTGTATACCCCCCTGGTTCGGAGAGAGGTATTGGTCTT] tttcatgtcaaaa [ATGCCAGGTCCTGGTGCTTATAATTTGCCCTGTCTA
1238  CTGTATACCCCCCTGGTTCGGAGAGAGGTATTGGTCTT] cttcatgtccaag [ATGCCAGGTCCTGGTGCTTATAATTTGCCCTGTCTA 1305  TTACCACAAGAGTACATTTCACATCTTGCTAGTGAACAAGCCCCTACTGTAGGTGAACAAGCCCCCTACTGTAGGTGAGGCTGCCCTGACCCTGATACC
1324  TTACCACAAGAGTACATTTCACATCTTGCTAGTGAACAAGCCCCTACTGTAGGTGAACAAGCCCCCTACTGTAGGTGAGGCTGCCCTGACCCTGATACC 1395  GGTCGGAATCTTGGGGA] a [TTCAAAGCATACCCTGATGGTTTCCTCACTTGTGTCCCAATGGGGCT] agc [TCGGGTCCACAAC
1414  GGTCGGAATCTTGGGGA] g [TTCAAAGCATACCCTGATGGTTTCCTCACTTGTGTCCCAATGGGGCT] tct [TCGGGTCCACAAC 1477  AGCTGCCGATCAATGGGGTCTTTGTCTTTTGTTTCATGGGTGTCCAGATTTTATCAATTAAAGCCTGTGGAACTGCCAGCTGCGGCAAGAG
1496  AGCTGCCGATCAATGGGGTCTTTGTCTTTTGTTTCATGGGTGTCCAGATTTTATCAATTAAAGCCTGTGGAACTGCCAGCTGCGGCAAGAG 1567  GTAGGCTTGGTCT] gcgcc [GATAATGGCCCAAGCCATAATTGCTGCTTCCACAGCAGTAGTGCTCTGGGAGCGGGCA
1586  GTAGGCTTGGTCT] ccgga [GATAATGGCCCAAGCCATAATTGCTGCTTCCACAGCAGTAGTGCTCTGGGAGCGGGCA 1653  TACAGGTTGGTGGCGAAGCGGCCCTCCAAAGCCAAAGTTATCAACAAAATTTGCAACTGCAAGAAAAATTCTTTTAAACATGACAGGGAAA
1672  TACAGGTTGGTGGCGAAGCGGCCCTCCAAAGCCAAAGTTATCAACAAAATTTGCAACTGCAAGAAAAATTCTTTTAAACATGACAGGGAAA 1743  TGATTGGGTATCAGGTTGA] a [GCTTTCAAATCAATTATTGGCTAAAAATTTGGCAACTAGATATTCACTCCTCCGTGCTGGGGTTTG
1762  TGATTGGGTATCAGGTTGA] g [GCTTTCAAATCAATTATTGGCTAAAAATTTGGCAACTAGATATTCACTCCTCCGTGCTGGGGTTTG 1829  ACCAGTGCTGATGCAGCAAGATCTGTGGCAGGAGCTCCAGTCACCCGCATTGTAGATTGGAATGCCGTGAGAGTGCTCGCTCCCGAGTCC
1848  ACCAGTGCTGATGCAGCAAGATCTGTGGCAGGAGCTCCAGTCACCCGCATTGTAGATTGGAATGCCGTGAGAGTGCTCGCTCCCGAGTCC
```

Figure 1C

```
1919  TCTGCTACCACCATTGAGATCCGGTGGCTTCATGTCAGTTCCATTTGCCTCTAAGCAAAAACAGGTTCAATCATCTGGTATTAGT
1938  TCTGCTACCACCATTGAGATCCGGTGGCTTCATGTCAGTTCCATTTGCCTCTAAGCAAAAACAGGTTCAATCATCTGGTATTAGT

2009  AATCCAAATTATTCCCCTTCATCCATTTCTCGAACCACTAGTTGGGTCGAGTCACAAAACTCATCGAGATTTGGAAATCTTTCTCCATAC
2028  AATCCAAATTATTCCCCTTCATCCATTTCTCGAACCACTAGTTGGGTCGAGTCACAAAACTCATCGAGATTTGGAAATCTTTCTCCATAC

2099  CACGCGGAGGCTCTCAATACAGTGGTTGACTCCACCCGGTTCAACAGCCTCTTCTACACTGTCTTCTGTGCCACGTGGTTATTCAAT
2118  CACGCGGAGGCTCTCAATACAGTGTGGTTGACTCCACCCGGTTCAACAGCCTCTTCTACACTGTCTTCTGTGCCACGTGGTTATTTCAAT

2189  ACAGACAGGTT] g [CCATTATTCGCAAATAATAGGCGATGATGTTGTAATATGAAATGTGGGCATCATATTCATTAATTAGGTTTAA
2208  ACAGACAGGTT] a [CCATTATTCGCAAATAATAGGCGATGATGTTGTAATATGAAATGTGGGCATCATATTCATTAATTAGGTTTAA

2275  TTAGGTTTAATTTGATGTT] .......
2294  TTAGGTTTAATTTGATGTT] gtcgac
```

Figure 2A

Translation of Norwalk Virus ORF2

```
AAGCTTACAAAACAAA
                                     1                                  10
                                     M   M   M   A   S   K   D   A   T   S   V   D   G   A
                                     ATG ATG ATG GCG TCT AAG GAC GCT ACA TCA AGC GTG GAT GGC GCT 20                                              30
    S   G   A   G   Q   L   V   P   E   V   N   A   S   D   P   L   A   M   D   P
    AGT GGC GCT GGT CAG TTG GTA CCG GAG GTT AAT GCT TCT GAC CCT CTT GCA ATG GAC CCT 40                                              50
    V   A   G   S   T   A   V   A   G   Q   N   P   I   D   P   W
    GTA GCA GGT TCT TCG ACA GCA GTC GCG ACT GCT GGA CAA AAT CCT ATT GAT CCC TGG 60                                              70
    I   I   N   E   V   Q   G   E   T   I   S   P   N   N   T
    ATA ATC AAT AAT TTT GTG CAA GGT GAA ACT ATT TCC CCA AAT AAT ACC 80                                              90
    P   G   D   V   L   F   D   L   S   L   G   P   H   L   N   P   F   L   L   H
    CCC GGT GAT GTT CTA TTT GAT TTG AGT TTG GGT CCC CAT CTT AAT CCT TTC TTG CTC CAT 100                                             110
    L   Q   M   Y   N   G   W   V   G   N   M   R   V   I   M   L   A   G
    CTA TCA CAA ATG TAT AAT GGT TGG GTT GGT AAC ATG AGA GTC AGG ATT ATG TTG GCT GGT 120                                             130
    N   A   F   T   A   G   K   I   I   V   S   C   I   P   P   G   F   G   S   H
    AAT GCC TTT ACT GCG GGG AAG ATA ATA GTT TCC TGC ATA CCC CCT GGT TTT GGT TCA CAT 140                                             150
    N   L   T   I   A   Q   A   T   L   F   P   H   V   I   A   D   V   R   T   L
    AAT CTT ACT ATA GCA CAA GCA ACT CTC TTT CCA CAT GTG ATT GCT GAT GTT AGG ACT CTA
```

Figure 2B

```
      D   P   I   E   V   P   L   E   D   V   R   N   V   L   F   H   N   N   D   R
      GAC CCC ATT GAG GTG CCT TTG GAA GAT GTT AGG AAT GTT CTC TTT CAT AAT AAT GAT AGA
                          160                             170
      N   Q   Q   T   M   R   L   V   C   M   L   Y   T   P   L   R   T   G   G   G
      AAT CAA CAA ACC ATG CGC CTT GTG TGC ATG CTG TAC ACC CCC CTC CGC ACT GGT GGT GGT
                          180                             190
      T   G   D   S   F   V   V   A   G   R   V   M   T   C   P   S   P   D   F   N
      ACT GGT GAT TCT TTT GTA GCA GGG CGA ATG ACT TGC CCC AGT CCT GAT TTT AAT
                          200                             210
      F   L   F   L   V   P   P   T   N   S   V   E   Q   K   T   R   P   F   T   L   P   N
      TTC TTG TTT TTA GTC CCT ACG AAC TCA GTG GAG CAG AAA ACC AGG CCC TTC ACA CTC CCA AAT
                          220                             230
      L   P   S   L   L   S   N   Q   V   S   R   A   P   L   P   I   S   I   G   I
      CTG CCA TTG TCT CTG AAC TCA CGT GCC CCT CTC CCA ATC AGT AGT ATC GGC ATT
                          240                             250
      S   P   D   N   V   Q   F   Q   N   G   R   C   T   L   D   G   R
      TCC CCA GAC AAT GTC CAG AGT CAG TTC CAA AAT GGT CGG TGT ACT CTG GAT GGC CGC
                          260                             270
      L   V   G   T   P   V   S   L   T   E   L   D   H   V   A   K   R   G   T   S   N
      CTG GTT GGC ACC CCA GTT TCA TTG ACT GAA GAT GTT GCC AAG AGA GGG ACC TCC AAT
                          280                             290
      G   T   V   N   I   N   L   T   P   D   G   D   P   F   H   P   E   G   P
      GGC ACT GTA AAC ATC AAC CTT ACT CCA GAT GGC ACA CCC TTT CAC CCT GAG GGC CCT
                          300                             310
      A   P   I   G   F   P   D   L   G   C   W   H   I   N   M   T   Q   F
      GCC CCC ATT GGG TTT CCA GAC CTC GGT TGT TGG CAT ATT AAT ATG ACA CAG TTT
                          320                             330
```

Figure 2C

```
     G    H    S    Q    T    Q    Y    D    V    D    T    P    T    F    V    P    H
                        340                                       350
     GGC  CAT  TCT  AGC  CAG  ACC  CAG  TAT  GAT  GTA  GAC  ACC  CCT  GAC  ACT  TTT  GTC  CCC  CAT

L    G    S    I    Q    A    N    G    I    G    S    G    N    Y    T    G    V    L    S    W
                        360                                       370
     CTT  GGT  TCA  ATT  CAG  GCA  AAT  GGC  ATT  GGC  AGT  GGT  AAT  TAT  ACT  GTT  GGT  CTT  AGC  TGG

I    S    P    P    S    H    P    S    G    S    Q    V    D    L    W    K    I    P    N    Y
                        380                                       390
     ATT  TCC  CCA  CCA  TCA  CAC  CCG  TCT  GGC  TCC  CAA  GTT  GAC  CTT  TGG  AAG  ATC  CCC  AAT  TAT

G    S    S    I    T    E    A    T    H    L    A    P    S    V    Y    P    P    G    F    G
                        400                                       410
     GGG  TCA  AGT  ATT  ACG  GAG  GCA  ACA  CAT  CTA  GCC  CCT  TCT  GTA  TAC  CCC  CCT  GGT  TTC  GGA

E    V    L    V    F    F    M    S    K    M    P    G    A    Y    P    T    V    G    E
                        420                                       430
     GAG  GTA  TTG  GTC  TTC  TTC  ATG  TCC  AAG  ATG  CCA  GGT  GCT  TAT  CCT  ACT  GTA  GGT  GAG

L    L    P    Q    Y    V    D    P    D    T    G    R    N    G    A    S    P    Q    Q    L
                        440                                       450
     CTA  TTA  CCA  CAA  TAT  GTT  GAC  CCT  GAT  ACC  GGT  CGG  AAT  GGG  GCC  AGC  CCT  CAA  CAG  CTG

A    A    L    H    Y    L    T    C    V    P    N    G    A    S    P    Q    Q    L
                        460                                       470
     GCT  GCC  CTC  CAC  TAT  CTC  ACT  TGT  GTC  CCC  AAT  GGG  GCT  TCT  CCA  CAA  CAG  CTG

Y    P    D    F    L    T    C    V    S    W    V    A    S    G    Y    L    K    P
                        480                                       490
     TAC  CCT  GAT  TTC  CTC  ACT  TGT  GTC  TCT  TGG  GTC  GCA  TCT  GGG  TAC  TTA  AAG  CCT

P    I    N    G    V    F    V    F    V    S    W    V    R    F    Y    Q    L
                        500                                       510
     CCG  ATC  AAT  GGG  GTC  TTT  GTC  TTT  GTG  TCA  TGG  GTG  AGA  TTT  TAT  CAA  TTA
```

Figure 2D

```
       520                          530
V  G   T   A   S   S   A   R   G   R   L   G   L   R   R   OC
GTG GGA ACT GCC AGC TCG GCA AGA GGT AGG CTT GGT CTC CGG AGA TA(A)
```

Translated Mol. Weight = 56580.91

Figure 2E

Translation of Norwalk Virus ORF3 (after frameshift)

```
     1
     M   A   Q   A   I   I   G   A   I   A   A   S
     ATG GCC CAA GCC ATA ATT GGT GCA ATT GCT GCT TCC

T   A   G   S   A   L   G   I   Q   V   G   30
                                                 L   Q   S
     ACA GCA GGT AGT GCT CTG GGA GCG ATA CAG GTT GGT GGC GAA GCG GCC CTC CAA AGC

Q   R   Y   Q   Q   N   L   Q   E   N   S   F   50
                                                     K   H   D   R   E   M
     CAA AGG TAT CAA CAA AAT TTG CAA CTG CAA GAA AAT TCT TTT AAA CAT GAC AGG GAA ATG

I   G   Y   Q   V   E   A   S   N   Q   L   A   70
                                                     K   N   L   A   T   R   Y
     ATT GGG TAT CAG GTT GAG GCT TCA AAT CAA TTA GCT AAA AAT TTG GCA ACT AGA TAT

S   L   L   R   A   G   G   L   T   S   A   D   90
                                                     A   R   S   V   A   G   A
     TCA CTC CTC CGT GCT GGG GGT TTG ACC AGT GCT GAT GCA AGA TCT GTG GCA GGA GCT

P   V   T   R   I   V   D   W   N   G   V   R   110
                                                     V   S   A   P   E   S   A
     CCA GTC ACC CGC ATT GTA GAT TGG AAT GGC GTG AGA GTG TCT GCT CCC GAG TCC TCT GCT

T   T   L   R   S   G   G   F   M   S   V   P   130
                                                     I   P   F   A   S   K   Q   K
     ACC ACA TTG AGA TCC GGT GGC TTC ATG TCA GTT CCC ATA CCA TTT GCC TCT AAG CAA AAA

Q   V   Q   S   S   G   I   S   N   P   N   Y   150
                                                     S   P   S   I   S   R   T
     CAG GTT CAA TCA TCT GGT ATT AGT AAT CCA AAT TAT TCC CCT TCA ATT TCT CGA ACC
```

Figure 2F

```
       T   S   W   V   E   S   Q   N   S   S   R   F   G   N   L   S   P   Y   H   A
                               160                         170
      ACT AGT TGG GTC GAG TCA CAA AAC TCA TCG AGA TTT GGA AAT CTT TCT CCA TAC CAC GCG

E   A   L   N   T   V   W   L   T   P   P   G   S   T   A   S   S   T   L   S
                               180                         190
      GAG GCT CTC AAT ACA GTG TGG TTG ACT CCA CCC GGT TCA ACA GCC TCT TCT ACA CTG TCT

S   V   P   R   G   G   Y   F   N   T   D   R   L   P   L   F   A   N   N   R   R
                               200                         210
      TCT GTG CCA CGT GGT TAT TTC AAT ACA GAC AGG TTA CCA TTA TTC GCA AAT AAT AGG CGA

212
      OP 3'UTR--------------------------------------------------
      TGA TGTTGTAATATGAAATGTGGGCATCATATTCATTTAATTAGGTTTAATTGATGTTGTCGAC

Translated Mol. Weight = 22482.97
```

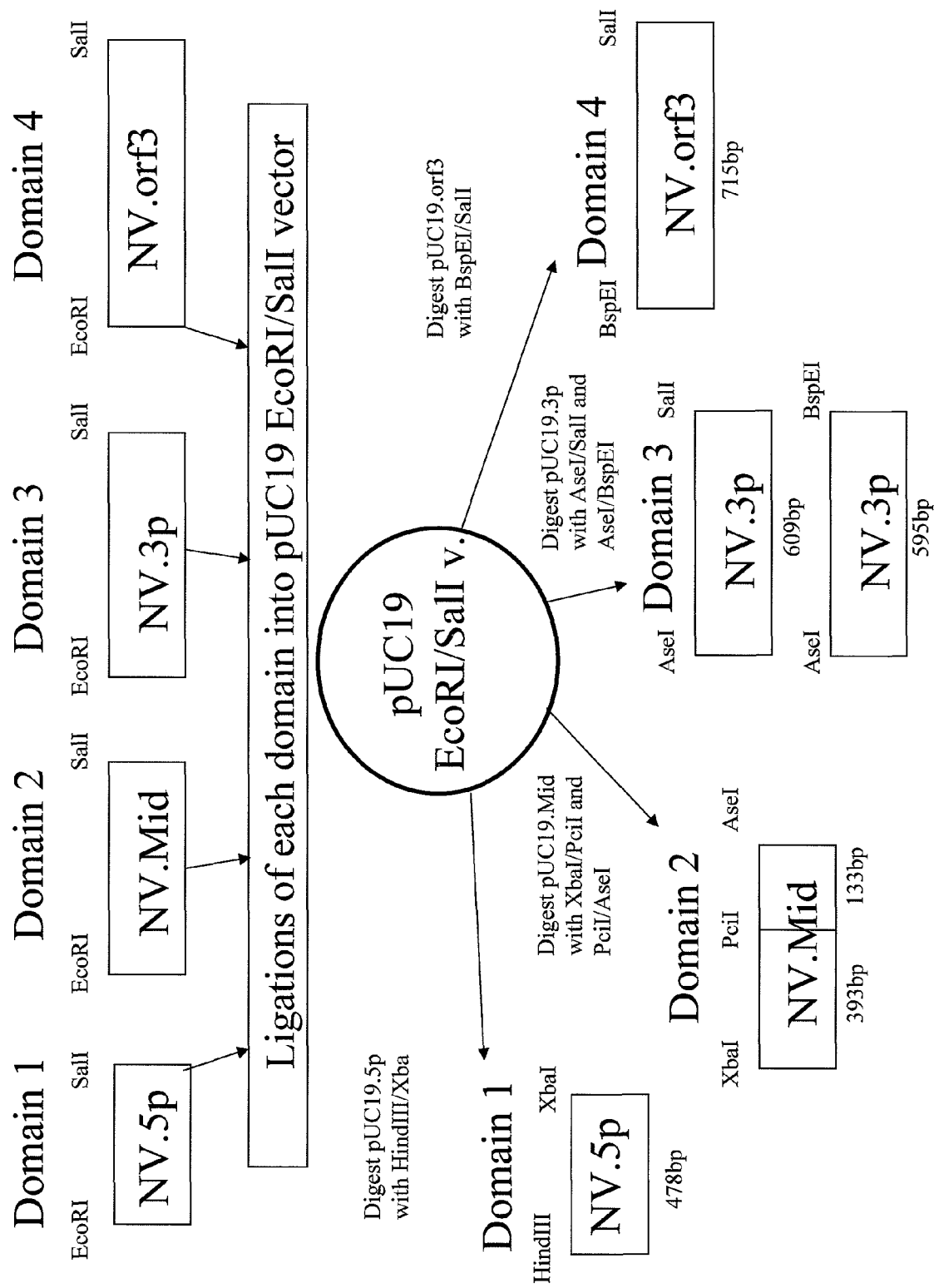

Figure 14A

NV.orf2: modified polynucleotide sequence of orf2 (SEQ ID NO:1)

```
aagcttacaa aacaaaatga tgatggcgtc taaggacgct acatcaagcg tggatggcgc     60
tagtggcgct ggtcagttgg taccggaggt taatgcttct gaccctcttg caatggaccc    120
tgtagcaggt tcttcgacag cagtcgcgac tgctggacaa gttaatccta ttgatccctg    180
gataatcaat aattttgtgc aagcccccca aggtgaattt actatttccc caaataatac    240
ccccggtgat gttttgtttg atttgagttt gggtccccat cttaatcctt tcttgctcca    300
tctatcacaa atgtataatg gttgggttgg taacatgaga gtcaggatta tgttggctgg    360
taatgccttt actgcgggga agataatagt ttcctgcata ccccctggtt ttggttcaca    420
taatcttact atagcacaag caactctctt tccacatgtg attgctgatg ttaggactct    480
agaccccatt gaggtgcctt tggaagatgt taggaatgtt ctctttcata ataatgatag    540
aaatcaacaa accatgcgcc ttgtgtgcat gctgtacacc cccctccgca ctggtggtgg    600
tactggtgat tcttttgtag ttgcagggcg agttatgact tgccccagtc ctgattttaa    660
tttcttgttt ttagtccctc ctacggtgga gcagaaaacc aggcccttca cactcccaaa    720
tctgccattg agttctctgt ctaactcacg tgcccctctc ccaatcagta gtatcggcat    780
ttccccagac aatgtccaga gtgtgcagtt ccaaaatggt cggtgtactc tggatggccg    840
cctggttggc accaccccag tttcattgtc acatgttgcc aagataagag ggacctccaa    900
tggcactgta atcaacctta ctgaattgga tggcacaccc tttcaccctt ttgagggccc    960
tgcccccatt gggtttccag acctcggtgg ttgtgattgg catattaata tgacacagtt   1020
tggccattct agccagaccc agtatgatgt agacaccacc cctgacactt ttgtccccca   1080
tcttggttca attcaggcaa atggcattgg cagtggtaat tatgttggtg ttcttagctg   1140
gatttcccca ccatcacacc cgtctggctc ccaagttgac ctttggaaga tccccaatta   1200
tgggtcaagt attacggagg caacacatct agccccttct gtataccccc ctggtttcgg   1260
agaggtattg gtcttcttca tgtccaagat gccaggtcct ggtgcttata atttgccctg   1320
tctattacca caagagtaca tttcacatct tgctagtgaa caagccccta ctgtaggtga   1380
ggctgccctg ctccactatg ttgaccctga taccggtcgg aatcttgggg agttcaaagc   1440
ataccctgat ggtttcctca cttgtgtccc caatggggct tcttcgggtc cacaacagct   1500
```

Figure 14B

```
gccgatcaat ggggtctttg tctttgtttc atgggtgtcc agattttatc aattaaagcc    1560
tgtgggaact gccagctcgg caagaggtag gcttggtctc cggagata                 1608
```

Figure 15A

NV.orf2+3: modified polynucleotide sequences of orf2 and orf3 (SEQ ID NO:2)

```
aagcttacaa aacaaaatga tgatggcgtc taaggacgct acatcaagcg tggatggcgc    60
tagtggcgct ggtcagttgg taccggaggt taatgcttct gaccctcttg caatggaccc   120
tgtagcaggt tcttcgacag cagtcgcgac tgctggacaa gttaatccta ttgatccctg   180
gataatcaat aattttgtgc aagcccccca aggtgaattt actatttccc caaataatac   240
ccccggtgat gttttgtttg atttgagttt gggtccccat cttaatcctt tcttgctcca   300
tctatcacaa atgtataatg gttgggttgg taacatgaga gtcaggatta tgttggctgg   360
taatgccttt actgcgggga agataatagt ttcctgcata cccctggtt ttggttcaca   420
taatcttact atagcacaag caactctctt ccacatgtg attgctgatg ttaggactct    480
agacccatt gaggtgcctt tggaagatgt taggaatgtt ctctttcata ataatgatag   540
aaatcaacaa accatgcgcc ttgtgtgcat gctgtacacc cccctccgca ctggtggtgg   600
tactggtgat tcttttgtag ttgcagggcg agttatgact tgccccagtc ctgattttaa   660
tttcttgttt ttagtccctc ctacggtgga gcagaaaacc aggcccttca cactcccaaa   720
tctgccattg agttctctgt ctaactcacg tgcccctctc ccaatcagta gtatcggcat   780
ttccccagac aatgtccaga gtgtgcagtt ccaaaatggt cggtgtactc tggatggccg   840
cctggttggc accaccccag tttcattgtc acatgttgcc aagataagag ggacctccaa   900
tggcactgta atcaacctta ctgaattgga tggcacaccc tttcaccctt ttgagggccc   960
tgcccccatt gggtttccag acctcggtgg ttgtgattgg catattaata tgacacagtt  1020
tggccattct agccagaccc agtatgatgt agacaccacc cctgacactt ttgtccccca  1080
tcttggttca attcaggcaa atggcattgg cagtggtaat tatgttggtg ttcttagctg  1140
gatttcccca ccatcacacc cgtctggctc ccaagttgac ctttggaaga tccccaatta  1200
tgggtcaagt attacggagg caacacatct agccccttct gtataccccc ctggtttcgg  1260
agaggtattg gtcttcttca tgtccaagat gccaggtcct ggtgcttata atttgcctg  1320
tctattacca caagagtaca tttcacatct tgctagtgaa caagccccta ctgtaggtga  1380
ggctgccctg ctccactatg ttgaccctga taccggtcgg aatcttgggg agttcaaagc  1440
ataccctgat ggtttcctca cttgtgtccc caatggggct tcttcgggtc cacaacagct  1500
```

Figure 15B

```
gccgatcaat ggggtctttg tctttgtttc atgggtgtcc agattttatc aattaaagcc    1560
tgtgggaact gccagctcgg caagaggtag gcttggtctc cggagataat ggcccaagcc    1620
ataattggtg caattgctgc ttccacagca ggtagtgctc tgggagcggg catacaggtt    1680
ggtggcgaag cggccctcca aagccaaagg tatcaacaaa atttgcaact gcaagaaaat    1740
tcttttaaac atgacaggga aatgattggg tatcaggttg aggcttcaaa tcaattattg    1800
gctaaaaatt tggcaactag atattcactc ctccgtgctg ggggtttgac cagtgctgat    1860
gcagcaagat ctgtggcagg agctccagtc acccgcattg tagattggaa tggcgtgaga    1920
gtgtctgctc ccgagtcctc tgctaccaca ttgagatccg gtggcttcat gtcagttccc    1980
ataccatttg cctctaagca aaaacaggtt caatcatctg gtattagtaa tccaaattat    2040 tcccttcat ccatttctcg aaccactagt tgggtcgagt cacaaaactc atcgagattt     2100
ggaaatcttt ctccatacca cgcggaggct ctcaatacag tgtggttgac tccacccggt    2160
tcaacagcct cttctacact gtcttctgtg ccacgtggtt atttcaatac agacaggtta    2220
ccattattcg caaataatag gcgatgatgt tgtaatatga aatgtgggca tcatattcat    2280
ttaattaggt ttaattaggt ttaatttgat gttgtcgac                           2319
```

Figure 16A

ORF1 Coding Sequence for NV-MD145-12 Polyprotein and Domain Boundaries

```
    |Nterm (amino acids 1-330)
gtga atg aag atg gcg tct aac gac gct tcc gct gcc gct gtt gcc aac        49
     Met Lys Met Ala Ser Asn Asp Ala Ser Ala Ala Ala Val Ala Asn
     1               5                   10                  15 agc aac aac gac acc gca aaa tct tca agt gac gga gtg ctt tct agc        97
Ser Asn Asn Asp Thr Ala Lys Ser Ser Ser Asp Gly Val Leu Ser Ser
                20                  25                  30 atg gct atc act ttt aaa cga gcc ctc ggg gcg cgg cct aaa cag cct       145
Met Ala Ile Thr Phe Lys Arg Ala Leu Gly Ala Arg Pro Lys Gln Pro
            35                  40                  45 ccc ccg agg gaa ata cta caa aga ccc cca cga cca cct acc cca gaa       193
Pro Pro Arg Glu Ile Leu Gln Arg Pro Pro Arg Pro Pro Thr Pro Glu
        50                  55                  60 ctg gtc aaa aag atc ccc cct ccc ccg ccc aac ggg gag gat gaa cta       241
Leu Val Lys Lys Ile Pro Pro Pro Pro Asn Gly Glu Asp Glu Leu
    65                  70                  75 gtg gtt tct tat agt gtc aaa gat ggc gtt tcc ggt ctg cct gag ctt       289
Val Val Ser Tyr Ser Val Lys Asp Gly Val Ser Gly Leu Pro Glu Leu
80                  85                  90                  95 tcc act gtc agg caa ccg gat gaa gcc aat acg gcc ttc agt gtt ccc       337
Ser Thr Val Arg Gln Pro Asp Glu Ala Asn Thr Ala Phe Ser Val Pro
                100                 105                 110 cca ctc aat cag agg gag aat agg gat gcc aag gag cca cta act gga       385
Pro Leu Asn Gln Arg Glu Asn Arg Asp Ala Lys Glu Pro Leu Thr Gly
            115                 120                 125 aca att ctg gaa atg tgg gat gga gag atc tac cat tac ggc cta tat       433
Thr Ile Leu Glu Met Trp Asp Gly Glu Ile Tyr His Tyr Gly Leu Tyr
        130                 135                 140 gtg gag cga ggt ctt gta ctt ggt gtg cac aaa cca cca gct gcc atc       481
Val Glu Arg Gly Leu Val Leu Gly Val His Lys Pro Pro Ala Ala Ile
    145                 150                 155 agc ctc gcc aag gtc gaa cta aca cca ctc tcc ttg ttc tgg aga cct       529
Ser Leu Ala Lys Val Glu Leu Thr Pro Leu Ser Leu Phe Trp Arg Pro
160                 165                 170                 175
```

Figure 16B

```
gta tac act ccc cag tat ctc atc tcc cca gac act ctc aag aga ttg      577
Val Tyr Thr Pro Gln Tyr Leu Ile Ser Pro Asp Thr Leu Lys Arg Leu
            180                 185                 190 cac gga gaa tcg ttc ccc tat aca gcc ttc gac aac aat tgc tat gcc      625
His Gly Glu Ser Phe Pro Tyr Thr Ala Phe Asp Asn Asn Cys Tyr Ala
            195                 200                 205 ttc tgt tgc tgg gtc tta gac cta aac gac tcg tgg ctg agt agg aga      673
Phe Cys Cys Trp Val Leu Asp Leu Asn Asp Ser Trp Leu Ser Arg Arg
            210                 215                 220 acg atc cag aga aca act ggt ttc ttt aga ccc tat caa gac tgg aat      721
Thr Ile Gln Arg Thr Thr Gly Phe Phe Arg Pro Tyr Gln Asp Trp Asn
            225                 230                 235 agg aaa ccc ctc cct act gtg gat gac tcc aaa tta aag aag gta gct      769
Arg Lys Pro Leu Pro Thr Val Asp Asp Ser Lys Leu Lys Lys Val Ala
240                 245                 250                 255 aac tta ttc ctg tgt gct cta tct tca cta ttc acc agg ccc atc aaa      817
Asn Leu Phe Leu Cys Ala Leu Ser Ser Leu Phe Thr Arg Pro Ile Lys
            260                 265                 270 gac ata ata ggg aaa cta aga cct ctc aac atc ctc aac atc ttg gcc      865
Asp Ile Ile Gly Lys Leu Arg Pro Leu Asn Ile Leu Asn Ile Leu Ala
            275                 280                 285 tca tgt gat tgg act ttc gca ggc ata gtg gaa tcc ttg ata ctc atg      913
Ser Cys Asp Trp Thr Phe Ala Gly Ile Val Glu Ser Leu Ile Leu Met
            290                 295                 300 gca gag ctc ttt gga gtt ttc tgg acg ccc cca gat gtg tct gcg atg      961
Ala Glu Leu Phe Gly Val Phe Trp Thr Pro Pro Asp Val Ser Ala Met
            305                 310                 315
                                            |  |NTPase (amino acids 331-696)
att gcc ccc ttg cta ggt gat tac gag tta caa ggg cct gag gac ctt     1009
Ile Ala Pro Leu Leu Gly Asp Tyr Glu Leu Gln Gly Pro Glu Asp Leu
320                 325                 330                 335 gca gtg gaa ctc gtt cct ata gtg atg ggg gga att ggt ttg gtg cta     1057
Ala Val Glu Leu Val Pro Ile Val Met Gly Gly Ile Gly Leu Val Leu
            340                 345                 350 gga ttt acc aaa gag aag att ggg aag atg ttg tca tct gct gca tcc     1105
Gly Phe Thr Lys Glu Lys Ile Gly Lys Met Leu Ser Ser Ala Ala Ser
            355                 360                 365 acc tta aga gct tgt aaa gat ctt ggt gca tac ggg ctg gaa atc cta     1153
Thr Leu Arg Ala Cys Lys Asp Leu Gly Ala Tyr Gly Leu Glu Ile Leu
            370                 375                 380
```

Figure 16C

| | |
|---|---|
| aaa tta gtc atg aag tgg ttc ttc cca aag aaa gag gaa gca aat gag<br>Lys Leu Val Met Lys Trp Phe Phe Pro Lys Lys Glu Glu Ala Asn Glu<br>    385                         390                         395 | 1201 |
| ctg gct atg gtg aga tcc atc gag gat gcg gtg ctg gac ctc gag gca<br>Leu Ala Met Val Arg Ser Ile Glu Asp Ala Val Leu Asp Leu Glu Ala<br>400                      405                    410                    415 | 1249 |
| att gaa aac aac cat atg acc agc ctg ctc aaa gac aaa gac agt ctg<br>Ile Glu Asn Asn His Met Thr Ser Leu Leu Lys Asp Lys Asp Ser Leu<br>                        420                    425                    430 | 1297 |
| gca acc tac atg aga acc ctt gac ctt gag gag gag aaa gcc agg aag<br>Ala Thr Tyr Met Arg Thr Leu Asp Leu Glu Glu Glu Lys Ala Arg Lys<br>                        435                    440                    445 | 1345 |
| ctc tca acc aag tct gct tca cct gat atc gtg ggt aca atc aac gcc<br>Leu Ser Thr Lys Ser Ala Ser Pro Asp Ile Val Gly Thr Ile Asn Ala<br>           450                    455                    460 | 1393 |
| ctt ctg gca aga atc gct gct gca cgt tcc ctg gtg cat cga gcg aag<br>Leu Leu Ala Arg Ile Ala Ala Ala Arg Ser Leu Val His Arg Ala Lys<br>    465                        470                    475 | 1441 |
| gag gag ctt tcc agc aga cca aga ccc gtt gtc gtg atg ata tca ggc<br>Glu Glu Leu Ser Ser Arg Pro Arg Pro Val Val Val Met Ile Ser Gly<br>480                      485                    490                    495 | 1489 |
| aga cca ggg ata ggg aag acc cac ctt gcc agg gaa ctg gcc aag aga<br>Arg Pro Gly Ile Gly Lys Thr His Leu Ala Arg Glu Leu Ala Lys Arg<br>                        500                    505                    510 | 1537 |
| atc gca gcc tcc ctc aca gga gac cag cgt gta ggt ctc atc cca cgc<br>Ile Ala Ala Ser Leu Thr Gly Asp Gln Arg Val Gly Leu Ile Pro Arg<br>                515                    520                    525 | 1585 |
| aat ggc gtc gac cac tgg gac gca tac aag ggg gag agg gtc gtc cta<br>Asn Gly Val Asp His Trp Asp Ala Tyr Lys Gly Glu Arg Val Val Leu<br>                    530                    535                    540 | 1633 |
| tgg gac gac tat gga atg agt aat ccc atc cat gat gcc ctc agg tta<br>Trp Asp Asp Tyr Gly Met Ser Asn Pro Ile His Asp Ala Leu Arg Leu<br>545                      550                    555 | 1681 |
| caa gaa ctc gct gac act tgc ccc ctc act cta aac tgt gac agg att<br>Gln Glu Leu Ala Asp Thr Cys Pro Leu Thr Leu Asn Cys Asp Arg Ile<br>560                      565                    570                    575 | 1729 |
| gag aac aaa gga aag gtc ttt gac agt gat gcc ata atc atc acc act<br>Glu Asn Lys Gly Lys Val Phe Asp Ser Asp Ala Ile Ile Ile Thr Thr<br>                    580                    585                    590 | 1777 |

Figure 16D

```
aat ctg gcc aac cca gca cca ctg gac tac gtc aac ttt gag gca tgc      1825
Asn Leu Ala Asn Pro Ala Pro Leu Asp Tyr Val Asn Phe Glu Ala Cys
            595             600             605 tcg agg cgc atc gat ttc ctc gtg tat gca gat gcc cct gaa gtc gag      1873
Ser Arg Arg Ile Asp Phe Leu Val Tyr Ala Asp Ala Pro Glu Val Glu
            610             615             620 aag gcg aaa cgt gat ttc cca ggc caa cct gac atg tgg aag aac gct      1921
Lys Ala Lys Arg Asp Phe Pro Gly Gln Pro Asp Met Trp Lys Asn Ala
            625             630             635 ttc agt cct gat ttc tcg cac ata aaa cta acg ctg gct cca cag ggt      1969
Phe Ser Pro Asp Phe Ser His Ile Lys Leu Thr Leu Ala Pro Gln Gly
640             645             650             655 ggc ttc gac aag aat gga aac acc cca cat ggg aag ggc gtc atg aag      2017
Gly Phe Asp Lys Asn Gly Asn Thr Pro His Gly Lys Gly Val Met Lys
            660             665             670 act ctc acc act ggc tcc ctc att gcc cgg gca tca ggg cta ctc cat      2065
Thr Leu Thr Thr Gly Ser Leu Ile Ala Arg Ala Ser Gly Leu Leu His
            675             680             685

| |P20 (amino acids 697-875)
gag agg tta gat gag tat gag cta cag ggc cca act ctc acc act ttc      2113
Glu Arg Leu Asp Glu Tyr Glu Leu Gln Gly Pro Thr Leu Thr Thr Phe
            690             695             700 aac ttt gat cgc aac aag gtg ctt gct ttt agg cag ctt gct gct gaa      2161
Asn Phe Asp Arg Asn Lys Val Leu Ala Phe Arg Gln Leu Ala Ala Glu
            705             710             715 aac aaa tac ggg ctg atg gac aca atg aaa gtt gga aga cag ctc aag      2209
Asn Lys Tyr Gly Leu Met Asp Thr Met Lys Val Gly Arg Gln Leu Lys
720             725             730             735 gat gtc aga acc atg cca gag ctt aaa caa gca ctc aag aat atc tca      2257
Asp Val Arg Thr Met Pro Glu Leu Lys Gln Ala Leu Lys Asn Ile Ser
            740             745             750 atc aag agg tgc cag ata gtg tac agt ggt tgc acc tat aca ctt gag      2305
Ile Lys Arg Cys Gln Ile Val Tyr Ser Gly Cys Thr Tyr Thr Leu Glu
            755             760             765 tct gat ggc aag ggc agt gtg aaa gtt gac aga gtt cag agc gcc acc      2353
Ser Asp Gly Lys Gly Ser Val Lys Val Asp Arg Val Gln Ser Ala Thr
            770             775             780 gtg cag acc aat aac gag ctg gcc ggc gcc cta cac cat cta agg tgc      2401
Val Gln Thr Asn Asn Glu Leu Ala Gly Ala Leu His His Leu Arg Cys
            785             790             795
```

Figure 16E

```
gcc aga att agg tac tat gtc aag tgt gtc cag gag gcc cta tat tcc      2449
Ala Arg Ile Arg Tyr Tyr Val Lys Cys Val Gln Glu Ala Leu Tyr Ser
800             805                 810                 815 atc atc caa att gct gga gct gca ttt gtc acc acg cgc atc gtc aag      2497
Ile Ile Gln Ile Ala Gly Ala Ala Phe Val Thr Thr Arg Ile Val Lys
                820                 825                 830 cgc atg aac ata caa gac ctc tgg tcc aag cca caa gtg gaa gac aca      2545
Arg Met Asn Ile Gln Asp Leu Trp Ser Lys Pro Gln Val Glu Asp Thr
            835                 840                 845 gag gag act atc aac aag gac ggg tgc cca aaa ccc aaa gat gat gag      2593
Glu Glu Thr Ile Asn Lys Asp Gly Cys Pro Lys Pro Lys Asp Asp Glu
    850                 855                 860
                                                    | |VPg (amino acids 876-1008)
gag ttc gtc gtc tca tct gac gac atc aaa act gag ggc aag aaa ggg      2641
Glu Phe Val Val Ser Ser Asp Asp Ile Lys Thr Glu Gly Lys Lys Gly
        865                 870                 875 aag aac aag act ggc cgt ggc aag aag cac aca gcc ttc tca agc aaa      2689
Lys Asn Lys Thr Gly Arg Gly Lys Lys His Thr Ala Phe Ser Ser Lys
880                 885                 890                 895 ggt ctc agt gat gaa gag tac gat gag tac aag aga atc aga gaa gaa      2737
Gly Leu Ser Asp Glu Glu Tyr Asp Glu Tyr Lys Arg Ile Arg Glu Glu
                900                 905                 910 aga aac ggc aag tac tcc ata gaa gag tac ctt cag gac agg gac aag      2785
Arg Asn Gly Lys Tyr Ser Ile Glu Glu Tyr Leu Gln Asp Arg Asp Lys
            915                 920                 925 tac tat gag gag gtg gcc att gcc agg gcg acc gaa gag gac ttc tgt      2833
Tyr Tyr Glu Glu Val Ala Ile Ala Arg Ala Thr Glu Glu Asp Phe Cys
        930                 935                 940 gaa gag gag gag gcc aag att cgg cag agg att ttc agg cca aca agg      2881
Glu Glu Glu Glu Ala Lys Ile Arg Gln Arg Ile Phe Arg Pro Thr Arg
945                 950                 955 aaa caa cgc aag gag gag agg gcc tct ctc ggt tta gtc aca ggc tct      2929
Lys Gln Arg Lys Glu Glu Arg Ala Ser Leu Gly Leu Val Thr Gly Ser
960                 965                 970                 975 gaa atc agg aag agg aac cca gat gat ttc aag ccc aag gga aaa ctg      2977
Glu Ile Arg Lys Arg Asn Pro Asp Asp Phe Lys Pro Lys Gly Lys Leu
                980                 985                 990 tgg gct gat gat gac agg agt gta gac tac aat gag aga ctc agt ttt     3025
Trp Ala Asp Asp Asp Arg Ser Val Asp Tyr Asn Glu Arg Leu Ser Phe
                995                 1000                1005
```

Figure 16F

```
| |Protease (amino acids 1009-1189)
gag gcc cca cca agc atc tgg tcg agg ata gtc aac ttt ggt tca      3070
Glu Ala Pro Pro Ser Ile Trp Ser Arg Ile Val Asn Phe Gly Ser
        1010            1015                1020 ggt tgg ggc ttc tgg gtt tct ccc agc ctg ttc ata aca tca act      3115
Gly Trp Gly Phe Trp Val Ser Pro Ser Leu Phe Ile Thr Ser Thr
        1025            1030                1035 cat gtc ata ccc cag ggc gca cag gag ttc ttt gga gtc ccc atc      3160
His Val Ile Pro Gln Gly Ala Gln Glu Phe Phe Gly Val Pro Ile
        1040            1045                1050 aag caa att cag ata cac aaa tcg ggc gaa ttc tgt cgc ttg agg      3205
Lys Gln Ile Gln Ile His Lys Ser Gly Glu Phe Cys Arg Leu Arg
        1055            1060                1065 ttc cca aaa cca atc agg act gat gtg acg ggc atg atc tta gaa      3250
Phe Pro Lys Pro Ile Arg Thr Asp Val Thr Gly Met Ile Leu Glu
        1070            1075                1080

| |Polymerase (amino acids 1090-1699)
gaa ggt gcg ccc gaa ggt acc gtg gcc acc cta ctc atc aag agg      3295
Glu Gly Ala Pro Glu Gly Thr Val Ala Thr Leu Leu Ile Lys Arg
        1085            1090                1095 cct act gga gaa ctt atg ccc tta gca gcc aga atg ggg acc cat      3340
Pro Thr Gly Glu Leu Met Pro Leu Ala Ala Arg Met Gly Thr His
        1100            1105                1110 gca acc atg aaa att caa ggg cgc act gtt gga ggt caa atg ggc      3385
Ala Thr Met Lys Ile Gln Gly Arg Thr Val Gly Gly Gln Met Gly
        1115            1120                1125 atg ctt ctg aca gga tcc aac gcc aaa agc atg gtt cta ggc acc      3430
Met Leu Leu Thr Gly Ser Asn Ala Lys Ser Met Val Leu Gly Thr
        1130            1135                1140 aca cca ggt gac tgc ggc tgc ccc tac atc tac aag agg gag aat      3475
Thr Pro Gly Asp Cys Gly Cys Pro Tyr Ile Tyr Lys Arg Glu Asn
        1145            1150                1155 gac tac gtg gtt att gga gtc cac acg gct gcc gct cgt ggg ggg      3520
Asp Tyr Val Val Ile Gly Val His Thr Ala Ala Ala Arg Gly Gly
        1160            1165                1170 aac act gtc ata tgt gcc acc cag ggg agt gag gga gag gct aca      3565
Asn Thr Val Ile Cys Ala Thr Gln Gly Ser Glu Gly Glu Ala Thr
        1175            1180                1185
```

Figure 16G

| | | | | | | | | | | | | | |
|---|---|---|---|---|---|---|---|---|---|---|---|---|---|
| ctt | gaa | ggc | ggt | gac | agt | aag | gga | acc | tac | tgt | ggt | gca | cca atc | 3610 |
| Leu | Glu | Gly | Gly | Asp | Ser | Lys | Gly | Thr | Tyr | Cys | Gly | Ala | Pro Ile |
| | | 1190 | | | | 1195 | | | | | 1200 | | |

```
ctt gaa ggc ggt gac agt aag gga acc tac tgt ggt gca cca atc    3610
Leu Glu Gly Gly Asp Ser Lys Gly Thr Tyr Cys Gly Ala Pro Ile
        1190            1195                1200 cta ggc cca gga agt gcc cca aaa ctc agc acc aag act aaa ttc    3655
Leu Gly Pro Gly Ser Ala Pro Lys Leu Ser Thr Lys Thr Lys Phe
        1205            1210                1215 tgg aga tca tct aca aca cca ctc cca cct ggc acc tat gaa cca    3700
Trp Arg Ser Ser Thr Thr Pro Leu Pro Pro Gly Thr Tyr Glu Pro
        1220            1225                1230 gcc tac ctt ggt ggt aag gac ccc aga gtc aag ggt ggc cct tca    3745
Ala Tyr Leu Gly Gly Lys Asp Pro Arg Val Lys Gly Gly Pro Ser
        1235            1240                1245 ttg caa caa gtc atg agg gat cag ctg aaa cca ttt aca gag ccc    3790
Leu Gln Gln Val Met Arg Asp Gln Leu Lys Pro Phe Thr Glu Pro
        1250            1255                1260 agg ggc aaa cca cca aag cca agt gtg ttg gag gct gcc aag aaa    3835
Arg Gly Lys Pro Pro Lys Pro Ser Val Leu Glu Ala Ala Lys Lys
        1265            1270                1275 acc atc atc aat gtc ctt gaa caa aca att gat cca cct cag aag    3880
Thr Ile Ile Asn Val Leu Glu Gln Thr Ile Asp Pro Pro Gln Lys
        1280            1285                1290 tgg tca ttc acg caa gct tgc gcg tcc ctc gac aag act act tcc    3925
Trp Ser Phe Thr Gln Ala Cys Ala Ser Leu Asp Lys Thr Thr Ser
        1295            1300                1305 agt ggc cat ccg cac cac ata cgg aaa aac gac tgc tgg aac ggg    3970
Ser Gly His Pro His His Ile Arg Lys Asn Asp Cys Trp Asn Gly
        1310            1315                1320 gaa tcc ttc aca ggc aag ttg gca gac cag gct tcc aag gcc aac    4015
Glu Ser Phe Thr Gly Lys Leu Ala Asp Gln Ala Ser Lys Ala Asn
        1325            1330                1335 ctg atg ttc gaa gag ggg aag aac atg acc ccg gtc tac aca ggt    4060
Leu Met Phe Glu Glu Gly Lys Asn Met Thr Pro Val Tyr Thr Gly
        1340            1345                1350 gcg ctt aag gat gag ttg gtc aaa act gac aaa att tat ggt aag    4105
Ala Leu Lys Asp Glu Leu Val Lys Thr Asp Lys Ile Tyr Gly Lys
        1355            1360                1365 atc aag aag agg ctt ctc tgg ggc tcg gac tta gcg acc atg atc    4150
Ile Lys Lys Arg Leu Leu Trp Gly Ser Asp Leu Ala Thr Met Ile
        1370            1375                1380
```

Figure 16H

```
cgg tgc gct cgg gca ttc gga ggc cta atg gat gaa ctc aaa gca    4195
Arg Cys Ala Arg Ala Phe Gly Gly Leu Met Asp Glu Leu Lys Ala
        1385            1390                1395 cac tgt gtt aca ctt cct gtc aga gtt ggt atg aat atg aat gag    4240
His Cys Val Thr Leu Pro Val Arg Val Gly Met Asn Met Asn Glu
        1400            1405                1410 gat ggc ccc atc atc ttc gag agg cat tcc agg tat aaa tat cac    4285
Asp Gly Pro Ile Ile Phe Glu Arg His Ser Arg Tyr Lys Tyr His
        1415            1420                1425 tat gat gct gat tac tct cgg tgg gat tca acg caa cag aga gcc    4330
Tyr Asp Ala Asp Tyr Ser Arg Trp Asp Ser Thr Gln Gln Arg Ala
        1430            1435                1440 gta tta gca gca gcc cta gaa atc atg gtt aaa ttc tcc cca gaa    4375
Val Leu Ala Ala Ala Leu Glu Ile Met Val Lys Phe Ser Pro Glu
        1445            1450                1455 cca cat ctg gcc cag ata gtt gca gaa gac ctt ctc tct cct agt    4420
Pro His Leu Ala Gln Ile Val Ala Glu Asp Leu Leu Ser Pro Ser
        1460            1465                1470 gtg atg gat gtg ggt gac ttc aaa ata tca atc aat gag ggt ctc    4465
Val Met Asp Val Gly Asp Phe Lys Ile Ser Ile Asn Glu Gly Leu
        1475            1480                1485 ccc tct ggg gtg ccc tgc acc tcc caa tgg aat tcc atc gcc cac    4510
Pro Ser Gly Val Pro Cys Thr Ser Gln Trp Asn Ser Ile Ala His
        1490            1495                1500 tgg ctc ctc act ctc tgt gca ctc tct gaa gtc aca aac ctg tcc    4555
Trp Leu Leu Thr Leu Cys Ala Leu Ser Glu Val Thr Asn Leu Ser
        1505            1510                1515 cct gat atc ata cag gct aat tcc ctc ttc tcc ttt tat ggc gat    4600
Pro Asp Ile Ile Gln Ala Asn Ser Leu Phe Ser Phe Tyr Gly Asp
        1520            1525                1530 gat gaa att gtc agt aca gat ata aag ttg gac cca gag aaa ttg    4645
Asp Glu Ile Val Ser Thr Asp Ile Lys Leu Asp Pro Glu Lys Leu
        1535            1540                1545 aca gca aaa ctc aag gaa tac ggg ttg aaa cca acc cgc cct gac    4690
Thr Ala Lys Leu Lys Glu Tyr Gly Leu Lys Pro Thr Arg Pro Asp
        1550            1555                1560 aaa act gaa gga ccc ctt act atc tct gaa gac ttg aat ggt ctg    4735
Lys Thr Glu Gly Pro Leu Thr Ile Ser Glu Asp Leu Asn Gly Leu
        1565            1570                1575
```

Figure 16I

```
acc ttc ctg cgg aga act gtg acc cgc gac cca gct ggc tgg ttt      4780
Thr Phe Leu Arg Arg Thr Val Thr Arg Asp Pro Ala Gly Trp Phe
        1580                1585                1590 gga aaa ttg gaa cag agt tca ata ctt agg caa atg tac tgg act      4825
Gly Lys Leu Glu Gln Ser Ser Ile Leu Arg Gln Met Tyr Trp Thr
        1595                1600                1605 agg ggc ccc aac cat gaa gac cca tct gaa aca atg ata cca cac      4870
Arg Gly Pro Asn His Glu Asp Pro Ser Glu Thr Met Ile Pro His
        1610                1615                1620 tcc caa aga ccc ata caa tta atg tcc cta ctg ggc gag gcc gca      4915
Ser Gln Arg Pro Ile Gln Leu Met Ser Leu Leu Gly Glu Ala Ala
        1625                1630                1635 ctc cac ggc cca gca ttc tac agc aaa att agc aag cta gtc att      4960
Leu His Gly Pro Ala Phe Tyr Ser Lys Ile Ser Lys Leu Val Ile
        1640                1645                1650 gca gag ctg aag gaa ggt ggc atg gat ttt tac gtg ccc aga caa      5005
Ala Glu Leu Lys Glu Gly Gly Met Asp Phe Tyr Val Pro Arg Gln
        1655                1660                1665 gag cca atg ttc aga tgg atg aga ttc tca gat ctg agc acg tgg      5050
Glu Pro Met Phe Arg Trp Met Arg Phe Ser Asp Leu Ser Thr Trp
        1670                1675                1680 gag ggc gat cgc aat ctg gct ccc agt ttt gtg aat gaa gat ggc      5095
Glu Gly Asp Arg Asn Leu Ala Pro Ser Phe Val Asn Glu Asp Gly
        1685                1690                1695 gtc gag tga cgccaaccca tctgatgggt ccgcagccaa cctcgtccca         5144
Val Glu
```

Figure 17A

ORF2 Coding Sequence for NV-MD145-12 Major Capsid Protein

| | |
|---|---:|
| gagcacgtgg gagggcgatc gcaatctggc tcccagtttt gtga atg aag atg gcg<br>                                                                               Met Lys Met Ala<br>                                                                                1 | 5096 |
| tcg agt gac gcc aac cca tct gat ggg tcc gca gcc aac ctc gtc cca<br>Ser Ser Asp Ala Asn Pro Ser Asp Gly Ser Ala Ala Asn Leu Val Pro<br>5                        10                        15                        20 | 5144 |
| gag gtc aac aat gag gtt atg gct ctg gag ccc gtt gtt ggt gcc gct<br>Glu Val Asn Asn Glu Val Met Ala Leu Glu Pro Val Val Gly Ala Ala<br>                      25                        30                        35 | 5192 |
| att gcg gca cct gta gcg ggc caa caa aat ata att gac ccc tgg att<br>Ile Ala Ala Pro Val Ala Gly Gln Gln Asn Ile Ile Asp Pro Trp Ile<br>                      40                        45                        50 | 5240 |
| aga aat aat ttt gta caa gcc cct ggt gga gag ttt aca gtg tcc cct<br>Arg Asn Asn Phe Val Gln Ala Pro Gly Gly Glu Phe Thr Val Ser Pro<br>                      55                        60                        65 | 5288 |
| aga aac gct cca ggt gag ata cta tgg agc gcg ccc ttg ggc cct gat<br>Arg Asn Ala Pro Gly Glu Ile Leu Trp Ser Ala Pro Leu Gly Pro Asp<br>                      70                        75                        80 | 5336 |
| ttg aac ccc tat ctt tct cat ttg tcc aga atg tac aat ggt tat gca<br>Leu Asn Pro Tyr Leu Ser His Leu Ser Arg Met Tyr Asn Gly Tyr Ala<br>85                        90                        95                        100 | 5384 |
| ggc ggt ttc gaa gtg caa gta atc ctc gcg ggg aac gcg ttc acc gcc<br>Gly Gly Phe Glu Val Gln Val Ile Leu Ala Gly Asn Ala Phe Thr Ala<br>                      105                      110                      115 | 5432 |
| ggg aaa gtt ata ttt gca gca gtt cca cca aac ttt cca act gaa ggc<br>Gly Lys Val Ile Phe Ala Ala Val Pro Pro Asn Phe Pro Thr Glu Gly<br>                      120                      125                      130 | 5480 |
| tta agc ccc agc cag gtt act atg ttc ccc cat ata att gta gat gtt<br>Leu Ser Pro Ser Gln Val Thr Met Phe Pro His Ile Ile Val Asp Val<br>                      135                      140                      145 | 5528 |
| agg caa ttg gaa cct gtg ttg atc ccc cta cct gat gtt agg aat aat<br>Arg Gln Leu Glu Pro Val Leu Ile Pro Leu Pro Asp Val Arg Asn Asn<br>                      150                      155                      160 | 5576 |
| ttc tat cat tac aat caa tca cat gat tct acc ctt aag ttg ata gca<br>Phe Tyr His Tyr Asn Gln Ser His Asp Ser Thr Leu Lys Leu Ile Ala<br>165                       170                      175                      180 | 5624 |

Figure 17B

```
atg ttg tat aca cca ctc agg gct aat aat gcc ggg gac gat gtc ttc    5672
Met Leu Tyr Thr Pro Leu Arg Ala Asn Asn Ala Gly Asp Asp Val Phe
            185                 190                 195 aca gtc tct tgt cga gtt ctc acg agg cca tcc ccc gat ttt gat ttc    5720
Thr Val Ser Cys Arg Val Leu Thr Arg Pro Ser Pro Asp Phe Asp Phe
            200                 205                 210 ata ttc ttg gtg cca ccc aca gtt gaa tca aga act aaa cca ttc acc    5768
Ile Phe Leu Val Pro Pro Thr Val Glu Ser Arg Thr Lys Pro Phe Thr
            215                 220                 225 gtc cca atc tta act gtt gag gaa atg tcc aat tca aga ttc ccc att    5816
Val Pro Ile Leu Thr Val Glu Glu Met Ser Asn Ser Arg Phe Pro Ile
        230                 235                 240 cct ttg gaa aag ttg tac acg ggt cct agc agt gct ttt gtt gtc caa    5864
Pro Leu Glu Lys Leu Tyr Thr Gly Pro Ser Ser Ala Phe Val Val Gln
245                 250                 255                 260 cca caa aat ggc aga tgc acg act gat ggc gtg ctc tta ggt act acc    5912
Pro Gln Asn Gly Arg Cys Thr Thr Asp Gly Val Leu Leu Gly Thr Thr
                265                 270                 275 cag ctg tca gct gtc aac atc tgt aac ttt agg ggg gat gtc acc cat    5960
Gln Leu Ser Ala Val Asn Ile Cys Asn Phe Arg Gly Asp Val Thr His
            280                 285                 290 att gtg ggc agc cat gat tat aca atg aat ctg gct tcc caa aat tgg    6008
Ile Val Gly Ser His Asp Tyr Thr Met Asn Leu Ala Ser Gln Asn Trp
            295                 300                 305 agc aat tat gac cca aca gaa gaa atc cca gcc ccc ctg gga aca cca    6056
Ser Asn Tyr Asp Pro Thr Glu Glu Ile Pro Ala Pro Leu Gly Thr Pro
            310                 315                 320 gat ttt gtg ggg aag atc caa ggc ctg ctc acc cag acc aca aga gcg    6104
Asp Phe Val Gly Lys Ile Gln Gly Leu Leu Thr Gln Thr Thr Arg Ala
325                 330                 335                 340 gat ggc tcg acc cgt gcc cac aaa gct aca gtg agc act ggg agt gtc    6152
Asp Gly Ser Thr Arg Ala His Lys Ala Thr Val Ser Thr Gly Ser Val
                345                 350                 355 cac ttc act cca aag ctg ggt agt gtt caa ttc acc act gac aca aac    6200
His Phe Thr Pro Lys Leu Gly Ser Val Gln Phe Thr Thr Asp Thr Asn
            360                 365                 370 aat gat ttc caa act ggc caa aac acg aaa ttc acc cca gtt ggc gtc    6248
Asn Asp Phe Gln Thr Gly Gln Asn Thr Lys Phe Thr Pro Val Gly Val
            375                 380                 385
```

Figure 17C

```
atc cag gac ggt gat cac cat cag aat gag ccc caa caa tgg gta ctc    6296
Ile Gln Asp Gly Asp His His Gln Asn Glu Pro Gln Gln Trp Val Leu
    390                 395                 400 cca aat tac tca ggt aga act ggt cat aat gtg cac ctg gcc cct gcc    6344
Pro Asn Tyr Ser Gly Arg Thr Gly His Asn Val His Leu Ala Pro Ala
405                 410                 415                 420 gtt gcc ccc act ttt ccg ggt gag caa ctc ctt ttc ttt aga tcc act    6392
Val Ala Pro Thr Phe Pro Gly Glu Gln Leu Leu Phe Phe Arg Ser Thr
                425                 430                 435 atg ccc gga tgt agc ggg tat ccc aac atg aat ttg gat tgc cta ctc    6440
Met Pro Gly Cys Ser Gly Tyr Pro Asn Met Asn Leu Asp Cys Leu Leu
            440                 445                 450 ccc cag gaa tgg gtg ctg cac ttc tac cag gaa gca gct cca gca caa    6488
Pro Gln Glu Trp Val Leu His Phe Tyr Gln Glu Ala Ala Pro Ala Gln
        455                 460                 465 tcc gat gtg gct ctg ctg aga ttt gtg aat cca gac aca ggt agg gtt    6536
Ser Asp Val Ala Leu Leu Arg Phe Val Asn Pro Asp Thr Gly Arg Val
    470                 475                 480 ctg ttt gag tgc aag ctc cat aaa tca ggc tat atc aca gtg gct cac    6584
Leu Phe Glu Cys Lys Leu His Lys Ser Gly Tyr Ile Thr Val Ala His
485                 490                 495                 500 acc ggc ccg tat gac ttg gtt atc ccc ccc aat ggt tat ttt aga ttt    6632
Thr Gly Pro Tyr Asp Leu Val Ile Pro Pro Asn Gly Tyr Phe Arg Phe
                505                 510                 515 gat tcc tgg gtc aac cag ttc tac aca ctt gcc ccc atg gga aat gga    6680
Asp Ser Trp Val Asn Gln Phe Tyr Thr Leu Ala Pro Met Gly Asn Gly
            520                 525                 530 acg ggg cgc agg cgt gca tta taa tggctggatc tttctttgct ggattggcat   6734
Thr Gly Arg Arg Arg Ala Leu
            535
```

Figure 18A

ORF3 Coding Sequence for NV-MD145-12 Minor Structural Protein

| | | | | | | | | | | | | | | | |
|---|---|---|---|---|---|---|---|---|---|---|---|---|---|---|---|
| ttgcccccat | gggaaatgga | acggggcgca | ggcgtgcatt | ata | atg<br>Met<br>1 | gct<br>Ala | gga<br>Gly | tct<br>Ser | | | | | | | 6715 |

| ttc<br>Phe<br>5 | ttt<br>Phe | gct<br>Ala | gga<br>Gly | ttg<br>Leu | gca<br>Ala<br>10 | tct<br>Ser | gat<br>Asp | gtc<br>Val | ctc<br>Leu | ggc<br>Gly<br>15 | tct<br>Ser | gga<br>Gly | ctt<br>Leu | ggt<br>Gly | tct<br>Ser<br>20 | 6763 |

| cta<br>Leu | atc<br>Ile | aat<br>Asn | gct<br>Ala | gga<br>Gly<br>25 | gct<br>Ala | ggg<br>Gly | gcc<br>Ala | atc<br>Ile | aac<br>Asn<br>30 | caa<br>Gln | aaa<br>Lys | gtt<br>Val | gaa<br>Glu | ttt<br>Phe<br>35 | gaa<br>Glu | 6811 |

| aat<br>Asn | aac<br>Asn | aga<br>Arg | aaa<br>Lys<br>40 | ttg<br>Leu | caa<br>Gln | caa<br>Gln | gct<br>Ala | tcc<br>Ser<br>45 | ttc<br>Phe | caa<br>Gln | ttt<br>Phe | agt<br>Ser | agc<br>Ser<br>50 | aat<br>Asn | cta<br>Leu | 6859 |

| caa<br>Gln | cag<br>Gln | gct<br>Ala | tcc<br>Ser<br>55 | ttc<br>Phe | caa<br>Gln | cat<br>His | gat<br>Asp | aaa<br>Lys<br>60 | gag<br>Glu | atg<br>Met | ctc<br>Leu | caa<br>Gln | gca<br>Ala<br>65 | caa<br>Gln | att<br>Ile | 6907 |

| gag<br>Glu | gct<br>Ala | act<br>Thr<br>70 | caa<br>Gln | aaa<br>Lys | ttg<br>Leu | caa<br>Gln | cag<br>Gln<br>75 | gat<br>Asp | ctg<br>Leu | atg<br>Met | aag<br>Lys | gtt<br>Val<br>80 | aaa<br>Lys | cag<br>Gln | gca<br>Ala | 6955 |

| gtg<br>Val<br>85 | ctc<br>Leu | cta<br>Leu | gag<br>Glu | ggt<br>Gly | gga<br>Gly<br>90 | ttt<br>Phe | tcc<br>Ser | aca<br>Thr | aca<br>Thr | gat<br>Asp<br>95 | gca<br>Ala | gcc<br>Ala | cgt<br>Arg | ggg<br>Gly | gca<br>Ala<br>100 | 7003 |

| atc<br>Ile | aac<br>Asn | gcc<br>Ala | ccc<br>Pro | atg<br>Met<br>105 | aca<br>Thr | aag<br>Lys | gct<br>Ala | ctg<br>Leu | gac<br>Asp<br>110 | tgg<br>Trp | agc<br>Ser | gga<br>Gly | aca<br>Thr | agg<br>Arg<br>115 | tac<br>Tyr | 7051 |

| tgg<br>Trp | gcc<br>Ala | cct<br>Pro | gat<br>Asp<br>120 | gcc<br>Ala | agg<br>Arg | acc<br>Thr | aca<br>Thr | aca<br>Thr<br>125 | tac<br>Tyr | aat<br>Asn | gca<br>Ala | ggc<br>Gly | cgc<br>Arg<br>130 | ttt<br>Phe | tcc<br>Ser | 7099 |

| acc<br>Thr | ctt<br>Leu | cag<br>Gln<br>135 | cct<br>Pro | tcg<br>Ser | ggg<br>Gly | gca<br>Ala | ctg<br>Leu<br>140 | cca<br>Pro | gga<br>Gly | aga<br>Arg | act<br>Thr | aat<br>Asn<br>145 | cct<br>Pro | agg<br>Arg | att<br>Ile | 7147 |

| acc<br>Thr | gtc<br>Val<br>150 | ccc<br>Pro | gct<br>Ala | cgg<br>Arg | ggc<br>Gly | ccc<br>Pro<br>155 | ccc<br>Pro | agc<br>Ser | aca<br>Thr | ctt<br>Leu | tct<br>Ser<br>160 | aat<br>Asn | gct<br>Ala | tct<br>Ser | act<br>Thr | 7195 |

| gct<br>Ala<br>165 | act<br>Thr | tct<br>Ser | gtg<br>Val | tat<br>Tyr | tca<br>Ser<br>170 | aat<br>Asn | caa<br>Gln | act<br>Thr | gtt<br>Val | tca<br>Ser<br>175 | acg<br>Thr | aga<br>Arg | cta<br>Leu | ggt<br>Gly | tct<br>Ser<br>180 | 7243 |

Figure 18B

```
tca gct ggt tct ggt acc ggt gtc tcg agt ctc ccg tca act gca agg    7291
Ser Ala Gly Ser Gly Thr Gly Val Ser Ser Leu Pro Ser Thr Ala Arg
            185                 190                 195 act agg aac tgg gtt gag gac caa aac agg aat ttg tca cct ttc atg    7339
Thr Arg Asn Trp Val Glu Asp Gln Asn Arg Asn Leu Ser Pro Phe Met
            200                 205                 210 agg ggg gct ctc aac aca tca ttc gtc acc cct cca tct agt aga tcc    7387
Arg Gly Ala Leu Asn Thr Ser Phe Val Thr Pro Pro Ser Ser Arg Ser
            215                 220                 225 tct aac caa ggc aca gtc tca acc gtg cct aaa gaa att ttg gac tcc    7435
Ser Asn Gln Gly Thr Val Ser Thr Val Pro Lys Glu Ile Leu Asp Ser
            230                 235                 240 tgg act ggc gct ttc aac acg cgc agg cag cct ctc ttc gct cac att    7483
Trp Thr Gly Ala Phe Asn Thr Arg Arg Gln Pro Leu Phe Ala His Ile
245                 250                 255                 260 cgc aaa cga ggg gag tca cgg gtg taa tgtgaaaaga caaaattgat           7530
Arg Lys Arg Gly Glu Ser Arg Val
                    265 tttctttctc ttctttagtg tctttt                                        7556
```

# METHODS FOR PRODUCING NOROVIRUS VLPS

CROSS REFERENCES TO RELATED APPLICATIONS

This application is a continuation of U.S. Ser. No. 11/603,913, filed Nov. 22, 2006, now U.S. Pat. No. 7,527,801 which application claims the benefit of U.S. provisional application No. 60/739,217, filed Nov. 22, 2005, which applications are hereby incorporated by reference in their entireties.

TECHNICAL FIELD

The present invention pertains generally to compositions that elicit immune responses against Noroviruses and/or Sapoviruses. In particular, the invention relates to immunogenic compositions comprising nucleic acids encoding Norovirus and/or Sapovirus antigens, and/or immunogenic polypeptides, including structural polypeptides, nonstructural polypeptides, and polyproteins, and fragments thereof, and/or multiepitope fusion proteins, and/or viral-like particles derived from one or more genotypes and/or isolates of Norovirus and Sapovirus. Immunogenic compositions, in addition may contain antigens other than Norovirus or Sapovirus antigens, including antigens that can be used in immunization against pathogens that cause diarrheal diseases, such as antigens derived from rotavirus. Methods of eliciting an immune response with the immunogenic compositions of the invention and methods of treating a Norovirus and/or Sapovirus infection are also described.

BACKGROUND

Noroviruses (also known as Norwalk-like viruses or Norwalk viruses) and Sapoviruses (also known as Sapporo-like viruses) are etiological agents of acute gastroenteritis in adults and children (Green et al. J. Infect. Dis. 181 (Suppl 2):S322-330). Norviruses and Sapoviruses are members of the Caliciviridae family of small, nonenveloped viruses, 27-35 nm in diameter, containing a single-strand of positive-sense genomic RNA. Currently, Norviruses and Sapoviruses are the only two genera of the Caliciviridae family known to cause human disease.

Noroviruses cause greater than 90% of nonbacterial gastroenteritis outbreaks and an estimated 23 million cases of gastroenteritis in the U.S. per year (Fankhauser et al. (2002) J. Infect. Dis. 186:1-7; MMWR Morb. Mortal Weekly Rep. (2000) 49:207-211). Although, the Norwalk strain of Norovirus was the first discovered, it is now apparent that the Norwalk virus causes less than 10% of gastroenteritis cases, whereas other members of the Norovirus family, such as the Lordsdale virus, Toronto virus, and Snow Mountain virus, may cause 90% of cases (Fankhauser et al. (1998) J. Infect. Dis. 178:1571-1578; Nishida et al. (2003) Appl. Environ. Microbiol. 69(10):5782-6).

The symptoms of Norovirus infection include simultaneous diarrhea and vomiting as well as fever, headaches, chills and stomach-aches. The cause of such symptoms may be related to the binding of Noroviruses to carbohydrate receptors of intestinal epithelial cells, which results in an imbalance in ion transfer (Marionneau et al. (2002) Gastroenterology 122:1967-1977; Hutson et al. (2003) J. Virol. 77:405-415). Extremely contagious, Noroviruses can cause disease by infection with as few as 10 virions. Although, otherwise healthy people infected with Noroviruses may recover within 2-4 days, they may still shed virus for up to 2 weeks after the onset of symptoms; hence, infected individuals should be quarantined for up to two weeks. Approximately 30-40% of infected people may remain symptom-free, though spread infection by shedding of virus to others who may be more susceptible to infection (Hutson et al. Trends Microbiol. 2004 June; 12(6):279-287).

In contrast, Sapoviruses are less prevalent in gastroenteritis outbreaks and infect mostly infants and children, though occasionally adults (Zintz et al. (2005) Infect. Genet. Evol. 5:281-290; Johansson et al. (2005) Scand. J. Infect. Dis. 37:200-204; Rockx et al. (2002) Clin. Infect. Dis. 35:246-253). Sapoviruses also cause diarrhea and vomiting and spread infection through viral shedding, which may last for up to 2 weeks.

There remains a need for an improved therapy for treating patients having gastroenteritis associated with Norovirus or Sapovirus infection and methods for preventing the spread of infection.

SUMMARY

The present invention provides immunogenic compositions comprising Norovirus and Sapovirus antigens. In particular, the invention provides polynucleotides encoding one or more capsid proteins or fragments thereof and/or other immunogenic viral polypeptides or peptides from one or more strains of Norovirus and/or Sapovirus.

Methods for producing Norovirus- or Sapovirus-derived multiple epitope fusion antigens or polyprotein fusion antigens are also described. Immunogenic polypeptides, peptides, and/or VLPs may be mixed or co-expressed with adjuvants (e.g., detoxified mutants of E. coli heat-labile toxins (LT) such as LT-K63 or LT-R72). The polynucleotides of the invention may be used in immunization or in production of immunogenic viral polypeptides and viral-like particles (VLPs). Immunogenic compositions may comprise one or more polynucleotides, polypeptides, peptides, VLPs, and/or adjuvants as described herein. Particularly preferred are immunogenic compositions including all or components of all the pathogenic Noroviruses and/or Saporoviruses. In addition, antigens, other than Norovirus or Sapovirus antigens, may be used in immunogenic compositions (e.g., combination vaccines). For example, immunogenic compositions may comprise other antigens that can be used in immunization against pathogens that cause diarrheal diseases, such as antigens derived from rotavirus.

The invention also provides various processes:

In one embodiment, the invention provides a process for producing a polypeptide of the invention, comprising the step of culturing a host cell transformed with a nucleic acid of the invention under conditions which induce polypeptide expression. By way of example, a Norovirus or Sapovirus protein may be expressed by recombinant technology and used to develop an immunogenic composition comprising a recombinant subunit Norwalk or Norwalk related vaccine. Alternatively the viral capsid protein genes may also be used to prepare Virus-like particles (VLPs) in yeast cells or using baculovirus/insect cell methodology or VEE/SIN alphavirus methodology.

The invention provides a process for producing a polypeptide of the invention, comprising the step of synthesising at least part of the polypeptide by chemical means.

The invention provides a process for producing nucleic acid of the invention, wherein the nucleic acid is prepared (at least in part) by chemical synthesis.

The invention provides a process for producing nucleic acid of the invention, comprising the step of amplifying nucleic acid using a primer-based amplification method (e.g. PCR).

The invention provides a process for producing a protein complex of the invention, comprising the step of contacting a class I MHC protein with a polypeptide of the invention, or a fragment thereof.

The invention provides a process for producing a protein complex of the invention, comprising the step of administering a polypeptide of the invention, or a fragment thereof, to a subject. The process may comprise the further step of purifying the complex from the subject.

The invention provides a process for producing a composition comprising admixing a polypeptide and/or a nucleic acid of the invention with a pharmaceutically acceptable carrier or diluent.

Thus, the subject invention is represented by, but not limited to, the following numbered embodiments:

1. A polynucleotide comprising the nucleotide sequence of SEQ ID NO:1.
2. A polynucleotide comprising the nucleotide sequence of SEQ ID NO:2.
3. A recombinant polynucleotide comprising a promoter operably linked to a polynucleotide of either embodiment 1 or 2.
4. The recombinant polynucleotide of embodiment 3, wherein said promoter is a hybrid ADH2/GAPDH promoter.
5. The recombinant polynucleotide of embodiment 3, further comprising an alpha-factor terminator.
6. The recombinant polynucleotide of embodiment 3, further comprising a polynucleotide encoding an adjuvant operably linked to a promoter.
7. A recombinant polynucleotide comprising a sequence encoding a Norovirus or Sapovirus antigen and a sequence encoding an adjuvant operably linked to a promoter.
8. The recombinant polynucleotide of either embodiment 6 or 7, wherein said adjuvant is a detoxified mutant of an *E. coli* heat-labile toxin (LT) selected from the group consisting of LT-K63 and LT-R72.
9. The recombinant polynucleotide of embodiment 8 comprising a polynucleotide selected from the group consisting of:
    a) a polynucleotide comprising the sequence of SEQ ID NO:1,
    b) a polynucleotide comprising a sequence at least 90% identical to the sequence of SEQ ID NO:1 that is capable of producing viral-like particles,
    c) a polynucleotide comprising the sequence of SEQ ID NO:2,
    d) a polynucleotide comprising a sequence at least 90% identical to the sequence of SEQ ID NO:2 that is capable of producing viral-like particles, a polynucleotide encoding a polypeptide comprising the sequence of SEQ ID NO:3,
    e) a polynucleotide encoding a polypeptide comprising a sequence at least 90% identical to the sequence of SEQ ID NO:3 that is capable of eliciting an immune response against Norwalk virus major capsid protein, a polynucleotide encoding a polypeptide comprising the sequence of SEQ ID NO:4, and
    h) a polynucleotide encoding a polypeptide comprising a sequence at least 90% identical to the sequence of SEQ ID NO:4 that is capable of eliciting an immune response against Norwalk virus minor structural protein.
10. The recombinant polynucleotide of embodiment 8 comprising a polynucleotide selected from the group consisting of:
    a) a polynucleotide encoding a polypeptide comprising at least one sequence selected from the group consisting of SEQ ID NOS:3-12, SEQ ID NOS:14-17, and SEQ ID NO:19,
    b) a polynucleotide encoding a polypeptide comprising at least one sequence at least 90% identical to a sequence selected from the group consisting of SEQ ID NOS:3-12, SEQ ID NOS:14-17, and SEQ ID NO:19 that is capable of eliciting an immune response against a Norovirus or Sapovirus, and
    c) a fragment of a polynucleotide of a) or b) comprising a sequence encoding an immunogenic fragment that is capable of eliciting an immune response against a Norovirus or Sapovirus.
11. A composition, comprising the recombinant polynucleotide of any of embodiments 3-10 and a pharmaceutically acceptable excipient.
12. The composition of embodiment 11, further comprising an adjuvant.
13. The composition of embodiment 12, wherein said adjuvant is selected from the group consisting of LT-K63, LT-R72, MF59, and alum.
14. The composition of any one of embodiments 11-13, further comprising a polynucleotide comprising a sequence encoding an adjuvant.
15. The composition of embodiment 14, wherein said adjuvant is LT-K63 or LT-R72.
16. The composition of any of embodiments 11-15, further comprising a microparticle.
17. The composition of embodiment 16, wherein said microparticle is a poly(L-lactide), poly(D,L-lactide) or poly (D,L-lactide-co-glycolide) microparticle.
18. The composition of any of embodiments 11-17, further comprising chitosan.
19. The composition of any of embodiments 11-17, further comprising a polypeptide from a Norovirus or Sapovirus.
20. The composition of embodiment 19, comprising a polypeptide selected from the group consisting of:
    a) a polypeptide comprising a sequence selected from the group consisting of SEQ ID NOS:3-12, SEQ ID NOS: 14-17, and SEQ ID NO:19,
    b) a polypeptide comprising a sequence at least 90% identical to a sequence selected from the group consisting of SEQ ID NOS:3-12, SEQ ID NOS:14-17, and SEQ ID NO:19, and
    c) an immunogenic fragment of a polypeptide of a) or b).
21. The composition of embodiment 19, comprising at least two polypeptides from different isolates of Norovirus or Sapovirus.
22. The composition of embodiment 21, wherein at least one polypeptide is from a virus selected from the group consisting of Norwalk virus (NV), Snow Mountain virus (SMV), and Hawaii virus (HV).
23. The composition of embodiment 22, comprising an NV polypeptide, an SMV polypeptide, and an HV polypeptide.
24. The composition of any of embodiments 11-23, further comprising a viral-like particle from a Norovirus or Sapovirus.
25. The composition of any of embodiments 11-24, further comprising a polynucleotide comprising an ORF1 sequence from a Norovirus or Sapovirus.
26. The composition of any of embodiments 11-25, further comprising a polynucleotide comprising an ORF2 sequence from a Norovirus or Sapovirus.

27. The composition of any of embodiments 11-26, further comprising a polynucleotide comprising an ORF3 sequence from a Norovirus.

28. A cell transformed with the recombinant polynucleotide of any of embodiments 3-10.

29. A composition comprising at least two polypeptides from two or more strains of Norovirus or Sapovirus.

30. The composition of claim 29 comprising at least two capsid polypeptides from two or more strains of Norovirus or Sapovirus.

31. The composition of embodiment 29 or 30, comprising a polypeptide selected from the group consisting of:
   a) a polypeptide comprising a sequence selected from the group consisting of SEQ ID NOS:3-12,
   b) a polypeptide comprising a sequence at least 90% identical to a sequence selected from the group consisting of SEQ ID NOS:3-12, and
   c) an immunogenic fragment of a polypeptide of a) or b).

32. The composition of embodiment 30, wherein at least one capsid polypeptide is from a virus selected from the group consisting of Norwalk virus (NV), Snow Mountain virus (SMV), and Hawaii virus (HV).

33. The composition of embodiment 32, comprising an NV ORF2-encoded polypeptide, an SMV ORF2-encoded polypeptide, and an HV ORF2-encoded polypeptide.

34. The composition of any of embodiments 31-33, further comprising a Sapovirus capsid polypeptide.

35. The composition of any of embodiments 29-34, further comprising a polypeptide encoded by ORF1 from a Norovirus or Sapovirus.

36. The composition of any of embodiments 29-35, further comprising a multi-epitope fusion protein comprising at least two polypeptides from one or more Norovirus or Sapovirus isolates.

37. The composition of embodiment 36, wherein the fusion protein comprises polypeptides from the same Norovirus or Sapovirus isolate.

38. The composition of embodiment 36, wherein the fusion protein comprises at least two polypeptides from different Norovirus or Sapovirus isolates.

39. The composition of embodiment 36, wherein the fusion protein comprises sequences that are not in the order in which they occur naturally in the Norovirus or Sapovirus polyprotein.

40. The composition of any of embodiments 29-39, further comprising an ORF1-encoded polyprotein of a Norovirus or Sapovirus or a fragment thereof.

41. The composition of any of embodiments 29-40, further comprising a polypeptide encoded by ORF3 from a Norovirus.

42. The composition of embodiment 41, comprising a polypeptide selected from the group consisting of:
   a) a polypeptide comprising a sequence selected from the group consisting of SEQ ID NO:4, SEQ ID NO:7, and SEQ ID NO:9;
   b) a polypeptide comprising a sequence at least 90% identical to a sequence selected from the group consisting of SEQ ID NO:4, SEQ ID NO:7, and SEQ ID NO:9 that is capable of eliciting an immune response against a Norovirus; and
   c) an immunogenic fragment of a polypeptide of a) or b) that is capable of eliciting an immune response against a Norovirus.

43. The composition of any of embodiments 29-42, further comprising a virus-like particle (VLP).

44. The composition of any of embodiments 29-42, further comprising one or more adjuvants.

45. The composition of embodiment 44, wherein the one or more adjuvants are selected from the group consisting of LT-K63, LT-R72, MF59, and alum.

46. The composition of any of embodiments 29-45, further comprising a microparticle.

47. The composition of embodiment 46, wherein said microparticle is a poly(L-lactide), poly(D,L-lactide) or poly(D,L-lactide-co-glycolide) microparticle.

48. The composition of any of embodiments 29-47 comprising all or components of all pathogenic Noroviruses.

49. The composition of any of embodiments 29-47 comprising all or components of all pathogenic Sapoviruses.

50. The composition of any of embodiments 29-47 comprising all or components of all pathogenic Noroviruses and Sapoviruses.

51. A composition comprising virus-like particles (VLPs) comprising at least two antigens from different strains of Norovirus or Sapovirus.

52. The composition of embodiment 51, wherein at least one antigen is from a virus selected from the group consisting of Norwalk virus (NV), Snow Mountain virus (SMV), and Hawaii virus (HV).

53. The composition of embodiment 52, comprising an NV antigen, an SMV antigen, and an HV antigen.

54. The composition of any of embodiments 29-53, further comprising a polynucleotide comprising an ORF2 sequence of a Norovirus or Sapovirus.

55. The composition of embodiment 54, wherein the polynucleotide comprises the sequence of SEQ ID NO:1 or a sequence at least 90% identical to SEQ ID NO:1.

56. The composition of any of embodiments 29-55, further comprising a polynucleotide comprising an ORF1 sequence of a Norovirus or Sapovirus.

57. The composition of any of embodiments 29-56, further comprising a polynucleotide comprising an ORF3 sequence of a Norovirus.

58. The composition of embodiment 57, wherein the polynucleotide comprises the sequence of SEQ ID NO:2 or a sequence at least 90% identical to SEQ ID NO:2.

59. A method for producing viral-like particles (VLPs), the method comprising:
   a) transforming a host cell with an expression vector comprising the sequence of SEQ ID NO:1 or SEQ ID NO:2;
   b) culturing the transformed host cell under conditions whereby capsid proteins are expressed and assembled into VLPs.

60. A method for producing viral-like particles (VLPs) from more than one Norovirus or Sapovirus isolate, the method comprising:
   a) transforming a host cell with one or more expression vectors comprising sequences encoding capsid proteins from more than one Norovirus or Sapovirus isolate;
   b) culturing the transformed host cell under conditions whereby said capsid proteins are expressed and assembled into VLPs.

61. The method of either embodiment 59 or 60, further comprising transforming said host cell with an expression vector comprising one or more sequences encoding a structural protein from a Norovirus or Sapovirus.

62. The method of embodiment 61, comprising transforming said host cell with an expression vector comprising an ORF3 sequence from a Norovirus.

63. The method of embodiment 60, wherein said expression vector comprises the nucleotide sequence of SEQ ID NO:2.

64. The method of embodiment 60, wherein said expression vector comprises a nucleotide sequence at least 90% identical to SEQ ID NO:2 that is capable of producing viral-like particles.

65. The method of any of embodiments 59-64, wherein said expression vector further comprises one or more ORF1 sequences from a Norovirus or Sapovirus.

66. The method of any of embodiments 59-65, further comprising transforming a host cell with an expression vector comprising a sequence encoding an adjuvant.

67. The method of embodiment 63, wherein said adjuvant is a detoxified mutant of an *E. coli* heat-labile toxin (LT) selected from the group consisting of LT-K63 and LT-R72.

68. A method for producing a mosaic VLP comprising capsid proteins from at least two viral strains of Norovirus or Sapovirus, the method comprising:

a) cloning polynucleotides encoding said capsid proteins into expression vectors; and b) expressing said vectors in the same host cell under conditions whereby said capsid proteins are expressed and assembled together into said VLP.

69. The method of any of embodiments 59-68, wherein the host cell is a yeast cell.

70. The method of embodiment 69 wherein the yeast is *Saccharomyces cerevisiae.*

71. The method of any of embodiments 59-68, wherein the host cell is an insect cell.

72. The method of embodiment 71, wherein the expression vector is a baculovirus vector.

73. The method of any of embodiments 59-68, wherein the expression vector is an alphavirus vector.

74. The composition of any one of embodiments 11-27 and 29-58, further comprising an antigen that is not a Norovirus or Sapovirus antigen.

75. The composition of embodiment 74, wherein the antigen is useful in a pediatric vaccine.

76. The composition of embodiment 74, wherein the antigen is useful in a vaccine designed to protect elderly or immunocompromised individuals.

77. The composition of embodiment 74, wherein the antigen elicits an immune response against a pathogen that causes diarrheal diseases.

78. The composition of embodiment 77, wherein the antigen is a rotavirus antigen.

79. A method of eliciting an immunological response in a subject, comprising administering the composition of any one of embodiments 11-27, 29-58, and 74-78 to said subject.

80. The method of embodiment 79, further comprising administering an adjuvant.

81. The method of embodiment 79 comprising administering said immunogenic composition to said subject topically.

82. The method of embodiment 79 comprising administering said immunogenic composition to said subject parenterally.

83. The method of embodiment 82, further comprising administering an adjuvant selected from the group consisting of MF59 and alum.

84. The method of embodiment 79 comprising administering said immunogenic composition to said subject mucosally.

85. The method of embodiment 84, further comprising administering an adjuvant comprising a detoxified mutant of an *E. coli* heat-labile toxin (LT) selected from the group consisting of LT-K63 and LT-R72.

86. The method of embodiment 79 comprising the following steps:

a) mucosally administering a first immunogenic composition comprising one or more Norovirus or Sapovirus antigens; and b) topically or parenterally administering a second immunogenic composition comprising one or more Norovirus or Sapovirus antigens.

87. The method of embodiment 86, wherein the one or more antigens is selected from the group consisting of a Norwalk virus (NV) antigen, a Snow Mountain virus (SMV) antigen, and a Hawaii virus (HV) antigen.

88. The method of embodiment 86, wherein the first immunogenic composition is the immunogenic composition of any of embodiments 11-27, 29-58, and 74-78.

89. The method of embodiment 86, wherein the second immunogenic composition is the immunogenic composition of any of embodiments 11-27, 29-58, and 74-78.

90. The method of embodiment 86, wherein the first immunogenic composition and the second immunogenic composition are the same.

91. The method of embodiment 86, wherein the first immunogenic composition and the second immunogenic composition are different.

92. The method of embodiment 86, wherein step (a) is performed two or more times.

93. The method of embodiment 86, wherein step (b) is performed two or more times.

94. The method of embodiment 86, wherein the mucosal administration is intranasal.

95. The method of embodiment 86, wherein the mucosal administration is oral.

96. The method of embodiment 86, wherein the mucosal administration is intrarectal.

97. The method of embodiment 86, wherein the mucosal administration is intravaginal.

98. The method of embodiment 86, where in the parenteral administration is transcutaneous.

99. A method for treating an infection by a Norovirus or Sapovirus, the method comprising administering to a subject in need thereof a therapeutically effective amount of the immunogenic composition of any of embodiments 11-27, 29-58, and 74-78.

100. The method of embodiment 99, wherein multiple therapeutically effective doses of the immunogenic composition are administered to said subject.

101. The method of embodiment 100, comprising the following steps:

a) mucosally administering a therapeutically effective amount of a first immunogenic composition comprising one or more Norovirus or Sapovirus antigens; and b) topically or parenterally administering a therapeutically effective amount of a second immunogenic composition comprising one or more Norovirus or Sapovirus antigens.

102. The method of embodiment 101, wherein one or more antigens is selected from the group consisting of a Norwalk virus (NV) antigen, a Snow Mountain virus (SMV) antigen, and a Hawaii virus (HV) antigen.

103. The method of embodiment 101, wherein the first immunogenic composition is the immunogenic composition of any of embodiments 11-27, 29-58, and, 74-78.

104. The method of embodiment 101, wherein the second immunogenic composition is the immunogenic composition of any of embodiments 11-27, 29-58, and 74-78.

105. The method of embodiment 101, wherein the first immunogenic composition and the second immunogenic composition are the same.

106. The method of embodiment 101, wherein the first immunogenic composition and the second immunogenic composition are different.

107. The method of embodiment 101, wherein step (a) is performed two or more times.

108. The method of embodiment 101, wherein step (b) is performed two or more times.

109. The method of embodiment 101, wherein the mucosal administration is intranasal.

110. The method of embodiment 101, wherein the mucosal administration is oral.

111. The method of embodiment 101, wherein the mucosal administration is intrarectal.

112. The method of embodiment 101, wherein the mucosal administration is intravaginal.

113. The method of embodiment 101, where in the parenteral administration is transcutaneous.

114. A method for treating an infection by a pathogen that causes diarrheal diseases, the method comprising administering to a subject in need thereof a therapeutically effective amount of the immunogenic composition of embodiment 77.

115. The method of embodiment 114, wherein multiple therapeutically effective doses of the immunogenic composition are administered to said subject.

116. The method of embodiment 115, comprising the following steps:
a) mucosally administering a therapeutically effective amount of a first immunogenic composition comprising one or more Norovirus or Sapovirus antigens; and
b) topically or parenterally administering a therapeutically effective amount of a second immunogenic composition comprising one or more Norovirus or Sapovirus antigens.

117. The method of any of embodiments 114-116, wherein one or more antigens is selected from the group consisting of a Norwalk virus (NV) antigen, a Snow Mountain virus (SMV) antigen, and a Hawaii virus (HV) antigen.

118. The method of embodiment 117, wherein the immunogenic composition comprises a rotavirus antigen.

119. A method of assessing efficacy of a therapeutic treatment of a subject infected by a Norovirus or Sapovirus, the method comprising:
a) administering to a subject in need thereof a therapeutically effective amount of the immunogenic composition of any of embodiments 11-27, 29-58, and 74-78; and
b) monitoring the subject for infection by the Norovirus or Sapovirus after administration of the composition.

120. A method of assessing efficacy of a prophylactic treatment of a subject, the method comprising:
a) administering to a subject in need thereof a therapeutically effective amount of the immunogenic composition of any of embodiments 11-27, 29-58, and 74-78; and
b) monitoring the subject for an immune response against one or more antigens in the composition after administration of the composition.

These and other embodiments of the subject invention will readily occur to those of skill in the art in view of the disclosure herein.

BRIEF DESCRIPTION OF THE DRAWINGS

FIGS. 1A-1C depict an alignment of the nucleotide sequence of Norwalk virus (SEQ ID NO:20), including orf2 and orf3 regions (GenBank Accession No. M87661, Mar. 26, 1997) and the nucleotide sequence of SEQ ID NO:2 (NV .orf2+3), comprising modified orf2 and orf3 sequences. The positions of sequence modifications in SEQ ID NO:2 are highlighted.

FIGS. 2A-2F depict a translation of the nucleotide sequence of SEQ ID NO:2. FIGS. 2A-2D show the translated amino acid sequence encoded by orf2 (SEQ ID NO:3) and FIGS. 2E-2F show the translated amino acid sequence encoded by orf3 (SEQ ID NO:4).

FIG. 3 depicts a schematic diagram illustrating the generation of oligonucleotide fragments for assembly of the NV .orf2 and NV .orf2+3 constructs. The sequence of SEQ ID NO:2 was divided into four domains as described in Example 1. Oligonucleotides for each of the four domains were engineered to include EcoR1 and SalI sites at their 5' and 3' ends and ligated into a pUC19 subcloning vector cut with the restriction enzymes EcoR1 and SalI. Further digests with the indicated restriction enzymes produced the oligonucleotide fragments as shown.

FIGS. 14A and 14B show the nucleotide sequence of SEQ ID NO:1 (NV .orf2).

FIGS. 15A and 15B show the nucleotide sequence of SEQ ID NO:2 (NV .orf2+3).

FIGS. 16A-16I show the ORF1 coding sequence (nucleotides 1-5144 of SEQ ID NO:13) for the Novirus MD145-12 polyprotein (SEQ ID NO:14) and the domain boundaries of the polyprotein.

FIGS. 17A-17C show the ORF2 coding sequence (nucleotides 5041-6734 of SEQ ID NO:13) for the Novirus MD145-12 major capsid protein (SEQ ID NO:21).

FIGS. 18A and 18B show the ORF3 coding sequence (nucleotides 6661-7556 of SEQ ID NO:13) for the Novirus MD145-12 minor structural protein (SEQ ID NO:22).

DETAILED DESCRIPTION

Figure 4:
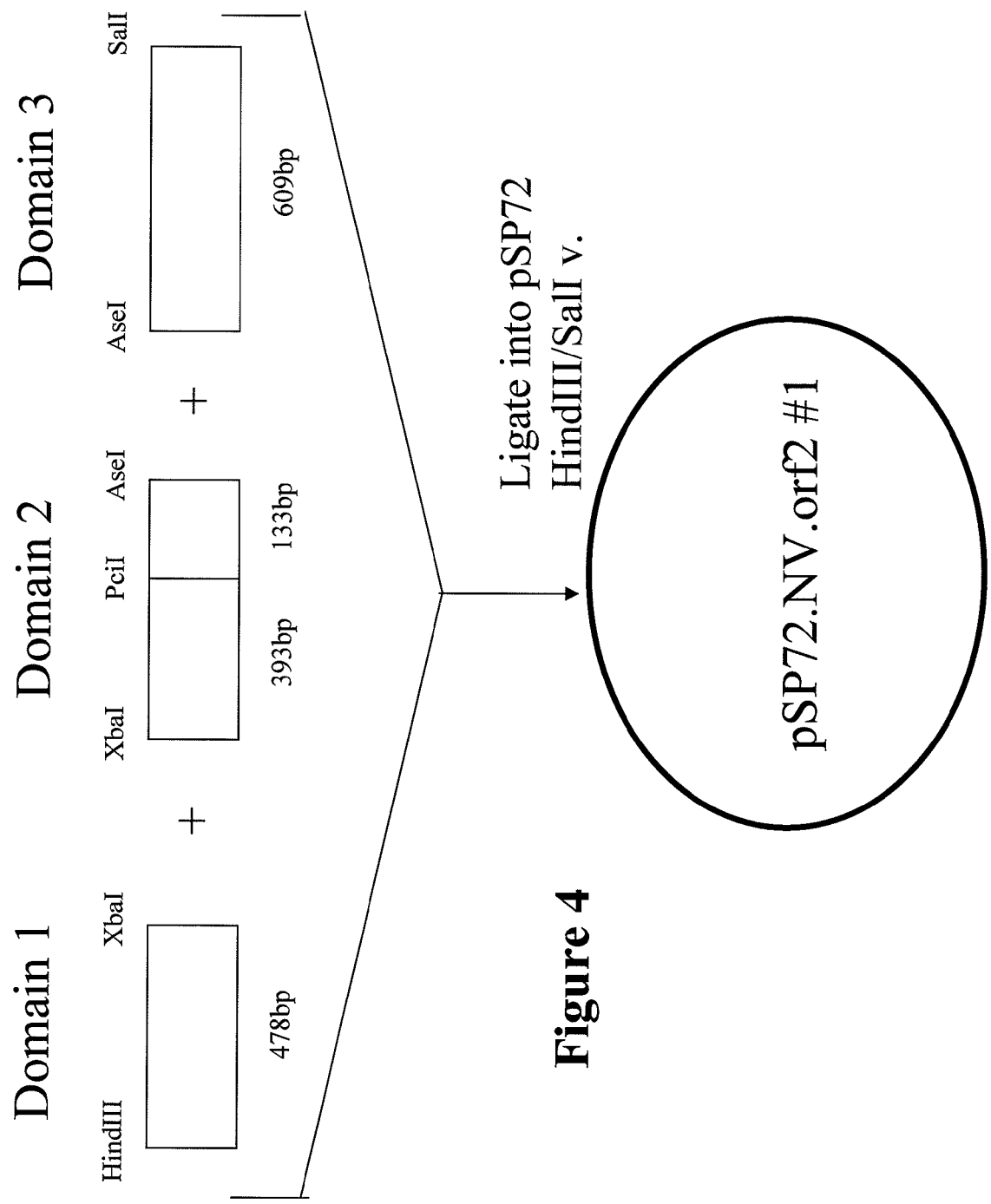
FIG. 4 depicts a schematic diagram illustrating the assembly of the NV .orf2 construct from oligonucleotide fragments. The full-length NV .orf2 construct was assembled from four oligonucleotide fragments produced from a series of digests with restriction enzymes as shown. All four fragments were gel purified and ligated into the pSP72 vector cut with the restriction enzymes HindIII and SalI, to create a 1613 base pair (bp) HindIII-SalI insert for the coding sequence of NV .orf2.

The practice of the present invention will employ, unless otherwise indicated, conventional methods of pharmacology, chemistry, biochemistry, recombinant DNA techniques and immunology, within the skill of the art. Such techniques are explained fully in the literature. See, e.g., *Handbook of Experimental Immunology*, Vols. I-IV (D. M. Weir and C. C. Blackwell eds., Blackwell Scientific Publications); A. L. Lehninger, *Biochemistry* (Worth Publishers, Inc., current addition); Sambrook, et al., *Molecular Cloning: A Laboratory Manual* (2nd Edition, 1989); *Methods In Enzymology* (S. Colowick and N. Kaplan eds., Academic Press, Inc.).

All publications, patents and patent applications cited herein, whether supra or infra, are hereby incorporated by reference in their entireties.

I. DEFINITIONS

All scientific and technical terms used in this application have meanings commonly used in the art unless otherwise specified. As used in this application, the following words or phrases have the meanings specified.

It must be noted that, as used in this specification and the appended claims, the singular forms "a", "an" and "the" include plural references unless the content clearly dictates otherwise. Thus, for example, reference to "a polynucleotide" includes a mixture of two or more such polynucleotides, and the like.

The term "comprising" means "including" as well as "consisting" e.g. a composition "comprising" X may consist exclusively of X or may include something additional e.g. X+Y.

The term "about" in relation to a numerical value x means, for example, x±10%.

As used herein, the terms "Norovirus" and "Norwalk-like virus" refer to members of the genus Norovirus of the family Caliciviridae of positive-sense, single-stranded RNA, nonenveloped viruses (Green et al., Human Caliciviruses, in Fields Virology Vol. 1, pp. 841-874. (Knipe and Howley, editors-in-chief, 4th ed., Lippincott Williams & Wilkins 2001)). The term Norovirus includes strains in all genogroups of the virus. Currently, Norovirus strains are divided into four genogroups (GI-GIV), which are subdivided into at least 20 genetic clusters. In particular, the term Norovirus includes, but is not limited to, the species Norwalk virus (NV), Lordsdale virus (LV), Mexico virus (MV), Hawaii virus (HV), Snow Mountain virus (SMV), Desert Shield virus (DSV), and Southhampton virus (SV). A large number of Norovirus isolates have been partially or completely sequenced. See, e.g., the Calicivirus Sequence Database, the Norovirus Database and the GenBank database. The term Norovirus also includes isolates not characterized at the time of filing.

As used herein, the terms "Sapovirus" and "Sapporo-like virus" refer to members of the genus Sapovirus of the family Caliciviridae of positive-sense, single-stranded RNA, nonenveloped viruses (Green et al., supra). The term Sapovirus includes strains in all genogroups of the virus. Currently, Sapovirus strains are divided into five genogroups (GI-GV) based on their capsid (VP1) sequences. In particular, the term Sapovirus includes, but is not limited to, the species Sapporo virus, London/29845 virus, Manchester virus, Houston/86 virus, Houston/90 virus, and Parkville virus. A large number of Sapovirus isolates have been partially or completely sequenced. See, e.g., the Calicivirus Sequence Database and the GenBank database. The term Sapovirus also includes isolates not characterized at the time of filing.

The terms "polypeptide" and "protein" refer to a polymer of amino acid residues and are not limited to a minimum length of the product. Thus, peptides, oligopeptides, dimers, multimers, and the like, are included within the definition. Both full-length proteins and fragments thereof are encompassed by the definition. The terms also include postexpression modifications of the polypeptide, for example, glycosylation, acetylation, phosphorylation and the like. Furthermore, for purposes of the present invention, a "polypeptide" refers to a protein which includes modifications, such as deletions, additions and substitutions (generally conservative in nature), to the native sequence, so long as the protein maintains the desired activity. These modifications may be deliberate, as through site-directed mutagenesis, or may be accidental, such as through mutations of hosts which produce the proteins or errors due to PCR amplification.

"Substantially purified" generally refers to isolation of a substance (compound, polynucleotide, protein, polypeptide, polypeptide composition) such that the substance comprises the majority percent of the sample in which it resides. Typically in a sample, a substantially purified component comprises 50%, preferably 80%-85%, more preferably 90-95% of the sample. Techniques for purifying polynucleotides and polypeptides of interest are well-known in the art and include, for example, ion-exchange chromatography, affinity chromatography and sedimentation according to density.

By "isolated" is meant, when referring to a polypeptide, that the indicated molecule is separate and discrete from the whole organism with which the molecule is found in nature or is present in the substantial absence of other biological macro-molecules of the same type. The term "isolated" with respect to a polynucleotide is a nucleic acid molecule devoid, in whole or part, of sequences normally associated with it in nature; or a sequence, as it exists in nature, but having heterologous sequences in association therewith; or a molecule disassociated from the chromosome.

As used herein, the terms "label" and "detectable label" refer to a molecule capable of detection, including, but not limited to, radioactive isotopes, fluorescers, chemiluminescers, enzymes, enzyme substrates, enzyme cofactors, enzyme inhibitors, chromophores, dyes, metal ions, metal sols, ligands (e.g., biotin or haptens) and the like. The term "fluorescer" refers to a substance or a portion thereof which is capable of exhibiting fluorescence in the detectable range. Particular examples of labels which may be used under the invention include fluorescein, rhodamine, dansyl, umbelliferone, Texas red, luminol, acradimum esters, NADPH and α-β-galactosidase.

"Homology" refers to the percent identity between two polynucleotide or two polypeptide moieties. Two nucleic acid, or two polypeptide sequences are "substantially homologous" to each other when the sequences exhibit at least about 50% sequence identity, preferably at least about 75% sequence identity, more preferably at least about 80%-85% sequence identity, more preferably at least about 90% sequence identity, and most preferably at least about 95%-98% sequence identity over a defined length of the molecules. As used herein, substantially homologous also refers to sequences showing complete identity to the specified sequence.

In general, "identity" refers to an exact nucleotide-to-nucleotide or amino acid-to-amino acid correspondence of two polynucleotides or polypeptide sequences, respectively. Percent identity can be determined by a direct comparison of the sequence information between two molecules by aligning the sequences, counting the exact number of matches between the two aligned sequences, dividing by the length of the shorter sequence, and multiplying the result by 100. Readily available computer programs can be used to aid in the analysis, such as ALIGN, Dayhoff, M. O. in *Atlas of Protein Sequence and Structure* M. O. Dayhoff ed., 5 Suppl. 3:353-358, National biomedical Research Foundation, Washington, D.C., which adapts the local homology algorithm of Smith and Waterman *Advances in Appl. Math.* 2:482-489, 1981 for peptide analysis. Programs for determining nucleotide sequence identity are available in the Wisconsin Sequence Analysis Package, Version 8 (available from Genetics Computer Group, Madison, Wis.) for example, the BESTFIT, FASTA and GAP programs, which also rely on the Smith and Waterman algorithm. These programs are readily utilized with the default parameters recommended by the manufacturer and described in the Wisconsin Sequence Analysis Package referred to above. For example, percent identity of a particular nucleotide sequence to a reference sequence can be determined using the homology algorithm of Smith and Waterman with a default scoring table and a gap penalty of six nucleotide positions.

Another method of establishing percent identity in the context of the present invention is to use the MPSRCH package of programs copyrighted by the University of Edinburgh, developed by John F. Collins and Shane S. Sturrok, and distributed by IntelliGenetics, Inc. (Mountain View, Calif.). From this suite of packages the Smith-Waterman algorithm can be employed where default parameters are used for the scoring table (for example, gap open penalty of 12, gap extension penalty of one, and a gap of six). From the data generated the "Match" value reflects "sequence identity." Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR. Details of these programs are readily available.

Alternatively, homology can be determined by hybridization of polynucleotides under conditions which form stable duplexes between homologous regions, followed by digestion with single-stranded-specific nuclease(s), and size determination of the digested fragments. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; *DNA Cloning, supra; Nucleic Acid Hybridization*, supra.

"Recombinant" as used herein to describe a nucleic acid molecule means a polynucleotide of genomic, cDNA, viral, semisynthetic, or synthetic origin which, by virtue of its origin or manipulation, is not associated with all or a portion of the polynucleotide with which it is associated in nature. The term "recombinant" as used with respect to a protein or polypeptide means a polypeptide produced by expression of a recombinant polynucleotide. In general, the gene of interest is cloned and then expressed in transformed organisms, as described further below. The host organism expresses the foreign gene to produce the protein under expression conditions.

The term "transformation" refers to the insertion of an exogenous polynucleotide into a host cell, irrespective of the method used for the insertion. For example, direct uptake, transduction or f-mating are included. The exogenous polynucleotide may be maintained as a non-integrated vector, for example, a plasmid, or alternatively, may be integrated into the host genome.

"Recombinant host cells", "host cells," "cells", "cell lines," "cell cultures", and other such terms denoting microorganisms or higher eukaryotic cell lines cultured as unicellular entities refer to cells which can be, or have been, used as recipients for recombinant vector or other transferred DNA, and include the original progeny of the original cell which has been transfected.

A "coding sequence" or a sequence which "encodes" a selected polypeptide, is a nucleic acid molecule which is transcribed (in the case of DNA) and translated (in the case of mRNA) into a polypeptide in vivo when placed under the control of appropriate regulatory sequences (or "control elements"). The boundaries of the coding sequence can be determined by a start codon at the 5' (amino) terminus and a translation stop codon at the 3' (carboxy) terminus. A coding sequence can include, but is not limited to, cDNA from viral, procaryotic or eucaryotic mRNA, genomic DNA sequences from viral or procaryotic DNA, and even synthetic DNA sequences. A transcription termination sequence may be located 3' to the coding sequence.

Typical "control elements," include, but are not limited to, transcription promoters, transcription enhancer elements, transcription termination signals, polyadenylation sequences (located 3' to the translation stop codon), sequences for optimization of initiation of translation (located 5' to the coding sequence), and translation termination sequences.

The term "nucleic acid" includes DNA and RNA, and also their analogues, such as those containing modified backbones (e.g. phosphorothioates, etc.), and also peptide nucleic acids (PNA), etc. The invention includes nucleic acids comprising sequences complementary to those described above (e.g. for antisense or probing purposes).

"Operably linked" refers to an arrangement of elements wherein the components so described are configured so as to perform their usual function. Thus, a given promoter operably linked to a coding sequence is capable of effecting the expression of the coding sequence when the proper enzymes are present. The promoter need not be contiguous with the coding sequence, so long as it functions to direct the expression thereof. Thus, for example, intervening untranslated yet transcribed sequences can be present between the promoter sequence and the coding sequence and the promoter sequence can still be considered "operably linked" to the coding sequence.

"Encoded by" refers to a nucleic acid sequence which codes for a polypeptide sequence, wherein the polypeptide sequence or a portion thereof contains an amino acid sequence of at least 3 to 5 amino acids, more preferably at least 8 to 10 amino acids, and even more preferably at least 15 to 20 amino acids from a polypeptide encoded by the nucleic acid sequence.

"Expression cassette" or "expression construct" refers to an assembly which is capable of directing the expression of the sequence(s) or gene(s) of interest. An expression cassette generally includes control elements, as described above, such as a promoter which is operably linked to (so as to direct transcription of) the sequence(s) or gene(s) of interest, and often includes a polyadenylation sequence as well. Within certain embodiments of the invention, the expression cassette described herein may be contained within a plasmid construct. In addition to the components of the expression cassette, the plasmid construct may also include, one or more selectable markers, a signal which allows the plasmid construct to exist as single-stranded DNA (e.g., a M13 origin of replication), at least one multiple cloning site, and a "mammalian" origin of replication (e.g., a SV40 or adenovirus origin of replication).

"Purified polynucleotide" refers to a polynucleotide of interest or fragment thereof which is essentially free, e.g., contains less than about 50%, preferably less than about 70%, and more preferably less than about at least 90%, of the protein with which the polynucleotide is naturally associated. Techniques for purifying polynucleotides of interest are well-known in the art and include, for example, disruption of the cell containing the polynucleotide with a chaotropic agent and separation of the polynucleotide(s) and proteins by ion-exchange chromatography, affinity chromatography and sedimentation according to density.

The term "transfection" is used to refer to the uptake of foreign DNA by a cell. A cell has been "transfected" when exogenous DNA has been introduced inside the cell membrane. A number of transfection techniques are generally known in the art. See, e.g., Graham et al. (1973) *Virology*, 52:456, Sambrook et al. (1989) *Molecular Cloning, a laboratory manual*, Cold Spring Harbor Laboratories, New York, Davis et al. (1986) *Basic Methods in Molecular Biology*, Elsevier, and Chu et al. (1981) *Gene* 13:197. Such techniques can be used to introduce one or more exogenous DNA moieties into suitable host cells. The term refers to both stable and transient uptake of the genetic material, and includes uptake of peptide- or antibody-linked DNAs.

A "vector" is capable of transferring nucleic acid sequences to target cells (e.g., viral vectors, non-viral vectors, particulate carriers, and liposomes). Typically, "vector construct," "expression vector," and "gene transfer vector," mean any nucleic acid construct capable of directing the expression of a nucleic acid of interest and which can transfer nucleic acid sequences to target cells. Thus, the term includes cloning and expression vehicles, as well as viral vectors.

"ADH II" refers to the glucose-repressible alcohol dehydrogenase II from yeast, particularly *Saccharomyces*, and in particular, *S. cerevisiae*. "ADH2" refers to the yeast gene encoding ADH II, as well as its associated regulatory sequences. See, e.g., Russell et al. (1983) J. Biol. Chem. 258:2674-2682.

"UAS" is an art-recognized term for upstream activation sequences or enhancer regions, which are usually short, repetitive DNA sequences located upstream from a promoter's TATA box. Of particular interest in the present invention is the ADH2 UAS, which is a 22-bp perfect inverted repeat located upstream from the ADH2 TATA box. See Shuster et al. (1986) Mol. Cell. Biol. 6:1894-1902.

"ADR1" refers to a positive regulatory gene from yeast required for the expression of ADH II. See, e.g., Denis et al. (1983) Mol. Cell. Biol. 3:360-370. The protein encoded by the ADR1 gene is referred to herein as "ADR I".

By "fragment" is intended a molecule consisting of only a part of the intact full-length sequence and structure. A fragment of a polypeptide can include a C-terminal deletion, an N-terminal deletion, and/or an internal deletion of the native polypeptide. A fragment of a polypeptide will generally include at least about 5-10 contiguous amino acid residues of the full-length molecule, preferably at least about 15-25 contiguous amino acid residues of the full-length molecule, and most preferably at least about 20-50 or more contiguous amino acid residues of the full-length molecule, or any integer between 5 amino acids and the number of amino acids in the full-length sequence, provided that the fragment in question retains the ability to elicit the desired biological response. A fragment of a nucleic acid can include a 5'-deletion, a 3'-deletion, and/or an internal deletion of a nucleic acid. Nucleic acid fragments will generally include at least about 5-1000 contiguous nucleotide bases of the full-length molecule and may include at least 5, 10, 15, 20, 25, 30, 40, 50, 60, 75, 100, 150, 250 or at least 500 contiguous nucleotides of the full-length molecule, or any integer between 5 nucleotides and the number of nucleotides in the full-length sequence. Such fragments may be useful in hybridization, amplification, production of immunogenic fragments, or nucleic acid immunization.

By "immunogenic fragment" is meant a fragment of an immunogen which includes one or more epitopes and thus can modulate an immune response or can act as an adjuvant for a co-administered antigen. Such fragments can be identified using any number of epitope mapping techniques, well known in the art. See, e.g., *Epitope Mapping Protocols* in Methods in Molecular Biology, Vol. 66 (Glenn E. Morris, Ed., 1996) Humana Press, Totowa, N.J. For example, linear epitopes may be determined by e.g., concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871; Geysen et al. (1984) *Proc. Natl. Acad. Sci. USA* 81:3998-4002; Geysen et al. (1986) *Molec. Immunol.* 23:709-715, all incorporated herein by reference in their entireties. Similarly, conformational epitopes are readily identified by determining spatial conformation of amino acids such as by, e.g., x-ray crystallography and 2-dimensional nuclear magnetic resonance. See, e.g., *Epitope Mapping Protocols*, supra. Antigenic regions of proteins can also be identified using standard antigenicity and hydropathy plots, such as those calculated using, e.g., the Omiga version 1.0 software program available from the Oxford Molecular Group. This computer program employs the Hopp/Woods method, Hopp et al., *Proc. Natl. Acad. Sci. USA* (1981) 78:3824-3828 for determining antigenicity profiles, and the Kyte-Doolittle technique, Kyte et al., *J. Mol. Biol.* (1982) 157:105-132 for hydropathy plots.

Immunogenic fragments, for purposes of the present invention, will usually be at least about 2 amino acids in length, more preferably about 5 amino acids in length, and most preferably at least about 10 to about 15 amino acids in length. There is no critical upper limit to the length of the fragment, which could comprise nearly the full-length of the protein sequence, or even a fusion protein comprising two or more epitopes.

As used herein, the term "epitope" generally refers to the site on an antigen which is recognised by a T-cell receptor and/or an antibody. Preferably it is a short peptide derived from or as part of a protein antigen. However the term is also intended to include peptides with glycopeptides and carbohydrate epitopes. Several different epitopes may be carried by a single antigenic molecule. The term "epitope" also includes modified sequences of amino acids or carbohydrates which stimulate responses which recognise the whole organism. It is advantageous if the selected epitope is an epitope of an infectious agent, which causes the infectious disease.

The epitope can be generated from knowledge of the amino acid and corresponding DNA sequences of the peptide or polypeptide, as well as from the nature of particular amino acids (e.g., size, charge, etc.) and the codon dictionary, without undue experimentation. See, e.g., Ivan Roitt, Essential Immunology, 1988; Kendrew, supra; Janis Kuby, Immunology, 1992 e.g., pp. 79-81. Some guidelines in determining whether a protein will stimulate a response, include: Peptide length—preferably the peptide is about 8 or 9 amino acids long to fit into the MHC class I complex and about 13-25 amino acids long to fit into a class II MHC complex. This length is a minimum for the peptide to bind to the MHC complex. It is preferred for the peptides to be longer than these lengths because cells may cut peptides. The peptide may contain an appropriate anchor motif which will enable it to bind to the various class I or class II molecules with high enough specificity to generate an immune response (See Bocchia, M. et al, Specific Binding of Leukemia Oncogene Fusion Protein Pentides to HLA Class I Molecules, Blood 85:2680-2684; Englehard, V H, Structure of peptides associated with class I and class II MHC molecules Ann. Rev. Immunol. 12:181 (1994)). This can be done, without undue experimentation, by comparing the sequence of the protein of interest with published structures of peptides associated with the MHC molecules. Thus, the skilled artisan can ascertain an epitope of interest by comparing the protein sequence with sequences listed in the protein database.

For a description of various Norovirus capsid epitopes, see, e.g., Hardy et al., U.S. Patent Application Publication No. 2005/0152911; incorporated herein by reference in its entirety. In particular, Hardy et al. have identified epitopes of the Norwalk virus capsid protein at residues 133-137 and of the Snow Mountain virus capsid protein at residues 319-327, comprising the following sequences: WTRGSHNL (SEQ ID NO:23), WTRGGHGL (SEQ ID NO:24), WTRGQHQL (SEQ ID NO:25), or WLPAPIDKL (SEQ ID NO:26) Immunogenic polypeptides comprising such capsid epitopes and nucleic acids encoding them may be used in the practice of the invention.

As used herein, the term "T cell epitope" refers generally to those features of a peptide structure which are capable of inducing a T cell response and a "B cell epitope" refers generally to those features of a peptide structure which are capable of inducing a B cell response.

An "immunological response" to an antigen or composition is the development in a subject of a humoral and/or a cellular immune response to an antigen present in the composition of interest. For purposes of the present invention, a "humoral immune response" refers to an immune response mediated by antibody molecules, while a "cellular immune response" is one mediated by T-lymphocytes and/or other white blood cells. One important aspect of cellular immunity involves an antigen-specific response by cytolytic T-cells ("CTL"s). CTLs have specificity for peptide antigens that are presented in association with proteins encoded by the major histocompatibility complex (MHC) and expressed on the surfaces of cells. CTLs help induce and promote the destruction of intracellular microbes, or the lysis of cells infected with such microbes. Another aspect of cellular immunity involves an antigen-specific response by helper T-cells. Helper T-cells act to help stimulate the function, and focus the activity of, nonspecific effector cells against cells displaying peptide antigens in association with MHC molecules on their surface. A "cellular immune response" also refers to the production of cytokines, chemokines and other such molecules produced by activated T-cells and/or other white blood cells, including those derived from CD4+ and CD8+ T-cells.

A composition or vaccine that elicits a cellular immune response may serve to sensitize a vertebrate subject by the presentation of antigen in association with MHC molecules at the cell surface. The cell-mediated immune response is directed at, or near, cells presenting antigen at their surface. In addition, antigen-specific T-lymphocytes can be generated to allow for the future protection of an immunized host.

The ability of a particular antigen to stimulate a cell-mediated immunological response may be determined by a number of assays, such as by lymphoproliferation (lymphocyte activation) assays, CTL cytotoxic cell assays, or by assaying for T-lymphocytes specific for the antigen in a sensitized subject. Such assays are well known in the art. See, e.g., Erickson et al., *J. Immunol.* (1993) 151:4189-4199; Doe et al., *Eur. J. Immunol.* (1994) 24:2369-2376. Recent methods of measuring cell-mediated immune response include measurement of intracellular cytokines or cytokine secretion by T-cell populations, or by measurement of epitope specific T-cells (e.g., by the tetramer technique)(reviewed by McMichael, A. J., and O'Callaghan, C. A., *J. Exp. Med.* 187(9) 1367-1371, 1998; Mcheyzer-Williams, M. G., et al, *Immunol. Rev.* 150: 5-21, 1996; Lalvani, A., et al, *J. Exp. Med.* 186:859-865, 1997).

Thus, an immunological response as used herein may be one that stimulates the production of antibodies (e.g., neutralizing antibodies that block bacterial toxins and pathogens such as viruses entering cells and replicating by binding to toxins and pathogens, typically protecting cells from infection and destruction). The antigen of interest may also elicit production of CTLs. Hence, an immunological response may include one or more of the following effects: the production of antibodies by B-cells; and/or the activation of suppressor T-cells and/or memory/effector T-cells directed specifically to an antigen or antigens present in the composition or vaccine of interest. These responses may serve to neutralize infectivity, and/or mediate antibody-complement, or antibody dependent cell cytotoxicity (ADCC) to provide protection to an immunized host. Such responses can be determined using standard immunoassays and neutralization assays, well known in the art. (See, e.g., Montefiori et al. (1988) *J. Clin Microbiol.* 26:231-235; Dreyer et al. (1999) *AIDS Res Hum Retroviruses* (1999) 15(17):1563-1571). The innate immune system of mammals also recognizes and responds to molecular features of pathogenic organisms via activation of Toll-like receptors and similar receptor molecules on immune cells. Upon activation of the innate immune system, various non-adaptive immune response cells are activated to, e.g., produce various cytokines, lymphokines and chemokines. Cells activated by an innate immune response include immature and mature Dendritic cells of the moncyte and plamsacytoid lineage (MDC, PDC), as well as gamma, delta, alpha and beta T cells and B cells and the like. Thus, the present invention also contemplates an immune response wherein the immune response involves both an innate and adaptive response.

An "immunogenic composition" is a composition that comprises an antigenic molecule where administration of the composition to a subject results in the development in the subject of a humoral and/or a cellular immune response to the antigenic molecule of interest.

The terms "immunogenic" protein or polypeptide refer to an amino acid sequence which elicits an immunological response as described above. An "immunogenic" protein or polypeptide, as used herein, includes the full-length sequence of the protein in question, including the precursor and mature forms, analogs thereof, or immunogenic fragments thereof.

By "nucleic acid immunization" is meant the introduction of a nucleic acid molecule encoding one or more selected antigens into a host cell, for the in vivo expression of an antigen, antigens, an epitope, or epitopes. The nucleic acid molecule can be introduced directly into a recipient subject, such as by injection, inhalation, oral, intranasal and mucosal administration, or the like, or can be introduced ex vivo, into cells which have been removed from the host. In the latter case, the transformed cells are reintroduced into the subject where an immune response can be mounted against the antigen encoded by the nucleic acid molecule.

"Gene transfer" or "gene delivery" refers to methods or systems for reliably inserting DNA or RNA of interest into a host cell. Such methods can result in transient expression of non-integrated transferred DNA, extrachromosomal replication and expression of transferred replicons (e.g., episomes), or integration of transferred genetic material into the genomic DNA of host cells. Gene delivery expression vectors include, but are not limited to, vectors derived from bacterial plasmid vectors, viral vectors, non-viral vectors, alphaviruses, pox viruses and vaccinia viruses. When used for immunization, such gene delivery expression vectors may be referred to as vaccines or vaccine vectors.

The term "derived from" is used herein to identify the original source of a molecule but is not meant to limit the method by which the molecule is made which can be, for example, by chemical synthesis or recombinant means.

Generally, a viral polypeptide is "derived from" a particular polypeptide of a virus (viral polypeptide) if it is (i) encoded by an open reading frame of a polynucleotide of that virus (viral polynucleotide), or (ii) displays sequence identity to polypeptides of that virus as described above.

A polynucleotide "derived from" a designated sequence refers to a polynucleotide sequence which comprises a contiguous sequence of approximately at least about 6 nucleotides, preferably at least about 8 nucleotides, more preferably at least about 10-12 nucleotides, and even more preferably at least about 15-20 nucleotides corresponding, i.e., identical or complementary to, a region of the designated nucleotide sequence. The derived polynucleotide will not necessarily be derived physically from the nucleotide sequence of interest, but may be generated in any manner, including, but not limited to, chemical synthesis, replication, reverse transcription or transcription, which is based on the information provided by the sequence of bases in the region(s) from which the polynucleotide is derived. As such, it may represent either a sense or an antisense orientation of the original polynucleotide.

A Norovirus or Sapovirus polynucleotide, oligonucleotide, nucleic acid, protein, polypeptide, or peptide, as defined above, is a molecule derived from a Norovirus or Sapovirus, respectively, including, without limitation, any of the various isolates of Norovirus or Sapovirus. The molecule need not be physically derived from the particular isolate in question, but may be synthetically or recombinantly produced.

In particular, the genomes of Norovirus strains contain three open reading frames: ORF1, which is transcribed into a polyprotein, ORF2, which is transcribed into the major capsid protein VP1, and ORF3, which is transcribed into the minor structural protein VP2. The Norovirus polyprotein encoded by ORF1 undergoes cleavage by a 3C-like protease to produce at least six distinct products, an N-terminal protein (Nterm), a 2C-like nucleoside triphosphatase (NTPase), p20 or p22 (depending on the genogroup), virus protein genome-linked (VPg), a 3C-like cysteine protease (Pro), and an RNA-dependent RNA polymerase (Pol). See, Belliot et al. (2003) *J. Virol.* 77:10957-10974, herein incorporated by reference in its entirety. The polyprotein comprises these polypeptides in the order of $NH_2$-Nterm-NTPase-p20/p22-VPg-Pro-Pol-COOH. In Norovirus strain MD145-12, the boundaries of the polypeptide domains within the polyprotein are as follows: Nterm at amino acid residues 1-330, NTPase at amino acid residues 331-696, P20 at amino acid residues 697-875, VPg at amino acid residues 876-1008, protease at amino acid residues 1009-1189, and polymerase at amino acid residues 1190-1699. Although, the foregoing numbering is relative to the polyprotein amino acid sequence of Norovirus strain MD145-12 (SEQ ID NO:14), it is to be understood that the corresponding amino acid positions in sequences obtained from other genotypes and isolates of Norovirus are also intended to be encompassed by the present invention. Any one of these polypeptides encoded by ORF1, or the full-length polyprotein, VP1, or VP2, as well as variants thereof, immunogenic fragments thereof, and nucleic acids encoding such polypeptides, variants or immunogenic fragments can be used in the practice of the invention.

The genomes of Sapovirus strains contain either two or three open reading frames. In strains of Sapovirus having two open reading frames, ORF1 encodes a polyprotein comprising both nonstructural and structural proteins. The capsid protein VP1 is encoded by ORF1 as a component of the Sapovirus polyprotein, and the minor structural protein VP10 is encoded by ORF2. In strains of Sapovirus having three open reading frames, a stop codon precedes the coding region for the capsid protein. A polyprotein not including the capsid protein is encoded by ORF1, the capsid protein VP1 is encoded by ORF2, and the minor structural protein VP10 is encoded by ORF3.

Cleavage of the Sapovirus strain Mc10 polyprotein (SEQ ID NO:19, GenBank Accession No. AY237420) by a 3C-like protease produces at least ten distinct products, p11, p28, p35 (NTPase), p32, p14 (VPg), p70 (Pro-Pol), p60 (VP1). See, Oka et al. (2005) *J. Virol.* 79:7283-7290, herein incorporated by reference in its entirety. The polyprotein comprises the polypeptides in the order of $NH_2$-p28-NTPase-p32-VPg-p70 (Pro-Pol)-VP1-COOH. The p70 (Pro-Pol) region of the polyprotein resides at residues 1056-1720, and the VP1 region of the polyprotein resides at residues 1721-2278 (numbered relative to Sapovirus strain Mc10 (SEQ ID NO:19, GenBank Accession No. AY237420; see Oka et al. (2005) *J. Virol.* 79:7283-7290 and Oka et al. (2005) Arch. Virol., August 1 electronic publication). Although, the foregoing numbering is relative to the polyprotein amino acid sequence of Sapovirus strain Mc10 (SEQ ID NO:19), it is to be understood that the corresponding amino acid positions in sequences obtained from other genotypes and isolates of Sapovirus are also intended to be encompassed by the present invention. Any one of the polypeptides encoded by ORF1, or the full-length polyprotein, VP1, or VP10, as well as variants thereof, immunogenic fragments thereof, and nucleic acids encoding such polypeptides, variants or immunogenic fragments can be used in the practice of the invention.

Nucleic acid and protein sequences for a number of Norovirus isolates are known. Representative Norovirus sequences are presented in FIGS. 1A-1C, 2A-2D, 14A-14B, and 15A-15B, and SEQ ID NOS:1-9 and SEQ ID NOS:13-17. Additional representative sequences, including sequences of ORF1, ORF2, ORF3, and their encoded polypeptides from Norovirus isolates are listed in the National Center for Biotechnology Information (NCBI) database. See, for example, GenBank entries: Norovirus genogroup 1 strain Hu/NoV/West Chester/2001/USA, GenBank Accession No. AY502016; Norovirus genogroup 2 strain Hu/NoV/Braddock Heights/1999/USA, GenBank Accession No. AY502015; Norovirus genogroup 2 strain Hu/NoV/Fayette/1999/USA, GenBank Accession No. AY502014; Norovirus genogroup 2 strain Hu/NoV/Fairfield/1999/USA, GenBank Accession No. AY502013; Norovirus genogroup. 2 strain Hu/NoV/Sandusky/1999/USA, GenBank Accession No. AY502012; Norovirus genogroup 2 strain Hu/NoV/Canton/1999/USA, GenBank Accession No. AY502011; Norovirus genogroup 2 strain Hu/NoV/Tiffin/1999/USA, GenBank Accession No. AY502010; Norovirus genogroup 2 strain Hu/NoV/CS-E1/2002/USA, GenBank Accession No. AY50200; Norovirus genogroup 1 strain Hu/NoV/Wisconsin/2001/USA, GenBank Accession No. AY502008; Norovirus genogroup 1 strain Hu/NoV/CS-841/2001/USA, GenBank Accession No. AY502007; Norovirus genogroup 2 strain Hu/NoV/Hiram/2000/USA, GenBank Accession No. AY502006; Norovirus genogroup 2 strain Hu/NoV/Tontogany/1999/USA, GenBank Accession No. AY502005; Norwalk virus, complete genome, GenBank Accession No. NC_001959; Norovirus Hu/GI/Otofuke/1979/JP genomic RNA, complete genome, GenBank Accession No. AB187514; Norovirus Hu/Hokkaido/133/2003/JP, GenBank Accession No. AB212306; Norovirus Sydney 2212, GenBank Accession No. AY588132; Norwalk virus strain SN2000JA, GenBank Accession No. AB 190457; Lordsdale virus complete genome, GenBank Accession No. X86557; Norwalk-like virus genomic RNA, Gifu'96, GenBank Accession No. AB045603; Norwalk virus strain Vietnam 026, complete genome, GenBank Accession No. AF504671; Norovirus Hu/GII.4/2004/NL, GenBank Accession No. AY883096; Norovirus Hu/GII/Hokushin/03/JP, GenBank Accession No. AB195227; Norovirus Hu/GII/Kamo/03/JP, GenBank Accession No. AB195228; Norovirus Hu/GII/Sinsiro/97/JP, GenBank Accession No. AB195226; Norovirus Hu/GII/Ina/02/JP, GenBank Accession No. AB195225; Norovirus Hu/NLV/GII/Neustrelitz260/2000/DE, GenBank Accession No. AY772730; Norovirus Hu/NLV/Dresden174/pUS-NorII/1997/GE, GenBank Accession No. AY741811; Norovirus Hu/NLV/Oxford/B2S16/2002/UK, GenBank Accession No. AY587989; Norovirus Hu/NLV/Oxford/B4S7/2002/UK, GenBank Accession No. AY587987; Norovirus Hu/NLV/Witney/B7S2/2003/UK, GenBank Accession No. AY588030; Norovirus Hu/NLV/Banbury/B9S23/2003/UK, GenBank Accession No. AY588029; Norovirus Hu/NLV/ChippingNorton/2003/UK, GenBank Accession No. AY588028; Norovirus Hu/NLV/Didcot/B9S2/2003/UK, GenBank Accession No. AY588027; Norovirus Hu/NLV/Oxford/B8S5/2002/UK, GenBank Accession No. AY588026; Norovirus Hu/NLV/Oxford/B6S4/2003/UK, GenBank Accession No. AY588025; Norovirus Hu/NLV/Oxford/B6S5/2003/UK, GenBank Accession No. AY588024; Norovirus Hu/NLV/Oxford/B5S23/2003/UK, GenBank Accession No. AY588023; Norovirus Hu/NLV/Oxford/B6S2/2003/UK, GenBank Accession No. AY588022; Norovirus Hu/NLV/Oxford/B6S6/2003/UK, GenBank Accession No. AY588021; Norwalk-like virus isolate Bo/Thirsk10/00/UK, GenBank Accession No. AY126468; Norwalk-like virus isolate Bo/Penrith55/00/UK, GenBank Accession No. AY126476; Norwalk-like virus isolate Bo/Aberystwyth24/00/UK, GenBank Accession No. AY126475; Norwalk-like virus isolate Bo/Dumfries/94/UK, GenBank Accession No. AY126474; Norovirus NLV/IF2036/2003/Iraq, GenBank Accession No. AY675555; Norovirus NLV/IF1998/2003/Iraq, GenBank Accession No. AY675554; Norovirus NLV/BUDS/2002/USA, GenBank Accession No. AY660568; Norovirus NLV/Paris Island/2003/USA, GenBank Accession No. AY652979; Snow Mountain virus, complete genome, GenBank Accession No. AY134748; Norwalk-like virus NLV/Fort Lauderdale/560/1998/US, GenBank Accession No. AF414-426; Hu/Norovirus/hiroshima/1999/JP(9912-02F), GenBank Accession No. AB044366; Norwalk-like virus strain 11MSU-MW, GenBank Accession No. AY274820; Norwalk-like virus strain B-1SVD, GenBank Accession No. AY274819; Norovirus genogroup 2 strain Hu/NoV/Farmington Hills/2002/USA, GenBank Accession No. AY502023; Norovirus genogroup 2 strain Hu/NoV/CS-G4/2002/USA, GenBank Accession No. AY502022; Norovirus genogroup 2 strain Hu/NoV/CS-G2/2002/USA, GenBank Accession No. AY502021; Norovirus genogroup 2 strain Hu/NoV/CS-G12002/USA, GenBank Accession No. AY502020; Norovirus genogroup 2 strain Hu/NoV/Anchorage/2002/USA, GenBank Accession No. AY502019; Norovirus genogroup 2 strain Hu/NoV/CS-D1/2002/CAN, GenBank Accession No. AY502018; Norovirus genogroup 2 strain Hu/NoV/Germanton/2002/USA, GenBank Accession No. AY502017; Human calicivirus NLV/GII/Langen1061/2002/DE, complete genome, GenBank Accession No. AY485642; Murine norovirus 1 polyprotein, GenBank Accession No. AY228235; Norwalk virus, GenBank Accession No. AB067536; Human calicivirus NLV/Mex7076/1999, GenBank Accession No. AF542090; Human calicivirus NLV/Oberhausen 455/01/DE, GenBank Accession No. AF539440; Human calicivirus NLV/Herzberg 385/01/DE, GenBank Accession No. AF539439; Human calicivirus NLV/Boxer/2001/US, GenBank Accession No. AF538679; Norwalk-like virus genomic RNA, complete genome, Gen- Bank Accession No. AB081723; Norwalk-like virus genomic RNA, complete genome, isolate:Saitama U201, GenBank Accession No. AB039782; Norwalk-like virus genomic RNA, complete genome, isolate:Saitama U18, GenBank Accession No. AB039781; Norwalk-like virus genomic RNA, complete genome, isolate:Saitama U25, GenBank Accession No. AB039780; Norwalk virus strain:U25GII, GenBank Accession No. AB067543; Norwalk virus strain: U201GII, GenBank Accession No. AB067542; Norwalk-like viruses strain 416/97003156/1996/LA, GenBank Accession No. AF080559; Norwalk-like viruses strain 408/97003012/1996/FL, GenBank Accession No. AF080558; Norwalk-like virus NLV/Burwash Landing/331/1995/US, GenBank Accession No. AF414425; Norwalk-like virus NLV/Miami Beach/326/1995/US, GenBank Accession No. AF414424; Norwalk-like virus NLV/White River/290/1994/US, GenBank Accession No. AF414423; Norwalk-like virus NLV/New Orleans/306/1994/US, GenBank Accession No. AF414422; Norwalk-like virus NLV/Port Canaveral/301/1994/US, GenBank Accession No. AF414421; Norwalk-like virus NLV/Honolulu/314/1994/US, GenBank Accession No. AF414420; Norwalk-like virus NLV/Richmond/283/1994/US, GenBank Accession No. AF414419; Norwalk-like virus NLV/Westover/302/1994/US, GenBank Accession No. AF414418; Norwalk-like virus NLV/UK3-17/12700/1992/GB, GenBank Accession No. AF414417; Norwalk-like virus NLV/Miami/81/1986/US, GenBank Accession No. AF414416; Snow Mountain strain, GenBank Accession No. U70059; Desert Shield virus DSV395, GenBank Accession No. U04469; Norwalk virus, complete genome, GenBank Accession No. AF093797; Hawaii calicivirus, GenBank Accession No. U07611; Southampton virus, GenBank Accession No. L07418; Norwalk virus (SRSV-KY-89/89/J), GenBank Accession No. L23828; Norwalk virus (SRSV-SMA/76/US), GenBank Accession No. L23831; Camberwell virus, GenBank Accession No. U46500; Human calicivirus strain Melksham, GenBank Accession No. X81879; Human calicivirus strain MX, GenBank Accession No. U22498; Minireovirus TV24, GenBank Accession No. U02030; and Norwalk-like virus NLV/Gwynedd/273/1994/US, GenBank Accession No. AF414409; all of which sequences (as entered by the date of filing of this application) are herein incorporated by reference. Additional Norovirus sequences are disclosed in the following patent publications: WO 05/030806, WO 00/79280, JP2002020399, US2003129588, U.S. Pat. No. 6,572,862, WO 94/05700, and WO 05/032457, all of which are herein incorporated by reference in their entireties. See also Green et al. (2000) J. Infect. Dis. 181 (Suppl. 2):S322-330; Wang et al. (1994) J. Virol. 68:5982-5990; Chen et al. (2004) J. Virol. 78: 6469-6479; Chakravarty et al. (2005) J. Virol. 79: 554-568; and Fankhauser et al. (1998) J. Infect. Dis. 178:1571-1578; for sequence comparisons and a discussion of genetic diversity and phylogenetic analysis of Noroviruses.

Nucleic acid and protein sequences for a number of Sapovirus isolates are also known. Representative Sapovirus sequences are presented in SEQ ID NOS:10-12. Additional representative sequences, including sequences of ORF1 and ORF2, and their encoded polypeptides from Sapovirus isolates are listed in the National Center for Biotechnology Information (NCBI) database. See, for example, GenBank entries: Sapovirus Mc10, GenBank Accession No. NC_010624; Sapporo virus, GenBank Accession No. U65427; Sapovirus Mc10, GenBank Accession No. AY237420; Sapovirus SaKaeo-15/Thailand, GenBank Accession No. AY646855; Sapporo virus, GenBank Accession No. NC_006269; Sapovirus C12, GenBank Accession No. NC_006554; Sapovirus C12, GenBank Accession No. AY603425; Sapovirus Hu/Dresden/pJG-Sap01/DE, GenBank Accession No. AY694184; Human calicivirus SLV/cruise ship/2000/USA, GenBank Accession No. AY289804; Human calicivirus SLV/Arg39, GenBank Accession No. AY289803; Porcine enteric calicivirus strain LL14, GenBank Accession No. AY425671; Porcine enteric calicivirus, GenBank Accession No. NC_000940; Human calicivirus strain Mc37, GenBank Accession No. AY237415; Mink enteric calicivirus strain Canada 151A, GenBank Accession No. AY144337; Human calicivirus SLV/Hou7-1181, GenBank Accession No. AF435814; Human calicivirus SLV/Mex14917/2000, GenBank Accession No. AF435813; Human calicivirus SLV/Mex340/1990, GenBank Accession No. AF435812; Porcine enteric calicivirus, GenBank Accession No. AF182760; Sapporo virus-London/29845, GenBank Accession No. U95645; Sapporo virus-Manchester, GenBank Accession No. X86560; Sapporo virus-Houston/86, GenBank Accession No. U95643; Sapporo virus-Houston/90, GenBank Accession No. U95644; and Human calicivirus strain HuCV/Potsdam/2000/DEU, GenBank Accession No. AF294739; all of which sequences (as entered by the date of filing of this application) are herein incorporated by reference. See also Schuffenecker et al. (2001) Arch Virol.; 146 (11):2115-2132; Zintz et al. (2005) Infect. Genet. Evol. 5:281-290; Farkas et al. (2004) Arch. Virol. 149:1309-1323; for sequence comparisons and a discussion of genetic diversity and phylogenetic analysis of Sapoviruses.

As used herein, the terms "major capsid protein" or "major capsid polypeptide" or "VP1" in reference to a Norovirus refer to a polypeptide comprising a sequence homologous or identical to the ORF2-encoded polypeptide of a Norovirus, and includes sequences displaying at least about 80-100% sequence identity thereto, including any percent identity within these ranges, such as 81, 82, 83, 84, 85, 86, 87, 88, 89, 90, 91, 92, 93, 94, 95, 96, 97, 98, 99, 100% sequence identity thereto.

As used herein, the terms "minor structural protein" or "minor structural polypeptide" or "VP2" or "small basic protein" in reference to a Norovirus refer to a polypeptide comprising a sequence homologous or identical to the ORF3-encoded polypeptide of a Norovirus, and include sequences displaying at least about 80-100% sequence identity thereto, including any percent identity within these ranges, such as 81, 82, 83, 84, 85, 86, 87, 88, 89, 90, 91, 92, 93, 94, 95, 96, 97, 98, 99, 100% sequence identity thereto.

As used herein, the terms "capsid protein" or "capsid polypeptide" or "VP1" in reference to a Sapovirus refer to a polypeptide comprising a sequence homologous or identical to the capsid polypeptide of a Sapovirus, and include sequences displaying at least about 80-100% sequence identity thereto, including any percent identity within these ranges, such as 81, 82, 83, 84, 85, 86, 87, 88, 89, 90, 91, 92, 93, 94, 95, 96, 97, 98, 99, 100% sequence identity thereto. The capsid polypeptide may be encoded by either ORF1 or ORF2 in different strains of Sapovirus. In some strains, the Sapovirus has two open reading frames: the capsid protein is encoded by ORF1 as part of a polyprotein and a minor structural protein (VP10) is encoded by ORF2. In other strains, the Sapovirus has three open reading frames: a stop codon precedes the coding region for the capsid protein, which is encoded by ORF2, and a minor structural protein (VP10) is encoded by ORF3.

As used herein, the terms "minor structural protein" or "minor structural polypeptide" or "VP10" in reference to a Sapovirus refer to a polypeptide comprising a sequence homologous or identical to the polypeptide encoded by the open reading frame following the coding region for the capsid protein in the Sapovirus genome (either ORF2 or ORF3 depending on the strain), and include sequences displaying at least about 80-100% sequence identity thereto, including any percent identity within these ranges, such as 81, 82, 83, 84, 85, 86, 87, 88, 89, 90, 91, 92, 93, 94, 95, 96, 97, 98, 99, 100% sequence identity thereto.

As used herein, the term "Norovirus polyprotein" refers to a polyprotein comprising a sequence homologous or identical to the ORF1-encoded polyprotein of a Norovirus, and includes sequences displaying at least about 80-100% sequence identity thereto, including any percent identity within these ranges, such as 81, 82, 83, 84, 85, 86, 87, 88, 89, 90, 91, 92, 93, 94, 95, 96, 97, 98, 99, 100% sequence identity thereto.

As used herein, the term "Sapovirus polyprotein" refers to a polyprotein comprising a sequence homologous or identical to the ORF1-encoded polyprotein of a Sapovirus, and includes sequences displaying at least about 80-100% sequence identity thereto, including any percent identity within these ranges, such as 81, 82, 83, 84, 85, 86, 87, 88, 89, 90, 91, 92, 93, 94, 95, 96, 97, 98, 99, 100% sequence identity thereto.

As used herein, the term "virus-like particle" or "VLP" refers to a nonreplicating, viral shell, derived from any of several viruses discussed further below. A virus-like particle in accordance with the invention is non replicative and non-infectious because it lacks all or part of the viral genome, in particular the replicative and infectious components of the viral genome. VLPs are generally composed of one or more viral proteins, such as, but not limited to those proteins referred to as capsid, coat, shell, surface, structural proteins (e.g., VP1, VP2), or particle-forming polypeptides derived from these proteins, including the proteins described herein. VLPs can form spontaneously upon recombinant expression of capsid proteins in an appropriate expression system. Methods for producing particular VLPs are known in the art and discussed more fully below. The presence of VLPs following recombinant expression of viral proteins can be detected using conventional techniques known in the art, such as by electron microscopy, biophysical characterization, and the like. For example, VLPs can be isolated by density gradient centrifugation and/or identified by characteristic density banding. Alternatively, cryoelectron microscopy can be performed on vitrified aqueous samples of the VLP preparation in question, and images recorded under appropriate exposure conditions.

As used herein, the term "mosaic VLP" refers to a VLP comprising capsid proteins from more than one type of virus. VLPs which result from intra- and/or inter-capsomeric association of the proteins are included.

By "particle-forming polypeptide" derived from a particular viral protein is meant a full-length or near full-length viral protein, as well as a fragment thereof, or a viral protein with internal deletions, which has the ability to form VLPs under conditions that favor VLP formation. Accordingly, the polypeptide may comprise the full-length sequence, fragments, truncated and partial sequences, as well as analogs and precursor forms of the reference molecule. The term therefore intends deletions, additions and substitutions to the sequence, so long as the polypeptide retains the ability to form a VLP. Thus, the term includes natural variations of the specified polypeptide since variations in coat proteins often occur between viral isolates. The term also includes deletions, additions and substitutions that do not naturally occur in the reference protein, so long as the protein retains the ability to form a VLP. Preferred substitutions are those which are conservative in nature, i.e., those substitutions that take place within a family of amino acids that are related in their side chains. Specifically, amino acids are generally divided into four families: (1) acidic—aspartate and glutamate; (2) basic—lysine, arginine, histidine; (3) non-polar—alanine, valine, leucine, isoleucine, proline, phenylalanine, methionine, tryptophan; and (4) uncharged polar—glycine, asparagine, glutamine, cystine, serine threonine, tyrosine. Phenylalanine, tryptophan, and tyrosine are sometimes classified as aromatic amino acids.

An "antigen" refers to a molecule containing one or more epitopes (either linear, conformational or both) that will stimulate a host's immune-system to make a humoral and/or cellular antigen-specific response. The term is used interchangeably with the term "immunogen." Normally, a B-cell epitope will include at least about 5 amino acids but can be as small as 3-4 amino acids. A T-cell epitope, such as a CTL epitope, will include at least about 7-9 amino acids, and a helper T-cell epitope at least about 12-20 amino acids. Normally, an epitope will include between about 7 and 15 amino acids, such as, 9, 10, 12 or 15 amino acids. The term "antigen" denotes both subunit antigens, (i.e., antigens which are separate and discrete from a whole organism with which the antigen is associated in nature), as well as, killed, attenuated or inactivated bacteria, viruses, fungi, parasites or other microbes. Antibodies such as anti-idiotype antibodies, or fragments thereof, and synthetic peptide mimotopes, which can mimic an antigen or antigenic determinant, are also captured under the definition of antigen as used herein. Similarly, an oligonucleotide or polynucleotide which expresses an antigen or antigenic determinant in vivo, such as in gene therapy and DNA immunization applications, is also included in the definition of antigen herein.

The term "antibody" encompasses polyclonal and monoclonal antibody preparations, as well as preparations including hybrid antibodies, altered antibodies, chimeric antibodies and, humanized antibodies, as well as: hybrid (chimeric) antibody molecules (see, for example, Winter et al. (1991) *Nature* 349:293-299; and U.S. Pat. No. 4,816,567); F(ab')$_2$ and F(ab) fragments; Fv molecules (noncovalent heterodimers, see, for example, Inbar et al. (1972) *Proc Natl Acad Sci USA* 69:2659-2662; and Ehrlich et al. (1980) *Biochem* 19:4091-4096); single-chain Fv molecules (sFv) (see, e.g., Huston et al. (1988) *Proc Natl Acad Sci USA* 85:5879-5883); dimeric and trimeric antibody fragment constructs; minibodies (see, e.g., Pack et al. (1992) *Biochem* 31:1579-1584; Cumber et al. (1992) *J Immunology* 149B:120-126); humanized antibody molecules (see, e.g., Riechmann et al. (1988) *Nature* 332:323-327; Verhoeyan et al. (1988) *Science* 239:1534-1536; and U.K. Patent Publication No. GB 2,276, 169, published 21 Sep. 1994); and, any functional fragments obtained from such molecules, wherein such fragments retain specific-binding properties of the parent antibody molecule.

The terms "hybridize" and "hybridization" refer to the formation of complexes between nucleotide sequences which are sufficiently complementary to form complexes via Watson-Crick base pairing. Where a primer "hybridizes" with target (template), such complexes (or hybrids) are sufficiently stable to serve the priming function required by, e.g., the DNA polymerase to initiate DNA synthesis.

As used herein, a "biological sample" refers to a sample of tissue or fluid isolated from a subject, including but not limited to, for example, blood, plasma, serum, fecal matter, urine, bone marrow, bile, spinal fluid, lymph fluid, samples of the skin, external secretions of the skin, respiratory, intestinal, and genitourinary tracts, tears, saliva, milk, blood cells, organs, biopsies and also samples of in vitro cell culture constituents including but not limited to conditioned media resulting from the growth of cells and tissues in culture medium, e.g., recombinant cells, and cell components. In particular, Norovirus or Sapovirus may be obtained from biological samples such as vomit or diarrhea from individuals infected with the viruses.

By "subject" is meant any member of the subphylum chordata, including, without limitation, humans and other primates, including non-human primates such as chimpanzees and other apes and monkey species; farm animals such as cattle, sheep, pigs, goats and horses; domestic mammals such as dogs and cats; laboratory animals including rodents such as mice, rats and guinea pigs; birds, including domestic, wild and game birds such as chickens, turkeys and other gallinaceous birds, ducks, geese, and the like. The term does not denote a particular age. Thus, both adult and newborn individuals are intended to be covered.

The terms "variant," "analog" and "mutein" refer to biologically active derivatives of the reference molecule that retain desired activity, such as antigenic activity in inducing an immune response against Norovirus or Sapovirus. In general, the terms "variant" and "analog" refer to compounds having a native polypeptide sequence and structure with one or more amino acid additions, substitutions (generally conservative in nature) and/or deletions, relative to the native molecule, so long as the modifications do not destroy biological activity and which are "substantially homologous" to the reference molecule as defined below. In general, the amino acid sequences of such analogs will have a high degree of sequence homology to the reference sequence, e.g., amino acid sequence homology of more than 50%, generally more than 60%-70%, even more particularly 80%-85% or more, such as at least 90%-95% or more, when the two sequences are aligned. Often, the analogs will include the same number of amino acids but will include substitutions, as explained herein: The term "mutein" further includes polypeptides having one or more amino acid-like molecules including but not limited to compounds comprising only amino and/or imino molecules, polypeptides containing one or more analogs of an amino acid (including, for example, unnatural amino acids, etc.), polypeptides with substituted linkages, as well as other modifications known in the art, both naturally occurring and non-naturally occurring (e.g., synthetic), cyclized, branched molecules and the like. The term also includes molecules comprising one or more N-substituted glycine residues (a "peptoid") and other synthetic amino acids or peptides. (See, e.g., U.S. Pat. Nos. 5,831,005; 5,877,278; and 5,977,301; Nguyen et al., Chem. Biol. (2000) 7:463-473; and Simon et al., Proc. Natl. Acad. Sci. USA (1992) 89:9367-9371 for descriptions of peptoids). Preferably, the analog or mutein has at least the same antigenic activity as the native molecule. Methods for making polypeptide analogs and muteins are known in the art and are described further below.

As explained above, analogs generally include substitutions that are conservative in nature, i.e., those substitutions that take place within a family of amino acids that are related in their side chains. Specifically, amino acids are generally divided into four families: (1) acidic—aspartate and glutamate; (2) basic—lysine, arginine, histidine; (3) non-polar—alanine, valine, leucine, isoleucine, proline, phenylalanine, methionine, tryptophan; and (4) uncharged polar—glycine, asparagine, glutamine, cysteine, serine thieonine, tyrosine. Phenylalanine, tryptophan, and tyrosine are sometimes classified as aromatic amino acids. For example, it is reasonably predictable that an isolated replacement of leucine with isoleucine or valine, an aspartate with a glutamate, a threonine with a serine, or a similar conservative replacement of an amino acid with a structurally related amino acid, will not have a major effect on the biological activity. For example, the polypeptide of interest may include up to about 5-10 conservative or non-conservative amino acid substitutions, or even up to about 15-25 conservative or non-conservative amino acid substitutions, or any integer between 5-25, so long as the desired function of the molecule remains intact. One of skill in the art may readily determine regions of the molecule of interest that can tolerate change by reference to Hopp/Woods and Kyte-Doolittle plots, well known in the art.

The term "multiple epitope fusion antigen" or "multiple epitope fusion protein" as used herein intends a polypeptide in which multiple Norovirus and/or Sapovirus antigens are part of a single, continuous chain of amino acids, which chain does not occur in nature. The Norovirus and Sapovirus antigens may be connected directly to each other by peptide bonds or may be separated by intervening amino acid sequences. The fusion antigens may contain ORF1-encoded, ORF2-encoded, and/or ORF3-encoded polypeptides or fragments thereof, including, for example, sequences of Norovirus polypeptides, such as N-terminal protein, NTPase, p20, VPg, protease, polymerase, VP1, and VP2; and/or sequences of Sapovirus polypeptides, such as N-terminal protein, p11, p28, NTPase, p32, VPg, protease, polymerase, VP1, and VP10. The fusion antigens may also contain sequences exogenous to the Norovirus or Sapovirus. Moreover, the sequences present may be from multiple genotypes and/or isolates of Norovirus and Sapovirus.

As used herein, "detoxified" refers to both completely nontoxic and low residual toxic mutants of the toxin in question. Toxic protein antigens may be detoxified where necessary, e.g., detoxification of pertussis toxin by chemical and/or genetic means is known in the art. Preferably, the detoxified protein retains a toxicity of less than 0.01% of the naturally occurring toxin counterpart, more preferably less than 0.001% and even more preferable, less than 0.0001% of the toxicity of the naturally occurring toxin counterpart. The toxicity may be measured in mouse CHO cells or preferably by evaluation of the morphological changes induced in Y1 cells. In particular, Y1 cells are adrenal tumor epithelial cells which become markedly more rounded when treated with a solution containing CT or LT (Ysamure et al., Cancer Res. (1966) 26:529-535). The toxicity of CT and LT is correlated with this morphological transition. Thus, the mutant toxins may be incubated with Y1 cells and the morphological changes of the cells assessed.

By "therapeutically effective amount" in the context of the immunogenic compositions is meant an amount of an immunogen (e.g., immunogenic polypeptide, fusion protein, polyprotein, VLP, or nucleic acid encoding an antigen) which will induce an immunological response, either for antibody production or for treatment or prevention of Norovirus or Sapovirus infection. Such a response will generally result in the development in the subject of an antibody-mediated and/or a secretory or cellular immune response to the composition. Usually, such a response includes but is not limited to one or more of the following effects; the production of antibodies from any of the immunological classes, such as immunoglobulins A, D, E, G or M; the proliferation of B and T lymphocytes; the provision of activation, growth and differentiation signals to immunological cells; expansion of helper T cell, suppressor T cell, and/or cytotoxic T cell and/or γδT cell populations.

For purposes of the present invention; an "effective amount" of an adjuvant will be that amount which enhances an immunological response to a coadministered antigen or nucleic acid encoding an antigen.

As used herein, "treatment" refers to any of (i) the prevention of infection or reinfection, as in a traditional vaccine, (ii) the reduction or elimination of symptoms, and (iii) the substantial or complete elimination of the pathogen in question. Treatment may be effected prophylactically (prior to infection) or therapeutically (following infection).

II. MODES OF CARRYING OUT THE INVENTION

Before describing the present invention in detail, it is to be understood that this invention is not limited to particularly exemplified molecules or process parameters as such may, of course, vary. It is also to be understood that the terminology used herein is for the purpose of describing particular embodiments of the invention only, and is not intended to be limiting. In addition, the practice of the present invention will employ, unless otherwise indicated, conventional methods of virology, microbiology, molecular biology, recombinant DNA techniques and immunology all of which are within the ordinary skill of the art. Such techniques are explained fully in the literature. See, e.g., Sambrook, et al., Molecular Cloning: A Laboratory Manual (2nd Edition, 1989); DNA Cloning: A Practical Approach, vol. I & II (D. Glover, ed.); Oligonucleotide Synthesis (N. Gait, ed., 1984); A Practical Guide to Molecular Cloning (1984); and Fundamental Virology, 2nd Edition, vol. I & II (B. N. Fields and D. M. Knipe, eds.). Although a number of methods and materials similar or equivalent to those described herein can be used in the practice of the present invention, the preferred materials and methods are described herein.

The present invention includes compositions and methods for immunizing a subject against Norovirus or Sapovirus infection. The invention provides immunogenic compositions comprising nucleic acids encoding capsid proteins and/or other immunogenic polypeptides from one or more strains of Norovirus and/or Sapovirus, compositions comprising immunogenic polypeptides derived from one or more strains of Norovirus and/or Sapovirus, compositions comprising VLPs derived from one or more strains of Norovirus and/or Sapovirus, and compositions comprising mixtures of such immunogenic nucleic acids, polypeptides, and/or VLPs. Nucleic acids encoding capsid proteins may further be used in the production of VLPs. Such VLPs are useful as vehicles for the presentation of antigens and stimulation of an immune response in a subject to whom the VLPs or nucleic acids encoding such VLPs are administered. Immunogenic polypeptides to be used in the practice of the invention may include Norovirus- or Sapovirus-derived polypeptides, including ORF1-encoded polypeptides, ORF2-encoded polypeptides, ORF3-encoded polypeptides, multiple epitope fusion antigens, and/or ORF1-encoded polyproteins. In addition, immunogenic compositions may comprise one or more adjuvants or nucleic acids encoding adjuvants, wherein immunogenic polypeptides and/or VLPs are mixed or co-expressed with adjuvants. Immunogenic compositions may also comprise additional antigens other than Norovirus or Sapovirus antigens, such as antigens that can be used in immunization against pathogens that cause diarrheal diseases.

In order to further an understanding of the invention, a more detailed discussion is provided below regarding the production of nucleic acids, polypeptides, and VLPs for use in immunogenic compositions and methods of using such compositions in the treatment or prevention of Norovirus or Sapovirus infection.

A. Polypeptides

Structural Polypeptides, Nonstructural Polypeptides, and Polyproteins

The immunogenic compositions described herein may comprise one or more polypeptides derived from one or more genotypes and/or isolates of Norovirus and Sapovirus. Polypeptides that can be used in the practice of the invention include structural proteins, nonstructural proteins, and polyproteins. Such polypeptides can be full-length proteins or variants or immunogenic fragments thereof capable of eliciting an immune response to a Norovirus or Sapovirus.

The genomes of Norovirus strains contain three open reading frames: ORF1, comprising approximately 5,000 to 5500 nucleotides, is transcribed into a 200 kDa polyprotein. ORF2, comprising approximately 1550 to 1650 nucleotides, is transcribed into the 60 kDa major capsid protein VP1. ORF3, comprising approximately 1550 to 1650 nucleotides, is transcribed into the minor structural protein VP2.

The Norovirus polyprotein undergoes cleavage by a 3C-like protease to produce at least six distinct products, an N-terminal protein (Nterm), a 2C-like nucleoside triphosphatase (NTPase), p20 or p22 (depending on the genogroup), virus protein genome-linked (VPg), a 3C-like cysteine protease (Pro), and an RNA-dependent RNA polymerase (Pol). See, Belliot et al. (2003) J. Virol. 77:10957-10974, herein incorporated by reference in its entirety. The polyprotein is initially cleaved into the three fragments, Nterm, NTPase, and a p20VPgProPol complex, by the 3C-like protease. Further proteolytic processing produces ProPol, P20VPgPro, Pol, P20VPg, VPgPro, p20 and Pro fragments. Completion of polyprotein maturation, catalyzed by the 3C-like cysteine protease, produces all the separate polypeptides. The 200 kDa polyprotein comprises these polypeptides in the order of $NH_2$-Nterm-NTPase-p20/p22-VPg-Pro-Pol-COOH. The approximate domain boundaries within the Norovirus polyprotein and the corresponding nucleotide positions of the ORF1 coding sequence are presented in Table 1.

TABLE 1

Norovirus Polyprotein

| Domain | Polyprotein Domain Boundaries Amino Acid Positions* | ORF1 Coding Sequence Nucleotide Positions* |
|---|---|---|
| Nterm | 1-330 | 5-994 |
| NTPase | 331-696 | 995-2092 |
| P20 | 697-875 | 2093-2629 |
| VPg | 876-1008 | 2630-3028 |
| protease | 1009-1189 | 3029-3271 |
| polymerase | 1190-1699 | 3272-5101 |

*Numbered relative to Norovirus strain MD145-12 (SEQ ID NO: 13, SEQ ID NO: 14, GenBank Accession No. AAK50354). See, Belliot et al. (2003) J. Virol. 77: 10957-10974.

The genomes of Sapovirus strains contain either two or three open reading frames. In strains of Sapovirus having two open reading frames, ORF1 encodes a polyprotein comprising both nonstructural and structural proteins. The capsid protein VP1 is encoded by ORF1 as a component of the Sapovirus polyprotein, and the minor structural protein VP10 is encoded by ORF2. In strains of Sapovirus having three open reading frames, a stop codon precedes the coding region for the capsid protein. A polyprotein not including the capsid protein is encoded by ORF1, the capsid protein VP1 is encoded by ORF2, and the minor structural protein VP10 is encoded by ORF3.

Cleavage of the Sapovirus strain Mc10 polyprotein (SEQ ID NO:19, GenBank Accession No. AY237420) by a 3C-like protease produces at least ten distinct products, p11, p28, p35 (NTPase), p32, p14 (VPg), p70 (Pro-Pol), p60 (VP1). See, Oka et al. (2005) *J. Virol.* 79:7283-7290, herein incorporated by reference in its entirety. Initial proteolytic processing produces p66 (p28-p35), p46 (p32-p14), and p120 (p32-p14-p70) fragments. The polyprotein comprises the polypeptides in the order of $NH_2$-p11-p28-NTPase-p32-VPg-p70(Pro-Pol)-VP1-COOH. The p70 (Pro-Pol) region of the polyprotein resides at residues 1056-1720, and the VP1 region of the polyprotein resides at residues 1721-2278 (numbered relative to Sapovirus strain Mc10 (SEQ ID NO:19, GenBank Accession No. AY237420; see Oka et al. (2005) *J. Virol.* 79:7283-7290 and Oka et al. (2005) Arch. Virol., August 1 electronic publication).

Nucleic acid and amino acid sequences of a number of Norovirus strains and isolates, including nucleic acid and amino acid sequences of VP1 and VP2 structural proteins and the various regions of Norovirus polyproteins, including Nterm, NTPase, p20/p22, VPg, Pro, and Pol genes and polypeptides have been determined. For example, Norwalk virus is described in Jiang et al. (1993) Virology 195:51-61 and Hardy and Estes (1996) Virus Genes 12:287-290; herein incorporated by reference in their entireties. Snow Mountain virus is described in Lochridge and Hardy (2003) Virus Genes 26:71-82; King and Green (1997) Virus Genes 15:5-7; Wang et al. (1994) J. Virol. 68, 5982-5990; herein incorporated by reference in their entireties. Hawaii virus is described in Lew et al. (1994) J. Infect. Dis. 170:535-542; herein incorporated by reference in its entirety.

Nucleic acid and amino acid sequences of a number of Sapovirus strains and isolates, including nucleic acid and amino acid sequences of VP1 and VP10 structural proteins and the various regions of Sapovirus polyproteins, including p11, p28, NTPase, p32, VPg, p70(Pro-Pol), VP1 genes and polypeptides have also been determined. For example, Sapporo virus is described in Numata et al. (1997) Arch. Virol. 142:1537-1552; herein incorporated by reference in its entirety. London/29845 virus, Houston/86 virus, and Houston/90 virus are described in Jiang et al. (1997) Arch. Virol. 142:1813-1827; herein incorporated by reference in its entirety. Parkville virus is described in Noel et al. (1997) J. Med. Virol. 52:173-178; herein incorporated by reference in its entirety.

The polypeptides in immunogenic compositions may be encoded by any region of a Norovirus or Sapovirus genome. Multiple polypeptides may be included in immunogenic compositions. Such compositions may comprise polypeptides from the same Norovirus or Sapovirus isolate or from different strains and isolates, including isolates having any of the various Norovirus or Sapovirus genotypes, to provide increased protection against a broad range of Norovirus and Sapovirus genotypes. Immunogenic compositions may contain both polypeptides derived from Norovirus strains as well as polypeptides derived from Sapovirus strains. Multiple viral strains of Norovirus and Sapovirus are known, and multiple polypeptides comprising epitopes derived from any of these strains can be used in immunogenic compositions.

The antigens used in the immunogenic compositions of the present invention may be present in the composition as individual separate polypeptides. Generally, the recombinant proteins of the present invention are prepared as a GST-fusion protein and/or a His-tagged fusion protein.

Multiepitope Fusion Proteins

The immunogenic compositions described herein may also comprise multiple epitope fusion proteins. See, e.g., International Publication No. WO 97/44469, U.S. Pat. No. 6,632,601, U.S. Pat. No. 6,630,298, U.S. Pat. No. 6,514,731, and U.S. Pat. No. 6,797,809; herein incorporated by reference in their entireties. Such fusion proteins include multiple epitopes derived from two or more viral polypeptides of one or more genotypes and/or isolates of Norovirus and Sapovirus. Multiple epitope fusion proteins offer two principal advantages: first, a polypeptide that may be unstable or poorly expressed on its own can be assisted by adding a suitable hybrid partner that overcomes the problem; second, commercial manufacture is simplified as only one expression and purification need be employed in order to produce two polypeptides which are both antigenically useful.

Multiepitope fusion proteins may contain one or more of the various domains of Norovirus or Sapovirus polyproteins (shown in Tables 1 and 2 above), full-length polyproteins, VP1 (also referred to herein as a capsid protein), VP2 (also referred to herein as a Norovirus minor structural protein), and/or VP10 (also referred to herein as a Sapovirus minor structural protein); or fragments thereof, derived from one or more Norovirus and/or Sapovirus isolates. The polypeptides in fusion proteins may be derived from the same Norovirus or Sapovirus isolate or from different strains and isolates, including isolates having any of the various Norovirus or Sapovirus genotypes, to provide increased protection against a broad range of Norovirus and Sapovirus genotypes. Multiple viral strains of Norovirus and Sapovirus are known, and epitopes derived from any of these strains can be used in a fusion protein.

It is well known that any given species of organism varies from one individual organism to another and further that a given organism such as a virus can have a number of different strains. For example, as explained above, Norovirus includes at least four genogroups (GI-GIV) and Sapovirus includes at least five genogroups (GI-GV). Each strain includes a number of antigenic determinants that are in homologous regions present in all strains of Noroviruses or Sapoviruses but are slightly different from one viral strain to another. Thus, a multiple epitope fusion antigen may include multiple polypeptides from different viral strains of Norovirus or Sapovirus, each comprising a particular homologous region but each having a different form of an antigenic determinant. In general, antigenic determinants may have a high degree of homology in terms of amino acid sequence, which degree of homology is generally 30% or more, preferably 40% or more, when aligned. A fusion protein may also comprise multiple copies of an epitope, wherein one or more polypeptides of the fusion protein comprise sequences comprising exact copies of the same epitope. Additionally, polypeptides can be selected based on the particular viral clades endemic in specific geographic regions where vaccine compositions containing the fusions will be used. It is readily apparent that the subject fusions provide an effective means of treating Norovirus and Sapovirus infection in a wide variety of contexts.

Multiple epitope fusion antigens can be represented by the formula $NH_2$-A-$\{$-X-L-$\}_n$-B—COOH, wherein: X is an amino acid sequence of a Norovirus or Sapovirus antigen or a fragment thereof; L is an optional linker amino acid sequence; A is an optional N-terminal amino acid sequence; B is an optional C-terminal amino acid sequence; and n is 2, 3, 4, 5, 6, 7, 8, 9, 10, 11, 12, 13, 14 or 15.

If an —X— moiety has a leader peptide sequence in its wild-type form, this may be included or omitted in the multiple epitope fusion antigen. In some embodiments, the leader peptides will be deleted except for that of the —X— moiety located at the N-terminus of the hybrid protein i.e. the leader peptide of $X_1$ will be retained, but the leader peptides of $X_2 \ldots X_n$ will be omitted. This is equivalent to deleting all leader peptides and using the leader peptide of $X_1$ as moiety -A-.

For each n instances of (—X-L-), linker amino acid sequence -L- may be present or absent. For instance, when n=2 the hybrid may be NH$_2$—X$_1$-L$_1$-X$_2$-L$_2$-COOH, NH$_2$—X$_1$—X$_2$—COOH, NH$_2$—X$_1$-L$_1$-X$_2$—COOH, NH$_2$—X$_1$—X$_2$-L$_2$-COOH, etc. Linker amino acid sequence(s)-L- will typically be short, e.g., 20 or fewer amino acids (i.e., 20, 19, 18, 17, 16; 15, 14, 13, 12, 11, 10, 9, 8, 7, 6, 5, 4, 3, 2, 1). Examples include short peptide sequences which facilitate cloning, poly-glycine linkers (Gly$_n$ where n=2, 3, 4, 5, 6, 7, 8, 9, 10 or more), and histidine tags (His$_n$ where n=3, 4, 5, 6, 7, 8, 9, 10 or more). Other suitable linker amino acid sequences will be apparent to those skilled in the art. A useful linker is GSGGGG, with the Gly-Ser dipeptide being formed from a BamHI restriction site, which aids cloning and manipulation, and the (Gly)$_4$ tetrapeptide being a typical poly-glycine linker.

-A- is an optional N-terminal amino acid sequence. This will typically be short, e.g., 40 or fewer amino acids (i.e., 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1). Examples include leader sequences to direct protein trafficking or short peptide sequences which facilitate cloning or purification (e.g., a histidine tag His$_n$ where n=3, 4, 5, 6, 7, 8, 9, 10 or more). Other suitable N-terminal amino acid sequences will be apparent to those skilled in the art. If X$_1$ lacks its own N-terminus methionine, -A- is preferably an oligopeptide (e.g., with 1, 2, 3, 4, 5, 6, 7 or 8 amino acids) which provides a N-terminus methionine.

—B— is an optional C-terminal amino acid sequence. This will typically be short, e.g., 40 or fewer amino acids (i.e., 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1). Examples include sequences to direct protein trafficking, short peptide sequences which facilitate cloning or purification (e.g., His$_n$ where n=3, 4, 5, 6, 7, 8, 9, 10 or more), or sequences which enhance protein stability. Other suitable C-terminal amino acid sequences will be apparent to those skilled in the art.

The individual antigens of the immunogenic composition within the multiple epitope fusion antigen (individual —X— moieties) may be from one or more strains or from one or more M types. Where n=2, for instance, X$_2$ may be from the same strain or type as X$_1$ or from a different strain or type. Where n=3, the strains might be (i) X$_1$=X$_2$=X$_3$, (ii) X$_1$≠X$_2$≠X$_3$, (iii) X$_1$≠X$_2$≠X$_3$, (iv) X$_1$≠X$_2$≠X$_3$, or (v) X$_1$=X$_3$≠X$_2$, etc.

Where multiple epitope fusion antigens are used, the individual antigens within the fusion protein (i.e. individual —X— moieties) may be from one or more strains. Where n=2, for instance, X$_2$ may be from the same strain as X$_1$ or from a different strain. Where n=3, the strains might be (i) X$_1$=X$_2$=X$_3$ (ii) X$_1$=X$_2$≠X$_3$ (iii) X$_1$≠X$_2$=X$_3$ (iv) X$_1$≠X$_2$≠X$_3$ or (v) X$_1$=X$_3$≠X$_2$, etc.

Accordingly, in certain embodiments of the invention antigenic determinants from different Norovirus and/or Sapovirus strains may be present. Representative multiepitope fusion proteins for use in the present invention, comprising polypeptides derived from Norovirus and Sapovirus isolates, are discussed below. However, it is to be understood that multiepitope fusion proteins comprising other epitopes derived from Norovirus and Sapovirus genomes or multi-epitope fusion proteins comprising different arrangements of epitopes will also find use in immunogenic compositions of the invention.

In certain embodiments, the fusion protein comprises one or more capsid and/or minor structural polypeptides from one or more isolates of Norovirus and/or Sapovirus. In one embodiment, the fusion protein comprises VP1 polypeptides from more than one Norovirus strain (e.g., VP1$_{NV}$-VP1$_{SMV}$, VP1$_{NV}$-VP1$_{SMV}$-VP1$_{HV}$, VP1$_{NV}$-VP1$_{SMV}$-VP1$_{HV}$-VP1$_{LV}$, VP1$_{SMV}$-VP1$_{LV}$-VP1$_{MV}$, VP1$_{NV}$-VP1$_{SMV}$-VP1$_{HV}$-VP1$_{LV}$-VP1$_{MV}$-VP1$_{DSV}$-VP1$_{SV}$).

In another embodiment, the fusion protein comprises VP1 polypeptides from more than one Sapovirus strain (e.g., VP1$_{Sapporo}$-VP1$_{London/29845}$, VP1$_{London/29845}$-VP1$_{Manchester}$-VP1$_{Sapporo}$, VP1$_{Manchester}$-VP1$_{Parkville}$-VP1$_{Sapporo}$-VP1$_{London/29845}$, VP1$_{Parkville}$-VP1$_{Houston/90}$-VP1$_{Houston/86}$-VP1$_{Manchester}$-VP1$_{Sapporo}$).

In another embodiment, the fusion protein comprises VP1 polypeptides from Norovirus and Sapovirus strains (e.g., VP1$_{NV}$-VP1$_{SMV}$-VP1$_{Sapporo}$-VP1$_{London/29845}$, VP1$_{Parkville}$-VP1$_{Houston/90}$-VP1$_{NV}$-VP1$_{SMV}$-VP1$_{HV}$, VP1$_{Manchester}$-VP1$_{NV}$-VP1$_{SMV}$-VP1$_{Sapporo}$-VP1$_{HV}$, VP1$_{LV}$, VP1$_{SMV}$-VP1$_{Houston/86}$-VP1$_{LV}$-VP1$_{MV}$, VP1$_{NV}$-VP1$_{SMV}$-VP1$_{HV}$-VP1$_{Sapporo}$-VP1$_{Houston/90}$-VP1$_{Houston/86}$, VP1$_{London/29845}$-VP1$_{LV}$-VP1$_{MV}$-VP1$_{DSV}$-VP1$_{SV}$).

In another embodiment, the fusion protein comprises VP2 polypeptides from more than one Norovirus strain (e.g., VP2$_{NV}$-VP2$_{SMV}$, VP2$_{NV}$-VP2$_{SMV}$-VP2$_{HV}$, VP2$_{NV}$-VP2$_{SMV}$-VP2$_{HV}$-VP2$_{LV}$, VP2$_{SMV}$-VP2$_{LV}$-VP2$_{MV}$, VP2$_{NV}$-VP2$_{SMV}$-VP2$_{HV}$-VP2$_{LV}$-VP2$_{MV}$-VP2$_{DSV}$-VP2$_{SV}$).

In another embodiment, the fusion protein comprises VP10 polypeptides from more than one Sapovirus strain (e.g., VP10$_{Sapporo}$-VP10$_{London/29845}$, VP10$_{London/29845}$-VP10$_{Manchester}$-VP10$_{Sapporo}$, VP10$_{Manchester}$-VP10$_{Parkville}$-VP10$_{Sapporo}$-VP10$_{London/29845}$, VP10$_{Parkville}$-VP10$_{Houston/90}$-VP10$_{Houston/86}$-VP10$_{Manchester}$-VP10$_{Sapporo}$).

In another embodiment, the fusion protein comprises VP2 from one or more. Norovirus strains and VP10 polypeptides from one or more Sapovirus strains (e.g., VP2$_{NV}$-VP2$_{SMV}$-VP10$_{Sapporo}$-VP10$_{London/29845}$, VP10$_{Parkville}$-VP10$_{Houston/90}$-VP2$_{NV}$-VP2$_{SMV}$-VP10$_{HV}$, VP10$_{Manchester}$-VP2$_{NV}$-VP2$_{SMV}$-VP10$_{Sapporo}$-VP2$_{HV}$, VP2$_{LV}$-VP2$_{SMV}$-VP10$_{Houston/86}$-VP2$_{LV}$-VP2$_{MV}$, VP2$_{NV}$-VP2$_{SMV}$-VP2$_{HV}$-VP10$_{Sapporo}$-VP10$_{Houston/90}$-VP10$_{Houston/86}$, VP10$_{London/29845}$-VP2$_{LV}$-VP2$_{MV}$-VP2$_{DSV}$-VP2$_{SV}$).

In another embodiment, the fusion protein comprises VP1 and VP2 polypeptides from one or more Norovirus strains and VP1 and VP10 polypeptides from one or more Sapovirus strains (e.g., VP1VP2$_{NV}$-VP1VP10$_{London/29845}$, VP1VP2$_{SMV}$-VP1VP10$_{Houston/86}$-VP1VP10$_{Houston/90}$-VP1VP2$_{HV}$, VP1VP2$_{NV}$-VP10$_{Sapporo}$-VP10$_{Houston/90}$-VP10$_{Houston/86}$-VP1VP2$_{SMV}$, VP1$_{NV}$-VP1VP2$_{SMV}$-VP2$_{HV}$-VP1$_{London/29845}$, VP1VP2$_{NV}$-VP10$_{Houston/90}$-VP1VP10$_{Houston/86}$-VP1VP2$_{SMV}$-VP1VP2$_{HV}$-VP1VP2$_{LV}$, VP1VP2$_{SMV}$-VP1VP2$_{LV}$-VP1VP2$_{MV}$-VP10$_{Sapporo}$-VP10$_{Houston/90}$-VP10$_{Houston/86}$, VP1VP2$_{LV}$-VP1VP2$_{MV}$-VP10$_{Sapporo}$-VP10$_{London/29845}$, VP10$_{Sapporo}$-VP10$_{London/29845}$-VP1$_{DSV}$-VP2$_{SV}$-VP1VP10$_{Houston/86}$).

The fusions may comprise any number of VP1 and VP2 polypeptides from different isolates of Norovirus and/or any number of VP1 and VP10 polypeptides from different isolates of Sapovirus, for example, fusion proteins may comprise at least 2, 3, 4, 5, 6, 7, 8, 9, 10, 11, 12, 13, 14, 15, 16, 17, 18, 19, or 20 or more VP1, VP2, and/or VP10 polypeptides, which may be present in any order in the multiepitope fusion protein. Fusion proteins may comprise the same or different numbers of VP1, VP2, and VP10 polypeptides.

In certain embodiments, the fusion proteins comprise one or more ORF1-encoded nonstructural polypeptides from one or more isolates of Norovirus (e.g., Nterm, NTPase, p20, p22, VPg, Pro, and Pol) and/or Sapovirus (e.g., p11, p28, NTPase, p32, VPg, Pro, Pol, and VP1). Fusion proteins may comprise at least 2, 3, 4, 5, 6, 7, 8, 9, 10, 11, 12, 13, 14, 15, 16, 17, 18, 19, or 20 or more nonstructural polypeptides. These nonstructural polypeptides need not be in the order in which they naturally occur in the native Norovirus or Sapovirus polyproteins. Thus, for example, an Nterm polypeptide may be at the N- and/or C-terminus of a fusion protein. Multiple copies of a particular nonstructural polypeptide from different isolates of Norovirus and/or Sapovirus may be present in the fusion protein. In certain embodiments, the fusion proteins may further comprise one or more structural proteins (e.g., VP1, VP2, and VP10) from one or more isolates of Norovirus and/or Sapovirus.

In all fusions described herein, the viral regions need not be in the order in which they occur naturally. Moreover, each of the regions can be derived from the same or different Norovirus or Sapovirus isolates. The various Norovirus and Sapovirus polypeptides present in the various fusions described above can either be full-length polypeptides or portions thereof.

In certain embodiments, the portions of the Norovirus and Sapovirus polypeptides making up the fusion protein comprise at least one epitope, which is recognized by a T cell receptor on an activated T cell. Epitopes of VP1, VP2, VP10, Nterm, NTPase, p20, p22, VPg, Pro, Pol, p11, p28, p35, and p32 from Norovirus and Sapovirus isolates can be identified by several methods. For example, the individual polypeptides or fusion proteins comprising any combination of the above, can be isolated, by, e.g., immunoaffinity purification using a monoclonal antibody for the polypeptide or protein. The isolated protein sequence can then be screened by preparing a series of short peptides by proteolytic cleavage of the purified protein, which together span the entire protein sequence. By starting with, for example, 100-mer polypeptides, each polypeptide can be tested for the presence of epitopes recognized by a T-cell receptor on a Norovirus or Sapovirus-activated T cell, progressively smaller and overlapping fragments can then be tested from an identified 100-mer to map the epitope of interest.

Epitopes recognized by a T-cell receptor on a Norovirus- or Sapovirus-activated T cell can be identified by, for example, $^{51}$Cr release assay (see Example 4) or by lymphoproliferation assay (see Example 6). In a $^{51}$Cr release assay, target cells can be constructed that display the epitope of interest by cloning a polynucleotide encoding the epitope into an expression vector and transforming the expression vector into the target cells. Norovirus-specific or Sapovirus-specific CD8$^+$ T cells will lyse target cells displaying, for example, one or more epitopes from one or more Norovirus or Sapovirus polypeptides found in the fusion, and will not lyse cells that do not display such an epitope. In a lymphoproliferation assay, Norovirus-activated and/or Sapovirus-activated CD4$^+$ T cells will proliferate when cultured with, for example, one or more epitopes from one or more Norovirus and/or Sapovirus polypeptides found in the fusion, but not in the absence of a Norovirus or Sapovirus epitopic peptide.

Useful polypeptides in the fusion include T-cell epitopes derived from any of the various regions in polyproteins or structural proteins, VP1, VP2, and VP10. In this regard, Norovirus capsid proteins are known to contain human T-cell epitopes (see, e.g., Nicollier-Jamot et al. (2004) Vaccine 22:1079-1086). Including one or more T-cell epitopes (both CD4+ and CD8+) serves to increase vaccine efficacy as well as to increase protective levels against multiple Norovirus and/or Sapovirus genotypes. Moreover, multiple copies of specific, conserved T-cell epitopes can also be used in the fusions, such as a composite of epitopes from different genotypes.

For example, polypeptides from the VP1 and VP2 regions can be used in the fusions of the present invention. Immunogenic fragments of VP1 and/or VP2 which comprise epitopes may be used in the subject fusions. For example, fragments of VP1 polypeptides can comprise from about 5 to nearly the full-length of the molecule, such as 6, 10, 25, 50, 75, 100, 125, 150, 175, 200, 250, 300, 350, 400, 500 or more amino acids of a VP1 polypeptide, or any integer between the stated numbers. Similarly, fragments of VP2 polypeptides can comprise 6, 10, 25, 50, 75, 100, 150, 175, or 200 amino acids of a VP2 polypeptide, or any integer between the stated numbers.

If desired, the fusion proteins, or the individual components of these proteins, also can contain other amino acid sequences, such as amino acid linkers or signal sequences, as well as ligands useful in protein purification, such as glutathione-S-transferase and staphylococcal protein A.

B. Nucleic Acids

Nucleic acids for use in the invention, for example, in polypeptide production, VLP production, and/or nucleic acid immunization, can be derived from any of the various regions of a Norovirus or Sapovirus genome, including from any of the ORF1, ORF2, or ORF3 regions. Representative sequences from Norovirus and Sapovirus isolates are listed herein. Thus, nucleic acids for use in the invention include those derived from one or more sequences from any pathogenic Norovirus or Sapovirus genotype or isolate.

Representative sequences from Norovirus are known and are presented in FIGS. 1A-1C, 2A-2D, 14A-14B, and 15A-15B, and SEQ ID NOS:1-9 and SEQ ID NOS:13-17. Additional representative Norovirus sequences are Norwalk virus, GenBank Accession No. M87661, Snow Mountain virus, GenBank Accession No. U70059; Snow Mountain virus, GenBank Accession No. AY134748, Hawaii virus; GenBank Accession No. U07611, and sequences disclosed in the following patent publications: WO 05/030806, WO 00/79280, JP2002020399, US2003129588, U.S. Pat. No. 6,572,862, WO 94/05700, and WO 05/032457. See also Green et al. (2000) J. Infect. Dis. 181(Suppl. 2):S322-330; Wang et al. (0.1994) J. Virol. 68:5982-5990; Chen et al. (2004) J. Virol. 78: 6469-6479; Chakravarty et al. (2005) J. Virol. 79: 554-568; and Fankhauser et al. (1998) J. Infect. Dis. 178:1571-1578; for sequence comparisons of different Norovirus strains.

Representative sequences from Sapovirus are also known and are presented in SEQ ID NOS:10-12, 18, and 19. Additional representative Sapovirus sequences are Sapporo virus-London/29845, GenBank Accession No. U95645, Parkville virus, GenBank Accession No. AF294739; and Sapporo virus-Houston/86, GenBank Accession No. U95643. See also Schuffenecker et al. (2001) Arch Virol.; 146(11):2115-2132; Zintz et al. (2005) Infect. Genet. Evol. 5:281-290; Farkas et al. (2004) Arch. Virol. 149:1309-1323; for sequence comparisons of different Sapovirus strains.

Any of these sequences, as well as fragments and variants thereof that can be used in nucleic acid immunization to elicit an immune response to a Norovirus or Sapovirus will find use in the present methods. Thus, the invention includes variants of the above sequences displaying at least about 80-100% sequence identity thereto, including any percent identity within these ranges, such as 81, 82, 83, 84, 85, 86, 87, 88, 89, 90, 91, 92, 93, 94, 95, 96, 97, 98, 99, 100% sequence identity thereto. The invention also includes polynucleotides encoding immunogenic fragments of a Norovirus or Sapovirus polypeptide derived from any of the above sequences or a variant thereof. Polynucleotides can also comprise coding sequences for polypeptides which occur naturally or can be artificial sequences which do not occur in nature.

Polynucleotides may contain less than an entire Norovirus or Sapovirus genome, or alternatively can include the sequence of an entire viral genomic RNA. For example, polynucleotides may comprise one or more sequences from the ORF1, ORF2, and ORF3 regions of a Norovirus or Sapovirus genome. Polynucleotides may also comprise the entire viral genomic RNA or less than the entire viral genomic RNA from multiple genotypes and/or isolates of Norovirus or Sapovirus.

In certain embodiments, polynucleotides comprise an ORF1 sequence coding for the full-length polyprotein of a Norovirus or Sapovirus. In other embodiments, polynucleotides comprise one or more portions of the ORF1 sequence of a Norovirus or Sapovirus, for example, polynucleotides may comprise sequences coding for one or more Norovirus ORF1-encoded polypeptides, such as the N-terminal protein, NTPase, p20, VPg, protease, polymerase, VP1, and VP2, or one or more Sapovirus polypeptides, such as the N-terminal protein, p11, p28, NTPase, p32; VPg, protease, polymerase, and VP1; or fragments thereof.

For example, a polynucleotide may comprise an ORF1 nucleotide sequence selected from the group consisting of: a) a sequence comprising contiguous nucleotides 5-994 of ORF1, b) a sequence comprising contiguous nucleotides 995-2092 of ORF1, c) a sequence comprising contiguous nucleotides 2093-2629 of ORF1, d) a sequence comprising contiguous nucleotides 2630-3028 of ORF1, e) a sequence comprising contiguous nucleotides 3029-3271 of ORF1, and f) a sequence comprising contiguous nucleotides 3272-5101 of ORF1. The foregoing numbering is relative to the ORF1 nucleotide sequence of Norovirus strain MD145-12 (SEQ ID NO:13), and it is to be understood that the corresponding nucleotide positions in ORF1 sequences obtained from other genotypes and isolates of Norovirus and Sapovirus are also intended to be encompassed by the present invention.

In another example, a polynucleotide may comprise a nucleotide sequence encoding a portion of a Norovirus or Sapovirus polyprotein. In certain embodiments, the polynucleotide is selected from the group consisting of: a) a polynucleotide encoding an amino acid sequence comprising contiguous amino acids 1-330 of an ORF1-encoded polyprotein, b) a polynucleotide encoding an amino acid sequence comprising contiguous amino acids 331-696 of an ORF1-encoded polyprotein, c) a polynucleotide encoding an amino acid sequence comprising contiguous amino acids 697-875 of an ORF1-encoded polyprotein, d) a polynucleotide encoding an amino acid sequence comprising contiguous amino acids 876-1008 of an ORF1-encoded polyprotein, e) a polynucleotide encoding an amino acid sequence comprising contiguous amino acids 1009-1189 of an ORF1-encoded polyprotein, and f) a polynucleotide encoding an amino acid sequence comprising contiguous amino acids 1090-1699 of an ORF1-encoded polyprotein. The foregoing numbering is relative to the polyprotein amino acid sequence of Norovirus strain MD145-12 (SEQ ID NO:14), and it is to be understood that the corresponding amino acid positions in polyprotein sequences obtained from other genotypes and isolates of Norovirus and Sapovirus are also intended to be encompassed by the present invention.

In certain embodiments, the polynucleotides comprise sequences encoding one or more capsid proteins of a Norovirus or Sapovirus. For example, polynucleotides may comprise one or more sequences coding for structural proteins (e.g., VP1, VP2, VP10) of a Norovirus or Sapovirus. In certain embodiments, the polynucleotide is selected from the group consisting of: a) a polynucleotide comprising contiguous nucleotides 5085-6701 of a Norovirus genomic nucleic acid numbered relative to Norovirus strain MD145-12 (SEQ ID NO:13), b) a polynucleotide comprising contiguous nucleotides 6704-7507 of a Norovirus genomic nucleic acid numbered relative to Norovirus strain MD145-12 (SEQ ID NO:13), c) a polynucleotide comprising contiguous nucleotides 5174-6847 of a Sapovirus genomic nucleic acid numbered relative to Sapovirus strain Mc10 (SEQ ID NO:18), and d) a polynucleotide comprising contiguous nucleotides 6856-7350 of a Sapovirus genomic nucleic acid numbered relative to Sapovirus strain Mc10 (SEQ ID NO:18). In certain embodiments, polynucleotides comprise sequences coding for at least two capsid proteins from multiple genotypes and/or isolates of Norovirus and Sapovirus.

In certain embodiments, polynucleotides comprise one or more Norovirus ORF2 and ORF3 sequences from one or more isolates of Norovirus. In one embodiment, polynucleotides comprise an ORF2 sequence coding for the major capsid protein (VP1) of a Norovirus. In another embodiment, polynucleotides comprise an ORF3 sequence coding for the minor structural protein (VP2) of a Norovirus. In yet another embodiment, polynucleotides comprise both a sequence coding for the major capsid protein and a sequence coding for the minor structural protein of a Norovirus.

In certain embodiments, polynucleotides comprise one or more Sapovirus sequences coding for the capsid proteins of one or more isolates of Sapovirus. In certain embodiments, polynucleotides comprise one or more sequences coding for the capsid proteins of one or more isolates of Sapovirus and one or more Norovirus ORF2 and/or ORF3 sequences of one or more isolates of Norovirus.

In certain embodiments, the invention provides polynucleotides encoding a multiepitope fusion protein as described herein. Multiepitope fusion proteins can comprise sequences from one or more genotypes and/or isolates of Norovirus or Sapovirus. The polynucleotides may encode fusion antigens comprising ORF1-encoded, ORF2-encoded, and/or ORF3-encoded polypeptides or fragments thereof, including, for example, sequences of Norovirus polypeptides, such as N-terminal protein, NTPase, p20, VPg, protease, polymerase, VP1, and VP2; and/or sequences of Sapovirus polypeptides, such as N-terminal protein, p11, p28, NTPase, p32, VPg, protease, polymerase, VP1, and VP10. The sequences may be derived from multiple genotypes and/or isolates of Norovirus and Sapovirus. The polynucleotides may also encode fusion antigens comprising sequences exogenous to the Noroviruses or Sapoviruses. A polynucleotide encoding a fusion protein can be constructed from multiple oligonucleotides comprising sequences encoding fragments of the fusion protein by ligating the oligonucleotides to form a coding sequence for the full-length fusion protein using standard molecular biology techniques. See, e.g., U.S. Pat. No. 6,632,601 and U.S. Pat. No. 6,630,298.

In certain embodiments, the polynucleotide encoding the multiepitope fusion protein comprises a Norovirus ORF2 sequence coding for the major capsid protein of a Norovirus and at least one other sequence coding for a capsid protein from a different isolate of Norovirus or Sapovirus. In certain embodiments, the polynucleotide encoding the multiepitope fusion protein comprises a Norovirus ORF2 sequence coding for the major capsid protein of a Norovirus and at least one other sequence from a different region of the Norovirus genome, such as an ORF1 or ORF3 sequence from the same or a different isolate of Norovirus or Sapovirus. In certain embodiments, the polynucleotide encoding the multiepitope fusion protein comprises one or more sequences from the ORF1 region of a Norovirus or Sapovirus. For example, polynucleotides may comprise sequences coding for one or more Norovirus ORF1-encoded polypeptides, such as the N-terminal protein, NTPase, p20, VPg, protease, polymerase, VP1, and VP2, or one or more Sapovirus polypeptides, such as the N-terminal protein, p11, p28, NTPase, p32, VPg, protease, polymerase, and VP1; or fragments thereof. In certain embodiments, the polynucleotide encoding the multiepitope fusion protein comprises one or more sequences from the ORF1 region of a Norovirus or Sapovirus and one or more sequences from the ORF2 or ORF3 regions of the same or a different isolate of Norovirus or Sapovirus. Polynucleotides of the invention can also comprise other nucleotide sequences, such as sequences coding for linkers, signal sequences, or ligands useful in protein purification such as glutathione-S-transferase and staphylococcal protein A.

Nucleic acids according to the invention can be prepared in many ways (e.g. by chemical synthesis, from genomic or cDNA libraries, from the organism itself, etc.) and can take various forms (e.g. single stranded, double stranded, vectors, probes, etc.). Preferably, nucleic acids are prepared in substantially pure form (i.e. substantially free from other host cell or non host cell nucleic acids).

For example, nucleic acids can be obtained by screening cDNA and/or genomic libraries from cells infected with virus, or by deriving the gene from a vector known to include the same. For example, polynucleotides of interest can be isolated from a genomic library derived from viral RNA, present in, for example, stool or vomit samples from an infected individual. Alternatively, Norovirus or Sapovirus nucleic acids can be isolated from infected humans or other mammals or from stool or vomit samples collected from infected individuals as described in e.g., Estes et al. U.S. Pat. No. 6,942,86; Guntapong et al. (2004) Jpn J. Infect. Dis. 57:276-278; Harrington et al. (2004) J. Virol. 78:3035-3045; Fankhauser et al. (1998) J. Infect. Dis. 178:1571-1578; and Dolin et al. (1971) J. Infect. Dis. 123:307-312. Viruses can be grown in LLC-PK cells in the presence of intestinal fluid containing bile acids (Chang et al. (2004.) Proc. Natl. Acad. Sci. U.S.A. 101:8733-8738). An amplification method such as PCR can be used to amplify polynucleotides from either Norovirus or Sapovirus genomic RNA or cDNA encoding therefor. Alternatively, polynucleotides can be synthesized in the laboratory, for example, using an automatic synthesizer. The nucleotide sequence can be designed with the appropriate codons for the particular amino acid sequence desired. In general, one will select preferred codons for the intended host in which the sequence will be expressed. The complete sequence of the polynucleotide of interest can be assembled from overlapping oligonucleotides prepared by standard methods and assembled into a complete coding sequence. See, e.g., Edge (1981) Nature 292:756; Nambair et al. (1984) Science 223:1299; Jay et al. (1984) J. Biol. Chem. 259:6311; Stemmer et al. (1995) Gene 164:49-53. The polynucleotides can be RNA or single- or double-stranded DNA. Preferably, the polynucleotides are isolated free of other components, such as proteins and lipids.

Thus, particular nucleotide sequences can be obtained from vectors harboring the desired sequences or synthesized completely or in part using various oligonucleotide synthesis techniques known in the art, such as site-directed mutagenesis and polymerase chain reaction (PCR) techniques where appropriate. See, e.g., Sambrook, supra. In particular, one method of obtaining nucleotide sequences encoding the desired sequences is by annealing complementary sets of overlapping synthetic oligonucleotides produced in a conventional, automated polynucleotide synthesizer, followed by ligation with an appropriate DNA ligase and amplification of the ligated nucleotide sequence via PCR. See, e.g., Jayaraman et al. (1991) Proc. Natl. Acad. Sci. USA 88:4084-4088. Additionally, oligonucleotide directed synthesis (Jones et al. (1986) Nature 54:75-82), oligonucleotide directed mutagenesis of pre-existing nucleotide regions (Riechmann et al. (1988) Nature 332:323-327 and Verhoeyen et al. (1988) Science 239:1534-1536), and enzymatic filling-in of gapped oligonucleotides using $T_4$ DNA polymerase (Queen et al. (1989) Proc. Natl. Acad. Sci. USA 86:10029-10033) can be used to provide molecules having altered or enhanced antigen-binding capabilities, and/or reduced immunogenicity.

C. Production of Immunogenic Polypeptides

Polypeptides described herein can be prepared in any suitable manner (e.g. recombinant expression, purification from cell culture, chemical synthesis, etc.) and in various forms (e.g. native, fusions, non-glycosylated, lipidated, etc.). Such polypeptides include naturally-occurring polypeptides, recombinantly produced polypeptides, synthetically produced polypeptides, or polypeptides produced by a combination of these methods. Means for preparing such polypeptides are well understood in the art. Polypeptides are preferably prepared in substantially pure form (i.e. substantially free from other host cell or non host cell proteins).

Polypeptides can be conveniently synthesized chemically, by any of several techniques that are known to those skilled in the peptide art. In general, these methods employ the sequential addition of one or more amino acids to a growing peptide chain. Normally, either the amino or carboxyl group of the first amino acid is protected by a suitable protecting group. The protected or derivatized amino acid can then be either attached to an inert solid support or utilized in solution by adding the next amino acid in the sequence having the complementary (amino or carboxyl) group suitably protected, under conditions that allow for the formation of an amide linkage. The protecting group is then removed from the newly added amino acid residue and the next amino acid (suitably protected) is then added, and so forth. After the desired amino acids have been linked in the proper sequence, any remaining protecting groups (and any solid support, if solid phase synthesis techniques are used) are removed sequentially or concurrently, to render the final polypeptide. By simple modification of this general procedure, it is possible to add more than one amino acid at a time to a growing chain, for example, by coupling (under conditions which do not racemize chiral centers) a protected tripeptide with a properly protected dipeptide to form, after deprotection, a pentapeptide. See, e.g., J. M. Stewart and J. D. Young, *Solid Phase Peptide Synthesis* (Pierce Chemical Co., Rockford, Ill. 1984) and G. Barany and R. B. Merrifield, *The Peptides: Analysis, Synthesis, Biology*, editors E. Gross and J. Meienhofer, Vol. 2, (Academic Press, New York, 1980), pp. 3-254, for solid phase peptide synthesis techniques; and M. Bodansky, *Principles of Peptide Synthesis*, (Springer-Verlag, Berlin 1984) and E. Gross and J. Meienhofer, Eds., *The Peptides: Analysis, Synthesis, Biology, Vol.* 1, for classical solution synthesis.

Typical protecting groups include t-butyloxycarbonyl (Boc), 9-fluorenylmethoxycarbonyl (Fmoc) benzyloxycarbonyl (Cbz); p-toluenesulfonyl (Tx); 2,4-dinitrophenyl; benzyl (Bzl); biphenylisopropyloxycarboxy-carbonyl, t-amyloxycarbonyl, isobornyloxycarbonyl, o-bromobenzyloxycarbonyl, cyclohexyl, isopropyl, acetyl, o-nitrophenylsulfonyl and the like. Typical solid supports are cross-linked polymeric supports. These can include divinylbenzene cross-linked-styrene-based polymers, for example, divinylbenzene-hydroxymethylstyrene copolymers, divinylbenzene-chloromethylstyrene copolymers and divinylbenzene-benzhydrylaminopolystyrene copolymers.

The polypeptides of the present invention can also be chemically prepared by other methods such as by the method of simultaneous multiple peptide synthesis. See, e.g., Houghten *Proc. Natl. Acad. Sci. USA* (1985) 82:5131-5135; U.S. Pat. No. 4,631,211.

Alternatively, the above-described immunogenic polypeptides, polyproteins, and multiepitope fusion proteins can be produced recombinantly. Once coding sequences for the desired proteins have been isolated or synthesized, they can be cloned into any suitable vector or replicon for expression. Numerous cloning vectors are known to those of skill in the art, and the selection of an appropriate cloning vector is a matter of choice. A variety of bacterial, yeast, plant, mammalian and insect expression systems are available in the art and any such expression system can be used (e.g., see Examples 1 and 2 for construction of exemplary expression cassettes for expression in yeast and insect cells, respectively). Optionally, a polynucleotide encoding these proteins can be translated in a cell-free translation system. Such methods are well known in the art.

Examples of recombinant DNA vectors for cloning and host cells which they can transform include the bacteriophage λ (*E. coli*), pBR322 (*E. coli*), pACYC177 (*E. coli*), pKT230 (gram-negative bacteria), pGV1106 (gram-negative bacteria), pLAFR1 (gram-negative bacteria), pME290 (non-*E. coli* gram-negative bacteria), pHV14 (*E. coli* and *Bacillus subtilis*), pBD9 (*Bacillus*), 0.161 (*Streptomyces*), pUC6 (*Streptomyces*), YIp5 (*Saccharomyces*), YCp19 (*Saccharomyces*) and bovine papilloma virus (mammalian cells). See, generally, DNA Cloning: Vols. I & II, supra; Sambrook et al., supra; B. Perbal, supra.

Insect cell expression systems, such as baculovirus systems, can also be used and are known to those of skill in the art and described in, e.g., Summers and Smith, Texas Agricultural Experiment Station Bulletin No. 1555 (1987). Materials and methods for baculovirus/insect cell expression systems are commercially available in kit form from, inter alfa, Invitrogen, San Diego Calif. ("MaxBac" kit).

Plant expression systems can also be used to produce the immunogenic proteins. Generally, such systems use virus-based vectors to transfect plant cells with, heterologous genes. For a description of such systems see, e.g., Porta et al., Mol. Biotech. (1996) 5:209-221; and Hackiand et al., Arch. Virol. (1994) 139:1-22.

Viral systems, such as a vaccinia based infection/transfection system, as described in Tomei et al., J. Virol. (1993) 67:4017-4026 and Selby et al., J. Gen. Virol. (1993) 74:1103-1113, will also find use with the present invention: In this system, cells are first transfected in vitro with a vaccinia virus recombinant that encodes the bacteriophage T7 RNA polymerase. This polymerase displays exquisite specificity in that it only transcribes templates bearing T7 promoters. Following infection, cells are transfected with the DNA of interest, driven by a T7 promoter. The polymerase expressed in the cytoplasm from the vaccinia virus recombinant transcribes the transfected DNA into RNA which is then translated into protein by the host translational machinery. The method provides for high level, transient, cytoplasmic production of large quantities of RNA and its translation product(s).

The gene can be placed under the control of a promoter, ribosome binding site (for bacterial expression) and, optionally, an operator (collectively referred to herein as "control" elements), so that the DNA sequence encoding the desired immunogenic polypeptide is transcribed into RNA in the host cell transformed by a vector containing this expression construction. The coding sequence may or may not contain a signal peptide or leader sequence. With the present invention, both the naturally occurring signal peptides or heterologous sequences can be used. Leader sequences can be removed by the host in post-translational processing. See, e.g., U.S. Pat. Nos. 4,431,739; 4,425,437; 4,338,397. Such sequences include, but are not limited to, the tpa leader, as well as the honey bee mellitin signal sequence.

Other regulatory sequences may also be desirable which allow for regulation of expression of the protein sequences relative to the growth of the host cell. Such regulatory sequences are known to those of skill in the art, and examples include those which cause the expression of a gene to be turned on or off in response to a chemical or physical stimulus, including the presence of a regulatory compound. Other types of regulatory elements may also be present in the vector, for example, enhancer sequences.

The control sequences and other regulatory sequences may be ligated to the coding sequence prior to insertion into a vector. Alternatively, the coding sequence can be cloned directly into an expression vector which already contains the control sequences and an appropriate restriction site.

In some cases it may be necessary to modify the coding sequence so that it may be attached to the control sequences with the appropriate orientation; i.e., to maintain the proper reading frame. It may also be desirable to produce mutants or analogs of the immunogenic polypeptides. Mutants or analogs may be prepared by the deletion of a portion of the sequence encoding the protein, by insertion of a sequence, and/or by substitution of one or more nucleotides within the sequence. Techniques for modifying nucleotide sequences, such as site-directed mutagenesis, are well known to those skilled in the art. See, e.g., Sambrook et al., supra; DNA Cloning, Vols. I and II, supra; Nucleic Acid Hybridization, supra.

The expression vector is then used to transform an appropriate host cell. A number of mammalian cell lines are known in the art and include immortalized cell lines available from the American Type Culture Collection (ATCC), such as, but not limited to, Chinese hamster ovary (CHO) cells, HeLa cells, baby hamster kidney (BHK) cells, monkey kidney cells (COS), human hepatocellular carcinoma cells (e.g., Hep G2), as well as others. Similarly, bacterial hosts such as *E. coli, Bacillus subtilis*, and *Streptococcus* spp., will find use with the present expression constructs. Yeast hosts useful in the present invention include inter alia, *Saccharomyces cerevisiae, Candida albicans, Candida maltosa, Hansenula polymorpha, Kluyveromyces fragilis, Kluyveromyces lactis, Pichia guillerimondii, Pichia pastoris, Schizosaccharomyces pombe* and *Yarrowia lipolytica*. Insect cells for use with baculovirus expression vectors include, inter alia, *Aedes aegypti, Autographa californica, Bombyx mori, Drosophila melanogaster, Spodoptera frugiperda*, and *Trichoplusia ni*.

Depending on the expression system and host selected, the proteins of the present invention are produced by growing host cells transformed by an expression vector described above under conditions whereby the protein of interest is expressed. The selection of the appropriate growth conditions is within the skill of the art. The cells are then disrupted, using chemical, physical or mechanical means, which lyse the cells yet keep the Norovirus and/or Sapovirus immunogenic polypeptides substantially intact. Intracellular proteins can also be obtained by removing components from the cell wall or membrane, e.g., by the use of detergents or organic solvents, such that leakage of the immunogenic polypeptides occurs. Such methods are known to those of skill in the art and are described in, e.g., Protein Purification Applications: A Practical Approach, (E. L. V. Har For example, methods of disrupting cells for use with the present invention include but are not limited to: sonication or ultrasonication; agitation; liquid or solid extrusion; heat treatment; freeze-thaw; desiccation; explosive decompression; osmotic shock; treatment with lytic enzymes including proteases such as trypsin, neuraminidase and lysozyme; alkali treatment; and the use of detergents and solvents such as bile salts, sodium dodecylsulphate, Triton, NP40 and CHAPS. The particular technique used to disrupt the cells is largely a matter of choice and will depend on the cell type in which the polypeptide is expressed, culture conditions and any pretreatment used.

Following disruption of the cells, cellular debris is removed, generally by centrifugation, and the intracellularly produced Norovirus and/or Sapovirus immunogenic polypeptides are further purified, using standard purification techniques such as but not limited to, column chromatography, ion-exchange chromatography, size-exclusion chromatography, electrophoresis, HPLC, immunoabsorbent techniques, affinity chromatography, immunoprecipitation, and the like.

For example, one method for obtaining the intracellular Norovirus and/or Sapovirus immunogenic polypeptides of the present invention involves affinity purification, such as by immunoaffinity chromatography using specific antibodies. The choice of a suitable affinity resin is within the skill in the art. After affinity purification, immunogenic polypeptides can be further purified using conventional techniques well known in the art, such as by any of the techniques described above.

It may be desirable to produce multiple polypeptides simultaneously (e.g., structural and/or nonstructural proteins from one or more viral strains or viral polypeptides in combination with polypeptide adjuvants). Production of two or more different polypeptides can readily be accomplished by e.g., co-transfecting host cells with constructs encoding the different polypeptides. Co-transfection can be accomplished either in trans or cis, i.e., by using separate vectors or by using a single vector encoding the polypeptides. If a single vector is used, expression of the polypeptides can be driven by a single set of control elements or, alternatively, the sequences coding for the polypeptides can be present on the vector in individual expression cassettes, regulated by individual control elements.

The polypeptides described herein may be attached to a solid support. The solid supports which can be used in the practice of the invention include substrates such as nitrocellulose (e.g., in membrane or microtiter well form); polyvinylchloride (e.g., sheets or microtiter wells); polystyrene latex (e.g., beads or microtiter plates); polyvinylidine fluoride; diazotized paper; nylon membranes; activated beads, magnetically responsive beads, and the like.

Typically, a solid support is first reacted with a solid phase component (e.g., one or more Norovirus or Sapovirus antigens) under suitable binding conditions such that the component is sufficiently immobilized to the support. Sometimes, immobilization of the antigen to the support can be enhanced by first coupling the antigen to a protein with better binding properties. Suitable coupling proteins include, but are not limited to, macromolecules such as serum albumins including bovine serum albumin (BSA), keyhole limpet hemocyanin, immunoglobulin molecules, thyroglobulin, ovalbumin, and other proteins well known to those skilled in the art. Other molecules that can be used to bind the antigens to the support include polysaccharides, polylactic acids, polyglycolic acids, polymeric amino acids, amino acid copolymers, and the like. Such molecules and methods of coupling these molecules to the antigens, are well known to those of ordinary skill in the art. See, e.g., Brinkley, M. A., *Bioconjugate Chem.* (1992) 3:2-13; Hashida et al., *J. Appl. Biochem.* (1984) 6:56-63; and Anjaneyulu and Staros, *International J. of Peptide and Protein Res.* (1987) 30:117-124.

If desired, polypeptides may be labeled using conventional techniques. Suitable labels include fluorophores, chromophores, radioactive atoms (particularly $^{32}P$ and $^{125}I$, electron-dense reagents, enzymes, and ligands having specific binding partners. Enzymes are typically detected by their activity. For example, horseradish peroxidase is usually detected by its ability to convert 3,3',5,5'-tetramethylbenzidine (TMB) to a blue pigment, quantifiable with a spectrophotometer. "Specific binding partner" refers to a protein capable of binding a ligand molecule with high specificity, as for example in the case of an antigen and a monoclonal antibody specific therefor. Other specific binding partners include biotin and avidin or streptavidin, IgG and protein A, and the numerous receptor-ligand couples known in the art. A single label or a combination of labels may be used in the practice of the invention.

D. Nucleic Acid Immunization

Nucleic acid immunization using nucleic acids, described herein, encoding immunogenic capsid polypeptides and/or other immunogenic viral polypeptides (e.g., structural and nonstructural proteins), and/or multiepitope fusion proteins, and/or VLPs can be used to elicit an immune response in a subject, for example, to treat or prevent Norovirus and/or Sapovirus infection.

Nucleic acids described herein can be inserted into an expression vector to create an expression cassette capable of producing the viral polypeptides and/or VLPs in a suitable host cell. The ability of VP1-encoding constructs to produce VLPs can be empirically determined (e.g, see Examples 1 and 2 describing detection of VLPs by electron microscopy).

Expression cassettes typically include control elements operably linked to the coding sequence, which allow for the expression of the gene in vivo in the subject species. For example, typical promoters for mammalian cell expression include the SV40 early promoter, a CMV promoter such as the CMV immediate early promoter, the mouse mammary tumor virus LTR promoter, the adenovirus major late promoter (Ad MLP), and the herpes simplex virus promoter, among others. Other nonviral promoters, such as a promoter derived from the murine metallothionein gene, will also find use for mammalian expression. Typically, transcription termination and polyadenylation sequences will also be present, located 3' to the translation stop codon. Preferably, a sequence for optimization of initiation of translation, located 5' to the coding sequence, is also present. Examples of transcription terminator/polyadenylation signals include those derived from SV40, as described in Sambrook et al., supra, as well as a bovine growth hormone terminator sequence.

Enhancer elements may also be used herein to increase expression levels of the mammalian constructs. Examples include the SV40 early gene enhancer, as described in Dijkema et al., EMPO J. (1985) 4:761, the enhancer/promoter derived from the long terminal repeat (LTR) of the Rous Sarcoma Virus, as described in Gorman et al., Proc. Natl. Acad. Sci. USA (1982b) 79:6777 and elements derived from human CMV, as described in Boshart et al., Cell (1985) 41:521, such as elements included in the CMV intron A sequence.

In addition, vectors can be constructed that include sequences coding for adjuvants. Particularly suitable are detoxified mutants of bacterial ADP-ribosylating toxins, for example, diphtheria toxin, pertussis toxin (PT), cholera toxin (CT), *E. coli* heat-labile toxins (LT1 and LT2), *Pseudomonas* endotoxin A, *C. botulinum* C2 and C3 toxins, as well as toxins from *C. perfringens, C. spiriforma* and *C. dfficile*. In a preferred embodiment, vectors include coding sequences for detoxified mutants of *E. coli* heat-labile toxins, such as the LT-K63 and LT-R72 detoxified mutants, described in U.S. Pat. No. 6,818,222, herein incorporated by reference in its entirety. One or more adjuvant polypeptides may be coexpressed with Norovirus and/or Sapovirus polypeptides. In certain embodiments, adjuvant and viral polypeptides may be coexpressed in the form of a fusion protein comprising one or more adjuvant polypeptides and one or more viral polypeptides. Alternatively, adjuvant and viral polypeptides may be coexpressed as separate proteins.

Furthermore, vectors can be constructed that include chimeric antigen-coding gene sequences, encoding, e.g., multiple antigens/epitopes of interest, for example derived from a single or from more than one viral isolate. In certain embodiments, adjuvant or antigen coding sequences precede or follow viral capsid coding sequences, and the chimeric transcription unit has a single open reading frame encoding the adjuvant and/or antigen of interest and the capsid polypeptide. Alternatively, multi-cistronic cassettes (e.g., bi-cistronic cassettes) can be constructed allowing expression of multiple adjuvants and/or antigens from a single mRNA using the EMCV IRES, or the like. Lastly, adjuvants and/or antigens can be encoded on separate transcripts from independent promoters on a single plasmid or other vector.

Once complete, the constructs are used for nucleic acid immunization or the like using standard gene delivery protocols. Methods for gene delivery are known in the art. See, e.g., U.S. Pat. Nos. 5,399,346, 5,580,859, 5,589,466. Genes can be delivered either directly to the vertebrate subject or, alternatively, delivered ex vivo, to cells derived from the subject and the cells reimplanted in the subject.

A number of viral based systems have been developed for gene transfer into mammalian cells. For example, retroviruses provide a convenient platform for gene delivery systems. Selected sequences can be inserted into a vector and packaged in retroviral particles using techniques known in the art. The recombinant virus can then be isolated and delivered to cells of the subject either in vivo or ex vivo. A number of retroviral systems have been described (U.S. Pat. No. 5,219,740; Miller and Rosman, BioTechniques (1989) 7:980-990; Miller, A. D., Human Gene Therapy (1990) 1:5-14; Scarpa et al., Virology (1991) 180:849-852; Burns et al., Proc. Natl. Acad. Sci. USA (1993) 90:8033-8037; and Boris-Lawrie and Temin, Cur. Opin. Genet. Develop. (1993) 3:102-109).

A number of adenovirus vectors have also been described. Unlike retroviruses which integrate into the host genome, adenoviruses persist extrachromosomally thus minimizing the risks associated with insertional mutagenesis (Haj-Ahmad and Graham, J. Virol. (1986) 57:267-274; Bett et al., J. Virol. (1993) 67:5911-5921; Mittereder et al., Human Gene Therapy (1994) 5:717-729; Seth et al., J. Virol. (1994) 68:933-940; Barr et al., Gene Therapy (1994) 1:51-58; Berkner, K. L. BioTechniques (1988) 6:616-629; and Rich et al., Human Gene Therapy (1993) 4:461-476). Additionally, various adeno-associated virus (AAV) vector systems have been developed for gene delivery. AAV vectors can be readily constructed using techniques well known in the art. See, e.g., U.S. Pat. Nos. 5,173,414 and 5,139,941; International Publication Nos. WO 92/01070 (published 23 Jan. 1992) and WO 93/03769 (published 4 Mar. 1993); Lebkowski et al., Molec. Cell. Biol. (1988) 8:3988-3996; Vincent et al., Vaccines 90 (1990) (Cold Spring Harbor Laboratory Press); Carter, B. J. Current Opinion in Biotechnology (1992) 3:533-539; Muzyczka, N. Current Topics in Microbiol. and Immunol. (1992) 158:97-129; Kotin, R. M. Human Gene Therapy (1994) 5:793-801; Shelling and Smith, Gene Therapy (1994) 1:165-169; and Zhou et al., J. Exp. Med. (1994) 179:1867-1875.

Another vector system useful for delivering the polynucleotides of the present invention is the enterically administered recombinant poxvirus vaccines described by Small, Jr., P. A., et al. (U.S. Pat. No. 5,676,950, issued Oct. 14, 1997, herein incorporated by reference).

Additional viral vectors which will find use for delivering the nucleic acid molecules encoding the antigens of interest include those derived from the pox family of viruses, including vaccinia virus and avian poxvirus. By way of example, vaccinia virus recombinants expressing the Norovirus and/or Sapovirus antigens can be constructed as follows. The DNA encoding the particular Norovirus or Sapovirus antigen coding sequence is first inserted into an appropriate vector so that it is adjacent to a vaccinia promoter and flanking vaccinia DNA sequences, such as the sequence encoding thymidine kinase (TK). This vector is then used to transfect cells which are simultaneously infected with vaccinia. Homologous recombination serves to insert the vaccinia promoter plus the gene encoding the coding sequences of interest into the viral genome. The resulting TK-recombinant can be selected by culturing the cells in the presence of 5-bromodeoxyuridine and picking viral plaques resistant thereto.

Alternatively, avipoxviruses, such as the fowlpox and canarypox viruses, can also be used to deliver the genes. Recombinant avipox viruses, expressing immunogens from mammalian pathogens, are known to confer protective immunity when administered to non-avian species. The use of an avipox vector is particularly desirable in human and other mammalian species since members of the avipox genus can only productively replicate in susceptible avian species and therefore are not infective in mammalian cells. Methods for producing recombinant avipoxviruses are known in the art and employ genetic recombination, as described above with respect to the production of vaccinia viruses. See, e.g., WO 91/12882; WO 89/03429; and WO 92/03545.

Molecular conjugate vectors, such as the adenovirus chimeric vectors described in Michael et al., J. Biol. Chem. (1993) 268:6866-6869 and Wagner et al., Proc. Natl. Acad. Sci. USA (1992) 89:6099-6103, can also be used for gene delivery.

Members of the Alphavirus genus, such as, but not limited to, vectors derived from the Sindbis virus (SIN), Semliki Forest virus (SFV), and Venezuelan Equine Encephalitis virus (VEE), will also find use as viral vectors for delivering the polynucleotides of the present invention. For a description of Sindbis-virus derived vectors useful for the practice of the instant methods, see, Dubensky et al. (1996) J. Virol. 70:508-519; and International Publication Nos. WO 95/07995, WO 96/17072; as well as, Dubensky, Jr., T. W., et al., U.S. Pat. No. 5,843,723, issued Dec. 1, 1998, and Dubensky, Jr., T. W., U.S. Pat. No. 5,789,245, issued Aug. 4, 1998, both herein incorporated by reference. Particularly preferred are chimeric alphavirus vectors comprised of sequences derived from Sindbis virus and Venezuelan equine encephalitis virus. See, e.g., Perri et al. (2003) J. Virol. 77: 10394-10403 and International Publication Nos. WO 02/099035, WO 02/080982, WO 01/81609, and WO 00/61772; herein incorporated by reference in their entireties.

A vaccinia based infection/transfection system can be conveniently used to provide for inducible, transient expression of the coding sequences of interest (for example, a VP1/VP2 expression cassette) in a host cell. In this system, cells are first infected in vitro with a vaccinia virus recombinant that encodes the bacteriophage T7 RNA polymerase. This polymerase displays exquisite specificity in that it only transcribes templates bearing T7 promoters. Following infection, cells are transfected with the polynucleotide of interest, driven by a T7 promoter. The polymerase expressed in the cytoplasm from the vaccinia virus recombinant transcribes the transfected DNA into RNA which is then translated into protein by the host translational machinery. The method provides for high level, transient, cytoplasmic production of large quantities of RNA and its translation products. See, e.g., Elroy-Stein and Moss, Proc. Natl. Acad. Sci. USA (1990) 87:6743-6747; Fuerst et al., Proc. Natl. Acad. Sci. USA (1986) 83:8122-8126.

As an alternative approach to infection with vaccinia or avipox virus recombinants, or to the delivery of genes using other viral vectors, an amplification system can be used that will lead to high level expression following introduction into host cells. Specifically, a T7 RNA polymerase promoter preceding the coding region for T7 RNA polymerase can be engineered. Translation of RNA derived from this template will generate T7 RNA polymerase which in turn will transcribe more template. Concomitantly, there will be a cDNA whose expression is under the control of the T7 promoter. Thus, some of the T7 RNA polymerase generated from translation of the amplification template RNA will lead to transcription of the desired gene. Because some T7 RNA polymerase is required to initiate the amplification, T7 RNA polymerase can be introduced into cells along with the template(s) to prime the transcription reaction. The polymerase can be introduced as a protein or on a plasmid encoding the RNA polymerase. For a further discussion of T7 systems and their use for transforming cells, see, e.g., International Publication No. WO 94/26911; Studier and Moffatt, J. Mol. Biol. (1986) 189:113-130; Deng and Wolff, Gene (1994) 143:245-249; Gao et al., Biochem. Biophys. Res. Commun. (1994) 200:1201-1206; Gao and Huang, Nuc. Acids Res. (1993) 21:2867-2872; Chen et al., Nuc. Acids Res. (1994) 22:2114-2120; and U.S. Pat. No. 5,135,855.

The synthetic expression cassette of interest can also be delivered without a viral vector. For example, the synthetic expression cassette can be packaged as DNA or RNA in liposomes prior to delivery to the subject or to cells derived therefrom. Lipid encapsulation is generally accomplished using liposomes which are able to stably bind or entrap and retain nucleic acid. The ratio of condensed DNA to lipid preparation can vary but will generally be around 1:1 (mg DNA:micromoles lipid), or more of lipid. For a review of the use of liposomes as carriers for delivery of nucleic acids, see, Hug and Sleight, Biochim. Biophys. Acta. (1991) 1097:1-17; Straubinger et al., in Methods of Enzymology (1983), Vol. 101, pp. 512-527.

Liposomal preparations for use in the present invention include cationic (positively charged), anionic (negatively charged) and neutral preparations, with cationic liposomes particularly preferred. Cationic liposomes have been shown to mediate intracellular delivery of plasmid DNA (Feigner et al., Proc. Natl. Acad. Sci. USA (1987) 84:7413-7416); mRNA (Malone et al., Proc. Natl. Acad. Sci. USA (1989) 86:6077-6081); and purified transcription factors (Debs et al., J. Biol. Chem. (1990) 265:10189-10192), in functional form.

Cationic liposomes are readily available. For example, N[1-2,3-dioleyloxy)propyl]-N,N,N-triethylammonium (DOTMA) liposomes are available under the trademark Lipofectin, from GIBCO BRL, Grand Island, N.Y. (See, also, Feigner et al., Proc. Natl. Acad. Sci. USA (1987) 84:7413-7416). Other commercially available lipids include (DDAB/DOPE) and DOTAP/DOPE (Boerhinger). Other cationic liposomes can be prepared from readily available materials using techniques well known in the art. See, e.g., Szoka et al., Proc. Natl. Acad. Sci. USA (1978) 75:4194-4198; PCT Publication No. WO 90/11092 for a description of the synthesis of DOTAP (1,2-bis(oleoyloxy)-3-(trimethylammonio)propane) liposomes.

Similarly, anionic and neutral liposomes are readily available, such as, from Avanti Polar Lipids (Birmingham, Ala.), or can be easily prepared using readily available materials. Such materials include phosphatidyl choline, cholesterol, phosphatidyl ethanolamine, dioleoylphosphatidyl choline (DOPC), dioleoylphosphatidyl glycerol (DOPG), dioleoylphoshatidyl ethanolamine (DOPE), among others. These materials can also be mixed with the DOTMA and DOTAP starting materials in appropriate ratios. Methods for making liposomes using these materials are well known in the art.

The liposomes can comprise multilammelar vesicles (MLVs), small unilamellar vesicles (SUVs), or large unilamellar vesicles (LUVs). The various liposome-nucleic acid complexes are prepared using methods known in the art. See, e.g., Straubinger et al., in METHODS OF IMMUNOLOGY (1983), Vol. 101, pp. 512-527; Szoka et al., Proc. Natl. Acad. Sci. USA (1978) 75:4194-4198; Papahadjopoulos et al., Biochim. Biophys. Acta (1975) 394:483; Wilson et al., Cell (1979) 17:77); Deamer and Bangham, Biochim Biophys. Acta (1976) 443:629; Ostro et al., Biochem. Biophys. Res. Commun. (1977) 76:836; Fraley et al., Proc. Natl. Acad. Sci. USA (1979) 76:3348); Enoch and Strittmatter, Proc. Natl. Acad. Sci. USA (1979) 76:145); Fraley et al., J. Biol. Chem. (1980) 255:10431; Szoka and Papahadjopoulos, Proc. Natl. Acad. Sci. USA (1978) 75:145; and Schaefer-Ridder et al., Science (1982) 215:166.

The DNA and/or protein antigen(s) can also be delivered in cochleate lipid compositions similar to those described by Papahadjopoulos et al., Biochem. Biophys. Acta. (1975) 394:483-491. See, also, U.S. Pat. Nos. 4,663,161 and 4,871,488.

The expression cassette of interest may also be encapsulated, adsorbed to, or associated with, particulate carriers. Such carriers present multiple copies of a selected antigen to the immune system and promote migration, trapping and retention of antigens in local lymph nodes. The particles can be taken up by profession antigen presenting cells such as macrophages and dendritic cells, and/or can enhance antigen presentation through other mechanisms such as stimulation of cytokine release. Examples of particulate carriers include those derived from polymethyl methacrylate polymers, as well as microparticles derived from poly(lactides) and poly (lactide-co-glycolides), known as PLG. See, e.g., Jeffery et al., Pharm. Res. (1993) 10:362-368; McGee J. P., et al., J. Microencapsul. 14(2):197-210, 1997; O'Hagan D. T., et al., Vaccine 11(2):149-54, 1993.

Furthermore, other particulate systems and polymers can be used for the in vivo or ex vivo delivery of the gene of interest. For example, polymers such as polylysine, polyarginine, polyornithine, spermine, spermidine, as well as conjugates of these molecules, are useful for transferring a nucleic acid of interest. Similarly, DEAE dextran-mediated transfection, calcium phosphate precipitation or precipitation using other insoluble inorganic salts, such as strontium phosphate, aluminum silicates including bentonite and kaolin, chromic oxide, magnesium silicate, talc, and the like, will find use with the present methods. See, e.g., Feigner, P. L., Advanced Drug Delivery Reviews (1990) 5:163-187, for a review of delivery systems useful for gene transfer. Peptoids (Zuckerman, R. N., et al., U.S. Pat. No. 5,831,005, issued Nov. 3, 1998, herein incorporated by reference) may also be used for delivery of a construct of the present invention.

Additionally, biolistic delivery systems employing particulate carriers such as gold and tungsten, are especially useful for delivering synthetic expression cassettes of the present invention. The particles are coated with the synthetic expression cassette(s) to be delivered and accelerated to high velocity, generally under a reduced atmosphere, using a gun powder discharge from a "gene gun." For a description of such techniques, and apparatuses useful therefore, see, e.g., U.S. Pat. Nos. 4,945,050; 5,036,006; 5,100,792; 5,179,022; 5,371,015; and 5,478,744. Also, needle-less injection systems can be used (Davis, H. L., et al, Vaccine 12:1503-1509, 1994; Bioject, Inc., Portland, Oreg.).

Recombinant vectors carrying a synthetic expression cassette of the present invention are formulated into compositions for delivery to a vertebrate subject. These compositions may either be prophylactic (to prevent infection) or therapeutic (to treat disease after infection). The compositions will comprise a "therapeutically effective amount" of the gene of interest such that an amount of the antigen can be produced in vivo so that an immune response is generated in the individual to which it is administered. The exact amount necessary will vary depending on the subject being treated; the age and general condition of the subject to be treated; the capacity of the subject's immune system to synthesize antibodies; the degree of protection desired; the severity of the condition being treated; the particular antigen selected and its mode of administration, among other factors. An appropriate effective amount can be readily determined by one of skill in the art. Thus, a "therapeutically effective amount" will fall in a relatively broad range that can be determined through routine trials.

The compositions will generally include one or more "pharmaceutically acceptable excipients or vehicles" such as water, saline, glycerol, polyethyleneglycol, hyaluronic acid, ethanol, etc. Additionally, auxiliary substances, such as wetting or emulsifying agents, pH buffering substances, surfactants and the like, may be present in such vehicles. Certain facilitators of immunogenicity or of nucleic acid uptake and/or expression can also be included in the compositions or coadministered, such as, but not limited to, bupivacaine, cardiotoxin and sucrose.

Once formulated, the compositions of the invention can be administered directly to the subject (e.g., as described above) or, alternatively, delivered ex vivo, to cells derived from the subject, using methods such as those described above. For example, methods for the ex vivo delivery and reimplantation of transformed cells into a subject are known in the art and can include, e.g., dextran-mediated transfection, calcium phosphate precipitation, polybrene mediated transfection, lipofectamine and LT-1 mediated transfection, protoplast fusion, electroporation, encapsulation of the polynucleotide(s) (with or without the corresponding antigen) in liposomes, and direct microinjection of the DNA into nuclei.

Direct delivery of synthetic expression cassette compositions in vivo will generally be accomplished with or without viral vectors, as described above, by injection using either a conventional syringe, needless devices such as Bioject™ or a gene gun, such as the Accell™ gene delivery system (PowderMed Ltd, Oxford, England). The constructs can be delivered (e.g., injected) either subcutaneously, epidermally, intradermally, intramuscularly, intravenously, intramucosally (such as nasally, rectally and vaginally), intraperitoneally or orally. Delivery of DNA into cells of the epidermis is particularly preferred as this mode of administration provides access to skin-associated lymphoid cells and provides for a transient presence of DNA in the recipient. Other modes of administration include oral ingestion and pulmonary administration, suppositories, needle-less injection, transcutaneous, topical, and transdermal applications. Dosage treatment may be a single dose schedule or a multiple dose schedule.

Ex Vivo Delivery

In one embodiment, T cells, and related cell types (including but not limited to antigen presenting cells, such as, macrophage, monocytes, lymphoid cells, dendritic cells, B-cells, T-cells, stem cells, and progenitor cells thereof), can be used for ex vivo delivery of expression cassettes of the present invention. T cells can be isolated from peripheral blood lymphocytes (PBLs) by a variety of procedures known to those skilled in the art. For example, T cell populations can be "enriched" from a population of PBLs through the removal of accessory and B cells. In particular, T cell enrichment can be accomplished by the elimination of non-T cells using anti-MHC class II monoclonal antibodies. Similarly, other antibodies can be used to deplete specific populations of non-T cells. For example, anti-Ig antibody molecules can be used to deplete B cells and anti-MacI antibody molecules can be used to deplete macrophages.

T cells can be further fractionated into a number of different subpopulations by techniques known to those skilled in the art. Two major subpopulations can be isolated based on their differential expression of the cell surface markers CD4 and CD8. For example, following the enrichment of T cells as described above, CD4$^+$ cells can be enriched using antibodies specific for CD4 (see Coligan et al., supra). The antibodies may be coupled to a solid support such as magnetic beads. Conversely, CD8+ cells can be enriched through the use of antibodies specific for CD4 (to remove CD4$^+$ cells), or can be isolated by the use of CD8 antibodies coupled to a solid support. CD4 lymphocytes from Norovirus or Sapovirus infected patients can be expanded ex vivo, before or after transduction as described by Wilson et. al. (1995) J. Infect. Dis. 172:88.

Following purification of T cells, a variety of methods of genetic modification known to those skilled in the art can be performed using non-viral or viral-based gene transfer vectors constructed as described herein. For example, one such approach involves transduction of the purified T cell population with vector-containing supernatant of cultures derived from vector producing cells. A second approach involves co-cultivation of an irradiated monolayer of vector-producing cells with the purified T cells. A third approach involves a similar co-cultivation approach; however, the purified T cells are pre-stimulated with various cytokines and cultured 48 hours prior to the co-cultivation with the irradiated vector producing cells. Pre-stimulation prior to such transduction increases effective gene transfer (Nolta et al. (1992) Exp. Hematol. 20:1065). Stimulation of these cultures to proliferate also provides increased cell populations for re-infusion into the patient. Subsequent to co-cultivation, T cells are collected from the vector producing cell monolayer, expanded, and frozen in liquid nitrogen.

Gene transfer vectors, containing one or more expression cassettes of the present invention (associated with appropriate control elements for delivery to the isolated T cells) can be assembled using known methods.

Selectable markers can also be used in the construction of gene transfer vectors. For example, a marker can be used which imparts to a mammalian cell transduced with the gene transfer vector resistance to a cytotoxic agent. The cytotoxic agent can be, but is not limited to, neomycin, aminoglycoside, tetracycline, chloramphenicol, sulfonamide, actinomycin, netropsin, distamycin A, anthracycline, or pyrazinamide. For example, neomycin phosphotransferase II imparts resistance to the neomycin analogue geneticin (G418).

The T cells can also be maintained in a medium containing at least one type of growth factor prior to being selected. A variety of growth factors are known in the art which sustain the growth of a particular cell type. Examples of such growth factors are cytokine mitogens such as rIL-2, IL-10, IL-12, and IL-15, which promote growth and activation of lymphocytes. Certain types of cells are stimulated by other growth factors such as hormones, including human chorionic gonadotropin (hCG) and human growth hormone. The selection of an appropriate growth factor for a particular cell population is readily accomplished by one of skill in the art.

For example, white blood cells such as differentiated progenitor and stem cells are stimulated by a variety of growth factors. More particularly, IL-3, IL-4, IL-5, IL-6, IL-9, GM-CSF, M-CSF, and G-CSF, produced by activated $T_H$ and activated macrophages, stimulate myeloid stem cells, which then differentiate into pluripotent stem cells, granulocyte-monocyte progenitors, eosinophil progenitors, basophil progenitors, megakaryocytes, and erythroid progenitors. Differentiation is modulated by growth factors such as GM-CSF, IL-3, IL-6, IL-11, and EPO.

Pluripotent stem cells then differentiate into lymphoid stem cells, bone marrow stromal cells, T cell progenitors, B cell progenitors, thymocytes, $T_H$ cells, $T_c$ cells, and B cells. This differentiation is modulated by growth factors such as IL-3, IL-4, IL-6, IL-7, GM-CSF, M-CSF, G-CSF, IL-2, and IL-5.

Granulocyte-monocyte progenitors differentiate to monocytes, macrophages, and neutrophils. Such differentiation is modulated by the growth factors GM-CSF, M-CSF, and IL-8. Eosinophil progenitors differentiate into eosinophils. This process is modulated by GM-CSF and IL-5.

The differentiation of basophil progenitors into mast cells and basophils is modulated by GM-CSF, IL-4, and IL-9. Megakaryocytes produce platelets in response to GM-CSF, EPO, and IL-6. Erythroid progenitor cells differentiate into red blood cells in response to EPO.

Thus, during activation by the CD3-binding agent, T cells can also be contacted with a mitogen, for example a cytokine such as IL-2. In particularly preferred embodiments, IL-2 is added to the population of T cells at a concentration of about 50 to 100 µg/ml. Activation with the CD3-binding agent can be carried out for 2 to 4 days.

Once suitably activated, the T cells are genetically modified by contacting the same with a suitable gene transfer vector under conditions that allow for transfection of the vectors into the T cells. Genetic modification is carried out when the cell density of the T cell population is between about $0.1 \times 10^6$ and $5 \times 10^6$, preferably between about $0.5 \times 10^6$ and $2 \times 10^6$. A number of suitable viral and nonviral-based gene transfer vectors have been described for use herein.

After transduction, transduced cells are selected away from non-transduced cells using known techniques. For example, if the gene transfer vector used in the transduction includes a selectable marker which confers resistance to a cytotoxic agent, the cells can be contacted with the appropriate cytotoxic agent, whereby non-transduced cells can be negatively selected away from the transduced cells. If the selectable marker is a cell surface marker, the cells can be contacted with a binding agent specific for the particular cell surface marker, whereby the transduced cells can be positively selected away from the population. The selection step can also entail fluorescence-activated cell sorting (FACS) techniques, such as where FACS is used to select cells from the population containing a particular surface marker, or the selection step can entail the use of magnetically responsive particles as retrievable supports for target cell capture and/or background removal.

More particularly, positive selection of the transduced cells can be performed using a FACS cell sorter (e.g. a FACSVantage™ Cell Sorter, Becton Dickinson Immunocytometry Systems, San Jose, Calif.) to sort and collect transduced cells expressing a selectable cell surface marker. Following transduction, the cells are stained with fluorescent-labeled antibody molecules directed against the particular cell surface marker. The amount of bound antibody on each cell can be measured by passing droplets containing the cells through the cell sorter. By imparting an electromagnetic charge to droplets containing the stained cells, the transduced cells can be separated from other cells. The positively selected cells are then harvested in sterile collection vessels. These cell sorting procedures are described in detail, for example, in the FACSVantage™ Training Manual, with particular reference to sections 3-11 to 3-28 and 10-1 to 10-17.

Positive selection of the transduced cells can also be performed using magnetic separation of cells based on expression or a particular cell surface marker. In such separation techniques, cells to be positively selected are first contacted with specific binding agent (e.g., an antibody or reagent the interacts specifically with the cell surface marker). The cells are then contacted with retrievable particles (e.g., magnetically responsive particles) which are coupled with a reagent that binds the specific binding agent (that has bound to the positive cells). The cell-binding agent-particle complex can then be physically separated from non-labeled cells, for example using a magnetic field. When using magnetically responsive particles, the labeled cells can be retained in a container using a magnetic filed while the negative cells are removed. These and similar separation procedures are known to those of ordinary skill in the art.

Expression of the vector in the selected transduced cells can be assessed by a number of assays known to those skilled in the art. For example, Western blot or Northern analysis can be employed depending on the nature of the inserted nucleotide sequence of interest. Once expression has been established and the transformed T cells have been tested for the presence of the selected synthetic expression cassette, they are ready for infusion into a patient via the peripheral blood stream. The invention includes a kit for genetic modification of an ex vivo population of primary mammalian cells. The kit typically contains a gene transfer vector coding for at least one selectable marker and at least one synthetic expression cassette contained in one or more containers, ancillary reagents or hardware, and instructions for use of the kit.

E. Production of Viral-Like Particles

The capsid proteins of Noroviruses and Sapoviruses self-assemble into noninfectious virus-like particles (VLP) when expressed in various eucaryotic cells (Taube et al. (2005) Arch Virol. 150:1425-1431; Ball et al. (1998) J. Virol. 72:1345-1353; Green et al. (1997) J. Clin. Microbiol. 35:1909-1914; Huang et al. (2005) Vaccine 23:1851-1858; Hansman et al. (2005) Arch. Virol. 150:21-36; herein incorporated by reference in their entireties). VLPs spontaneously form when a particle-forming polypeptide of interest, for example, a Norovirus or Sapovirus VP1 polypeptide or a variant or fragment thereof capable of producing VLPs, is recombinantly expressed in an appropriate host cell.

Expression vectors comprising Norovirus and/or Sapovirus capsid coding sequences are conveniently prepared using recombinant techniques. As discussed below, VP1 polypeptide-encoding expression vectors of the present invention can include other polypeptide coding sequences of interest, for example, ORF1-encoded nonstructural proteins (e.g., Norovirus Nterm, NTPase, p20, p22, VPg, Pro, and Pol; and Sapovirus p11, p28, NTPase, p32, VPg, Pro, and Pol) and minor structural proteins, such as Norovirus VP2 and Sapovirus VP10. Such expression vectors can produce VLPs comprising VP1, as well as, any additional polypeptide of interest.

In certain embodiments, expression vectors may encode one or more structural proteins from one or more genotypes and/or isolates of Norovirus and Sapovirus. For example, expression vectors capable of producing VLPs can comprise one or more VP1 capsid proteins from one or more isolates and/or genotypes of Norovirus and Sapovirus. In addition, expression vectors may further comprise coding sequences for one or more minor structural proteins (e.g., VP2, VP10) from one or more isolates and/or genotypes of Norovirus and Sapovirus.

Once coding sequences for the desired particle-forming polypeptides have been isolated or synthesized, they can be cloned into any suitable vector or replicon for expression. Numerous cloning vectors are known to those of skill in the art, and the selection of an appropriate cloning vector is a matter of choice. See, generally, Ausubel et al, supra or Sambrook et al, supra. The vector is then used to transform an appropriate host cell. Suitable recombinant expression systems include, but are not limited to, bacterial, baculovirus/insect, vaccinia, Semliki Forest virus (SFV), Alphaviruses (such as, Sindbis, Venezuelan Equine Encephalitis (VEE)), mammalian, yeast, plant, and *Xenopus* expression systems, well known in the art. Particularly preferred expression systems are mammalian cell lines, vaccinia, Sindbis, insect and yeast systems.

For example, a number of mammalian cell lines are known in the art and include immortalized cell lines available from the American Type Culture Collection (A.T.C.C.), such as, but not limited to, Chinese hamster ovary (CHO) cells, 293 cells, HeLa cells, baby hamster kidney (BHK) cells, mouse myeloma (SB20), monkey kidney cells (COS), as well as others. Similarly, bacterial hosts such as *E. coli, Bacillus subtilis,* and *Streptococcus* spp., will find use with the present expression constructs. Yeast hosts useful in the present invention include inter alia, *Saccharomyces cerevisiae, Candida albicans, Candida maltosa, Hansenula polymorpha, Kluyveromyces fragilis, Kluyveromyces lactis, Pichia guilerimondii, Pichia pastoris, Schizosaccharomyces pombe* and *Yarrowia lipolytica.* See, e.g., Shuster et al. U.S. Pat. No. 6,183,985, herein incorporated by reference in its entirety. See also Example 1, which describes the expression of Norwalk virus VP1 and VP2 structural proteins and production of viral particles in *Saccharomyces cerevisiae*. Insect cells for use with baculovirus expression vectors include, inter alia, *Aedes aegypti, Autographa californica, Bombyx mori, Drosophila melanogaster, Spodoptera frugiperda,* and *Trichoplusia ni.* See, e.g., Summers and Smith, Texas Agricultural Experiment Station Bulletin No. 1555 (1987). See also Example 2, which describes the expression of Norwalk virus VP1 and VP2 structural proteins and production of viral particles in SF9 cells. Fungal hosts include, for example, *Aspergillus.* Plant hosts include tobacco, soybean, potato leaf and tuber tissues, and tomato fruit. See, e.g., Huang et al. (2005) Vaccine 23:1851-1858.

Viral vectors can be used for the production of particles in eucaryotic cells, such as those derived from the pox family of viruses, including vaccinia virus and avian poxvirus. Additionally, a vaccinia based infection/transfection system, as described in Tomei et al., J. Virol. (1993) 67:4017-4026 and Selby et al., J. Gen. Virol. (1993) 74:1103-1113, will also find use with the present invention. In this system, cells are first infected in vitro with a vaccinia virus recombinant that encodes the bacteriophage T7 RNA polymerase. This polymerase displays exquisite specificity in that it only transcribes templates bearing T7 promoters. Following infection, cells are transfected with the DNA of interest, driven by a T7 promoter. The polymerase expressed in the cytoplasm from the vaccinia virus recombinant transcribes the transfected DNA into RNA which is then translated into protein by the host translational machinery. Alternately, T7 can be added as a purified protein or enzyme as in the "Progenitor" system (Studier and Moffatt, J. Mol. Biol. (1986) 189:113-130). The method provides for high level, transient, cytoplasmic production of large quantities of RNA and its translation product(s).

Depending on the expression system and host selected, the VLPs are produced by growing host cells transformed by an expression vector under conditions whereby the particle-forming polypeptide is expressed and VLPs can be formed. The selection of the appropriate growth conditions is within the skill of the art.

If the VLPs are formed intracellularly, the cells are then disrupted, using chemical, physical or mechanical means, which lyse the cells yet keep the VLPs substantially intact. Such methods are known to those of skill in the art and are described in, e.g., Protein Purification Applications: A Practical Approach, (E. L. V. Harris and S. Angal, Eds., 1990).

The particles are then isolated (or substantially purified) using methods that preserve the integrity thereof, such as, by density gradient centrifugation, e.g., sucrose gradients, PEG-precipitation, pelleting, and the like (see, e.g., Kirnbauer et al. J. Virol. (1993) 67:6929-6936), as well as standard purification techniques including, e.g., ion exchange and gel filtration chromatography.

In a further aspect, the present invention provides vectors and hosts cells for production of mosaic VLPs comprising antigens from more than one viral strain. Mosaic VLPs comprising capsid proteins from at least two types of viruses, are produced by coexpressing capsid proteins from at least two different genotypes and/or isolates of Norovirus and/or Sapovirus in the same host cell. Coding sequences for capsid polypeptides derived from at least two different genotypes and/or isolates of Norovirus and/or Sapovirus can be cloned into one or more expression vectors and coexpressed in cis or trans. In addition, expression vectors may further comprise coding sequences for one or more minor structural proteins or nonstructural proteins from one or more isolates and/or genotypes of Norovirus and/or Sapovirus.

Mosaic VLPs may comprise one or more VP1 polypeptides from multiple strains of Norovirus (e.g., NV, SMV, and HV) or one or more VP1 polypeptides from multiple strains of Sapovirus (e.g., Sapporo, London/29845, Parkville, Houston/90). Alternatively, mosaic VLPs may comprise a combination of Norovirus and Sapovirus capsid proteins, such mosaic VLPs comprising one or more VP1 polypeptides from one or more strains of Norovirus and one or more VP1 polypeptides from one or more strains of Sapovirus.

Mosaic VLPs can be produced by coexpression of multiple capsid proteins using any suitable recombinant expression system, such as those described above for expression of capsid proteins and production of VLPs. In a preferred embodiment, capsid polypeptides can be expressed in an *S. cerevisiae* diploid strain produced by mating two haploid strains, each expressing different capsid proteins. See, e.g., International Patent Publication WO 00/09699, herein incorporated by reference in its entirety, which describes the production of mosaic VLPs in yeast by expression of multiple capsid polypeptides using the episomal expression vector pBS24.1 comprising an ADH2/GAPD glucose-repressible hybrid promoter.

VLPs of the present invention, including those comprising capsid proteins from a single viral strain and mosaic VLPs, can be used to elicit an immune response when administered to a subject. As discussed above, the VLPs can comprise a variety of antigens in addition to the VP1 polypeptides (e.g., minor structural proteins and nonstructural proteins). Purified VLPs, produced using the expression cassettes of the present invention, can be administered to a vertebrate subject, usually in the form of immunogenic compositions, such as vaccine compositions. Combination vaccines may also be used, where such immunogenic compositions contain, for example, other proteins derived from Noroviruses, Sapoviruses, or other organisms or nucleic acids encoding such antigens. Administration can take place using the VLPs formulated alone or formulated with other antigens. Further, the VLPs can be administered prior to, concurrent with, or subsequent to, delivery of expression cassettes for nucleic acid immunization (see below) and/or delivery of other vaccines. Also, the site of VLP administration may be the same or different as other immunogenic compositions that are being administered. Gene delivery can be accomplished by a number of methods including, but are not limited to, immunization with DNA, alphavirus vectors, pox virus vectors, and vaccinia virus vectors.

F. Immunogenic Compositions

The invention also provides compositions comprising one or more of the immunogenic nucleic acids, polypeptides, polyproteins multiepitope fusion proteins, and/or VLPs, described herein. Different polypeptides, polyproteins, and multiple epitope fusion proteins may be mixed together in a single formulation. Within such combinations, an antigen of the immunogenic composition may be present in more than one polypeptide, or multiple epitope polypeptide, or polyprotein.

The immunogenic compositions may comprise a mixture of polypeptides and nucleic acids, which in turn may be delivered using the same or different vehicles. Antigens may be administered individually or in combination, in e.g., prophylactic (i.e., to prevent infection) or therapeutic (to treat infection) immunogenic compositions. The immunogenic composition may be given more than once (e.g., a "prime" administration followed by one or more "boosts") to achieve the desired effects. The same composition can be administered in one or more priming and one or more boosting steps. Alternatively, different compositions can be used for priming and boosting.

The immunogenic compositions will generally include one or more "pharmaceutically acceptable excipients or vehicles" such as water, saline, glycerol, ethanol, etc. Additionally, auxiliary substances, such as wetting or emulsifying agents, pH buffering substances, and the like, may be present in such vehicles.

Immunogenic compositions will typically, in addition to the components mentioned above, comprise one or more "pharmaceutically acceptable carriers." These include any carrier which does not itself induce the production of antibodies harmful to the individual receiving the composition. Suitable carriers typically are large, slowly metabolized macromolecules such as proteins, polysaccharides, polylactic acids, polyglycolic acids, polymeric amino acids, amino acid copolymers, and lipid aggregates (such as oil droplets or liposomes). Such carriers are well known to those of ordinary skill in the art. A composition may also contain a diluent, such as water, saline, glycerol, etc. Additionally, an auxiliary substance, such as a wetting or emulsifying agent, pH buffering substance, and the like, may be present. A thorough discussion of pharmaceutically acceptable components is available in Gennaro (2000) *Remington: The Science and Practice of Pharmacy.* 20th ed., ISBN: 0683306472.

Pharmaceutically acceptable salts can also be used in compositions of the invention, for example, mineral salts such as hydrochlorides, hydrobromides, phosphates, or sulfates, as well as salts of organic acids such as acetates, proprionates, malonates, or benzoates. Especially useful protein substrates are serum albumins, keyhole limpet hemocyanin, immunoglobulin molecules, thyroglobulin, ovalbumin, tetanus toxoid, and other proteins well known to those of skill in the art. Compositions of the invention can also contain liquids or excipients, such as water, saline, glycerol, dextrose, ethanol, or the like, singly or in combination, as well as substances such as wetting agents, emulsifying agents, or pH buffering agents. Antigens can also be adsorbed to, entrapped within or otherwise associated with liposomes and particulate carriers such as PLG.

Antigens can be conjugated to a carrier protein in order to enhance immunogenicity. This is particularly useful in compositions in which a saccharide or carbohydrate antigen is used. See Ramsay et al. (2001) *Lancet* 357(9251):195-196; Lindberg (1999) *Vaccine* 17 Suppl 2:S28-36; Buttery & Moxon (2000) *J R Coll Physicians Lond* 34:163-168; Ahmad & Chapnick (1999) *Infect Dis Clin North Am* 13:113-133, vii; Goldblatt (1998) *J. Med. Microbiol.* 47:563-567; European patent 0 477 508; U.S. Pat. No. 5,306,492; WO98/42721; *Conjugate Vaccines* (eds. Cruse et al.) ISBN 3805549326, particularly vol. 10:48-114; Hermanson (1996) *Bioconjugate Techniques* ISBN: 0123423368 or 012342335X.

Preferred carrier proteins are bacterial toxins or toxoids, such as diphtheria or tetanus toxoids. The $CRM_{197}$ diphtheria toxoid is particularly preferred. Other carrier polypeptides include the *N. meningitidis* outer membrane protein (EP-A-0372501), synthetic peptides (EP-A-0378881 and EP-A-0427347), heat shock proteins (WO 93/17712 and WO 94/03208), pertussis proteins (WO 98/58668 and EP-A-0471177), protein D from H influenzae (WO 00/56360), cytokines (WO 91/01146), lymphokines, hormones, growth factors, toxin A or B from *C. difficile* (WO 00/61761), iron-uptake proteins, such as transferring (WO 01/72337), etc. Where a mixture comprises capsular saccharide from both serigraphs A and C, it may be preferred that the ratio (w/w) of MenA saccharide:MenC saccharide is greater than 1 (e.g., 2:1, 3:1, 4:1, 5:1, 10:1 or higher). Different saccharides can be conjugated to the same or different type of carrier protein. Any suitable conjugation reaction can be used, with any suitable linker where necessary.

Immunogenic compositions, preferably vaccines of the present invention may be administered in conjunction with other immunoregulatory agents. For example, a vaccine of the invention can include an adjuvant. Preferred adjuvants include, but are not limited to, one or more of the following types of adjuvants described below.

A. Mineral Containing Compositions

Mineral containing compositions suitable for use as adjuvants in the invention include mineral salts, such as aluminum salts and calcium salts. The invention includes mineral salts such as hydroxides (e.g. oxyhydroxides), phosphates (e.g. hydroxyphosphates, orthophosphates), sulfates, etc. (e.g. see chapters 8 & 9 of *Vaccine Design* . . . (1995) eds. Powell & Newman. ISBN: 030644867X. Plenum.), or mixtures of different mineral compounds (e.g. a mixture of a phosphate and a hydroxide adjuvant, optionally with an excess of the phosphate), with the compounds taking any suitable form (e.g. gel, crystalline, amorphous, etc.), and with adsorption to the salt(s) being preferred. The mineral containing compositions may also be formulated as a particle of metal salt (WO00/23105).

Aluminum salts may be included in vaccines of the invention such that the dose of $Al^{3+}$ is between 0.2 and 1.0 mg per dose.

In one embodiment the aluminum based adjuvant for use in the present invention is alum (aluminum potassium sulfate $(AlK(SO_4)_2)$), or an alum derivative, such as that formed in-situ by mixing an antigen in phosphate buffer with alum, followed by titration and precipitation with a base such as ammonium hydroxide or sodium hydroxide.

Another aluminum-based adjuvant for use in vaccine formulations of the present invention is aluminum hydroxide adjuvant $(Al(OH)_3)$ or crystalline aluminum oxyhydroxide (AlOOH), which is an excellent adsorbant, having a surface area of approximately 500 $m^2/g$. Alternatively, aluminum phosphate adjuvant $(AlPO_4)$ or aluminum hydroxyphosphate, which contains phosphate groups in place of some or all of the hydroxyl groups of aluminum hydroxide adjuvant is provided. Preferred aluminum phosphate adjuvants provided herein are amorphous and soluble in acidic, basic and neutral media.

In another embodiment the adjuvant of the invention comprises both aluminum phosphate and aluminum hydroxide. In a more particular embodiment thereof, the adjuvant has a greater amount of aluminum phosphate than aluminum hydroxide, such as a ratio of 2:1, 3:1, 4:1, 5:1, 6:1, 7:1, 8:1, 9:1 or greater than 9:1, by weight aluminum phosphate to aluminum hydroxide. More particular still, aluminum salts in the vaccine are present at 0.4 to 1.0 mg per vaccine dose, or 0.4 to 0.8 mg per vaccine dose, or 0.5 to 0.7 mg per vaccine dose, or about 0.6 mg per vaccine dose.

Generally, the preferred aluminum-based adjuvant(s), or ratio of multiple aluminum-based adjuvants, such as aluminum phosphate to aluminum hydroxide is selected by optimization of electrostatic attraction between molecules such that the antigen carries an opposite charge as the adjuvant at the desired pH. For example, aluminum phosphate adjuvant (iep=4) adsorbs lysozyme, but not albumin at pH 7.4. Should albumin be the target, aluminum hydroxide adjuvant would be selected (iep 11.4). Alternatively, pretreatment of aluminum hydroxide with phosphate lowers its isoelectric point, making it a preferred adjuvant for more basic antigens.

B. Oil-Emulsions

Oil-emulsion compositions suitable for use as adjuvants in the invention include squalene-water emulsions, such as MF59 (5% Squalene, 0.5% Tween 80, and 0.5% Span 85, formulated into submicron particles using a microfluidizer). See WO90/14837. See also, Podda, "The adjuvanted influenza vaccines with novel adjuvants: experience with the MF59-adjuvanted vaccine", Vaccine (2001) 19: 2673-2680; Frey et al., "Comparison of the safety, tolerability, and immunogenicity of a MF59-adjuvanted influenza vaccine and a non-adjuvanted influenza vaccine in non-elderly adults", Vaccine (2003) 21:4234-4237. MF59 is used as the adjuvant in the FLUAD™ influenza virus trivalent subunit vaccine.

Particularly preferred adjuvants for use in the compositions are submicron oil-in-water emulsions. Preferred submicron oil-in-water emulsions for use herein are squalene/water emulsions optionally containing varying amounts of MTP-PE, such as a submicron oil-in-water emulsion containing 4-5% w/v squalene, 0.25-1.0% w/v Tween 80™ (polyoxyelthylenesorbitan monooleate), and/or 0.25-1.0% Span85™ (sorbitan trioleate), and, optionally, N-acetylmuramyl-L-alanyl-D-isogluatminyl-L-alanine-2-(1'-2'-dipalmitoyl-sn-glycero-3-huydroxyphosphosphoryloxy)-ethylamine (MTP-PE), for example, the submicron oil-in-water emulsion known as "MF59" (International Publication No. WO90/14837; U.S. Pat. Nos. 6,299,884 and 6,451,325, and Ott et al., "MF59—Design and Evaluation of a Safe and Potent Adjuvant for Human Vaccines" in *Vaccine Design The Subunit and Adjuvant Approach* (Powell, M. F. and Newman, M. J. eds.) Plenum Press, New York, 1995, pp. 277-296). MF59 contains 4-5% w/v Squalene (e.g. 4.3%), 0.25-0.5% w/v Tween 80™, and 0.5% w/v Span 85™ and optionally contains various amounts of MTP-PE, formulated into submicron particles using a microfluidizer such as Model 110Y microfluidizer (Microfluidics, Newton, Mass.). For example, MTP-PE may be present in an amount of about 0-500 μg/dose, more preferably 0-250 μg/dose and most preferably, 0-100 μg/dose. As used herein, the term "MF59-0" refers to the above submicron oil-in-water emulsion lacking MTP-PE, while the term MF59-MTP denotes a formulation that contains MTP-PE. For instance, "MF59-100" contains 100 μg MTP-PE per dose, and so on. MF69, another submicron oil-in-water emulsion for use herein, contains 4.3% w/v squalene, 0.25% w/v Tween 80™, and 0.75% w/v Span 85™ and optionally MTP-PE. Yet another submicron oil-in-water emulsion is MF75, also known as SAF, containing 10% squalene, 0.4% Tween 80™, 5% pluronic-blocked polymer L121, and thr-MDP, also microfluidized into a submicron emulsion. MF75-MTP denotes an MF75 formulation that includes MTP, such as from 100-400 μg MTP-PE per dose.

Submicron oil-in-water emulsions, methods of making the same and immunostimulating agents, such as muramyl peptides, for use in the compositions, are described in detail in International Publication No. WO90/14837 and U.S. Pat. Nos. 6,299,884 and 6,451,325.

Complete Freund's adjuvant (CFA) and incomplete Freund's adjuvant (IFA) may also be used as adjuvants in the invention.

C. Saponin Formulations

Saponin formulations, may also be used as adjuvants in the invention. Saponins are a heterologous group of sterol glycosides and triterpenoid glycosides that are found in the bark, leaves, stems, roots and even flowers of a wide range of plant species. Saponins isolated from the bark of the *Quillaia saponaria* Molina tree have been widely studied as adjuvants. Saponins can also be commercially obtained from *Smilax ornata* (sarsaprilla), *Gypsophilla paniculata* (brides veil), and *Saponaria officianalis* (soap root). Saponin adjuvant formulations include purified formulations, such as QS21, as well as lipid formulations, such as ISCOMs.

Saponin compositions have been purified using High Performance Thin Layer Chromatography (HP-TLC) and Reversed Phase High Performance Liquid Chromatography (RP-HPLC), Specific purified fractions using these techniques have been identified, including QS7, QS17, QS18, QS21, QH-A, QH-B and QH-C. Preferably, the saponin is QS21. A method of production of QS21 is disclosed in U.S. Pat. No. 5,057,540. Saponin formulations may also comprise a sterol, such as cholesterol (see WO96/33739).

Combinations of saponins and cholesterols can be used to form unique particles called Immunostimulating Complexes (ISCOMs). ISCOMs typically also include a phospholipid such as phosphatidylethanolamine or phosphatidylcholine. Any known saponin can be used in ISCOMs. Preferably, the ISCOM includes one or more of Quil A, QHA and QHC. ISCOMs are further described in EP0109942, WO96/11711 and WO96/33739. Optionally, the ISCOMS may be devoid of (an) additional detergent(s). See WO00/07621.

A review of the development of saponin based adjuvants can be found in Barr, et al., "ISCOMs and other saponin based adjuvants", Advanced Drug Delivery Reviews (1998) 32:247-271. See also Sjolander, et al., "Uptake and adjuvant activity of orally delivered saponin and ISCOM vaccines", Advanced Drug Delivery Reviews (1998) 32:321-338.

D. Virosomes and Virus Like Particles (VLPs)

Virosomes and Virus Like Particles (VLPs) can also be used as adjuvants in the invention. These structures generally contain one or more proteins from a virus optionally combined or formulated with a phospholipid. They are generally non-pathogenic, non-replicating and generally do not contain any of the native viral genome. The viral proteins may be recombinantly produced or isolated from whole viruses. These viral proteins suitable for use in virosomes or VLPs include proteins derived from influenza virus (such as HA or NA), Hepatitis B virus (such as core or capsid proteins), Hepatitis E virus, measles virus, Sindbis virus, Rotavirus, Foot-and-Mouth Disease virus, Retrovirus, Norwalk virus, human Papilloma virus, HIV, RNA-phages, Qβ-phage (such as coat proteins), GA-phage, fr-phage; AP205 phage, and Ty (such as retrotransposon Ty protein p1). VLPs are discussed further in WO03/024480, WO03/024481, and Niikura et al., "Chimeric Recombinant Hepatitis E Virus-Like Particles as an Oral Vaccine Vehicle Presenting Foreign Epitopes", Virology (2002) 293:273-280; Lenz et al., "Papillomarivurs-Like Particles Induce Acute Activation of Dendritic Cells", Journal of Immunology (2001) 5246-5355; Pinto, et al., "Cellular Immune Responses to Human Papillomavirus (HPV)-16 μl Healthy Volunteers Immunized with Recombinant HPV-16 L1 Virus-Like Particles", Journal of Infectious Diseases (2003) 188:327-338; and Gerber et al., "Human Papillomavrisu Virus-Like Particles Are Efficient Oral Immunogens when Coadministered with *Escherichia coli* Heat-Labile Entertoxin Mutant R192G or CpG", Journal of Virology (2001) 75(10):4752-4760. Virosomes are discussed further in, for example, Gluck et al., "New Technology Platforms in the Development of Vaccines for the Future", Vaccine (2002) 20:B10-B16. Immunopotentiating reconstituted influenza virosomes (IRIV) are used as the subunit antigen delivery system in the intranasal trivalent INFLEXAL™ product {Mischler & Metcalfe (2002) *Vaccine* 20 Suppl 5:B17-23} and the INFLUVAC PLUS™ product.

E. Bacterial or Microbial Derivatives

Adjuvants suitable for use in the invention include bacterial or microbial derivatives such as:

(1) Non-Toxic Derivatives of Enterobacterial Lipopolysaccharide (LPS)

Such derivatives include Monophosphoryl lipid A (MPL) and 3-O-deacylated MPL (3dMPL). 3dMPL is a mixture of 3 De-O-acylated monophosphoryl lipid A with 4, 5 or 6 acylated chains. A preferred "small particle" form of 3 De-O-acylated monophosphoryl lipid A is disclosed in EP 0 689 454. Such "small particles" of 3dMPL are small enough to be sterile filtered through a 0.22 micron membrane (see EP 0 689 454). Other non-toxic LPS derivatives include monophosphoryl lipid A mimics, such as aminoalkyl glucosaminide phosphate derivatives e.g. RC-529. See Johnson et al. (1999) *Bioorg Med Chem Lett* 9:2273-2278.

(2) Lipid A Derivatives

Lipid A derivatives include derivatives of lipid A from *Escherichia coli* such as OM-174. OM-174 is described for example in Meraldi et al., "OM-174, a New Adjuvant with a Potential for Human Use, Induces a Protective Response when Administered with the Synthetic C-Terminal Fragment 242-310 from the circumsporozoite protein of *Plasmodium berghei*", Vaccine (2003) 21:2485-2491; and Pajak, et al., "The Adjuvant OM-174 induces both the migration and maturation of murine dendritic cells in vivo", Vaccine (2003) 21:836-842.

(3) Immunostimulatory Oligonucleotides

Immunostimulatory oligonucleotides suitable for use as adjuvants in the invention include nucleotide sequences containing a CpG motif (a sequence containing an unmethylated cytosine followed by guanosine and linked by a phosphate bond). Bacterial double stranded RNA or oligonucleotides containing palindromic or poly(dG) sequences have also been shown to be immunostimulatory.

The CpG's can include nucleotide modifications/analogs such as phosphorothioate modifications and can be double-stranded or single-stranded. Optionally, the guanosine may be replaced with an analog such as 2'-deoxy-7-deazaguanosine. See Kandimalla, et al., "Divergent synthetic nucleotide motif recognition pattern: design and development of potent immunomodulatory oligodeoxyribonucleotide agents with distinct cytokine induction profiles", Nucleic Acids Research (2003) 31(9): 2393-2400; WO02/26757 and WO99/62923 for examples of possible analog substitutions. The adjuvant effect of CpG oligonucleotides is further discussed in Krieg, "CpG motifs: the active ingredient in bacterial extracts?", Nature Medicine (2003) 9(7): 831-835; McCluskie, et al., "Parenteral and mucosal prime-boost immunization strategies in mice with hepatitis B surface antigen and CpG DNA", FEMS Immunology and Medical Microbiology (2002) 32:179-185; WO98/40100; U.S. Pat. No. 6,207,646; U.S. Pat. No. 6,239,116 and U.S. Pat. No. 6,429,199.

The CpG sequence may be directed to TLR9, such as the motif GTCGTT or TTCGTT. See Kandimalla, et al., "Toll-like receptor 9: modulation of recognition and cytokine induction by novel synthetic CpG DNAs", Biochemical Society Transactions (2003) 31 (part 3): 654-658. The CpG sequence may be specific for inducing a Th1 immune response, such as a CpG-A ODN, or it may be more specific for inducing a B cell response, such a CpG-B ODN. CpG-A and CpG-B ODNs are discussed in Blackwell, et al., "CpG-A-Induced Monocyte IFN-gamma-Inducible Protein-10 Production is Regulated by Plasmacytoid Dendritic Cell Derived IFN-alpha", J. Immunol. (2003) 170(8):4061-4068; Krieg, "From A to Z on CpG", TRENDS in Immunology (2002) 23(2): 64-65 and WO01/95935. Preferably, the CpG is a CpG-A ODN.

Preferably, the CpG oligonucleotide is constructed so that the 5' end is accessible for receptor recognition. Optionally, two CpG oligonucleotide sequences may be attached at their 3' ends to form "immunomers". See, for example, Kandimalla, et al., "Secondary structures in CpG oligonucleotides affect immunostimulatory activity", BBRC (2003) 306:948-953; Kandimalla, et al., "Toll-like receptor 9: modulation of recognition and cytokine induction by novel synthetic GpG DNAs", Biochemical Society Transactions (2003) 31(part 3):664-658; Bhagat et al., "CpG penta- and hexadeoxyribonucleotides as potent immunomodulatory agents" BBRC (2003) 300:853-861 and WO03/035836.

(4) ADP-Ribosylating Toxins and Detoxified Derivatives Thereof.

Bacterial ADP-ribosylating toxins and detoxified derivatives thereof may be used as adjuvants in the invention. Preferably, the protein is derived from *E. coli* (i.e., *E. coli* heat labile enterotoxin "LT), cholera ("CT"), or pertussis ("PT"). The use of detoxified ADP-ribosylating toxins as mucosal adjuvants is described in WO95/17211 and as parenteral adjuvants in WO98/42375. Preferably, the adjuvant is a detoxified LT mutant such as LT-K63, LT-R72, and LTR192G. The use of ADP-ribosylating toxins and detoxified derivatives thereof, particularly LT-K63 and LT-R72, as adjuvants can be found in the following references: Beignon, et al., "The LTR72Mutant of Heat-Labile Enterotoxin of *Escherichia coli* Enhances the Ability of Peptide Antigens to Elicit CD4+ T Cells and Secrete Gamma Interferon after Coapplication onto Bare Skin", Infection and Immunity (2002) 70(6):3012-3019; Pizza, et al., "Mucosal vaccines: non toxic derivatives of LT and CT as mucosal adjuvants", Vaccine (2001) 19:2534-2541; Pizza, et al., "LTK63 and LTR72, two mucosal adjuvants ready for clinical trials" Int. J. Med. Microbiol. (2000) 290(4-5):455-461; Scharton-Kersten et al., "Transcutaneous Immunization with Bacterial ADP-Ribosylating Exotoxins, Subunits and Unrelated Adjuvants", Infection and Immunity (2000) 68(9):5306-5313; Ryan et al., "Mutants of *Escherichia coli* Heat-Labile Toxin Act as Effective Mucosal Adjuvants for Nasal Delivery of an Acellular Pertussis Vaccine: Differential Effects of the Nontoxic AB Complex and Enzyme Activity on Th1 and Th2 Cells" Infection and Immunity (1999) 67(12):6270-6280; Partidos et al., "Heat-labile enterotoxin of *Escherichia coli* and its site-directed mutant LT-K63 enhance the proliferative and cytotoxic T-cell responses to intranasally co-immunized synthetic peptides", Immunol. Lett. (1999) 67(3):209-216; Peppoloni et al., "Mutants of the *Escherichia coli* heat-labile enterotoxin as safe and strong adjuvants for intranasal delivery of vaccines", Vaccines (2003) 2(2):285-293; and Pine et al., (2002) "Intranasal immunization with influenza vaccine and a detoxified mutant of heat labile enterotoxin from *Escherichia coli* (LTK63)" J. Control Release (2002) 85(1-3):263-270. Numerical reference for amino acid substitutions is preferably based on the alignments of the A and B subunits of ADP-ribosylating toxins set forth in Domenighini et al., Mol. Microbiol. (1995) 15(6):1165-1167.

F. Bioadhesives and Mucoadhesives

Bioadhesives and mucoadhesives may also be used as adjuvants in the invention. Suitable bioadhesives include esterified hyaluronic acid microspheres (Singh et al. (2001) *J. Cont. Rele.* 70:267-276) or mucoadhesives such as cross-linked derivatives of polyacrylic acid, polyvinyl alcohol, polyvinyl pyrollidone, polysaccharides and carboxymethylcellulose. Chitosan and derivatives thereof may also be used as adjuvants in the invention. E.g. WO99/27960.

G. Microparticles

Microparticles may also be used as adjuvants in the invention. Microparticles (i.e. a particle of ~100 nm to ~150 μm in diameter, more preferably ~200 nm to ~30 μm in diameter, and most preferably ~500 nm to ~10 μm in diameter) formed from materials that are biodegradable and non-toxic (e.g. a poly(α-hydroxy acid), a polyhydroxybutyric acid, a polyorthoester, a polyanhydride, a polycaprolactone, etc.), with poly(lactide-co-glycolide) are preferred, optionally treated to have a negatively-charged surface (e.g. with SDS) or a positively-charged surface (e.g. with a cationic detergent, such as CTAB).

H. Liposomes

Examples of liposome formulations suitable for use as adjuvants are described in U.S. Pat. No. 6,090,406, U.S. Pat. No. 5,916,588, and EP 0 626 169.

I. Polyoxyethylene ether and Polyoxyethylene Ester Formulations

Adjuvants suitable for use in the invention include polyoxyethylene ethers and polyoxyethylene esters. WO99/52549. Such formulations further include polyoxyethylene sorbitan ester surfactants in combination with an octoxynol (WO01/21207) as well as polyoxyethylene alkyl ethers or ester surfactants in combination with at least one additional non-ionic surfactant such as an octoxynol (WO01/21152).

Preferred polyoxyethylene ethers are selected from the following group: polyoxyethylene-9-lauryl ether (laureth 9), polyoxyethylene-9-steoryl ether, polyoxytheylene-8-steoryl ether, polyoxyethylene-4-lauryl ether, polyoxyethylene-35-lauryl ether, and polyoxyethylene-23-lauryl ether.

J. Polyphosphazene (PCPP)

PCPP formulations are described, for example, in Andrianov et al., "Preparation of hydrogel microspheres by coacervation of aqueous polyphophazene solutions", Biomaterials (1998) 19(1-3):109-115 and Payne et al., "Protein Release from Polyphosphazene Matrices", Adv. Drug. Delivery Review (1998) 31(3):185-196.

K. Muramyl Peptides

Examples of muramyl peptides suitable for use as adjuvants in the invention include N-acetyl-muramyl-L-threonyl-D-isoglutamine (thr-MDP), N-acetyl-normuramyl-1-alanyl-d-isoglutamine (nor-MDP), and N-acetylmuramyl-1-alanyl-d-isoglutaminyl-1-alanine-2-(1'-2'-dipalmitoyl-sn-glycero-3-hydroxyphosphoryloxy)-ethylamine MTP-PE).

L. Imidazoquinoline Compounds

Examples of imidazoquinoline compounds suitable for use adjuvants in the invention include Imiquimod and its analogues, described further in Stanley, "Imiquimod and the imidazoquinolines: mechanism of action and therapeutic potential" Clin Exp Dermatol (2002) 27(7):571-577; Jones, "Resiquimod 3M", Curr Opin Investig Drugs (2003) 4(2): 214-218; and U.S. Pat. Nos. 4,689,338, 5,389,640, 5,268, 376, 4,929,624, 5,266,575, 5,352,784, 5,494,916, 5,482,936, 5,346,905, 5,395,937, 5,238,944, and 5,525,612.

M. Thiosemicarbazone Compounds.

Examples of thiosemicarbazone compounds, as well as methods of formulating, manufacturing, and screening for compounds all suitable for use as adjuvants in the invention include those described in WO04/60308. The thiosemicarbazones are particularly effective in the stimulation of human peripheral blood mononuclear cells for the production of cytokines, such as TNF-α.

N. Tryptanthrin Compounds.

Examples of tryptanthrin compounds, as well as methods of formulating, manufacturing, and screening for compounds all suitable for use as adjuvants in the invention include those described in WO04/64759. The tryptanthrin compounds are particularly effective in the stimulation of human peripheral blood mononuclear cells for the production of cytokines, such as TNF-α.

The invention may also comprise combinations of aspects of one or more of the adjuvants identified above. For example, the following adjuvant compositions may be used in the invention:

(1) a saponin and an oil-in-water emulsion (WO99/11241);

(2) a saponin (e.g., QS21)+a non-toxic LPS derivative (e.g. 3dMPL) (see WO94/00153);

(3) a saponin (e.g., QS21)+a non-toxic LPS derivative (e.g. 3dMPL)+a cholesterol;

(4) a saponin (e.g. QS21)+3dMPL+IL-12 (optionally+a sterol) (WO98/57659);

(5) combinations of 3dMPL with, for example, QS21 and/or oil-in-water emulsions (See European patent applications 0835318, 0735898 and 0761231);

(6) SAF, containing 10% Squalane, 0.4% Tween 80, 5% pluronic-block polymer L121, and thr-MDP, either microfluidized into a submicron emulsion or vortexed to generate a larger particle size emulsion.

(7) Ribi™ adjuvant system (RAS), (Ribi Immunochem) containing 2% Squalene, 0.2% Tween 80, and one or more bacterial cell wall components from the group consisting of monophosphorylipid A (MPL), trehalose dimycolate (TDM), and cell wall skeleton (CWS), preferably MPL+CWS (Detox™); and (8) one or more mineral salts (such as an aluminum salt)+a non-toxic derivative of LPS (such as 3dPML).

(9) one or more mineral salts (such as an aluminum salt) and one or more immunostimulatory oligonucleotides (such as a nucleotide sequence including a CpG motif) and one or more detoxified ADP-ribosylating toxins (such as LT-K63 and LT-R72).

O. Human Immunomodulators

Human immunomodulators suitable for use as adjuvants in the invention include cytokines, such as interleukins (e.g. IL-1, IL-2, IL-4, IL-6, IL-7, IL-12, etc.), interferons (e.g. interferon-γ), macrophage colony stimulating factor, and tumor necrosis factor.

Aluminum salts and MF59 are preferred adjuvants for use with injectable Norovirus and Sapovirus vaccines. Bacterial toxins and bioadhesives are preferred adjuvants for use with mucosally-delivered vaccines, such as nasal vaccines.

The contents of all of the above cited patents, patent applications and journal articles are incorporated by reference as if set forth fully herein.

Additional Antigens

Compositions of the invention optionally can comprise one or more additional polypeptide antigens which are not derived from Norovirus or Sapovirus proteins. Such antigens include bacterial, viral, or parasitic antigens.

In some embodiments, a Norovirus or Sapovirus antigen is combined with one or more antigens which are useful in a pediatric vaccine. Such antigens are well known in the art and include, but are not limited to, antigens derived from a bacteria or virus, such as Orthomyxovirus (influenza), Pneumovirus (RSV), Paramyxovirus (PIV and Mumps), Morbillivirus (measles), Togavirus (Rubella), Enterovirus HBV, Coronavirus (SARS), and Varicella-zoster virus (VZV), Epstein Barr virus (EBV), *Streptococcus pneumoniae, Neisseria meningitides, Streptococcus pyogenes* (Group A *Streptococcus*), *Moraxella catarrhalis, Bordetella pertussis, Staphylococcus aureus, Clostridium tetani* (Tetanus), *Cornynebacterium diphtheriae* (Diphtheria), *Haemophilus influenzae* B (Hib), *Pseudomonas aeruginosa, Streptococcus agalactiae* (Group B *Streptococcus*), and *E. coli*.

In other embodiments, a Norovirus or Sapovirus antigen is combined with one or more antigens useful in a vaccine designed to protect elderly or immunocompromised individuals. Antigens of this type are well known in the art and include, but are not limited to, *Neisseria meningitides, Streptococcus pneumoniae, Streptococcus pyogenes* (Group A *Streptococcus*), *Moraxella catarrhalis, Bordetella pertussis, Staphylococcus aureus, Staphylococcus epidermis, Clostridium tetani* (Tetanus), *Cornynebacterium diphtheriae* (Diphtheria), *Haemophilus influenzae* B (Hib), *Pseudomonas aeruginosa, Legionella pneumophila, Streptococcus agalactiae* (Group B *Streptococcus*), *Enterococcus faecalis, Helicobacter pylori, Clamydia pneumoniae*, Orthomyxovirus (influenza), Pneumovirus (RSV), Paramyxovirus (PIV and Mumps), Morbillivirus (measles), Togavirus (Rubella), Enterovirus (polio), HBV, Coronavirus (SARS), Varicella-zoster virus (VZV), Epstein Barr virus (EBV), Cytomegalovirus (CMV).

In other embodiments, a Norovirus or Sapovirus antigen is combined with one or more antigens which are useful in a vaccine designed to protect individuals against pathogens that cause diarrheal diseases. Such antigens include, but are not limited to, rotavirus, *Shigella* spp., enterotoxigenic *Escherichia coli* (ETEC), *Vibrio cholerae*, and *Campylobacter jejuni* antigens. In a preferred embodiment, one or more Norovirus antigens derived from Norwalk virus, Snow Mountain virus, and/or Hawaii virus are combined with a rotavirus antigen in an immunogenic composition.

Antigens for use with the invention include, but are not limited to, one or more of the following antigens set forth below, or antigens derived from one or more of the pathogens set forth below:

A. BACTERIAL ANTIGENS

Bacterial antigens suitable for use in the invention include proteins, polysaccharides, lipopolysaccharides, and outer membrane vesicles which may be isolated, purified or derived from a bacteria. In addition, bacterial antigens may include bacterial lysates and inactivated bacteria formulations. Bacteria antigens may be produced by recombinant expression. Bacterial antigens preferably include epitopes which are exposed on the surface of the bacteria during at least one stage of its life cycle. Bacterial antigens are preferably conserved across multiple serotypes. Bacterial antigens include antigens derived from one or more of the bacteria set forth below as well as the specific antigens examples identified below.

*Neisseria meningitides*: Meningitides antigens may include proteins (such as those identified in References 1-7), saccharides (including a polysaccharide, oligosaccharide or lipopolysaccharide), or outer-membrane vesicles (References 8, 9, 10, 11) purified or derived from *N. meningitides* serogroup such as A, C, W135, Y, and/or B. Meningitides protein antigens may be selected from adhesions, autotransporters, toxins, Fe acquisition proteins, and membrane associated proteins (preferably integral outer membrane protein).

*Streptococcus pneumoniae*: *Streptococcus pneumoniae* antigens may include a saccharide (including a polysaccharide or an oligosaccharide) and/or protein from *Streptococcus pneumoniae*. Saccharide antigens may be selected from serotypes 1, 2, 3, 4, 5, 6B, 7F, 8, 9N, 9V, 10A, 11A, 12F, 14, 15B, 17F, 18C, 19A, 19F, 20, 22F, 23F, and 33F. Protein antigens may be selected from a protein identified in WO 98/18931, WO 98/18930, U.S. Pat. No. 6,699,703, U.S. Pat. No. 6,800, 744, WO 97/43303, and WO 97/37026. *Streptococcus pneumoniae* proteins may be selected from the Poly Histidine Triad family (PhtX), the Choline Binding Protein family (CbpX), CbpX truncates, LytX family, LytX truncates, CbpX truncate-LytX truncate chimeric proteins, pneumolysin (Ply), PspA, PsaA, Sp128, Sp101, Sp130, Sp125 or Sp133.

*Streptococcus pyogenes* (Group A *Streptococcus*): Group A *Streptococcus* antigens may include a protein identified in WO 02/34771 or WO 2005/032582 (including GAS 40), fusions of fragments of GAS M proteins (including those described in WO 02/094851, and Dale, Vaccine (1999) 17:193-200, and Dale, Vaccine 14(10): 944-948), fibronectin binding protein (Sfb1), Streptococcal heme-associated protein (Shp), and Streptolysin S (SagA).

*Moraxella catarrhalis*: *Moraxella* antigens include antigens identified in WO 02/18595 and WO 99/58562, outer membrane protein antigens (HMW-OMP), C-antigen, and/or LPS.

*Bordetella pertussis*: Pertussis antigens include *petussis* holotoxin (PT) and filamentous haemagglutinin (FHA) from *B. pertussis*, optionally also combination with pertactin and/or agglutinogens 2 and 3 antigen.

*Staphylococcus aureus*: Staph aureus antigens include *S. aureus* type 5 and 8 capsular polysaccharides optionally conjugated to nontoxic recombinant *Pseudomonas aeruginosa* exotoxin A, such as StaphVAX™, or antigens derived from surface proteins, invasins (leukocidin, kinases, hyaluronidase), surface factors that inhibit phagocytic engulfment (capsule, Protein A), carotenoids, catalase production, Protein A, coagulase, clotting factor, and/or membrane-damaging toxins (optionally detoxified) that lyse eukaryotic cell membranes (hemolysins, leukotoxin, leukocidin).

*Staphylococcus epidermis*: *S. epidermidis* antigens include slime-associated antigen (SAA).

*Clostridium tetani* (Tetanus): Tetanus antigens include tetanus toxoid (TT), preferably used as a carrier protein in conjunction/conjugated with the compositions of the present invention.

*Cornynebacterium diphtheriae* (Diphtheria): Diphtheria antigens include diphtheria toxin, preferably detoxified, such as $CRM_{197}$. Additionally antigens capable of modulating, inhibiting or associated with ADP ribosylation are contemplated for combination/co-administration/conjugation with the compositions of the present invention. The diphtheria toxoids may be used as carrier proteins.

*Haemophilus influenzae* B (Hib): Hib antigens include a Hib saccharide antigen.

*Pseudomonas aeruginosa*: *Pseudomonas* antigens include endotoxin A, Wzz protein, *P. aeruginosa* LPS, more particularly LPS isolated from PAO1 (O5 serotype), and/or Outer Membrane Proteins, including Outer Membrane Proteins F (OprF) (*Infect Immun.* 2001 May; 69(5): 3510-3515).

*Legionella pneumophila*. Bacterial antigens may be derived from *Legionella pneumophila*.

*Streptococcus agalactiae* (Group B *Streptococcus*): Group B *Streptococcus* antigens include a protein or saccharide antigen identified in WO 02/34771, WO 03/093306, WO 04/041157, or WO 2005/002619 (including proteins GBS 80, GBS 104, GBS 276 and GBS 322, and including saccharide antigens derived from serotypes 1a, 1b, Ia/c, II, III, IV, V, VI, VII and VIII).

*Neiserria gonorrhoeae*: Gonorrhoeae antigens include Por (or porin) protein, such as PorB (see Zhu et al., Vaccine (2004) 22:660-669), a transferring binding protein, such as TbpA and TbpB (See Price et al., Infection and Immunity (2004) 71(1):277-283), a opacity protein (such as Opa), a reduction-modifiable protein (Rmp), and outer membrane vesicle (OMV) preparations (see Plante et al., J Infectious Disease (2000) 182:848-855), also see e.g. WO99/24578, WO99/36544, WO99/57280, WO02/079243).

*Chlamydia trachomatis*: *Chlamydia trachomatis* antigens include antigens derived from serotypes A, B, Ba and C (agents of trachoma, a cause of blindness), serotypes $L_1$, $L_2$ & $L_3$ (associated with Lymphogranuloma venereum), and serotypes, D-K. *Chlamydia* trachomas antigens may also include an antigen identified in WO 00/37494, WO 03/049762, WO 03/068811, or WO 05/002619; including PepA (CT045), LcrE (CT089), ArtJ (CT381), DnaK (CT396), CT398, OmpH-like (CT242), L7/L12 (CT316), OmcA (CT444), AtosS (CT467), CT547, Eno (CT587), HrtA (CT823), and MurG (CT761).

*Treponema pallidum* (Syphilis): Syphilis antigens include TmpA antigen.

*Haemophilus ducreyi* (causing chancroid): Ducreyi antigens include outer membrane protein (DsrA).

*Enterococcus faecalis* or *Enterococcus faecium*: Antigens include a trisaccharide repeat or other *Enterococcus* derived antigens provided in U.S. Pat. No. 6,756,361.

*Helicobacter pylori*: *H pylori* antigens include Cag, Vac, Nap, HopX, HopY and/or urease antigen.

*Staphylococcus saprophyticus*: Antigens include the 160 kDa hemagglutinin of *S. saprophyticus* antigen.

*Yersinia enterocolitica* Antigens include LPS (*Infect Immun.* 2002 August; 70(8): 4414).

*E. coli*: *E. coli* antigens may be derived from enterotoxigenic *E. coli* (ETEC), enteroaggregative *E. coli* (EAggEC), diffusely adhering *E. coli* (DAEC), enteropathogehic *E. coli* (EPEC), and/or enterohemorrhagic *E. coli* (EHEC).

*Bacillus anthracis* (anthrax): *B. anthracis* antigens are optionally detoxified and may be selected from A-components (lethal factor (LF) and edema factor (EF)), both of which can share a common B-component known as protective antigen (PA).

*Yersinia pestis* (plague): Plague antigens include F1 capsular antigen (*Infect Immun.* 2003 January; 71(1)): 374-383, LPS (*Infect Immun.* 1999 October; 67(10): 5395), *Yersinia pestis* V antigen (*Infect Immun.* 1997 November; 65(11): 4476-4482).

*Mycobacterium tuberculosis*: Tuberculosis antigens include lipoproteins, LPS, BCG antigens, a fusion protein of antigen 85B (Ag85B) and/or ESAT-6 optionally formulated in cationic lipid vesicles (Infect Immun. 2004 October; 72(10): 6148), *Mycobacterium tuberculosis* (Mtb) isocitrate dehydrogenase associated antigens (*Proc Natl Acad Sci USA.* 2004 Aug. 24; 101(34): 12652), and/or MPT51 antigens (Infect Immun. 2004 July; 72(7): 3829).

*Rickettsia*: Antigens include outer membrane proteins, including the outer membrane protein A and/or B (OmpB) (*Biochim Biophys Acta.* 2004 Nov. 1; 1702(2):145), LPS, and surface protein antigen (SPA) (*J Autoimmun.* 1989 June; 2 Suppl:81).

*Listeria monocytogenes*. Bacterial antigens may be derived from *Listeria monocytogenes*.

*Chlamydia pneumoniae*: Antigens include those identified in WO 02/02606.

*Vibrio cholerae*: Antigens include proteinase antigens, LPS, particularly lipopolysaccharides of *Vibrio cholerae* II, O1 Inaba O-specific polysaccharides, *V. cholera* 0139, antigens of IEM108 vaccine (*Infect Immun.* 2003 October; 71(10):5498-504), and/or Zonula occludens toxin (Zot).

*Salmonella typhi* (typhoid fever): Antigens include capsular polysaccharides preferably conjugates (Vi, i.e. vax-TyVi).

*Borrelia burgdorferi* (Lyme disease): Antigens include lipoproteins (such as OspA, OspB, Osp C and Osp D), other surface proteins such as OspE-related proteins (Erps), decorin-binding proteins (such as DbpA), and antigenically variable VI proteins., such as antigens associated with P39 and P13 (an integral membrane protein, *Infect Immun.* 2001 May; 69(5): 3323-3334), V1sE Antigenic Variation Protein (*J Clin Microbiol.* 1999 December; 37(12): 3997).

*Porphyromonas gingivalis*: Antigens include *P. gingivalis* outer membrane protein (OMP).

*Klebsiella*: Antigens include an OMP, including OMP A, or a polysaccharide optionally conjugated to tetanus toxoid.

Further bacterial antigens of the invention may be capsular antigens, polysaccharide antigens or protein antigens of any of the above. Further bacterial antigens may also include an outer membrane vesicle (OMV) preparation. Additionally, antigens include live, attenuated, and/or purified versions of any of the aforementioned bacteria. The antigens of the present invention may be derived from gram-negative or gram-positive bacteria. The antigens of the present invention may be derived from aerobic or anaerobic bacteria.

Additionally, any of the above bacterial-derived saccharides (polysaccharides, LPS, LOS or oligosaccharides) can be conjugated to another agent or antigen, such as a carrier protein (for example $CRM_{197}$). Such conjugation may be direct conjugation effected by reductive amination of carbonyl moieties on the saccharide to amino groups on the protein, as provided in U.S. Pat. No. 5,360,897 and *Can J Biochem Cell Biol.* 1984 May; 62(5):270-5. Alternatively, the saccharides can be conjugated through a linker, such as, with succinamide or other linkages provided in *Bioconjugate Techniques,* 1996 and *CRC, Chemistry of Protein Conjugation and Cross-Linking,* 1993.

B. VIRAL ANTIGENS

Viral antigens suitable for use in the invention include inactivated (or killed) virus, attenuated virus, split virus formulations, purified subunit formulations, viral proteins which may be isolated, purified or derived from a virus, and Virus Like Particles (VLPs). Viral antigens may be derived from viruses propagated on cell culture or other substrate. Alternatively, viral antigens may be expressed recombinantly. Viral antigens preferably include epitopes which are exposed on the surface of the virus during at least one stage of its life cycle. Viral antigens are preferably conserved across multiple serotypes or isolates. Viral antigens include antigens derived from one or more of the Viruses set forth below as well as the specific antigens examples identified below.

Orthomyxovirus: Viral antigens may be derived from an Orthomyxovirus, such as Influenza A, B and C. Orthomyxovirus antigens may be selected from one or more of the viral proteins, including hemagglutinin (HA), neuraminidase (NA), nucleoprotein (NP), matrix protein (M1), membrane protein (M2), one or more of the transcriptase components (PB1, PB2 and PA). Preferred antigens include HA and NA.

Influenza antigens may be derived from interpandemic (annual) flu strains. Alternatively influenza antigens may be derived from strains with the potential to cause pandemic a pandemic outbreak (i.e., influenza strains with new haemagglutinin compared to the haemagglutinin in currently circulating strains, or influenza strains which are pathogenic in avian subjects and have the potential to be transmitted horizontally in the human population, or influenza strains which are pathogenic to humans).

Paramyxoviridae viruses: Viral antigens may be derived from Paramyxoviridae viruses, such as Pneumoviruses (RSV), Paramyxoviruses (PIV) and Morbilliviruses (Measles).

Pneumovirus: Viral antigens may be derived from a Pneumovirus, such as Respiratory syncytial virus (RSV), Bovine respiratory syncytial virus, Pneumonia virus of mice, and Turkey rhinotracheitis virus. Preferably, the Pneumovirus is RSV. Pneumovirus antigens may be selected from one or more of the following proteins, including surface proteins Fusion (F), Glycoprotein (G) and Small Hydrophobic protein (SH), matrix proteins M and M2, nucleocapsid proteins N, P and L and nonstructural proteins NS1 and NS2. Preferred Pneumovirus antigens include F, G and M. See e.g., *J Gen Virol.* 2004 November; 85(Pt 11):3229). Pneumovirus antigens may also be formulated in or derived from chimeric viruses. For example, chimeric RSV/PIV viruses may comprise components of both RSV and PIV.

Paramyxovirus: Viral antigens may be derived from a Paramyxovirus, such as Parainfluenza virus types 1-4 (PIV), Mumps, Sendai viruses, Simian virus 5, Bovine parainfluenza virus and Newcastle disease virus. Preferably, the Paramyxovirus is PIV or Mumps. Paramyxovirus antigens may be selected from one or more of the following proteins: Hemagglutinin-Neuraminidase (HN), Fusion proteins F1 and F2, Nucleoprotein (NP), Phosphoprotein (P), Large protein (L), and Matrix protein (M). Preferred Paramyxovirus proteins include HN, F1 and F2. Paramyxovirus antigens may also be formulated in or derived from chimeric viruses. For example, chimeric RSV/PIV viruses may comprise components of both RSV and PIV. Commercially available mumps vaccines include live attenuated mumps virus, in either a monovalent form or in combination with measles and rubella vaccines (MMR).

Morbillivirus: Viral antigens may be derived from a Morbillivirus, such as Measles. Morbillivirus antigens may be selected from one or more of the following proteins: hemagglutinin (H), Glycoprotein (G), Fusion factor (F), Large protein (L), Nucleoprotein (NP), Polymerase phosphoprotein (P), and Matrix (M). Commercially available measles vaccines include live attenuated measles virus, typically in combination with mumps and rubella (MMR).

Picornavirus: Viral antigens may be derived from Picornaviruses, such as Enteroviruses, Rhinoviruses, Heparnavirus, Cardioviruses and Aphthoviruses. Antigens derived from Enteroviruses, such as Poliovirus are preferred.

Enterovirus: Viral antigens may be derived from an Enterovirus, such as Poliovirus types 1, 2 or 3, Coxsackie A virus types 1 to 22 and 24, Coxsackie B virus types 1 to 6, Echovirus (ECHO) virus) types 1 to 9, 11 to 27 and 29 to 34 and Enterovirus 68 to 71. Preferably, the Enterovirus is poliovirus. Enterovirus antigens are preferably selected from one or more of the following Capsid proteins VP1, VP2, VP3 and VP4. Commercially available polio vaccines include Inactivated Polio Vaccine (IPV) and Oral poliovirus vaccine (OPV).

Heparnavirus: Viral antigens may be derived from an Heparnavirus, such as Hepatitis A virus (HAV). Commercially available HAV vaccines include inactivated HAV vaccine.

Togavirus: Viral antigens may be derived from a Togavirus, such as a Rubivirus, an Alphavirus, or an Arterivirus. Antigens derived from Rubivirus, such as Rubella virus, are preferred. Togavirus antigens may be selected from E1, E2, E3, C, NSP-1, NSPO-2, NSP-3 or NSP-4. Togavirus antigens are preferably selected from E1, E2 or E3. Commercially available Rubella vaccines include a live cold-adapted virus, typically in combination with mumps and measles vaccines (MMR).

Flavivirus: Viral antigens may be derived from a Flavivirus, such as Tick-borne encephalitis (TBE), Dengue (types 1, 2, 3 or 4), Yellow Fever, Japanese encephalitis, West Nile encephalitis, St. Louis encephalitis, Russian spring-summer encephalitis, Powassan encephalitis. Flavivirus antigens may be selected from PrM, M, C, E, NS-1, NS-2a, NS2b, NS3, NS4a, NS4b, and NS5. Flavivirus antigens are preferably selected from PrM, M and E. Commercially available TBE vaccine include inactivated virus vaccines.

Pestivirus: Viral antigens may be derived from a Pestivirus, such as Bovine viral diarrhea (BVDV), Classical swine fever (CSFV) or Border disease (BDV).

Hepadnavirus: Viral antigens may be derived from a Hepadnavirus, such as Hepatitis B virus. Hepadnavirus antigens may be selected from surface antigens (L, M and S), core antigens (HBc, HBe). Commercially available HBV vaccines include subunit vaccines comprising the surface antigen S protein.

Hepatitis C virus: Viral antigens may be derived from a Hepatitis C virus (HCV). HCV antigens may be selected from one or more of E1, E2, E1/E2, NS345 polyprotein, NS 345-core polyprotein, core, and/or peptides from the nonstructural regions (Houghton et al., *Hepatology* (1991) 14:381).

Rhabdovirus: Viral antigens may be derived from a Rhabdovirus, such as a Lyssavirus (Rabies virus) and Vesiculovirus (VSV). Rhabdovirus antigens may be selected from glycoprotein (G), nucleoprotein (N), large protein (L), nonstructural proteins (NS). Commercially available Rabies virus vaccine comprise killed virus grown on human diploid cells or fetal rhesus lung cells.

Caliciviridae; Viral antigens may be derived from Caliciviridae, such as Norwalk virus, and Norwalk-like Viruses, such as Hawaii Virus and Snow Mountain Virus.

Coronavirus: Viral antigens may be derived from a Coronavirus, SARS, Human respiratory coronavirus, Avian infectious bronchitis (IBV), Mouse hepatitis virus (MHV), and Porcine transmissible gastroenteritis virus (TGEV). Coronavirus antigens may be selected from spike (S), envelope (E), matrix (M), nucleocapsid (N), and Hemagglutinin-esterase glycoprotein (HE). Preferably, the Coronavirus antigen is derived from a SARS virus. SARS viral antigens are described in WO 04/92360;

Retrovirus: Viral antigens may be derived from a Retrovirus, such as an Oncovirus, a Lentivirus or a Spumavirus. Oncovirus antigens may be derived from HTLV-1, HTLV-2 or HTLV-5. Lentivirus antigens may be derived from HIV-1 or HIV-2. Retrovirus antigens may be selected from gag, pol, env, tax, tat, rex, rev, nef, vif, vpu, and vpr. HIV antigens may be selected from gag (p24gag and p55gag), env (gp160 and gp41), pol, tat, nef, rev vpu, miniproteins, (preferably p55 gag and gp140v delete). HIV antigens may be derived from one or more of the following strains: $HIV_{IIIb}$, $HIV_{SF2}$, $HIV_{LAV}$, $HIV_{LA1}$, $HIV_{MN}$, $HIV-1_{CM235}$, $HIV-1_{US4}$.

Reovirus: Viral antigens may be derived from a Reovirus, such as an Orthoreovirus, a Rotavirus, an Orbivirus, or a Coltivirus. Reovirus antigens may be selected from structural proteins λ1, λ2, λ3, μ1, μ2, σ1, σ2, or σ3, or nonstructural proteins σNS, μNS, or σ1s. Preferred Reovirus antigens may be derived from a Rotavirus. Rotavirus antigens may be selected from VP1, VP2, VP3, VP4 (or the cleaved product VP5 and VP8), NSP 1, VP6, NSP3, NSP2, VP7, NSP4, or NSP5. Preferred Rotavirus antigens include VP4 (or the cleaved product VP5 and VP8), and VP7. See, e.g., WO 2005/021033, WO 2003/072716, WO 2002/11540, WO 2001/12797, WO 01/08495, WO 00/26380, WO 02/036172; herein incorporated by reference in their entireties.

Parvovirus: Viral antigens may be derived from a Parvovirus, such as Parvovirus B19. Parvovirus antigens may be selected from VP-1, VP-2, VP-3, NS-1 and NS-2. Preferably, the Parvovirus antigen is capsid protein VP-2.

Delta hepatitis virus (HDV): Viral antigens may be derived HDV, particularly δ-antigen from HDV (see, e.g., U.S. Pat. No. 5,378,814).

Hepatitis E-virus (HEV): Viral antigens may be derived from HEV.

Hepatitis G virus (HGV): Viral antigens may be derived from HGV.

Human Herpesvirus: Viral antigens may be derived from a Human Herpesvirus, such as Herpes Simplex Viruses (HSV), Varicella-zoster virus (VZV), Epstein-Barr virus (EBV), Cytomegalovirus (CMV), Human Herpesvirus 6 (HHV6), Human Herpesvirus 7 (HHV7), and Human Herpesvirus 8 (HHV8). Human Herpesvirus antigens may be selected from immediate early proteins (α), early proteins (β), and late proteins (γ). HSV antigens may be derived from HSV-1 or HSV-2 strains. HSV antigens may be selected from glycoproteins gB, gC, gD and gH, fusion protein (gB), or immune escape proteins (gC, gE, or gI). VZV antigens may be selected from core, nucleocapsid, tegument, or envelope proteins. A live attenuated VZV vaccine is commercially available. EBV antigens may be selected from early antigen (EA) proteins, viral capsid antigen (VCA), and glycoproteins of the membrane antigen (MA). CMV antigens may be selected from capsid proteins, envelope glycoproteins (such as gB and gH), and tegument proteins Papovaviruses: Antigens may be derived from Papovaviruses, such as Papillomaviruses and Polyomaviruses. Papillomaviruses include HPV serotypes 1, 2, 4, 5, 6, 8, 11, 13, 16, 18, 31, 33, 35, 39, 41, 42, 47, 51, 57, 58, 63 and 65. Preferably, HPV antigens are derived from serotypes 6, 11, 16 or 18. HPV antigens may be selected from capsid proteins (L1) and (L2), or E1-E7, or fusions thereof HPV antigens are preferably formulated into virus-like particles (VLPs). Polyomavirus viruses include BK virus and JK virus. Polyomavirus antigens may be selected from VP1, VP2 or VP3.

Further provided are antigens, compositions, methods, and microbes included in *Vaccines*, 4$^{th}$ Edition (Plotkin and Orenstein ed. 2004); *Medical Microbiology* 4$^{th}$ Edition (Murray et al. ed. 2002); Virology, 3rd Edition (W. K. Joklik ed. 1988); *Fundamental Virology*, 2nd Edition (B. N. Fields and D. M. Knipe, eds. 1991), which are contemplated in conjunction with the compositions of the present invention.

C. FUNGAL ANTIGENS

Fungal antigens for use in the invention may be derived from one or more of the fungi set forth below.

Fungal antigens may be derived from Dermatophytres, including: *Epidermophyton floccusum, Microsporum audouini, Microsporum canis, Microsporum distortum, Microsporum equinum, Microsporum gypsum, Microsporum nanum, Trichophyton concentricum, Trichophyton equinum, Trichophyton gallinae, Trichophyton gypseum, Trichophyton megnini, Trichophyton mentagrophytes, Trichophyton quinckeanum, Trichophyton rubrum, Trichophyton schoenleini, Trichophyton tonsurans, Trichophyton verrucosum, T. verrucosum* var. *album*, var. *discoides*, var. *ochraceum, Trichophyton violaceum*, and/or *Trichophyton faviforme*.

Fungal pathogens may be derived from *Aspergillus fumigatus, Aspergillus flavus, Aspergillus niger, Aspergillus nidulans, Aspergillus terreus, Aspergillus sydowi, Aspergillus flavatus, Aspergillus glaucus, Blastoschizomyces capitatus, Candida albicans, Candida enolase, Candida tropicalis, Candida glabrata, Candida krusei, Candida parapsilosis, Candida stellatoidea, Candida kusei, Candida parakwsei, Candida lusitaniae, Candida pseudotropicalis, Candida guilliermondi, Cladosporium carrionii, Coccidioides immitis, Blastomyces dermatidis, Cryptococcus neoformans, Geotrichum clavatum, Histoplasma capsulatum, Klebsiella pneumoniae, Paracoccidioides brasiliensis, Pneumocystis carinii, Pythiumn insidiosum, Pityrosporum ovale, Sacharomyces cerevisae, Saccharomyces boulardii, Saccharomyces pombe, Scedosporium apiosperum, Sporothrix schenckii, Trichosporon beigelii, Toxoplasma gondii, Penicillium marneffei, Malassezia* spp., *Fonsecaea* spp., *Wangiella* spp., *Sporothrix* spp., *Basidiobolus* spp., *Conidiobolus* spp., *Rhizopus* spp, *Mucor* spp, *Absidia* spp, *Mortierella* spp, *Cunninghamella* spp, *Saksenaea* spp., *Alternaria* spp, *Curvularia* spp, *Helminthosporium* spp, *Fusarium* spp, *Aspergillus* spp, *Penicillium* spp, *Monolinia* spp, *Rhizoctonia* spp, *Paecilomyces* spp, *Pithomyces* spp, and *Cladosporium* spp.

Processes for producing a fungal antigens are well known in the art (see U.S. Pat. No. 6,333,164). In a preferred method a solubilized fraction extracted and separated from an insoluble fraction obtainable from fungal cells of which cell wall has been substantially removed or at least partially removed, characterized in that the process comprises the steps of: obtaining living fungal cells; obtaining fungal cells of which cell wall has been substantially removed or at least partially removed; bursting the fungal cells of which cell wall has been substantially removed or at least partially removed;

obtaining an insoluble fraction; and extracting and separating a solubilized fraction from the insoluble fraction.

D. STD ANTIGENS

The compositions of the invention may include one or more antigens derived from a sexually transmitted disease (STD). Such antigens may provide for prophylactis or therapy for STD's such as chlamydia, genital herpes, hepatitis (such as HCV), genital warts, gonorrhoea, syphilis and/or chancroid (See, WO00/15255). Antigens may be derived from one or more viral or bacterial STD's. Viral STD antigens for use in the invention may be derived from, for example, HIV, herpes simplex virus (HSV-1 and HSV-2), human papillomavirus (HPV), and hepatitis (HCV). Bacterial STD antigens for use in the invention may be derived from, for example, *Neiserria gonorrhoeae*, *Chlamydia trachomatis*, *Treponema pallidum*, *Haemophilus ducreyi*, *E. coli*, and *Streptococcus agalactiae*. Examples of specific antigens derived from these pathogens are described above.

E. RESPIRATORY ANTIGENS

The compositions of the invention may include one or more antigens derived from a pathogen which causes respiratory disease. For example, respiratory antigens may be derived from a respiratory virus such as Orthomyxoviruses (influenza), Pneumovirus (RSV), Paramyxovirus (Hy), Morbillivirus (measles), Togavirus (Rubella), VZV, and Coronavirus (SARS). Respiratory antigens may be derived from a bacteria which causes respiratory disease, such as *Streptococcus pneumoniae*, *Pseudomonas aeruginosa*, *Bordetella pertussis*, *Mycobacterium tuberculosis*, *Mycoplasma pneumoniae*, *Chlamydia pneumoniae*, *Bacillus anthracis*, and *Moraxella catarrhalis*. Examples of specific antigens derived from these pathogens are described above.

F. PEDIATRIC VACCINE ANTIGENS

The compositions of the invention may include one or more antigens suitable for use in pediatric subjects. Pediatric subjects are typically less than about 3 years old, or less than about 2 years old, or less than about 1 years old. Pediatric antigens may be administered multiple times over the course of 6 months, 1, 2 or 3 years. Pediatric antigens may be derived from a virus which may target pediatric populations and/or a virus from which pediatric populations are susceptible to infection. Pediatric viral antigens include antigens derived from one or more of Orthomyxovirus (influenza), Pneumovirus (RSV), Paramyxovirus (PIV and Mumps), Morbillivirus (measles), Togavirus (Rubella), Enterovirus (polio), HBV, Coronavirus (SARS), and Varicella-zoster virus (VZV), Epstein Barr virus (EBV). Pediatric bacterial antigens include antigens derived from one or more of *Streptococcus pneumoniae*, *Neisseria meningitides*, *Streptococcus pyogenes* (Group A *Streptococcus*), *Moraxella catarrhalis*, *Bordetella pertussis*, *Staphylococcus aureus*, *Clostridium tetani* (Tetanus), *Cornynebacterium diphtheriae* (Diphtheria), *Haemophilus influenzae* B (Hib), *Pseudomonas aeruginosa*, *Streptococcus agalactiae* (Group B *Streptococcus*), and *E. coli*. Examples of specific antigens derived from these pathogens are described above.

G. ANTIGENS SUITABLE FOR USE IN ELDERLY OR IMMUNOCOMPROMISED INDIVIDUALS

The compositions of the invention may include one or more antigens suitable for use in elderly or immunocompromised individuals. Such individuals may need to be vaccinated more frequently, with higher doses or with adjuvanted formulations to improve their-immune response to the targeted antigens. Antigens which may be targeted for use in elderly or immunocompromised individuals include antigens derived from one or more of the following pathogens: *Neisseria meningitides*, *Streptococcus pneumoniae*, *Streptococcus pyogenes* (Group A *Streptococcus*), *Moraxella catarrhalis*, *Bordetella pertussis*, *Staphylococcus aureus*, *Staphylococcus epidermis*, *Clostridium tetani* (Tetanus), *Cornynebacterium diphtheriae* (Diphtheria), *Haemophilus influenzae* B (Hib), *Pseudomonas aeruginosa*, *Legionella pneumophila*, *Streptococcus agalactiae* (Group B *Streptococcus*), *Enterococcus faecalis*, *Helicobacter pylori*, *Clamydia pneumoniae*, Orthomyxovirus (influenza), Pneumovirus (RSV), Paramyxovirus (PTV and Mumps), Morbillivirus (measles), Togavirus (Rubella), Enterovirus (polio), HBV, Coronavirus (SARS), Varicella-zoster virus (VZV), Epstein Barr virus (EBV), Cytomegalovirus (CMV). Examples of specific antigens derived from these pathogens are described above.

H. ANTIGENS SUITABLE FOR USE IN ADOLESCENT VACCINES

The compositions of the invention may include one or more antigens suitable for use in adolescent subjects. Adolescents may be in need of a boost of a previously administered pediatric antigen. Pediatric antigens which may be suitable for use in adolescents are described above. In addition, adolescents may be targeted to receive antigens derived from an STD pathogen in order to ensure protective or therapeutic immunity before the beginning of sexual activity. STD antigens which may be suitable for use in adolescents are described above.

I. ANTIGEN FORMULATIONS

In other aspects of the invention, methods of producing microparticles having adsorbed antigens are provided. The methods comprise: (a) providing an emulsion by dispersing a mixture comprising (i) water, (ii) a detergent, (iii) an organic solvent, and (iv) a biodegradable polymer selected from the group consisting of a poly(α-hydroxy acid), a polyhydroxy butyric acid, a polycaprolactone, a polyorthoester, a polyanhydride, and a polycyanoacrylate. The polymer is typically present in the mixture at a concentration of about 1% to about 30% relative to the organic solvent, while the detergent is typically present in the mixture at a weight-to-weight detergent-to-polymer ratio of from about 0.00001:1 to about 0.1:1 (more typically about 0.0001:1 to about 0.1:1, about 0.001:1 to about 0.1:1, or about 0.005:1 to about 0.1:1); (b) removing the organic solvent from the emulsion; and (c) adsorbing an antigen on the surface of the microparticles. In certain embodiments, the biodegradable polymer is present at a concentration of about 3% to about 10% relative to the organic solvent.

Microparticles for use herein will be formed from materials that are sterilizable, non-toxic and biodegradable. Such materials include, without limitation, poly(α-hydroxy acid), polyhydroxybutyric acid, polycaprolactone, polyorthoester, polyanhydride, PACA, and polycyanoacrylate. Preferably, microparticles for use with the present invention are derived from a poly(α-hydroxy acid), in particular, from a poly(lactide) ("PLA") or a copolymer of D,L-lactide and glycolic acid, such as a poly(D,L-lactide-co-glycolide) ("PLG" or "PLGA"), or a copolymer of D,L-lactide and caprolactone. The microparticles may be derived from any of various polymeric starting materials which have a variety of molecular weights and, in the case of the copolymers such as PLG, a variety of lactide:glycolide ratios, the selection of which will be largely a matter of choice, depending in part on the coadministered macromolecule. These parameters are discussed more fully below.

Further antigens may also include an outer membrane vesicle (OMV) preparation. Additional formulation methods and antigens (especially tumor antigens) are provided in U.S. patent Ser. No. 09/581,772.

J. ANTIGEN REFERENCES

The following references include antigens useful in conjunction with the compositions of the present invention:
1 International patent application WO99/24578
2 International patent application WO99/36544.
3 International patent application WO99/57280.
4 International patent application WO00/22430.
5 Tettelin et al. (2000) Science 287:1809-1815.
6 International patent application WO96/29412.
7 Pizza et al. (2000) Science 287:1816-1820.
8 PCT WO 01/52885.
9 Bjune et al. (1991) Lancet 338(8775).
10 Fuskasawa et al. (1999) Vaccine 17:2951-2958.
11 Rosenqist et al. (1998) Dev. Biol. Strand 92:323-333.
12 Constantino et al. (1992) Vaccine 10:691-698.
13 Constantino et al. (1999) Vaccine 17:1251-1263.
14 Watson (2000) Pediatr Infect Dis J 19:331-332.
15 Rubin (20000) Pediatr Clin North Am 47:269-285, v.
16 Jedrzeja's (2001) Microbiol Mol Biol Rev 65:187-207.
17 International patent application filed on $3^{rd}$ July 2001 claiming priority from GB-0016363.4; WO 02/02606; PCT IB/01/00166.
18 Kalman et al. (1999) Nature Genetics 21:385-389.
19 Read et al. (2000) Nucleic Acids Res 28:1397-406.
20 Shirai et al. (2000) J. Infect. Dis 181(Suppl 3):S524-5527.
21 International patent application WO99/27105.
22 International patent application WO00/27994.
23 International patent application WO00/37494.
24 International patent application WO99/28475.
25 Bell (2000) Pediatr Infect Dis J 19:1187-1188.
26 Iwarson (1995) APMIS103:321-326.
27 Gerlich et al. (1990) Vaccine 8 Suppl:S63-68 & 79-80.
28 Hsu et al. (1999) Clin Liver Dis 3:901-915.
29 Gastofsson et al. (1996) N. Engl. J. Med. 334-:349-355.
30 Rappuoli et al. (1991) TIBTECH 9:232-238.
31 Vaccines (1988) eds. Plotkin & Mortimer. ISBN 0-7216-1946-0.
32 Del Guidice et al. (1998) Molecular Aspects of Medicine 19:1-70.
33 International patent application WO93/018150.
34 International patent application WO99/53310.
35 International patent application WO98/04702.
36 Ross et al. (2001) Vaccine 19:135-142.
37 Sutter et al. (2000) Pediatr Clin North Am 47:287-308.
38 Zimmerman & Spann (1999) Am Fan Physician 59:113-118, 125-126.
39 Dreensen (1997) Vaccine 15 Suppl" S2-6.
40 MMWR Morb Mortal Wkly rep 1998 January 16:47(1): 12, 9.
41 McMichael (2000) Vaccine 19 Suppl 1:S101-107.
42 Schuchat (1999) Lancer 353(9146):51-6.
43 GB patent applications 0026333.5, 0028727.6 & 0105640.7.
44 Dale (1999) Infect Disclin North Am 13:227-43, viii.
45 Ferretti et al. (2001) PNAS USA 98: 4658-4663.
46 Kuroda et al. (2001) Lancet 357(9264):1225-1240; see also pages 1218-1219.
47 Ramsay et al. (2001) Lancet 357(9251):195-196.
48 Lindberg (1999) Vaccine 17 Suppl 2:S28-36.
49 Buttery & Moxon (2000) J R Coil Physicians Long 34:163-168.
50 Ahmad & Chapnick (1999) Infect Dis Clin North Am 13:113-133, vii.
51 Goldblatt (1998) J. Med. Microbiol. 47:663-567.
52 European patent 0 477 508.
53 U.S. Pat. No. 5,306,492.
54 International patent application WO98/42721.
55 Conjugate Vaccines (eds. Cruse et al.) ISBN 3805549326, particularly vol. 10:48-114.
56 Hermanson (1996) Bioconjugate Techniques ISBN: 012323368 & 012342335X.
57 European patent application 0372501.
58 European patent application 0378881.
59 European patent application 0427347.
60 International patent application WO93/17712.
61 International patent application WO98/58668.
62 European patent application 0471177.
63 International patent application WO00/56360.
64 International patent application WO00/67161.

The contents of all of the above cited patents, patent applications and journal articles are incorporated by reference as if set forth fully herein.

The immunogenic compositions of the invention may be prepared in various forms. For example, the compositions may be prepared as injectables, either as liquid solutions or suspensions. Solid forms suitable for solution in, or suspension in, liquid vehicles prior to injection can also be prepared (e.g. a lyophilized composition or a spray-freeze dried composition). The composition may be prepared for topical administration e.g. as an ointment, cream or powder. The composition may be prepared for oral administration e.g. as a tablet or capsule, as a spray, or as a syrup (optionally flavoured) and/or a fast dissolving dosage form. The composition may be prepared for pulmonary administration e.g. as an inhaler, using a fine powder or a spray. The composition may be prepared as a suppository or pessary. The composition may be prepared for nasal, aural or ocular administration e.g. as drops. Preparation of such pharmaceutical compositions is within the general skill of the art. See, e.g., Remington's Pharmaceutical Sciences, Mack Publishing Company, Easton, Pa., 18th edition, 1990.

The composition may be in kit form, designed such that a combined composition is reconstituted just prior to administration to a patient. Such kits may comprise one or more Norovirus and/or Sapovirus antigens or nucleic acids encoding such antigens in liquid form, and any of the additional antigens and adjuvants as described herein.

Immunogenic compositions of the invention comprising polypeptide antigens or nucleic acid molecules are preferably vaccine compositions. The pH of such compositions preferably is between 6 and 8, preferably about 7. The pH can be maintained by the use of a buffer. The composition can be sterile and/or pyrogen-free. The composition can be isotonic with respect to humans. Vaccines according to the invention may be used either prophylactically or therapeutically, but will typically be prophylactic and can be used to treat animals (including companion and laboratory mammals), particularly humans.

Immunogenic compositions used as vaccines comprise an immunologically effective amount of antigen(s) and/or nucleic acids encoding antigen(s), as well as any other components, as needed. By 'immunologically effective amount', it is meant that the administration of that amount to an individual, either in a single dose or as part of a series, is effective for treatment or prevention. This amount varies depending upon the health and physical condition of the individual to be treated, age, the taxonomic group of individual to be treated (e.g. human, non-human primate, etc.), the capacity of the individual's immune system to synthesize antibodies, the degree of protection desired, the formulation of the vaccine, the treating doctor's assessment of the medical situation, and other relevant factors. It is expected that the amount will fall in a relatively broad range that can be determined through routine trials.

G. Administration

Compositions of the invention will generally be administered directly to a patient. Direct delivery may be accomplished by parenteral injection (e.g. subcutaneously, intraperitoneally, intravenously, intramuscularly, or to the interstitial space of a tissue), or mucosally, such as by rectal, oral (e.g. tablet, spray), vaginal, topical, transdermal (See e.g. WO99/27961) or transcutaneous (See e.g. WO02/074244 and WO02/064162), intranasal (See e.g. WO03/028760), ocular, aural, pulmonary or other mucosal administration Immunogenic compositions can also be administered topically by direct transfer to the surface of the skin. Topical administration can be accomplished without utilizing any devices, or by contacting naked skin with the immunogenic composition utilizing a bandage or a bandage-like device (see, e.g., U.S. Pat. No. 6,348,450).

Preferably the mode of administration is parenteral, mucosal or a combination of mucosal and parenteral immunizations. Even more preferably, the mode of administration is parenteral, mucosal or a combination of mucosal and parenteral immunizations in a total of 1-2 vaccinations 1-3 weeks apart. Preferably the route of administration includes but is not limited to oral delivery, intra-muscular delivery and a combination of oral and intra-muscular delivery.

It has already been demonstrated that mucosal and systemic immune responses to antigens, such as *Helicobacter pylori* antigens can be enhanced through mucosal priming followed by systemic boosting immunizations (see Vajdy et al (2003) Immunology 110: 86-94). In a preferred embodiment, the method for treating an infection by a Norovirus or Sapovirus, comprises mucosally administering to a subject in need thereof a first immunogenic composition comprising one or more Norovirus or Sapovirus antigens followed by parenterally administering a therapeutically effective amount of a second immunogenic composition comprising one or more Norovirus or Sapovirus antigens.

The immunogenic composition may be used to elicit systemic and/or mucosal immunity, preferably to elicit an enhanced systemic and/or mucosal immunity.

Preferably the immune response is characterized by the induction of a serum IgG and/or intestinal IgA immune response.

As noted above, prime-boost methods are preferably employed where one or more gene delivery vectors and/or polypeptide antigens are delivered in a "priming" step and, subsequently, one or more second gene delivery vectors and/or polypeptide antigens are delivered in a "boosting" step. In certain embodiments, priming and boosting with one or more gene delivery vectors or polypeptide antigens described herein is followed by additional boosting with one or more polypeptide-containing compositions (e.g., polypeptides comprising Norovirus and/or Sapovirus antigens).

In any method involving co-administration, the various compositions can be delivered in any order. Thus, in embodiments including delivery of multiple different compositions or molecules, the nucleic acids need not be all delivered before the polypeptides. For example, the priming step may include delivery of one or more polypeptides and the boosting comprises delivery of one or more nucleic acids and/or one or more polypeptides. Multiple polypeptide administrations can be followed by multiple nucleic acid administrations or polypeptide and nucleic acid administrations can be performed in any order. Thus, one or more of the gene delivery vectors described herein and one or more of the polypeptides described herein can be co-administered in any order and via any administration route. Therefore, any combination of polynucleotides and polypeptides described herein can be used to elicit an immune reaction.

Dosage Regime

Dosage treatment can be according to a single dose schedule or a multiple dose schedule. Multiple doses may be used in a primary immunization schedule and/or in a booster immunization schedule. In a multiple dose schedule, the various doses may be given by the same or different routes, e.g. a parenteral prime and mucosal boost, a mucosal prime and parenteral boost, etc.

Preferably the dosage regime enhances the avidity of the antibody response leading to antibodies with a neutralizing characteristic. An in-vitro neutralization assay may be used to test for neutralizing antibodies (see for example Asanaka et al (2005) J of Virology 102: 10327; Wobus et al (2004) PLOS Biology 2(12); e432; and Dubekti et al (2002) J Medical Virology 66: 400).

There is a strong case for a correlation between serum antibody levels and protection from disease caused by Norovirus and/or Saporovirus. For example, in multiple challenge studies, serum antibody levels were associated with protection after repeated (2-3) oral challenges with high doses of Norwalk virus (Journal of Infectious Disease (1990) 161:18). In another study, 18 of 23 infants without pre-existing antibodies developed gastroenteritis caused by human Caliciviruses, whereas 15 of 18 with pre-existing antibody levels did not become ill (Journal of Infectious Disease (1985). In yet another study, 47% of persons with a baseline Norwalk antibody titre of less than 1:100 developed Norwalk infection compared to 13% of persons with a baseline antibody titre of greater than 1:100 (p<0.001) (Journal of Infectious Disease (1985) 151: 99).

H. Tests to Determine the Efficacy of an Immune Response

One way of assessing efficacy of therapeutic treatment involves monitoring infection after administration of a composition of the invention. One way of assessing efficacy of prophylactic treatment involves monitoring immune responses against the antigens in the compositions of the invention after administration of the composition.

Another way of assessing the immunogenicity of the component proteins of the immunogenic compositions of the present invention is to express the proteins recombinantly and to screen patient sera or mucosal secretions by immunoblot. A positive reaction between the protein and the patient serum indicates that the patient has previously mounted an immune response to the protein in question—that is, the protein is an immunogen. This method may also be used to identify immunodominant proteins and/or epitopes.

Another way of checking efficacy of therapeutic treatment involves monitoring infection after administration of the compositions of the invention. One way of checking efficacy of prophylactic treatment involves monitoring immune responses both systemically (such as monitoring the level of IgG1 and IgG2a production) and mucosally (such as monitoring the level of IgA production) against the antigens in the compositions of the invention after administration of the composition. Typically, serum specific antibody responses are determined post-immunization but pre-challenge whereas mucosal specific antibody body responses are determined post-immunization and post-challenge.

The immunogenic compositions of the present invention can be evaluated in in vitro and in vivo animal models prior to host, e.g., human, administration. Particularly useful mouse models include those in which intraperitoneal immunization is followed by either intraperitoneal challenge or intranasal challenge.

The efficacy of immunogenic compositions of the invention can also be determined in vivo by challenging animal models of infection, e.g., guinea pigs or mice or rhesus macaques, with the immunogenic compositions. The immunogenic compositions may or may not be derived from the same strains as the challenge strains. Preferably the immunogenic compositions are derivable from the same strains as the challenge strains.

In vivo efficacy models include but are not limited to: (i) A murine infection model using human strains; (ii) a murine disease model which is a murine model using a mouse-adapted strain, such as strains which are particularly virulent in mice and (iii) a primate model using human isolates. A human challenge model, which is supported by the NIH and Center for Disease Control (CDC) is also available (see for example, Lindesmith et al (2003) Nature Medicine 9: 548-553 and Journal of Virology (2005) 79: 2900).

The immune response may be one or both of a TH1 immune response and a TH2 response. The immune response may be an improved or an enhanced or an altered immune response. The immune response may be one or both of a systemic and a mucosal immune response. Preferably the immune response is an enhanced systemic and/or mucosal response.

An enhanced systemic and/or mucosal immunity is reflected in an enhanced TH1 and/or TH2 immune response. Preferably, the enhanced immune response includes an increase in the production of IgG1 and/or IgG2a and/or IgA. Preferably the mucosal immune response is a TH2 immune response. Preferably, the mucosal immune response includes an increase in the production of IgA.

Activated TH2 cells enhance antibody production and are therefore of value in responding to extracellular infections. Activated TH2 cells may secrete one or more of IL-4, IL-5, IL-6, and IL-10. A TH2 immune response may result in the production of IgG1, IgE, IgA and memory B cells for future protection.

A TH2 immune response may include one or more of an increase in one or more of the cytokines associated with a TH2 immune response (such as IL-4, IL-5, IL-6 and IL-10), or an increase in the production of IgG1, IgE, IgA and memory B cells. Preferably, the enhanced TH2 immune response will include an increase in IgG1 production.

A TH1 immune response may include one or more of an increase in CTLs, an increase in one or more of the cytokines associated with a TH1 immune response (such as IL-2, IFNγ, and TNFβ), an increase in activated macrophages, an increase in NK activity, or an increase in the production of IgG2a. Preferably, the enhanced TH1 immune response will include an increase in IgG2a production.

Immunogenic compositions of the invention, in particular, immunogenic composition comprising one or more antigens of the present invention may be used either alone or in combination with other antigens optionally with an immunoregulatory agent capable of eliciting a Th1 and/or Th2 response.

The invention also comprises an immunogenic composition comprising one or more immunoregulatory agent, such as a mineral salt, such as an aluminium salt and an oligonucleotide containing a CpG motif. Most preferably, the immunogenic composition includes both an aluminium salt and an oligonucleotide containing a CpG motif. Alternatively, the immunogenic composition includes an ADP ribosylating toxin, such as a detoxified ADP ribosylating toxin and an oligonucleotide containing a CpG motif. Preferably, the one or more immunoregulatory agents include an adjuvant. The adjuvant may be selected from one or more of the group consisting of a TH1 adjuvant and TH2 adjuvant, further discussed above.

The immunogenic compositions of the invention will preferably elicit both a cell mediated immune response as well as a humoral immune response in order to effectively address an infection. This immune response will preferably induce long lasting (e.g., neutralizing) antibodies and a cell mediated immunity that can quickly respond upon exposure to one or more infectious antigens. By way of example, evidence of neutralizing antibodies in patients blood samples is considered as a surrogate parameter for protection since their formation is of decisive importance for virus elimination in TBE infections (see Kaiser and Holzmann (2000) Infection 28; 78-84).

I. Use of the Immunogenic Compositions as Medicaments

The invention also provides a composition of the invention for use as a medicament. The medicament is preferably able to raise an immune response in a mammal (i.e. it is an immunogenic composition) and is more preferably a vaccine. The invention also provides the use of the compositions of the invention in the manufacture of a medicament for raising an immune response in a mammal. The medicament is preferably a vaccine. Preferably the vaccine is used to prevent and/or treat an intestinal infection such as gastroenteritis, preferably acute gastroenteritis. The gastroenteritis may result from an imbalance in ion and/or water transfer resulting in both watery diarrhea and/or intestinal peristalisis and/or motility (vomiting).

The invention provides methods for inducing or increasing an immune response using the compositions described above. The immune response is preferably protective and can include antibodies and/or cell-mediated immunity (including systemic and mucosal immunity). Immune responses include booster responses.

The invention also provides a method for raising an immune response in a mammal comprising the step of administering an effective amount of a composition of the invention. The immune response is preferably protective and preferably involves antibodies and/or cell-mediated immunity. Preferably, the immune response includes one or both of a TH1 immune response and a TH2 immune response. The method may raise a booster response.

The mammal is preferably a human. Where the immunogenic composition, preferably a vaccine is for prophylactic use, the human is preferably a child (e.g. a toddler or infant, preferably pre-school, preferably one year or less or from three years (preferably 1-4 years) onwards) or a teenager; where the vaccine is for therapeutic use, the human is preferably a teenager or an adult. A vaccine intended for children may also be administered to adults e.g. to assess safety, dosage, immunogenicity, etc. Preferably, the human is a teenager. More preferably, the human is a pre-adolescent teenager. Even more preferably, the human is a pre-adolescent female or male. Preferably the pre-adolescent male or female is around 9-12 years of age. Preferably the adolescent male or female is around 15-19 years of age. Preferably the male or female is around 20-49 years of age. Preferably the male or female is over 49 years of age. Preferably the human is elderly, preferably around 60-80 years of age.

Other target groups for the immunogenic compositions (e.g., vaccines) of the present invention include: transplant and immunocompromised individuals; Adults and children in USA, Canada and Europe including but not limited to the following:

Food handlers;

Healthcare workers such as but not limited to Hospital and Nursing home personnel;

Day care children;

Travellers including cruise ship travelers;

Military personnel; and

Paediatric and/or elderly populations as discussed above.

J. Kits

The invention also provides kits comprising one or more containers of compositions of the invention. Compositions can be in liquid form or can be lyophilized, as can individual antigens. Suitable containers for the compositions include, for example, bottles, vials, syringes, and test tubes. Containers can be formed from a variety of materials, including glass or plastic. A container may have a sterile access port (for example, the container may be an intravenous solution bag or a vial having a stopper pierceable by a hypodermic injection needle).

The kit can further comprise a second container comprising a pharmaceutically-acceptable buffer, such as phosphate-buffered saline, Ringer's solution, or dextrose solution. It can also contain other materials useful to the end-user, including other pharmaceutically acceptable formulating solutions such as buffers, diluents, filters, needles, and syringes or other delivery device. The kit may further include a third component comprising an adjuvant.

The kit can also comprise a package insert containing written instructions for methods of inducing immunity or for treating infections. The package insert can be an unapproved draft package insert or can be a package insert approved by the Food and Drug Administration (FDA) or other regulatory body.

The invention also provides a delivery device pre-filled with the immunogenic compositions of the invention.

K. Methods of Producing Norovirus or Sapovirus-Specific Antibodies

The Norovirus and Sapovirus polypeptides described herein can be used to produce Norovirus or Sapovirus-specific polyclonal and monoclonal antibodies that specifically bind to Norovirus or Sapovirus antigens, respectively. Polyclonal antibodies can be produced by administering a Norovirus or Sapovirus polypeptide to a mammal, such as a mouse, a rabbit, a goat, or a horse. Serum from the immunized animal is collected and the antibodies are purified from the plasma by, for example, precipitation with ammonium sulfate, followed by chromatography, preferably affinity chromatography. Techniques for producing and processing polyclonal antisera are known in the art.

Monoclonal antibodies directed against Norovirus or Sapovirus-specific epitopes present in the polypeptides can also be readily produced. Normal B cells from a mammal, such as a mouse, immunized with a Norovirus or Sapovirus polypeptide, can be fused with, for example, HAT-sensitive mouse myeloma cells to produce hybridomas. Hybridomas producing Norovirus or Sapovirus-specific antibodies can be identified using RIA or ELISA and isolated by cloning in semi-solid agar or by limiting dilution. Clones producing Norovirus or Sapovirus-specific antibodies are isolated by another round of screening.

Antibodies, either monoclonal and polyclonal, which are directed against Norovirus or Sapovirus epitopes, are particularly useful for detecting the presence of Norovirus or Sapovirus antigens in a sample, such as a serum sample from a Norovirus or Sapovirus-infected human. An immunoassay for a Norovirus or Sapovirus antigen may utilize one antibody or several antibodies. An immunoassay for a Norovirus or Sapovirus antigen may use, for example, a monoclonal antibody directed towards a Norovirus or Sapovirus epitope, a combination of monoclonal antibodies directed towards epitopes of one Norovirus or Sapovirus polypeptide, monoclonal antibodies directed towards epitopes of different Norovirus or Sapovirus polypeptides, polyclonal antibodies directed towards the same Norovirus or Sapovirus antigen, polyclonal antibodies directed towards different Norovirus or Sapovirus antigens, or a combination of monoclonal and polyclonal antibodies. Immunoassay protocols may be based, for example, upon competition, direct reaction, or sandwich type assays using, for example, labeled antibody. The labels may be, for example, fluorescent, chemiluminescent, or radioactive.

The polyclonal or monoclonal antibodies may further be used to isolate Norovirus or Sapovirus particles or antigens by immunoaffinity columns. The antibodies can be affixed to a solid support by, for example, adsorption or by covalent linkage so that the antibodies retain their immunoselective activity. Optionally, spacer groups may be included so that the antigen binding site of the antibody remains accessible. The immobilized antibodies can then be used to bind Norovirus or Sapovirus particles or antigens from a biological sample, such as blood or plasma. The bound Norovirus or Sapovirus particles or antigens are recovered from the column matrix by, for example, a change in pH.

L. Norovirus and Sapovirus Specific T Cells

Norovirus or Sapovirus-specific T cells, which are activated by the above-described immunogenic polypeptides, polyproteins, multiepitope fusion proteins, or VLPs expressed in vivo or in vitro, preferably recognize an epitope of a Norovirus or Sapovirus polypeptide, such as a VP1 or VP2 polypeptide or a nonstructural polypeptide. Norovirus or Sapovirus-specific T cells can be $CD8^+$ or $CD4^+$.

Norovirus or Sapovirus-specific $CD8^+$ T cells can be cytotoxic T lymphocytes (CTL) which can kill Norovirus or Sapovirus-infected cells that display any of these epitopes complexed with an MHC class I molecule. Norovirus or Sapovirus-specific $CD8^+$ T cells can be detected by, for example, $^{51}Cr$ release assays (see Example 4). $^{51}Cr$ release assays measure the ability of Norovirus or Sapovirus-specific $CD8^+$ T cells to lyse target cells displaying one or more of these epitopes. Norovirus or Sapovirus-specific $CD8^+$ T cells which express antiviral agents, such as IFN-γ, are also contemplated herein and can also be detected by immunological methods, preferably by intracellular staining for IFN-γ or like cytokine after in vitro stimulation with one or more of the Norovirus or Sapovirus polypeptides, such as but not limited to a VP1, VP2, VP10, or nonstructural polypeptide, (see Example 5).

Norovirus or Sapovirus-specific $CD4^+$ T cells can be detected by a lymphoproliferation assay (see Example 6). Lymphoproliferation assays measure the ability of Norovirus or Sapovirus-specific $CD4^+$ T cells to proliferate in response to, e.g., a VP1, VP2, VP10, and/or a nonstuctural polypeptide epitope.

Methods of Activating Norovirus or Sapovirus-Specific T Cells

The Norovirus or Sapovirus polynucleotides and/or immunogenic polypeptides, polyproteins, and/or multiepitope fusion proteins can be used to activate Norovirus or Sapovirus-specific T cells either in vitro or in vivo. Activation of Norovirus or Sapovirus-specific T cells can be used, inter alia, to provide model systems to optimize CTL responses to Norovirus or Sapovirus and to provide prophylactic or therapeutic treatment against Norovirus or Sapovirus infection. For in vitro activation, proteins are preferably supplied to T cells via a plasmid or a viral vector, such as an adenovirus vector, as described above.

Polyclonal populations of T cells can be derived from the blood, and preferably from peripheral lymphoid organs, such as lymph nodes, spleen, or thymus, of mammals that have been infected with a Norovirus or Sapovirus. Preferred mammals include mice, chimpanzees, baboons, and humans. Infection with Norovirus or Sapovirus serves to expand the number of activated Norovirus or Sapovirus-specific T cells in the mammal. The Norovirus or Sapovirus-specific T cells derived from the mammal can then be restimulated in vitro by adding, a Norovirus or Sapovirus immunogenic polypeptide, polyprotein, and/or multiepitope fusion protein. The Norovirus or Sapovirus-specific T cells can then be tested for, inter alia, proliferation, the production of IFN-γ, and the ability to lyse target cells displaying, for example, VP1, VP2, VP10, or nonstructural polypeptide epitopes in vitro.

In a lymphoproliferation assay (see Example 6), Norovirus or Sapovirus-activated $CD4^+$ T cells proliferate when cultured with a Norovirus or Sapovirus immunogenic polypeptide, polyprotein, and/or multiepitope fusion protein, but not in the absence of such an immunogenic polypeptide. Thus, particular Norovirus or Sapovirus epitopes, such as derived from VP1, VP2, VP10, and nonstructural polypeptides, and fusions of these epitopes that are recognized by Norovirus or Sapovirus-specific $CD4^+$ T cells can be identified using a lymphoproliferation assay.

Similarly, detection of IFN-γ in Norovirus or Sapovirus-specific CD4+ and/or $CD8^+$ T cells after in vitro stimulation with the above-described immunogenic polypeptides, can be used to identify, for example, epitopes, such as but not limited to VP1, VP2, VP10, and nonstructural polypeptides, and fusions of these epitopes that are particularly effective at stimulating CD4+ and/or $CD8^+$ T cells to produce IFN-γ (see Example 5).

Further, $^{51}Cr$ release assays are useful for determining the level of CTL response to Norovirus or Sapovirus. See Cooper et al. Immunity 10:439-449. For example, Norovirus or Sapovirus-specific $CD8^+$ T cells can be derived from the liver of an Norovirus or Sapovirus infected mammal. These T cells can be tested in $^{51}Cr$ release assays against target cells displaying, e.g., VP1, VP2, VP10, and nonstructural polypeptides epitopes. Several target cell populations expressing different VP1, VP2, VP10, and nonstructural polypeptides epitopes can be constructed so that each target cell population displays different epitopes of VP1, VP2, VP10, and nonstructural polypeptides. The Norovirus or Sapovirus-specific $CD8^+$ cells can be assayed against each of these target cell populations. The results of the $^{51}Cr$ release assays can be used to determine which epitopes of VP1, VP2, VP10, and nonstructural polypeptides are responsible for the strongest CTL response to Norovirus or Sapovirus.

Norovirus or Sapovirus immunogenic polypeptides, polyproteins, multiepitope fusion proteins, and/or VLPs as described above, and/or polynucleotides encoding such polypeptides, can be administered to a mammal, such as a mouse, baboon, chimpanzee, or human, to activate Norovirus or Sapovirus-specific T cells in vivo. Administration can be by any means known in the art, including parenteral, intranasal, intramuscular or subcutaneous injection, including injection using a biological ballistic gun ("gene gun"), as discussed above.

Preferably, injection of a Norovirus or Sapovirus polynucleotide is used to activate T cells. In addition to the practical advantages of simplicity of construction and modification, injection of the polynucleotides results in the synthesis of immunogenic polypeptide in the host. Thus, these immunogens are presented to the host immune system with native post-translational modifications, structure, and conformation. The polynucleotides are preferably injected intramuscularly to a large mammal, such as a human, at a dose of 0.5, 0.75, 1.0, 1.5, 2.0, 2.5, 5 or 10 mg/kg.

A composition of the invention comprising a Norovirus or Sapovirus immunogenic polypeptide, VLP, or polynucleotide is administered in a manner compatible with the particular composition used and in an amount which is effective to activate Norovirus or Sapovirus-specific T cells as measured by, inter alia, a $^{51}Cr$ release assay, a lymphoproliferation assay, or by intracellular staining for IFN-γ. The proteins and/or polynucleotides can be administered either to a mammal which is not infected with a Norovirus or Sapovirus or can be administered to a Norovirus or Sapovirus-infected mammal. The particular dosages of the polynucleotides or fusion proteins in a composition will depend on many factors including, but not limited to the species, age, and general condition of the mammal to which the composition is administered, and the mode of administration of the composition. An effective amount of the composition of the invention can be readily determined using only routine experimentation. In vitro and in vivo models described above can be employed to identify appropriate doses. The amount of polynucleotide used in the example described below provides general guidance which can be used to optimize the activation of Norovirus or Sapovirus-specific T cells either in vivo or in vitro. Generally, 0.5, 0.75, 1.0, 1.5, 2.0, 2.5, 5 or 10 mg of a Norovirus or Sapovirus polypeptide or polynucleotide, will be administered to a large mammal, such as a baboon, chimpanzee, or human. If desired, co-stimulatory molecules or adjuvants can also be provided before, after, or together with the compositions.

Immune responses of the mammal generated by the delivery of a composition of the invention, including activation of Norovirus or Sapovirus-specific T cells, can be enhanced by varying the dosage, route of administration, or boosting regimens. Compositions of the invention may be given in a single dose schedule, or preferably in a multiple dose schedule in which a primary course of vaccination includes 1-10 separate doses, followed by other doses given at subsequent time intervals required to maintain and/or reinforce an immune response, for example, at 1-4 months for a second dose, and if needed, a subsequent dose or doses after several months.

III. EXPERIMENTAL

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

Example 1

Expression of Norwalk Virus Capsid Protein in Yeast

Constructs for production of Norwalk virus (NV) VLPs in *Saccharomyces cerevisiae* were created by cloning sequences encoding viral capsid proteins into the yeast expression vector pBS24.1. The pBS24.1 vector is described in detail in commonly owned U.S. patent application Ser. No. 382,805, filed Jul. 19, 1989, which application is hereby incorporated by reference in its entirety herein. The pBS24.1 vector contains the 2μ sequence for autonomous replication in yeast and the yeast genes leu2d and URA3 as selectable markers. The β-lactamase gene and the ColE1 origin of replication, required for plasmid replication in bacteria, are also present in this expression vector. Regulation of expression was put under the control of a hybrid ADH2/GAPDH promoter (described in U.S. Pat. No. 6,183,985) and an alpha-factor terminator.

The constructs created and utilized for expression of NV capsid proteins included: NV .orf2 comprising a modified polynucleotide sequence of orf2 (SEQ ID NO:1) and NV .orf2+3 comprising modified polynucleotide sequences of orf2 and orf3 (SEQ ID NO:2). The coding sequences for orf2 (major capsid gene) and orf2+3 were generated using synthetic oligonucleotides, based on the DNA sequence from GenBank accession number M87661. A number of silent mutations were introduced into orf2 and orf3 to facilitate the cloning of NV .orf2 and NV .orf2+3 in the expression vector (FIG. 1).

The full-length orf2+3 coding and 3'UTR sequence was divided into four domains as follows (FIG. 2):

Domain 1 ("5p") encodes a 5' HindIII cloning site followed by the sequence ACAAAACAAA (SEQ ID NO:27), the initiator ATG, and the first 154 amino acids of the capsid protein, ending with a unique XbaI cloning site.

Domain 2 ("mid") encodes the next 175 amino acids, from the XbaI site to a unique AseI cloning site.

Domain 3 ("3p") encodes the final 200 amino acids for orf2, from AseI to a unique Bspe1 site near the end of the orf2 coding sequence, then followed by two stop codons and a SalI cloning site.

Domain 4 ("orf3") includes the following: a unique BspE1 site, a stop codon, a frame-shift/reinitiation codon that subsequently begins the translation of orf3 (212 amino acids), 66 bp of 3' UTR, and finally a SalI cloning site.

The oligonucleotides for each domain were engineered to include EcoR1 and SalI sites at the 5' and 3' ends, flanking the unique cloning sites described above. Then the kinased, annealed oligos for each domain were ligated into a pUC19 EcoR1/SalI subcloning vector (FIG. 3). After transformation into HB101 competent cells (commercially available), miniscreen analysis and sequence verification, the clones with the correct sequence were identified as follows and amplified:
pUC19.NV.5p #4
pUC19.NV.mid #11 and #13
pUC19.NV.3p #22
pUC19.NV .orf3 #31

To assemble the full-length NV .orf2 as a HindIII/SalI fragment, a series of digests were performed: pUC19.NV.5p #13 was digested with HindIII and XbaI to isolate a 478 bp fragment; pUC19.NV.mid #13 was digested with XbaI and PciI to isolate a 393 bp fragment; pUC19.NV.mid #11 was digested with PciI and AseI to isolate a 133 bp fragment; and pUC19.NV.3p #22 was digested with AseI and SalI to isolate a 609 bp fragment. All four fragments were gel purified and ligated into the pSP72 HindIII/SalI vector, to create a 1613 bp HindIII-SalI insert for the coding sequence of NV .orf2 (FIGS. 3 and 4).

Figure 5:
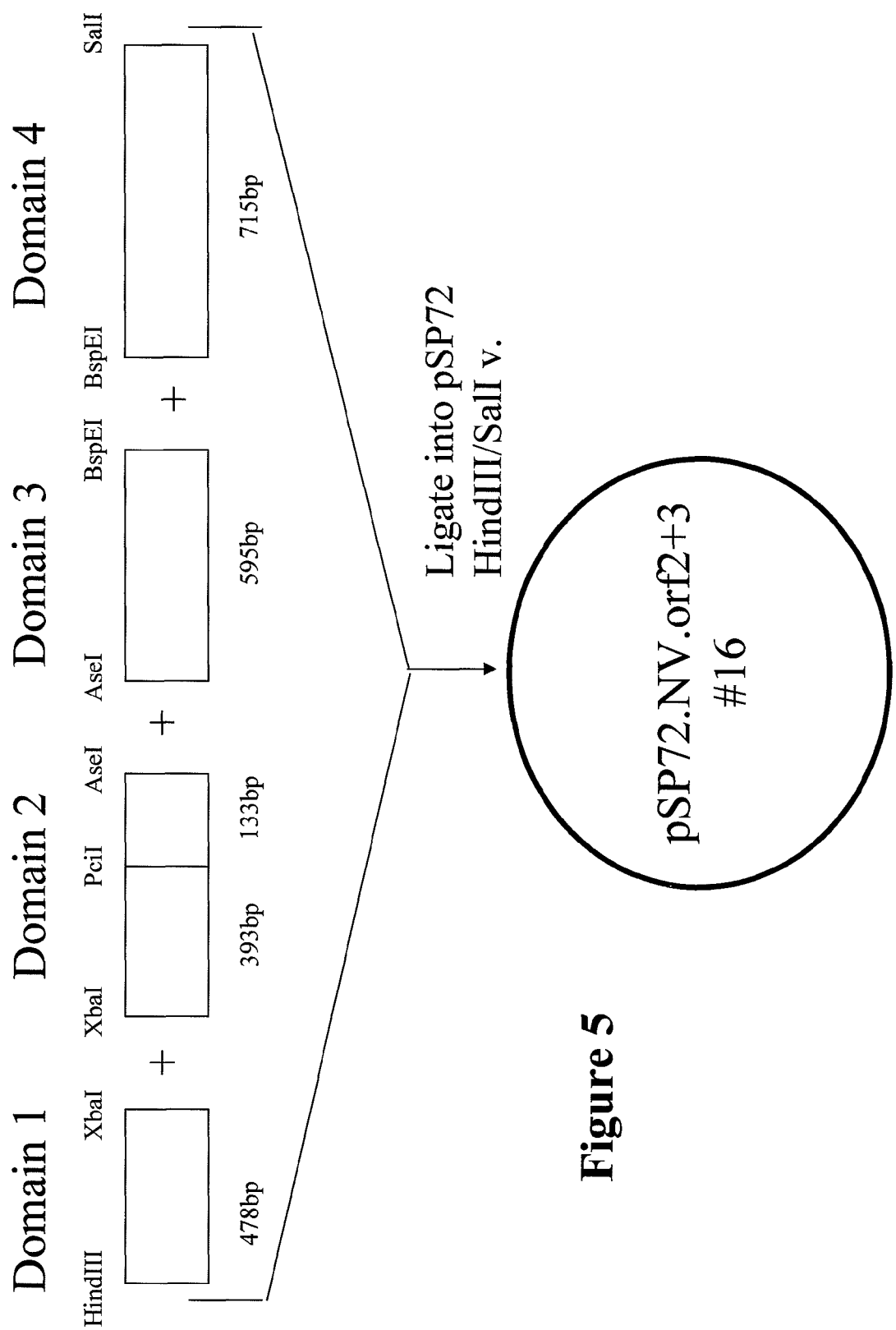
FIG. 5 depicts a schematic diagram illustrating the assembly of the NV .orf2+3 construct from oligonucleotide fragments. The full-length NV .orf2+3 construct was assembled by ligating the HindIII/XbaI, XbaI/PciI, and PciI/AseI fragments shown with a 595 bp gel purified fragment obtained from digesting pUC19.NV .3p #22 with AseI and BspE1, and a gel purified BspEI/SalI fragment of 715 bp, obtained from pUC19.NV .orf3 #31, into the pSP72 HindIII/SalI vector (see Example 1).
Figure 6:
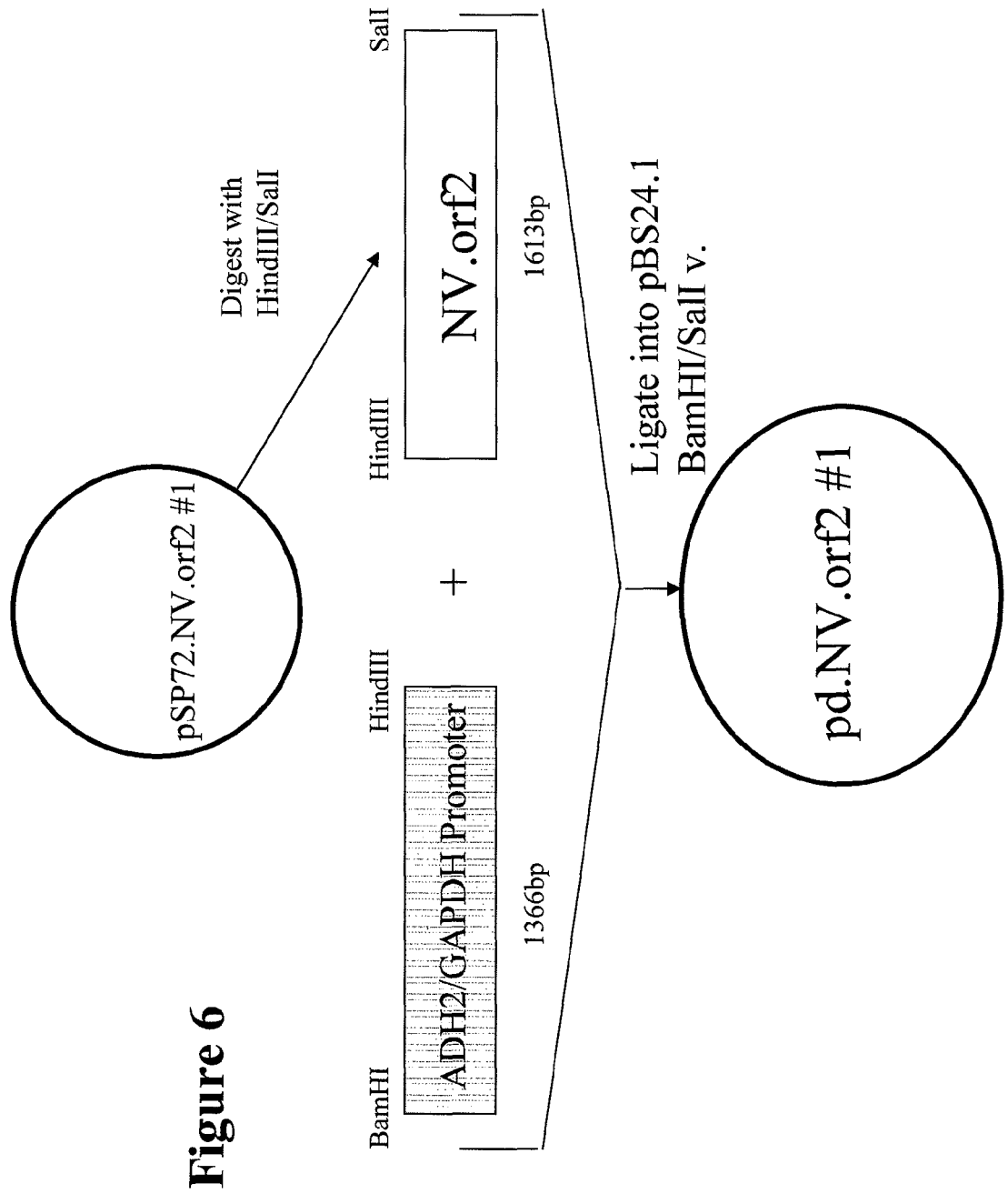
FIG. 6 depicts a schematic diagram illustrating the subcloning of the full-length pSP72.NV .orf2 #1 into the pBS24.1 vector to produce the pd.NV .orf2#1 construct for expression in yeast. A 1613 bp NV .orf2 fragment, obtained by digestion with the restriction enzymes HindIII and SalI, was gel isolated and purified. This fragment was ligated with the BamHI/HindIII ADH2/GAPDH yeast hybrid promoter of 1366 bp into the pBS24.1 BamHI/SalI yeast expression vector, as described in Example 1.
Figure 7:
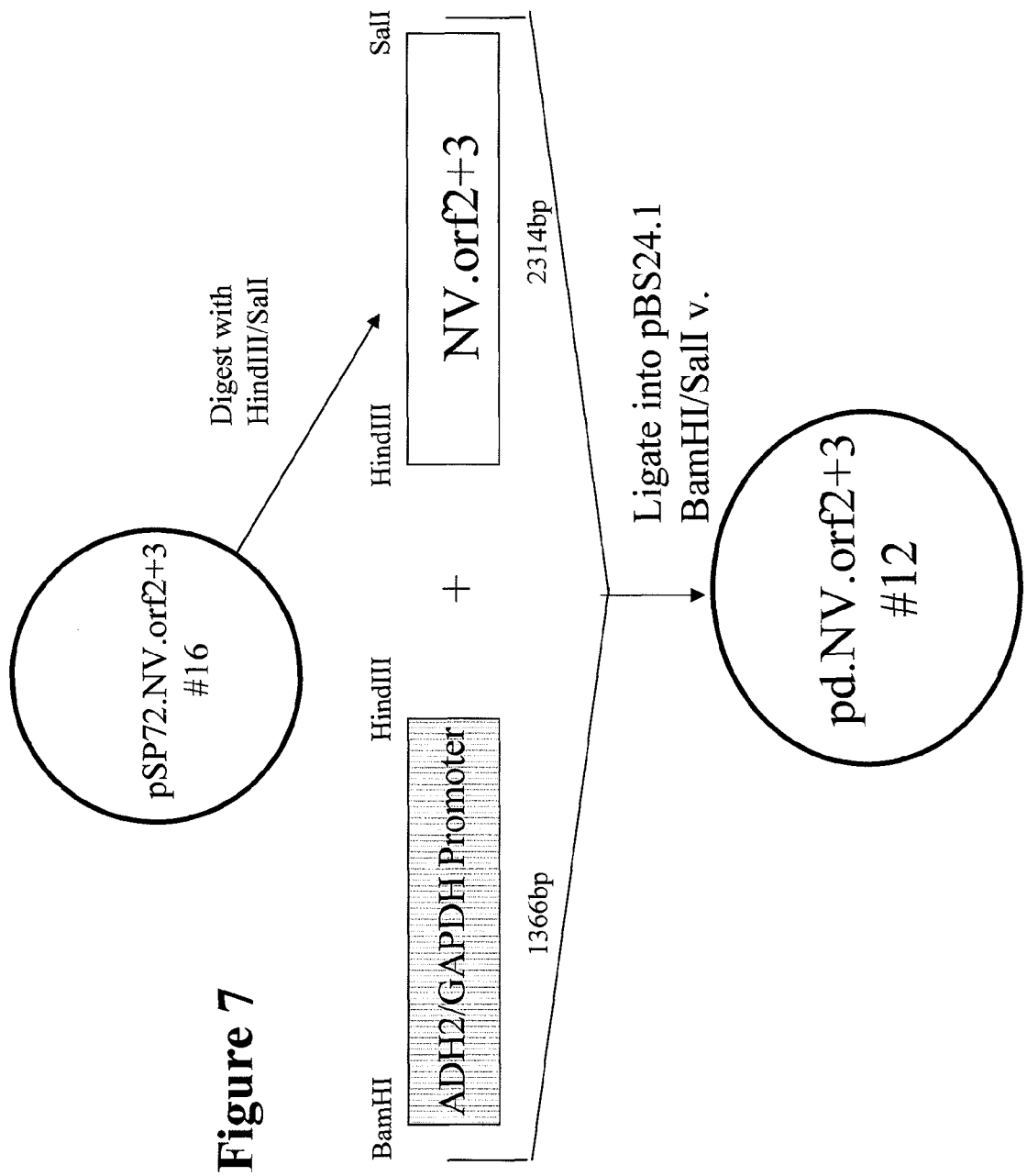
FIG. 7 depicts a schematic diagram illustrating the subcloning of the full-length pSP72.NV .orf2+3 #16 into the pBS24.1 vector to produce the pd.NV .orf2+3#12 construct for expression in yeast. A 2314 bp NV .orf2+3 fragment, obtained by digestion with the restriction enzymes HindIII and SalI, was gel isolated and purified. This fragment was ligated with the BamHI/HindIII ADH2/GAPDH yeast hybrid promoter of 1366 bp into the pBS24.1 BamHI/SalI yeast expression vector, as described in Example 1.

The full-length NV .orf2+3 coding sequence was assembled by ligating the HindIII/XbaI, XbaI/PciI, and PciI/AseI fragments (described above) with a 595 bp gel purified fragment obtained from digesting pUC19.NV.3p #22 with AseI and BspE1, and a gel purified BspEI/SalI fragment of 715 bp, obtained from pUC19.NV .orf3 #31, into the pSP72 HindIII/SalI vector (FIG. 5). After transformation into HB101 and miniscreen analysis, the full-length subclones pSP72.NV .orf2 #1 and pSP72.NV .orf2+3 #16 were obtained. The 1613 bp HindIII/SalI NV .orf2 fragment and the 2314 bp NV .orf2+3 fragment were gel isolated and purified after restriction digestion of the respective pSP72 subclones. Each HindIII-SalI fragment was ligated with the BamHI/HindIII ADH2/GAPDH yeast hybrid promoter of 1366 bp into the pBS24.1 BamHI/SalI yeast expression vector, containing the elements described above. After HB101 transformation and miniscreen analysis, the following yeast expression plasmids were identified and amplified: pd.NV .orf2 #1 and pd.NV .orf2+3 #12 (FIGS. 6 and 7).

Figure 8:
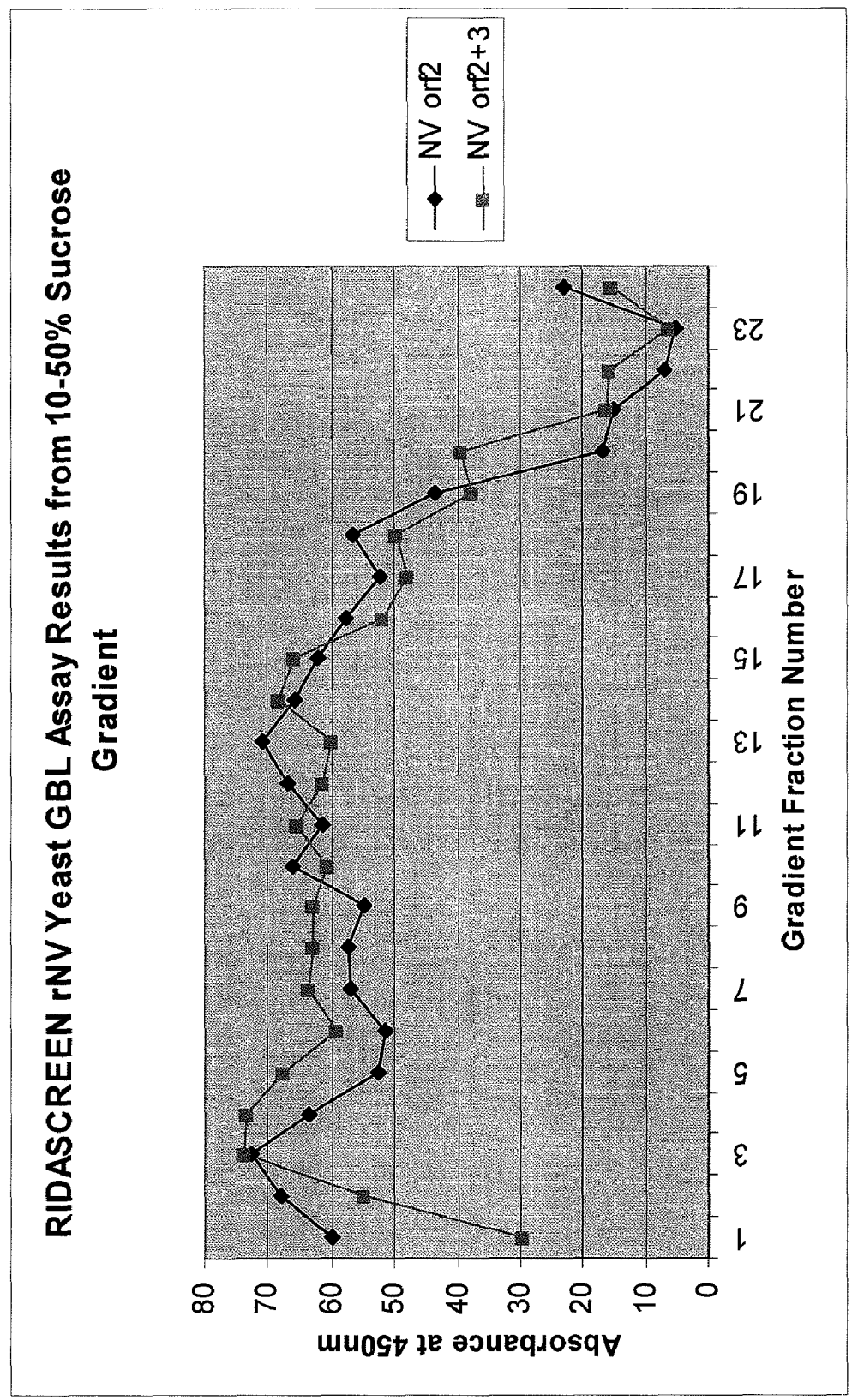
FIG. 8 depicts results from expression of recombinant Norwalk virus antigens in yeast. The expression plasmids, pd.NV .orf2 #1 and pd.NV .orf2+3 #12, were expressed in S. cerevisiae strain AD3 [matα, leu2Δ, trp1, ura3-52, prb-1122, pep4-3, prc1-407, cir°, trp+, ::DM15[GAP/ADR]. Cell lysates were subjected to sucrose gradient sedimentation, and the recombinant proteins in collected fractions were detected using the RIDASCREEN Norovirus immunoassay (SciMedx Corporation).
Figure 9:
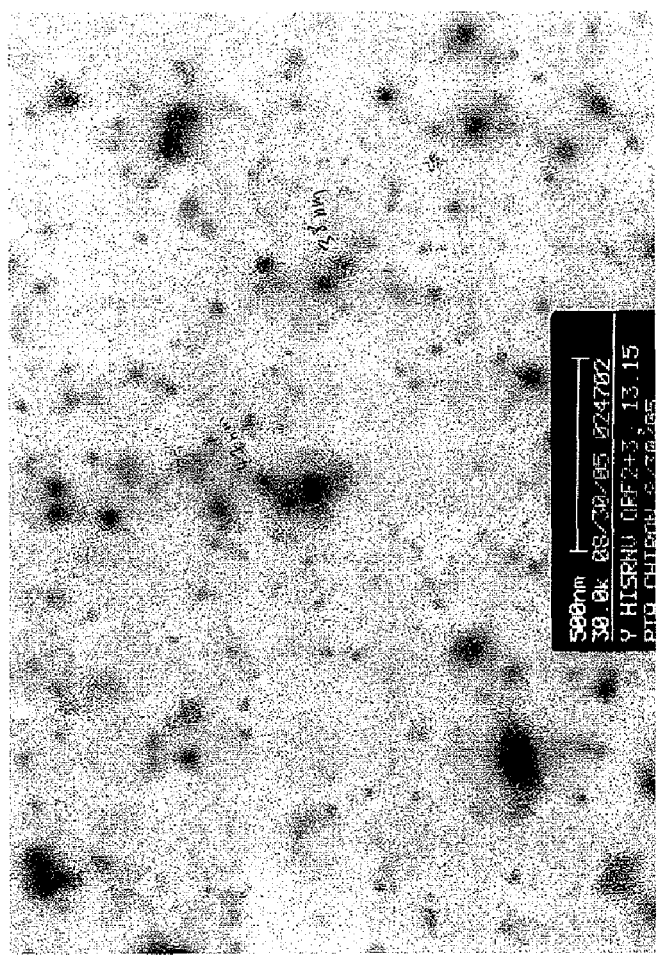
FIG. 9 shows an electron micrograph of recombinant Norovirus particles produced by expression of pd.NV .orf2+3 #12 in yeast.

S. cerevisiae strain AD3 [matα, leu2Δ, trp1, ura3-52, prb-1122, pep4-3, prc1-407, cir°, trp+, ::DM15[GAP/ADR] was transformed with the expression plasmids pd.NV .orf2 #1 and pd.NV .orf2+3 #12 using a lithium acetate protocol (Invitrogen EasyComp). After transformation, several Ura-transformants were streaked onto Ura-8% glucose plates in order to obtain single colonies. The single colonies were subsequently patched onto Leu-8% glucose plates to increase the plasmid copy number. Leu-starter cultures were grown for 24 hours at 30° C. and then diluted 1:20 in YEPD (yeast extract bactopeptone 2% glucose) media. Cells were grown for 48 hours at 30° C. to allow depletion of the glucose in the media and then harvested. Then aliquots of the yeast cells were lysed with glass beads in lysis buffer (10 mM NaPO4 pH7.5 0.1% Triton X-100). The lysates were cleared by centrifugation in 4° microfuge. The recombinant proteins were detected in the cleared glass bead lysate using the commercially available RIDASCREEN Norovirus Immunoassay (SciMedx Corporation) (FIG. 8). The lysates were subjected to sucrose gradient sedimentation, and the fractions were assayed using the Norovirus kit to determine if the expression of the capsid protein in S. cerevisiae resulted in the self-assembly of recombinant NV empty virus-like particles. Preliminary results of electron microscopy indicated the formation of virus-like particles in the peak fractions of the sucrose gradients (FIG. 9).

Example 2

Expression of Norwalk Virus Capsid Protein in Insect Cells

Figure 10:
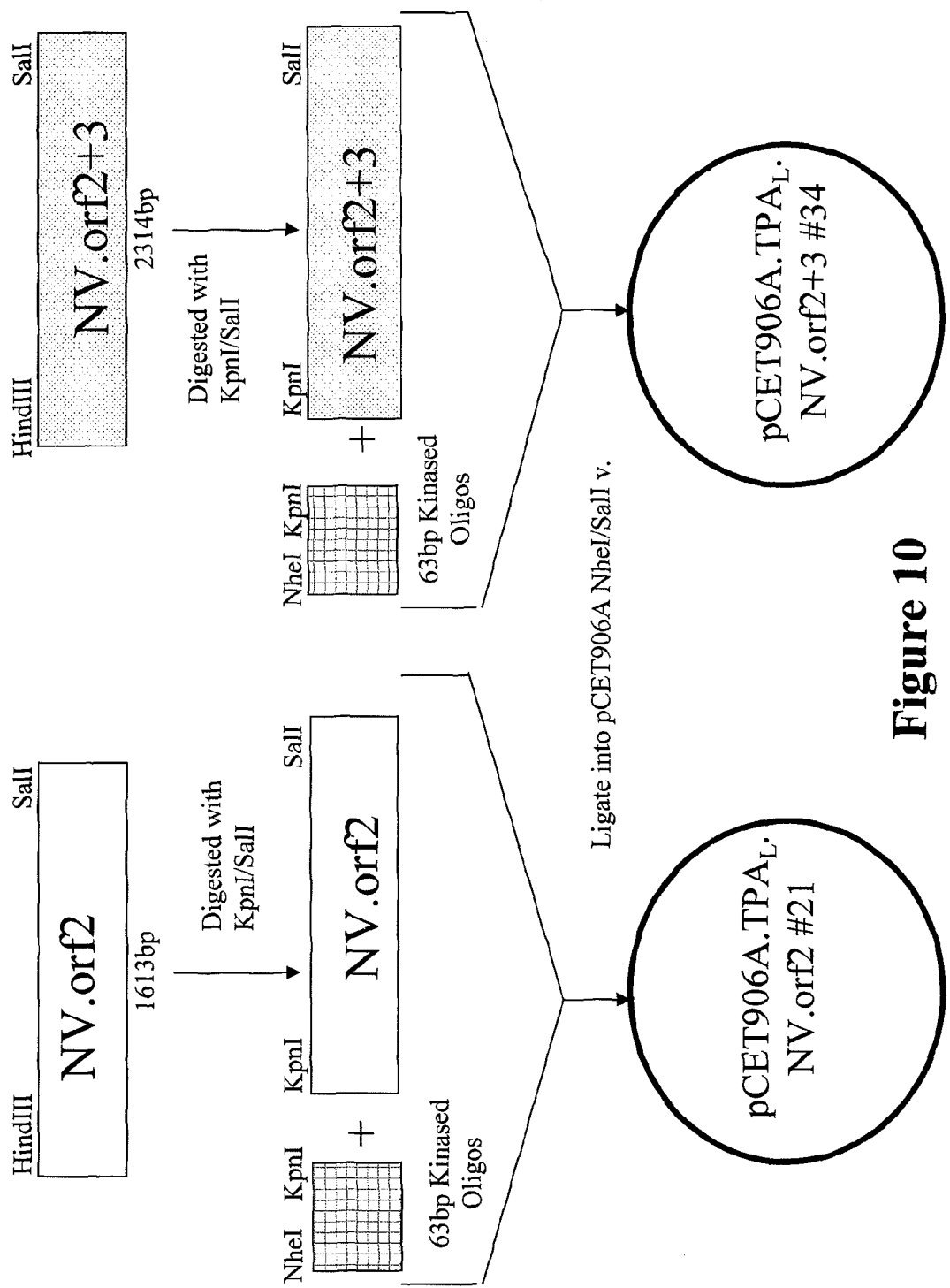
FIG. 10 depicts a schematic diagram illustrating the subcloning of the full-length NV .orf2 and NV .orf2+3 into the PCET906A shuttle vector. A 1534 bp KpnI/SalI NV .orf2 fragment and a 2235 bp KpnI/SalI NV .orf2+3 fragment were isolated by digesting pSP72.NV .orf2 #1 and pSP72.NV .orf2+3 #16, respectively, with KpnI and SalI. The gel purified KpnI/SalI NV .orf2 and KpnI/SalI NV .orf2+3 fragments were ligated with a 63 bp synthetic oligo that included an NheI site at the beginning, a sequence encoding amino acids 1-21 of the capsid protein, and a KpnI site at the end and cloned into the PCET906A NheI/SalI v. shuttle vector (ML Labs).

For the expression of NV capsid orf2 and NV capsid orf2+3 in the insect cell system, the following manipulations were undertaken to create an NheI/SalI fragment that could be cloned into PBLUEBAC4.5 baculovirus expression vector. First, the 5' end of the orf2 and orf2+3 HindIII/SalI fragments were modified to replace the HindIII restriction site with a NheI restriction site. This was accomplished with a 63 bp synthetic oligo that included the NheI site at the beginning, a sequence encoding amino acids 1-21 of the capsid protein, and a KpnI site at the end. Next, a 1534 bp KpnI/SalI NV .orf2 fragment and a 2235 bp KpnI/SalI NV .orf2+3 fragment were isolated by digesting pSP72.NV .orf2 #1 and pSP72.NV .orf2+3 #16, respectively, with KpnI and SalI followed by gel electrophoretic separation and purification of the isolated bands. The NheI/KpnI oligos and the KpnI/SalI fragments were ligated into the PCET906A shuttle vector (ML Labs). Competent HB101 were transformed with the ligation mixture and plated onto Luria-ampicillin plates. After miniprep analysis, identification of the desired clones, and sequence confirmation, the plasmids pCET906A.TPA$_L$.orf2 #21 and pCET906A.TPA$_L$.orf2+3 #34 were amplified (FIG. 10).

Figure 11:
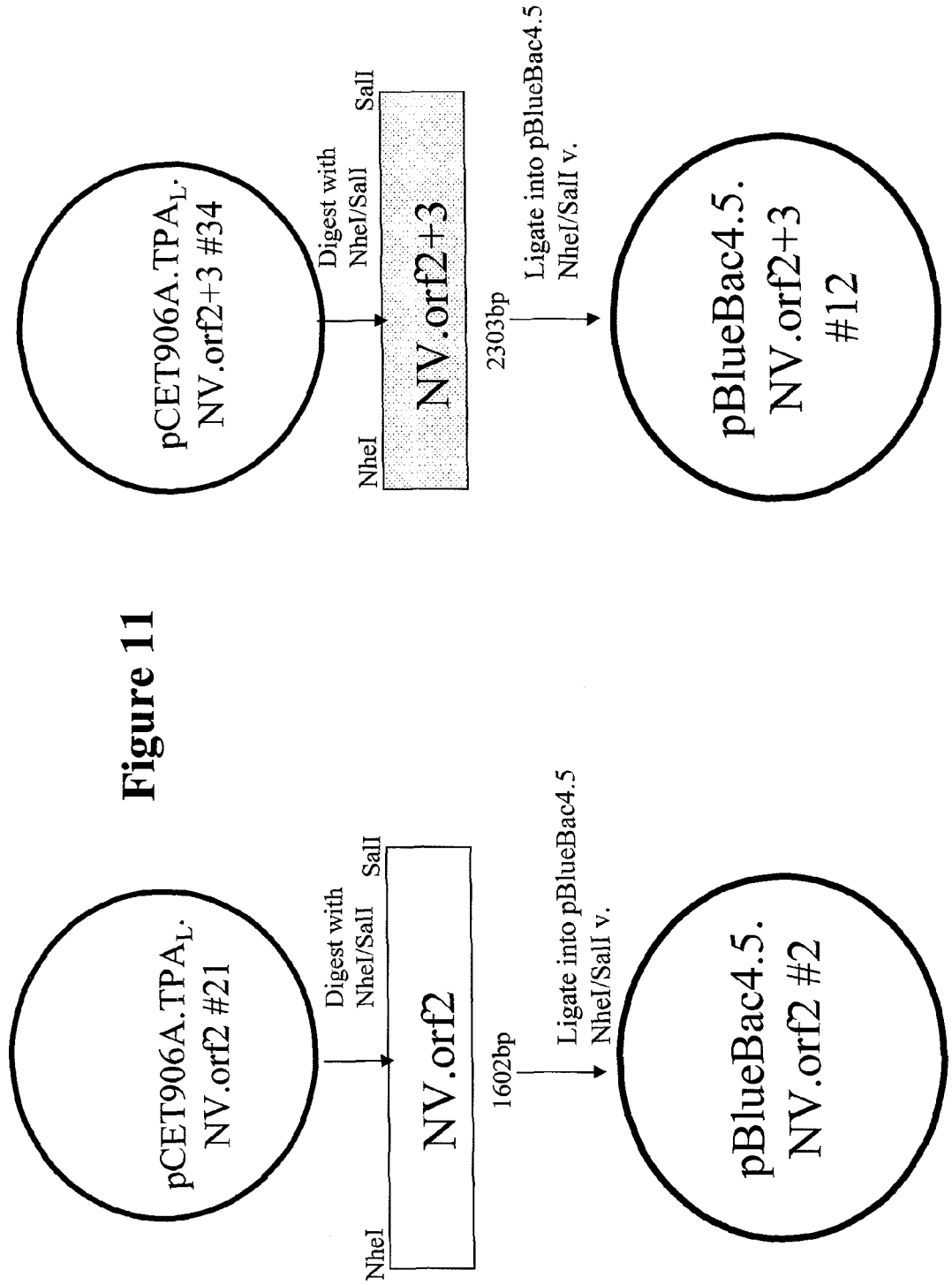
FIG. 11 depicts a schematic diagram illustrating the subcloning of the full-length NV .orf2 and NV .orf2+3 into the PBLUEBAC4.5 baculovirus expression vector. Clones pCET906A.TPA$_L$.orf2 #21 and pCET906A.TPA$_L$.orf2+3 #34 were digested with NheI and SalI to gel isolate a 1602 bp fragment coding for NV .orf2 and a 2303 bp fragment coding for NV .orf2+3, respectively. Each of the orf2 and orf2+3 NheI/SalI fragments was ligated into the PBLUEBAC4.5 NheI/SalI insect cell expression vector (Invitrogen), creating the plasmids PBLUEBAC4.5.NV .orf2 #2 and PBLUEBAC4.5.NV .orf2+3 #12.

Next pCET906A.TPA$_L$.orf2 #21 and pCET906A.TPA$_L$.orf2+3 #34 were digested with NheI and SalI to gel isolate a 1602 bp fragment coding for NV .orf2 and a 2303 bp fragment coding for NV .orf2+3, respectively. Each of the orf2 and orf2+3 NheI/SalI fragments was ligated into the PBLUEBAC4.5 NheI/SalI insect cell expression vector (Invitrogen), creating the plasmids PBLUEBAC4.5.NV .orf2 #2 and PBLUEBAC4.5.NV .orf2+3 #12 (FIG. 11).

Figure 12:
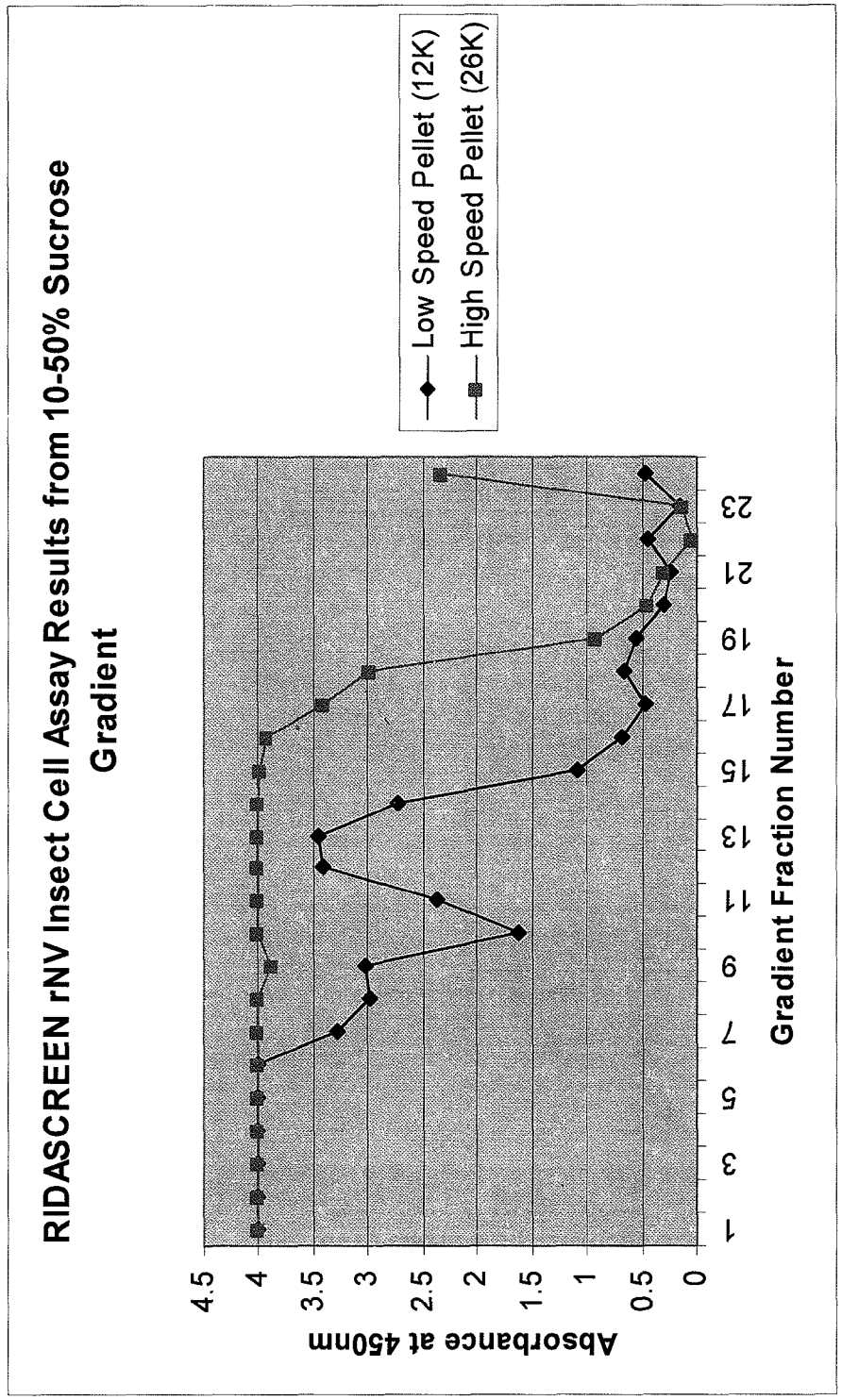
FIG. 12 depicts results from expression of recombinant Norwalk virus antigens in SF9 insect cells infected with baculovirus. Cell lysates were subjected to sucrose gradient sedimentation, and the recombinant proteins in collected fractions were detected using the RIDASCREEN Norovirus immunoassay (SciMedx Corporation).
Figure 13:
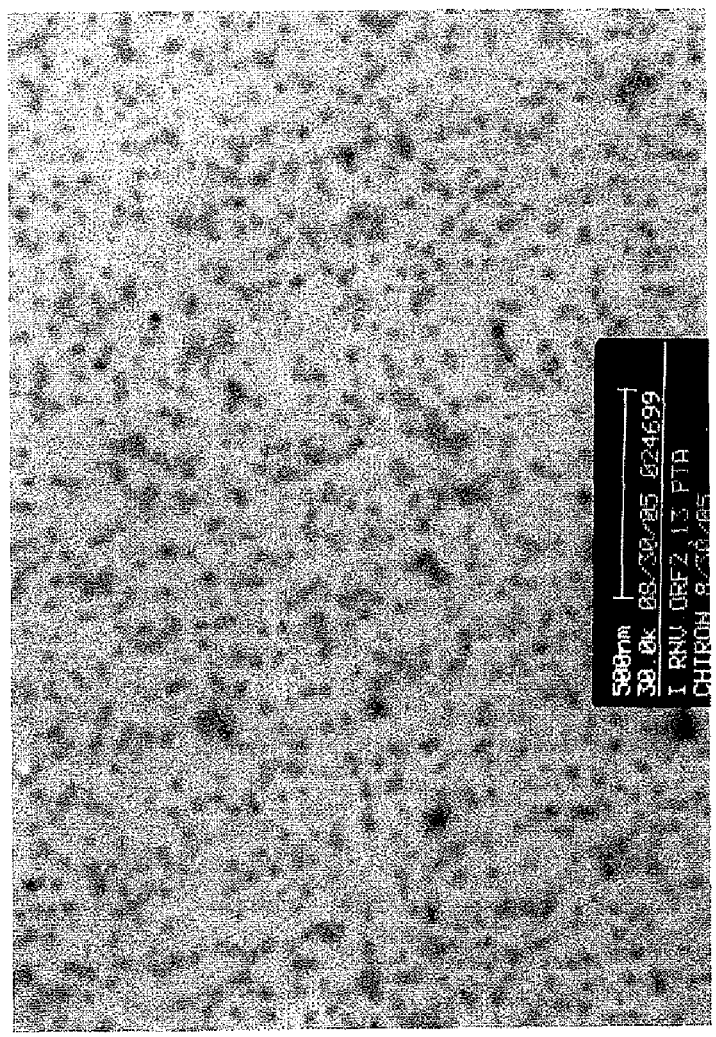
FIG. 13 shows an electron micrograph of recombinant Norovirus particles produced by expression of PBLUEBAC4.5.NV .orf2+3 #12 in SF9 insect cells.

The sequences encoding NV .orf2 or orf2+3 were recombined into the *Autographa californica* baculovirus (AcNPV) via the PBLUEBAC4.5 transfer vector by co-transfecting 2 μg of transfer vector with 0.5 μg of linearized, wild-type viral DNA into SF9 cells as described (Kitts et al., 1991). Recombinant baculovirus was isolated by plaque purification (Smith et al, 1983). Suspension cultures of $1.5 \times 10^6$ SF9 cells per ml were harvested following 48 hours of infection with the relevant baculovirus at a multiplicity of infection (moi) of 2-10 in serum free medium (Maiorella et al., 1988). The recombinant proteins were detected in the media using the commercially available RIDASCREEN Norovirus immunoassay (SciMedx Corporation) (FIG. 12). VLPs were purified from the media by sucrose gradient sedimentation (see, e.g., Kirnbauer et al. J. Virol. (1993) 67:6929-6936), and the presence of VLPs in peak fractions was confirmed by electron microscopy (FIG. 13).

Example 3

Production of a Multiepitope Fusion Protein

A polynucleotide encoding an Nterm-NTPase fusion, comprising approximately amino acids 1 to 696, numbered relative to Norovirus MD145-12 (SEQ ID NO:13), is isolated from a Norovirus. This construct is fused with a polynucleotide encoding a polymerase polypeptide which includes approximately amino acids 1190-1699 of the polyprotein numbered relative to Norovirus MD145-12. The polymerase-encoding polynucleotide sequence is fused downstream from the Nterm-NTPase-encoding portion of the construct such that the resulting fusion protein includes the polymerase polypeptide at its C-terminus. The construct is cloned into plasmid, vaccinia virus, adenovirus, alphavirus, and yeast vectors. Additionally, the construct is inserted into a recombinant expression vector and used to transform host cells to produce the Nterm-NTPase-Pol fusion protein.

Example 4

Activation of CD8$^+$ T Cells $^{51}$Cr Release Assay. A $^{51}$Cr release assay is used to measure the ability of T cells to lyse target cells displaying a Norovirus or Sapovirus epitope. Spleen cells are pooled from the immunized animals. These cells are stimulated in vitro for 6 days with a CTL epitopic peptide, derived from a Norovirus or Sapovirus, in the presence of IL-2. The spleen cells are then assayed for cytotoxic activity in a standard $^{51}$Cr release assay against peptide-sensitized target cells (L929) expressing class I, but not class II MHC molecules, as described in Weiss (1980) J. Biol. Chem. 255:9912-9917. Ratios of effector (T cells) to target (B cells) of 60:1, 20:1, and 7:1 are tested. Percent specific lysis is calculated for each effector to target ratio.

Example 5

Activation of Norovirus and Sapovirus-Specific CD8$^+$ T Cells which Express IFN-γ

Intracellular Staining for Interferon-gamma (IFN-γ). Intracellular staining for IFN-γ is used to identify the CD8$^+$ T cells that secrete IFN-γ after in vitro stimulation with a Norovirus and/or Sapovirus antigen. Spleen cells of individual immunized animals are restimulated in vitro either with an immunogenic composition described herein or with a non-specific peptide for 6-12 hours in the presence of IL-2 and monensin. The cells are then stained for surface CD8 and for intracellular IFN-γ and analyzed by flow cytometry. The percent of CD8$^+$ T cells which are also positive for IFN-γ is then calculated.

Example 6

Proliferation of Norovirus and Sapovirus-Specific CD4$^+$ T Cells

Lymphoproliferation assay. Spleen cells from pooled immunized animals are depleted of CD8$^+$ T cells using magnetic beads and are cultured in triplicate with either an immunogenic composition described herein, or in medium alone. After 72 hours, cells are pulsed with 1 μCi per well of $^3$H-thymidine and harvested 6-8 hours later. Incorporation of radioactivity is measured after harvesting. The mean cpm is calculated.

Example 7

Ability of VP1-VP2 Encoding DNA Vaccine Formulations to Prime CTLs

Animals are immunized with 10-250 μg of plasmid DNA encoding VP1 and VP2 as described in Example 1 and plasmid DNA encoding the Nterm-NTPase-Pol fusion protein as described in Example 3. DNA is delivered either by using PLG-linked DNA (see below), or by electroporation (see, e.g., International Publication No. WO/0045823 for this delivery technique). The immunizations are followed by a booster injection 6 weeks later of plasmid DNA encoding Nterm-NTPase-Pol and plasmid DNA encoding VP1 and VP2.

PLG-delivered DNA. The polylactide-co-glycolide (PLG) polymers are obtained from Boehringer Ingelheim, U.S.A. The PLG polymer is RG505, which has a copolymer ratio of 50/50 and a molecular weight of 65 kDa (manufacturers data). Cationic microparticles with adsorbed DNA are prepared using a modified solvent evaporation process, essentially as described in Singh et al., Proc. Natl. Acad. Sci. USA (2000) 97:811-816. Briefly, the microparticles are prepared by emulsifying 10 ml of a 5% w/v polymer solution in methylene chloride with 1 ml of PBS at high speed using an IKA homogenizer. The primary emulsion is then added to 50 ml of distilled water containing cetyl trimethyl ammonium bromide (CTAB) (0.5% w/v). This results in the formation of a w/o/w emulsion which is stirred at 6000 rpm for 12 hours at room temperature, allowing the methylene chloride to evaporate. The resulting microparticles are washed twice in distilled water by centrifugation at 10,000 g and freeze dried. Following preparation, washing and collection, DNA is adsorbed onto the microparticles by incubating 100 mg of cationic microparticles in a 1 mg/ml solution of DNA at 4 C for 6 hours. The microparticles are then separated by centrifugation, the pellet washed with TE buffer and the microparticles are freeze dried.

CTL activity and IFN-γ expression is measured by $^{51}$Cr release assay or intracellular staining as described in the examples above.

Example 8

Immunization Routes and Replicon Particles SINCR (DC+) Encoding for VP1 and VP2

Alphavirus replicon particles, for example, SINCR (DC+) are prepared as described in Polo et al., *Proc. Natl. Acad. Sci. USA* (1999) 96:4598-4603. Animals are injected with 5×10$^6$ IU SINCR (DC+) replicon particles encoding Norovirus VP1 and VP2 intramuscularly (IM), or subcutaneously (S/C) at the base of the tail (BoT) and foot pad (FP), or with a combination of ⅔ of the DNA delivered via IM administration and ⅓ via a BoT route. The immunizations are followed by a booster injection of vaccinia virus encoding VP1. IFN-γ expression is measured by intracellular staining as described in Example 5.

Example 9

Alphavirus Replicon Priming, Followed by Various Boosting Regimes

Alphavirus replicon particles, for example, SINCR (DC+) are prepared as described in Polo et al., *Proc. Natl. Acad. Sci. USA* (1999) 96:4598-4603. Animals are primed with SINCR (DC+), $1.5\times10^6$ IU replicon particles encoding Norovirus VP1 and VP2, by intramuscular injection into the tibialis anterior, followed by a booster of either 10-100 μg of plasmid DNA encoding for VP1, $10^{10}$ adenovirus particles encoding VP1 and VP2, $1.5\times10^6$ IU SINCR (DC+) replicon particles encoding VP1 and VP2, or $10^7$ pfu vaccinia virus encoding VP1 at 6 weeks. IFN-γ expression is measured by intracellular staining as described in Example 5.

Example 10

Alphaviruses Expressing VP1 and VP2

Alphavirus replicon particles, for example, SINCR (DC+) and SINCR (LP) are prepared as described in Polo et al., Proc. Natl. Acad. Sci. USA (1999) 96:4598-4603. Animals are immunized with $1\times10^2$ to $1\times10^6$ IU SINCR (DC+) replicons encoding VP1 and VP2 via a combination of delivery routes (⅔ IM and ⅓ S/C) as well as by S/C alone, or with $1\times10^2$ to $1\times10^6$ IU SINCR (LP) replicon particles encoding VP1 and VP2 via a combination of delivery routes (⅔ IM and ⅓ S/C) as well as by S/C alone. The immunizations are followed by a booster injection of $10^7$ pfu vaccinia virus encoding VP1 at 6 weeks. IFN-γ expression is measured by intracellular staining as described in Example 5.

Example 11

Immunization with Combinations of Norovirus Antigens and Adjuvants

The following example illustrates immunization with various combinations of NV, SMV and HV antigens in a mouse model. The NV, SMV and HV antigens are prepared and characterized as described herein. CD1 mice are divided into nine groups and immunized as follows:

TABLE 3

Immunization Schedule

| Group | Immunizing Composition | Route of Delivery |
|---|---|---|
| 1 | Mixture of NV, SMV, HV antigens (5 μg/each) + CFA | Intra-peritoneal or intra-nasal or mucosal (oral) following by parenteral (intra-muscular admin) |
| 2 | Mixture of NV, SMV, HV antigens (5 μg/each) + AlOH (200 μg) | Intra-peritoneal or intra-nasal or mucosal (oral) following by parenteral (intra-muscular admin) |
| 3 | Mixture of NV, SMV, HV antigens (5 μg/each) + CpG (10 ug) | Intra-peritoneal or intra-nasal or mucosal (oral) following by parenteral (intra-muscular admin) |
| 4 | Mixture of NV, SMV, HV antigens (5 μg/each) + AlOH (200 μg) + CpG (10 μg) | Intra-peritoneal or intra-nasal or mucosal (oral) following by parenteral (intra-muscular admin) |
| 5 | Complete Freunds Adjuvant (CFA) | Intra-peritoneal or intra-nasal or mucosal (oral) following by parenteral (intra-muscular admin) |
| 6 | Mixture of NV, SMV, HV (5 μg/each) + LTK63 (5 μg) | Intra-peritoneal or Intranasal or mucosal (oral) following by parenteral (intra-muscular admin) |
| 7 | AlOH (200 μg) + CpG (10 μg) | Intra-peritoneal or intra-nasal or mucosal (oral) following by parenteral (intra-muscular admin) |
| 8 | CpG (10 μg) | Intra-peritoneal or intra-nasal or mucosal (oral) following by parenteral (intra-muscular admin) |
| 9 | LTK63 (5 μg) | Intra-peritoneal or intra-nasal or mucosal (oral) following by parenteral (intra-muscular admin) |

Mice are immunized at two week intervals. Two weeks after the last immunization, all mice are challenged with the appropriate strain. When mucosal immunization (e.g., intranasal(in)) is used, the animal model is also challenged mucosally to test the protective effect of the mucosal immunogen.

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be covered by the present invention.

The invention claimed is:

1. A method for producing viral-like particles (VLPs), the method comprising:
   a) transforming an isolated host cell with an expression vector comprising a recombinant polynucleotide, wherein the polynucleotide comprises a nucleotide sequence selected from the group consisting of: (i) a polynucleotide comprising a sequence with at least 98% sequence identity to the sequence of SEQ ID NO:1; and (ii) a polynucleotide comprising the sequence of SEQ ID NO:2,
   wherein the polynucleotide is operably linked to control elements that direct the expression of said nucleotide sequence in a yeast host cell, and further wherein the polynucleotide contains less than an entire Norovirus genome; and
   b) culturing the transformed host cell under conditions whereby capsid proteins are expressed and assembled into VLPs.

2. The method of claim 1, wherein one or more of the expression vectors comprise sequences encoding capsid proteins from more than one Norovirus isolate.

3. The method of claim 1, further comprising transforming said isolated host cell with one or more sequences encoding a structural protein from a Norovirus.

4. The method of claim 1, wherein said expression vector further comprises one or more ORF1- and/or ORF3-encoding sequences from a Norovirus.

5. The method of claim 1, wherein a mosaic VLP comprising capsid proteins from at least two viral strains of Norovirus is assembled.

6. The method of claim 1, wherein said expression vector comprises the sequence of SEQ ID NO:1.

7. The method of claim 1, wherein the expression vector comprises an ADH2 promoter.

8. The method of claim 7, wherein the promoter is a hybrid ADH2/GAPDH promoter.

* * * * *

SEQUENCE LISTING

```
<160> NUMBER OF SEQ ID NOS: 27

<210> SEQ ID NO 1
<211> LENGTH: 1608
<212> TYPE: DNA
<213> ORGANISM: Norwalk virus
```

<400> SEQUENCE: 1

```
aagcttacaa aacaaaatga tgatggcgtc taaggacgct acatcaagcg tggatggcgc 60
tagtggcgct ggtcagttgg taccggaggt taatgcttct gaccctcttg caatggaccc 120
tgtagcaggt tcttcgacag cagtcgcgac tgctggacaa gttaatccta ttgatccctg 180
gataatcaat aattttgtgc aagcccccca aggtgaattt actatttccc caaataatac 240
ccccggtgat gttttgtttg atttgagttt gggtccccat cttaatcctt tcttgctcca 300
tctatcacaa atgtataatg gttgggttgg taacatgaga gtcaggatta tgttggctgg 360
taatgccttt actgcgggga agataatagt ttcctgcata ccccctggtt ttggttcaca 420
taatcttact atagcacaag caactctctt tccacatgtg attgctgatg ttaggactct 480
agaccccatt gaggtgcctt tggaagatgt taggaatgtt ctctttcata ataatgatag 540
aaatcaacaa accatgcgcc ttgtgtgcat gctgtacacc cccctccgca ctggtggtgg 600
tactggtgat tcttttgtag ttgcagggcg agttatgact tgccccagtc ctgattttaa 660
tttcttgttt ttagtccctc ctacggtgga gcagaaaacc aggcccttca cactcccaaa 720
tctgccattg agttctctgt ctaactcacg tgcccctctc ccaatcagta gtatcggcat 780
ttccccagac aatgtccaga gtgtgcagtt ccaaaatggt cggtgtactc tggatggccg 840
cctggttggc accaccccag tttcattgtc acatgttgcc aagataagag ggacctccaa 900
tggcactgta atcaacctta ctgaattgga tggcacaccc tttcaccctt ttgagggccc 960
tgcccccatt gggtttccag acctcggtgg ttgtgattgg catattaata tgacacagtt 1020
tggccattct agccagaccc agtatgatgt agacaccacc cctgacactt ttgtccccca 1080
tcttggttca attcaggcaa atggcattgg cagtggtaat tatgttggtg ttcttagctg 1140
gatttcccca ccatcacacc cgtctggctc ccaagttgac ctttggaaga tcccccaatta 1200
tgggtcaagt attacggagg caacacatct agccccttct gtataccccc ctggtttcgg 1260
agaggtattg gtcttcttca tgtccaagat gccaggtcct ggtgcttata atttgccctg 1320
tctattacca caagagtaca tttcacatct tgctagtgaa caagccccta ctgtaggtga 1380
ggctgccctg ctccactatg ttgaccctga taccggtcgg aatcttgggg agttcaaagc 1440
ataccctgat ggtttcctca cttgtgtccc caatggggct tcttcgggtc cacaacagct 1500
gccgatcaat ggggtctttg tctttgtttc atgggtgtcc agattttatc aattaaagcc 1560
tgtgggaact gccagctcgg caagaggtag gcttggtctc cggagata 1608
```

<210> SEQ ID NO 2
<211> LENGTH: 2319
<212> TYPE: DNA
<213> ORGANISM: Norwalk virus

<400> SEQUENCE: 2

```
aagcttacaa aacaaaatga tgatggcgtc taaggacgct acatcaagcg tggatggcgc 60
tagtggcgct ggtcagttgg taccggaggt taatgcttct gaccctcttg caatggaccc 120
tgtagcaggt tcttcgacag cagtcgcgac tgctggacaa gttaatccta ttgatccctg 180
gataatcaat aattttgtgc aagcccccca aggtgaattt actatttccc caaataatac 240
ccccggtgat gttttgtttg atttgagttt gggtccccat cttaatcctt tcttgctcca 300
tctatcacaa atgtataatg gttgggttgg taacatgaga gtcaggatta tgttggctgg 360
taatgccttt actgcgggga agataatagt ttcctgcata ccccctggtt ttggttcaca 420
taatcttact atagcacaag caactctctt tccacatgtg attgctgatg ttaggactct 480
```

-continued

```
agaccccatt gaggtgcctt tggaagatgt taggaatgtt ctctttcata ataatgatag    540
aaatcaacaa accatgcgcc ttgtgtgcat gctgtacacc cccctccgca ctggtggtgg    600
tactggtgat tcttttgtag ttgcagggcg agttatgact tgccccagtc ctgattttaa    660
tttcttgttt ttagtccctc ctacggtgga gcagaaaacc aggcccttca cactcccaaa    720
tctgccattg agttctctgt ctaactcacg tgcccctctc ccaatcagta gtatcggcat    780
ttccccagac aatgtccaga gtgtgcagtt ccaaaatggt cggtgtactc tggatggccg    840
cctggttggc accaccccag tttcattgtc acatgttgcc aagataagag ggacctccaa    900
tggcactgta atcaacctta ctgaattgga tggcacaccc tttcaccctt ttgagggccc    960
tgcccccatt gggtttccag acctcggtgg ttgtgattgg catattaata tgacacagtt   1020
tggccattct agccagaccc agtatgatgt agacaccacc cctgacactt ttgtccccca   1080
tcttggttca attcaggcaa atggcattgg cagtggtaat tatgttggtg ttcttagctg   1140
gatttcccca ccatcacacc cgtctggctc ccaagttgac ctttggaaga tccccaatta   1200
tgggtcaagt attacggagg caacacatct agcccccttct gtataccccc ctggtttcgg   1260
agaggtattg gtcttcttca tgtccaagat gccaggtcct ggtgcttata atttgccctg   1320
tctattacca caagagtaca tttcacatct tgctagtgaa caagccccta ctgtaggtga   1380
ggctgccctg ctccactatg ttgaccctga taccggtcgg aatcttgggg agttcaaagc   1440
ataccctgat ggtttcctca cttgtgtccc caatggggct tcttcgggtc cacaacagct   1500
gccgatcaat ggggtctttg tctttgtttc atgggtgtcc agattttatc aattaaagcc   1560
tgtgggaact gccagctcgg caagaggtag gcttggtctc cggagataat ggcccaagcc   1620
ataattggtg caattgctgc ttccacagca ggtagtgctc tgggagcggg catacaggtt   1680
ggtggcgaag cggccctcca aagccaaagg tatcaacaaa atttgcaact gcaagaaaat   1740
tcttttaaac atgacaggga aatgattggg tatcaggttg aggcttcaaa tcaattattg   1800
gctaaaaatt tggcaactag atattcactc ctccgtgctg gggggtttgac cagtgctgat   1860
gcagcaagat ctgtggcagg agctccagtc acccgcattg tagattggaa tggcgtgaga   1920
gtgtctgctc ccgagtcctc tgctaccaca ttgagatccg gtggcttcat gtcagttccc   1980
ataccatttg cctctaagca aaaacaggtt caatcatctg gtattagtaa tccaaattat   2040
tccccttcat ccatttctcg aaccactagt tgggtcgagt cacaaaactc atcgagattt   2100
ggaaatcttt ctccatacca cgcggaggct ctcaatacag tgtggttgac tccacccggt   2160
tcaacagcct cttctacact gtcttctgtg ccacgtggtt atttcaatac agacaggtta   2220
ccattattcg caaataatag gcgatgatgt tgtaatatga aatgtgggca tcatattcat   2280
ttaattaggt ttaattaggt ttaatttgat gttgtcgac                          2319
```

<210> SEQ ID NO 3
<211> LENGTH: 530
<212> TYPE: PRT
<213> ORGANISM: Norwalk virus

<400> SEQUENCE: 3

```
Met Met Met Ala Ser Lys Asp Ala Thr Ser Ser Val Asp Gly Ala Ser
1               5                   10                  15

Gly Ala Gly Gln Leu Val Pro Glu Val Asn Ala Ser Asp Pro Leu Ala
            20                  25                  30

Met Asp Pro Val Ala Gly Ser Ser Thr Ala Val Ala Thr Ala Gly Gln
        35                  40                  45
```

-continued

```
Val Asn Pro Ile Asp Pro Trp Ile Ile Asn Asn Phe Val Gln Ala Pro
 50                  55                  60

Gln Gly Glu Phe Thr Ile Ser Pro Asn Asn Thr Pro Gly Asp Val Leu
 65                  70                  75                  80

Phe Asp Leu Ser Leu Gly Pro His Leu Asn Pro Phe Leu Leu His Leu
                 85                  90                  95

Ser Gln Met Tyr Asn Gly Trp Val Gly Asn Met Arg Val Arg Ile Met
            100                 105                 110

Leu Ala Gly Asn Ala Phe Thr Ala Gly Lys Ile Ile Val Ser Cys Ile
        115                 120                 125

Pro Pro Gly Phe Gly Ser His Asn Leu Thr Ile Ala Gln Ala Thr Leu
    130                 135                 140

Phe Pro His Val Ile Ala Asp Val Arg Thr Leu Asp Pro Ile Glu Val
145                 150                 155                 160

Pro Leu Glu Asp Val Arg Asn Val Leu Phe His Asn Asn Asp Arg Asn
                165                 170                 175

Gln Gln Thr Met Arg Leu Val Cys Met Leu Tyr Thr Pro Leu Arg Thr
            180                 185                 190

Gly Gly Gly Thr Gly Asp Ser Phe Val Val Ala Gly Arg Val Met Thr
        195                 200                 205

Cys Pro Ser Pro Asp Phe Asn Phe Leu Phe Leu Val Pro Pro Thr Val
    210                 215                 220

Glu Gln Lys Thr Arg Pro Phe Thr Leu Pro Asn Leu Pro Leu Ser Ser
225                 230                 235                 240

Leu Ser Asn Ser Arg Ala Pro Leu Pro Ile Ser Ser Ile Gly Ile Ser
                245                 250                 255

Pro Asp Asn Val Gln Ser Val Gln Phe Gln Asn Gly Arg Cys Thr Leu
            260                 265                 270

Asp Gly Arg Leu Val Gly Thr Thr Pro Val Ser Leu Ser His Val Ala
        275                 280                 285

Lys Ile Arg Gly Thr Ser Asn Gly Thr Val Ile Asn Leu Thr Glu Leu
    290                 295                 300

Asp Gly Thr Pro Phe His Pro Phe Glu Gly Pro Ala Pro Ile Gly Phe
305                 310                 315                 320

Pro Asp Leu Gly Gly Cys Asp Trp His Ile Asn Met Thr Gln Phe Gly
                325                 330                 335

His Ser Ser Gln Thr Gln Tyr Asp Val Asp Thr Thr Pro Asp Thr Phe
            340                 345                 350

Val Pro His Leu Gly Ser Ile Gln Ala Asn Gly Ile Gly Ser Gly Asn
        355                 360                 365

Tyr Val Gly Val Leu Ser Trp Ile Ser Pro Ser His Pro Ser Gly
    370                 375                 380

Ser Gln Val Asp Leu Trp Lys Ile Pro Asn Tyr Gly Ser Ser Ile Thr
385                 390                 395                 400

Glu Ala Thr His Leu Ala Pro Ser Val Tyr Pro Pro Gly Phe Gly Glu
                405                 410                 415

Val Leu Val Phe Phe Met Ser Lys Met Pro Gly Pro Gly Ala Tyr Asn
            420                 425                 430

Leu Pro Cys Leu Leu Pro Gln Glu Tyr Ile Ser His Leu Ala Ser Glu
        435                 440                 445

Gln Ala Pro Thr Val Gly Glu Ala Leu Leu His Tyr Val Asp Pro
    450                 455                 460

Asp Thr Gly Arg Asn Leu Gly Glu Phe Lys Ala Tyr Pro Asp Gly Phe
465                 470                 475                 480
```

-continued

```
Leu Thr Cys Val Pro Asn Gly Ala Ser Ser Gly Pro Gln Gln Leu Pro
                485                 490                 495

Ile Asn Gly Val Phe Val Phe Val Ser Trp Val Ser Arg Phe Tyr Gln
            500                 505                 510

Leu Lys Pro Val Gly Thr Ala Ser Ser Ala Arg Gly Arg Gly Leu Gly Leu
        515                 520                 525

Arg Arg
    530

<210> SEQ ID NO 4
<211> LENGTH: 212
<212> TYPE: PRT
<213> ORGANISM: Norwalk virus

<400> SEQUENCE: 4

Met Ala Gln Ala Ile Ile Gly Ala Ile Ala Ala Ser Thr Ala Gly Ser
1               5                   10                  15

Ala Leu Gly Ala Gly Ile Gln Val Gly Glu Ala Ala Leu Gln Ser
            20                  25                  30

Gln Arg Tyr Gln Gln Asn Leu Gln Leu Gln Glu Asn Ser Phe Lys His
        35                  40                  45

Asp Arg Glu Met Ile Gly Tyr Gln Val Glu Ala Ser Asn Gln Leu Leu
    50                  55                  60

Ala Lys Asn Leu Ala Thr Arg Tyr Ser Leu Leu Arg Ala Gly Gly Leu
65                  70                  75                  80

Thr Ser Ala Asp Ala Ala Arg Ser Val Ala Gly Ala Pro Val Thr Arg
                85                  90                  95

Ile Val Asp Trp Asn Gly Val Arg Val Ser Ala Pro Glu Ser Ser Ala
            100                 105                 110

Thr Thr Leu Arg Ser Gly Gly Phe Met Ser Val Pro Ile Pro Phe Ala
        115                 120                 125

Ser Lys Gln Lys Gln Val Gln Ser Ser Gly Ile Ser Asn Pro Asn Tyr
    130                 135                 140

Ser Pro Ser Ser Ile Ser Arg Thr Thr Ser Trp Val Glu Ser Gln Asn
145                 150                 155                 160

Ser Ser Arg Phe Gly Asn Leu Ser Pro Tyr His Ala Glu Ala Leu Asn
                165                 170                 175

Thr Val Trp Leu Thr Pro Pro Gly Ser Thr Ala Ser Ser Thr Leu Ser
            180                 185                 190

Ser Val Pro Arg Gly Tyr Phe Asn Thr Asp Arg Leu Pro Leu Phe Ala
        195                 200                 205

Asn Asn Arg Arg
    210

<210> SEQ ID NO 5
<211> LENGTH: 542
<212> TYPE: PRT
<213> ORGANISM: Snow Mountain virus
<300> PUBLICATION INFORMATION:
<308> DATABASE ACCESSION NUMBER: GenBank/U70059
<309> DATABASE ENTRY DATE: 2000-10-02
<313> RELEVANT RESIDUES IN SEQ ID NO: (1)..(542)

<400> SEQUENCE: 5

Met Lys Met Ala Ser Asn Asp Ala Ala Pro Ser Thr Asp Gly Ala Ala
1               5                   10                  15

Gly Leu Val Pro Glu Ser Asn Asn Glu Val Met Ala Leu Glu Pro Val
            20                  25                  30
```

```
Ala Gly Ala Ala Leu Ala Ala Pro Val Thr Gly Gln Thr Asn Ile Ile
             35                  40                  45

Asp Pro Trp Ile Arg Ala Asn Phe Val Gln Ala Pro Asn Gly Glu Phe
 50                  55                  60

Thr Val Ser Pro Arg Asn Ala Pro Gly Glu Val Leu Leu Asn Leu Glu
 65                  70                  75                  80

Leu Gly Pro Glu Leu Asn Pro Tyr Leu Ala His Leu Ala Arg Met Tyr
                 85                  90                  95

Asn Gly Tyr Ala Gly Gly Met Glu Val Gln Val Met Leu Ala Gly Asn
            100                 105                 110

Ala Phe Thr Ala Gly Lys Leu Val Phe Ala Ala Val Pro Pro His Phe
            115                 120                 125

Pro Val Glu Asn Leu Ser Pro Gln Gln Ile Thr Met Phe Pro His Val
            130                 135                 140

Ile Ile Asp Val Arg Thr Leu Glu Pro Val Leu Leu Pro Leu Pro Asp
145                 150                 155                 160

Val Arg Asn Asn Phe Phe His Tyr Asn Gln Lys Asp Pro Lys Met
                165                 170                 175

Arg Ile Val Ala Met Leu Tyr Thr Pro Leu Arg Ser Asn Gly Ser Gly
            180                 185                 190

Asp Asp Val Phe Thr Val Ser Cys Arg Val Leu Thr Arg Pro Ser Pro
            195                 200                 205

Asp Phe Asp Phe Thr Tyr Leu Val Pro Pro Thr Val Glu Ser Lys Thr
210                 215                 220

Lys Pro Phe Thr Leu Pro Ile Leu Thr Leu Gly Glu Leu Ser Asn Ser
225                 230                 235                 240

Arg Phe Pro Val Ser Ile Asp Gln Met Tyr Thr Ser Pro Asn Glu Val
                245                 250                 255

Ile Ser Val Gln Cys Gln Asn Gly Arg Cys Thr Leu Asp Gly Glu Leu
            260                 265                 270

Gln Gly Thr Thr Gln Leu Gln Val Ser Gly Ile Cys Ala Ser Lys Gly
            275                 280                 285

Glu Val Thr Ala His Leu Gln Asp Asn Asp His Leu Tyr Asn Ile Thr
            290                 295                 300

Ile Thr Asn Leu Asn Gly Ser Pro Phe Asp Pro Ser Glu Asp Ile Pro
305                 310                 315                 320

Ala Pro Leu Gly Val Pro Asp Phe Gln Gly Arg Val Phe Gly Val Ile
                325                 330                 335

Thr Gln Arg Asp Lys Gln Asn Ala Ala Gly Gln Ser Gln Pro Ala Asn
            340                 345                 350

Arg Gly His Asp Ala Val Val Pro Thr Tyr Thr Ala Gln Tyr Thr Pro
            355                 360                 365

Lys Leu Gly Gln Val Gln Ile Gly Thr Trp Gln Thr Asp Asp Leu Lys
            370                 375                 380

Val Asn Gln Pro Val Lys Phe Thr Pro Val Gly Leu Asn Asp Thr Glu
385                 390                 395                 400

His Phe Asn Gln Trp Val Val Pro Arg Tyr Ala Gly Ala Leu Asn Leu
                405                 410                 415

Asn Thr Asn Leu Ala Pro Ser Val Ala Pro Val Phe Pro Gly Glu Arg
            420                 425                 430

Leu Leu Phe Phe Arg Ser Tyr Leu Pro Leu Lys Gly Gly Tyr Gly Asn
            435                 440                 445

Pro Ala Ile Asp Cys Leu Leu Pro Gln Glu Trp Val Gln His Phe Tyr
```

```
                 450                 455                 460
Gln Glu Ala Ala Pro Ser Met Ser Glu Val Ala Leu Val Arg Tyr Ile
465                 470                 475                 480

Asn Pro Asp Thr Gly Arg Ala Leu Phe Glu Ala Lys Leu His Arg Ala
                485                 490                 495

Gly Phe Met Thr Val Ser Ser Asn Thr Ser Ala Pro Val Val Val Pro
            500                 505                 510

Ala Asn Gly Tyr Phe Arg Phe Asp Ser Trp Val Asn Gln Phe Tyr Ser
            515                 520                 525

Leu Ala Pro Met Gly Thr Gly Asn Gly Arg Arg Val Gln
            530                 535                 540

<210> SEQ ID NO 6
<211> LENGTH: 542
<212> TYPE: PRT
<213> ORGANISM: Snow Mountain virus
<300> PUBLICATION INFORMATION:
<308> DATABASE ACCESSION NUMBER: GenBank/AY134748
<309> DATABASE ENTRY DATE: 2004-07-01
<313> RELEVANT RESIDUES IN SEQ ID NO: (1)..(542)

<400> SEQUENCE: 6

Met Lys Met Ala Ser Asn Asp Ala Ala Pro Ser Thr Asp Gly Ala Ala
1               5                   10                  15

Gly Leu Val Pro Glu Ser Asn Asn Glu Val Met Ala Leu Glu Pro Val
                20                  25                  30

Ala Gly Ala Ala Leu Ala Ala Pro Val Thr Gly Gln Thr Asn Ile Ile
            35                  40                  45

Asp Pro Trp Ile Arg Ala Asn Phe Val Gln Ala Pro Asn Gly Glu Phe
50                  55                  60

Thr Val Ser Pro Arg Asn Ala Pro Gly Glu Val Leu Leu Asn Leu Glu
65                  70                  75                  80

Leu Gly Pro Glu Leu Asn Pro Tyr Leu Ala His Leu Ala Arg Met Tyr
                85                  90                  95

Asn Gly Tyr Ala Gly Gly Met Glu Val Gln Val Met Leu Ala Gly Asn
            100                 105                 110

Ala Phe Thr Ala Gly Lys Leu Val Phe Ala Ala Val Pro Pro His Phe
        115                 120                 125

Pro Val Glu Asn Leu Ser Pro Gln Gln Ile Thr Met Phe Pro His Val
    130                 135                 140

Ile Ile Asp Val Arg Thr Leu Glu Pro Val Leu Leu Pro Leu Pro Asp
145                 150                 155                 160

Val Arg Asn Asn Phe Phe His Tyr Asn Gln Lys Asp Asp Pro Lys Met
                165                 170                 175

Arg Ile Val Ala Met Leu Tyr Thr Pro Leu Arg Ser Asn Gly Ser Gly
            180                 185                 190

Asp Asp Val Phe Thr Val Ser Cys Arg Val Leu Thr Arg Pro Ser Pro
        195                 200                 205

Asp Phe Asp Phe Thr Tyr Leu Val Pro Pro Thr Val Glu Ser Lys Thr
    210                 215                 220

Lys Pro Phe Thr Leu Pro Ile Leu Thr Leu Gly Glu Leu Ser Asn Ser
225                 230                 235                 240

Arg Phe Pro Val Ser Ile Asp Gln Met Tyr Thr Ser Pro Asn Glu Val
                245                 250                 255

Ile Ser Val Gln Cys Gln Asn Gly Arg Cys Thr Leu Asp Gly Glu Leu
            260                 265                 270
```

Gln Gly Thr Thr Gln Leu Gln Val Ser Gly Ile Cys Ala Phe Lys Gly
    275                 280                 285

Glu Val Thr Ala His Leu Gln Asp Asn Asp His Leu Tyr Asn Ile Thr
    290                 295                 300

Ile Thr Asn Leu Asn Gly Ser Pro Phe Asp Pro Ser Glu Asp Ile Pro
305                 310                 315                 320

Ala Pro Leu Gly Val Pro Asp Phe Gln Gly Arg Val Phe Gly Val Ile
                325                 330                 335

Thr Gln Arg Asp Lys Gln Asn Ala Ala Gly Gln Ser Gln Pro Ala Asn
                340                 345                 350

Arg Gly His Asp Ala Val Val Pro Thr Tyr Thr Ala Gln Tyr Thr Pro
                355                 360                 365

Lys Leu Gly Gln Val Gln Ile Gly Thr Trp Gln Thr Asp Asp Leu Lys
    370                 375                 380

Val Asn Gln Pro Val Lys Phe Thr Pro Val Gly Leu Asn Asp Thr Glu
385                 390                 395                 400

His Phe Asn Gln Trp Val Val Pro Arg Tyr Ala Gly Ala Leu Asn Leu
                405                 410                 415

Asn Thr Asn Leu Ala Pro Ser Val Ala Pro Val Phe Pro Gly Glu Arg
                420                 425                 430

Leu Leu Phe Phe Arg Ser Tyr Leu Pro Leu Lys Gly Gly Tyr Gly Asn
    435                 440                 445

Pro Ala Ile Asp Cys Leu Leu Pro Gln Glu Trp Val Gln His Phe Tyr
450                 455                 460

Gln Glu Ala Ala Pro Ser Met Ser Glu Val Ala Leu Val Arg Tyr Ile
465                 470                 475                 480

Asn Pro Asp Thr Gly Arg Ala Leu Phe Glu Ala Lys Leu His Arg Ala
                485                 490                 495

Gly Phe Met Thr Val Ser Ser Asn Thr Ser Ala Pro Val Val Val Pro
                500                 505                 510

Ala Asn Gly Tyr Phe Arg Phe Asp Ser Trp Val Asn Gln Phe Tyr Ser
    515                 520                 525

Leu Ala Pro Met Gly Thr Gly Asn Gly Arg Arg Arg Ile Gln
    530                 535                 540

<210> SEQ ID NO 7
<211> LENGTH: 259
<212> TYPE: PRT
<213> ORGANISM: Snow Mountain virus
<300> PUBLICATION INFORMATION

```
Ala Leu Asp Trp Asn Gly Thr Arg Tyr Trp Ala Pro Gly Ser Met Arg
            100                 105                 110

Thr Thr Ser Tyr Ser Gly Arg Phe Thr Ser Thr Ala Pro Ala Arg Gln
        115                 120                 125

Ala Asp Leu Gln His Thr Gln Asn Arg Pro Ser Ser Gly Ser Ser Val
    130                 135                 140

Ser Ser Tyr Ala Thr Gln Ser Ser Arg Pro Thr Leu Thr Thr Thr Thr
145                 150                 155                 160

Gly Ser Ser His Ser Thr Thr Ser Ser Asn Ser Thr Arg Ser Thr Asn
                165                 170                 175

Leu Ser Gln Ser Thr Val Ser Arg Ala Ala Ser Arg Thr Ser Glu Trp
            180                 185                 190

Val Arg Asp Gln Asn Arg Asn Leu Glu Pro Tyr Met His Gly Ala Leu
        195                 200                 205

Gln Thr Ala Phe Val Thr Pro Pro Ser Ser Arg Ala Ser Asp Gly Thr
    210                 215                 220

Val Ser Thr Val Pro Lys Gly Val Leu Asp Ser Trp Thr Pro Ala Phe
225                 230                 235                 240

Asn Thr Arg Arg Gln Pro Leu Phe Ala His Leu Arg Lys Arg Gly Glu
                245                 250                 255

Ser Gln Ala

<210> SEQ ID NO 8
<211> LENGTH: 535
<212> TYPE: PRT
<213> ORGANISM: Hawaii virus
<300> PUBLICATION INFORMATION:
<308> DATABASE ACCESSION NUMBER: GenBank/U07611
<309> DATABASE ENTRY DATE: 2000-09-05
<313> RELEVANT RESIDUES IN SEQ ID NO: (1)..(535)

<400> SEQUENCE: 8

Met Lys Met Ala Ser Asn Asp Ala Ala Pro Ser Asn Asp Gly Ala Ala
1               5                   10                  15

Gly Leu Val Pro Glu Val Asn Asn Glu Thr Met Ala Leu Glu Pro Val
            20                  25                  30

Ala Gly Ala Ser Ile Ala Ala Pro Leu Thr Gly Gln Asn Asn Val Ile
        35                  40                  45

Asp Pro Trp Ile Arg Met Asn Phe Val Gln Ala Pro Asn Gly Glu Phe
    50                  55                  60

Thr Val Ser Pro Arg Asn Ser Pro Gly Glu Ile Leu Leu Asn Leu Glu
65                  70                  75                  80

Leu Gly Pro Glu Leu Asn Pro Phe Leu Ala His Leu Ser Arg Met Tyr
                85                  90                  95

Asn Gly Tyr Ala Gly Gly Val Glu Val Gln Val Leu Leu Ala Gly Asn
            100                 105                 110

Ala Phe Thr Ala Gly Lys Leu Val Phe Ala Ala Ile Pro Pro His Phe
        115                 120                 125

Pro Leu Glu Asn Leu Ser Pro Gly Gln Ile Thr Met Phe Pro His Val
    130                 135                 140

Ile Ile Asp Val Arg Thr Leu Glu Pro Val Leu Leu Pro Leu Pro Asp
145                 150                 155                 160

Val Arg Asn Asn Phe Phe His Tyr Asn Gln Gln Pro Glu Pro Arg Met
                165                 170                 175

Arg Leu Val Ala Met Leu Tyr Thr Pro Leu Arg Ser Asn Gly Ser Gly
            180                 185                 190
```

Asp Asp Val Phe Thr Val Ser Cys Arg Val Leu Thr Arg Pro Ser Pro
            195                 200                 205

Asp Phe Asp Phe Asn Tyr Leu Val Pro Pro Thr Val Glu Ser Lys Thr
            210                 215                 220

Lys Pro Phe Thr Leu Pro Ile Leu Thr Ile Gly Glu Leu Ser Asn Ser
225                 230                 235                 240

Arg Phe Pro Val Pro Ile Asp Glu Leu Tyr Thr Ser Pro Asn Glu Gly
            245                 250                 255

Val Ile Val Gln Pro Gln Asn Gly Arg Ser Thr Leu Asp Gly Glu Leu
            260                 265                 270

Leu Gly Thr Thr Gln Leu Val Pro Ser Asn Ile Cys Ala Leu Arg Gly
            275                 280                 285

Arg Ile Asn Ala Gln Val Pro Asp Asp His His Gln Trp Asn Leu Gln
            290                 295                 300

Val Thr Asn Thr Asn Gly Thr Pro Phe Asp Pro Thr Glu Asp Val Pro
305                 310                 315                 320

Ala Pro Leu Gly Thr Pro Asp Phe Leu Ala Asn Ile Tyr Gly Val Thr
            325                 330                 335

Ser Gln Arg Asn Pro Asn Asn Thr Cys Arg Ala His Asp Gly Val Leu
            340                 345                 350

Ala Thr Trp Ser Pro Lys Phe Thr Pro Lys Leu Gly Ser Val Ile Leu
            355                 360                 365

Gly Thr Trp Glu Glu Ser Asp Leu Asp Leu Asn Gln Pro Thr Arg Phe
            370                 375                 380

Thr Pro Val Gly Leu Phe Asn Thr Asp His Phe Asp Gln Trp Ala Leu
385                 390                 395                 400

Pro Ser Tyr Ser Gly Arg Leu Thr Leu Asn Met Asn Leu Ala Pro Ser
            405                 410                 415

Val Ser Pro Leu Phe Pro Gly Glu Gln Leu Leu Phe Phe Arg Ser His
            420                 425                 430

Ile Pro Leu Lys Gly Gly Thr Ser Asp Gly Ala Ile Asp Cys Leu Leu
            435                 440                 445

Pro Gln Glu Trp Ile Gln His Phe Tyr Gln Glu Ser Ala Pro Ser Pro
            450                 455                 460

Thr Asp Val Ala Leu Ile Arg Tyr Thr Asn Pro Asp Thr Gly Arg Val
465                 470                 475                 480

Leu Phe Glu Ala Lys Leu His Arg Gln Gly Phe Ile Thr Val Ala Asn
            485                 490                 495

Ser Gly Ser Arg Pro Ile Val Val Pro Pro Asn Gly Tyr Phe Arg Phe
            500                 505                 510

Asp Ser Trp Val Asn Gln Phe Tyr Ser Leu Ala Pro Met Gly Thr Gly
            515                 520                 525

Asn Gly Arg Arg Arg Val Gln
            530                 535

<210> SEQ ID NO 9
<211> LENGTH: 259
<212> TYPE: PRT
<213> ORGANISM: Hawaii virus
<300> PUBLICATION INFORMATION:
<308> DATABASE ACCESSION NUMBER: GenBank/U07611
<309> DATABASE ENTRY DATE: 2000-09-05
<313> RELEVANT RESIDUES IN SEQ ID NO: (1)..(259)

<400> SEQUENCE: 9

Met Ala Gly Ala Phe Ile Ala Gly Leu Ala Gly Asp Ile Val Thr Asn

```
               1               5                   10                  15
Ser Val Gly Ser Leu Val Asn Ala Gly Ala Asn Ala Ile Asn Gln Lys
                20                  25                  30

Val Asp Phe Glu Asn Asn Lys Gln Leu Gln Gln Ala Ser Phe Asn His
            35                  40                  45

Asp Lys Glu Met Leu Gln Ala Gln Ile Gln Ala Thr Lys Gln Leu Gln
        50                  55                  60

Ala Asp Met Ile Ala Leu Arg Gln Gly Val Leu Thr Ala Gly Gly Phe
65                  70                  75                  80

Ser Pro Thr Asp Ala Ala Arg Gly Ala Val Asn Ala Pro Met Thr Gln
                85                  90                  95

Val Leu Asp Trp Asn Gly Thr Arg Tyr Trp Ala Pro Gly Ala Thr Lys
            100                 105                 110

Thr Thr Ala Phe Ser Gly Gly Phe Thr Ser Ser His Ala Arg Thr
        115                 120                 125

Val Asp Leu Pro Lys Lys Thr Ala Ala Pro Ala Thr Met Pro Val
    130                 135                 140

Ser Arg Pro Ser Ser Ser Ala Ser Thr Ala Ser Thr Arg Ser Thr Leu
145                 150                 155                 160

Val Ser Gly Ser Ser Asn Leu Pro Ser Ser Ala Arg Ser Ser Ser Ser
                165                 170                 175

Val Phe Ser Gln Ser Thr Ser Pro Ser Ser Arg Thr Ser Glu Trp Val
            180                 185                 190

Arg Ser Gln Asn Arg Ala Leu Glu Pro Tyr Met Arg Gly Ala Leu Gln
        195                 200                 205

Thr Ala Tyr Val Thr Pro Pro Ser Ser Arg Ala Ser Ser Asn Gly Thr
    210                 215                 220

Val Ser Thr Val Pro Lys Glu Val Leu Asp Ser Trp Thr Ser Val Phe
225                 230                 235                 240

Asn Thr His Arg Gln Pro Leu Phe Ala His Leu Arg Arg Arg Gly Glu
                245                 250                 255

Ser Gln Val

<210> SEQ ID NO 10
<211> LENGTH: 849
<212> TYPE: PRT
<213> ORGANISM: London/29845 Sapovirus
<300> PUBLICATION INFORMATION:
<308> DATABASE ACCESSION NUMBER: GenBank/U95645
<309> DATABASE ENTRY DATE: 2005-07-12
<313> RELEVANT RESIDUES IN SEQ ID NO: (1)..(849)

<400> SEQUENCE: 10

Asp Ser Tyr Gln Val Glu Val Leu Asn Glu Ser Leu Lys Gly Gly Val
1               5                   10                  15

Val Tyr Cys Leu Asp Tyr Ser Lys Trp Asp Ser Thr Gln His Pro Ala
            20                  25                  30

Val Thr Ala Ala Ser Leu Ala Ile Leu Glu Arg Leu Ser Glu Ala Thr
        35                  40                  45

Pro Ile Thr Thr Ser Ala Val Arg Leu Leu Ser Ser Pro Ala Arg Gly
    50                  55                  60

His Leu Asn Asp Ile Ile Phe Val Thr Lys Ser Gly Leu Pro Ser Gly
65                  70                  75                  80

Met Pro Phe Thr Ser Val Val Asn Ser Leu Asn His Met Thr Tyr Phe
                85                  90                  95

Ala Ala Ala Val Leu Lys Ala Tyr Glu Gln His Gly Ala Pro Tyr Thr
```

```
                    100                 105                 110
Gly Asn Val Phe Gln Val Lys Thr Val His Thr Tyr Gly Asp Asp Cys
            115                 120                 125

Ile Tyr Ser Leu Cys Pro Ala Thr Ala Ser Ile Phe Glu Thr Val Leu
        130                 135                 140

Ala Asn Leu Ser Ala Phe Gly Leu Arg Pro Thr Ala Ala Asp Lys Thr
145                 150                 155                 160

Asp Lys Ile Ala Pro Thr His Thr Pro Val Phe Leu Lys Arg Thr Leu
                165                 170                 175

Thr Cys Thr Pro Arg Gly Ile Arg Gly Leu Leu Asp Ile Thr Ser Ile
            180                 185                 190

Arg Arg Gln Phe Phe Trp Ile Lys Ala Asn Arg Thr Thr Asp Ile Ser
        195                 200                 205

Ser Pro Pro Ala Tyr Asp Arg Glu Ala Arg Ser Val Gln Leu Glu Asn
            210                 215                 220

Ala Leu Ala Tyr Ala Ser Gln His Gly His Ala Ile Phe Glu Glu Ile
225                 230                 235                 240

Ala Glu Ile Ala Lys Arg Thr Ala Gln Ser Glu Gly Leu Val Leu Thr
                245                 250                 255

Asn Val Asn Tyr Asp Gln Ala Leu Ala Thr Tyr Glu Ala Trp Phe Ile
            260                 265                 270

Gly Gly Thr Gly Thr Gly Gln Asp Ser Pro Ser Glu Glu Thr Thr Lys
        275                 280                 285

Leu Val Phe Glu Met Glu Gly Leu Ala Ser His Ser Pro Lys Gly Gln
        290                 295                 300

Gln Val Met Glu Gln Val Val Thr Pro Gln Asp Thr Ile Gly Pro Thr
305                 310                 315                 320

Ser Ala Leu Leu Leu Pro Thr Gln Val Glu Thr Pro Asn Ala Ser Ala
                325                 330                 335

Gln Arg Val Glu Leu Ala Met Ala Thr Gly Ala Val Thr Ser Asn Val
            340                 345                 350

Pro Asn Cys Ile Arg Glu Cys Phe Ala Ala Val Thr Thr Ile Pro Trp
        355                 360                 365

Thr Thr Arg Gln Ala Ala Asn Thr Phe Leu Gly Ala Ile His Leu Gly
        370                 375                 380

Pro Arg Ile Asn Pro Tyr Thr Ala His Leu Ser Ala Met Phe Ala Gly
385                 390                 395                 400

Trp Gly Gly Phe Gln Val Arg Val Thr Ile Ser Gly Ser Gly Leu
                405                 410                 415

Phe Ala Gly Arg Ala Ile Thr Ala Ile Leu Pro Pro Gly Val Asn Pro
            420                 425                 430

Ala Ala Val Gln Asn Pro Gly Val Phe Pro His Ala Phe Ile Asp Ala
        435                 440                 445

Arg Thr Thr Asp Pro Ile Leu Ile Asn Leu Pro Asp Ile Arg Pro Ile
        450                 455                 460

Asp Phe His Arg Val Asp Gly Asp Ala Thr Val Cys Gly Val Val
465                 470                 475                 480

Gly Arg Asp Pro Leu Ile Asn Pro Phe Gln Thr Gly Ser Val Ser Thr
                485                 490                 495

Cys Trp Leu Ser Phe Glu Thr Arg Pro Gly Asp Phe Asp Phe Cys
            500                 505                 510

Leu Leu Lys Ala Pro Glu Gln Glu Met Asp Asn Gly Ile Ser Pro Ala
        515                 520                 525
```

-continued

Asn Leu Leu Pro Arg Arg Leu Gly Ser Arg Gly Asn Arg Leu Gly Arg
            530                 535                 540

Val Val Gly Leu Val Val Ala Ala Ala Glu Gln Val Asn His His
545                 550                 555                 560

Phe Gly Ala Asn Ser Thr Thr Leu Gly Trp Ser Thr Leu Pro Ile Glu
                565                 570                 575

Pro Ile Ala Gly Gly Ile Ser Trp Tyr Asp Asp Asn Asn Glu His Thr
                580                 585                 590

Lys Ile Arg Gly Leu Leu Ser Ala Gln Gly Lys Gly Ile Ile Phe Pro
            595                 600                 605

Asn Ile Val Asn His Trp Thr Asp Val Ser Leu Ser Ala Lys Thr Ser
610                 615                 620

Gly Gln Thr Thr Ile Pro Ile Ala Ala Asp Asn Leu Asn Asn Ser Pro
625                 630                 635                 640

Trp Gly Ser Trp Pro Val Val Met Phe Glu Asn Asn Gly Asp Val Asn
                645                 650                 655

Glu Ser Thr Ala Asn His Gly Ile Leu Thr Ala Ala Ser His Asp Phe
                660                 665                 670

Thr Ser Leu Ser Gln Thr Phe Asp Ala Ala Gly Leu Trp Val Trp Met
            675                 680                 685

Pro Trp Thr Arg Asn Lys Pro Asp Gly Arg Thr Asn Thr Asn Val Tyr
690                 695                 700

Ile Thr Pro Thr Trp Ile Asn Gly Asn Pro Ala Arg Pro Ile His Glu
705                 710                 715                 720

Lys Cys Thr Asn Met Val Gly Thr Asn Phe Gln Phe Gly Gly Thr Gly
                725                 730                 735

Thr Asn Asn Ile Met Leu Trp Gln Glu Gln His Phe Thr Ser Phe Pro
                740                 745                 750

Gly Ala Ala Glu Val Tyr Cys Ser Gln Leu Glu Ser Thr Ala Glu Met
            755                 760                 765

Phe Gln Asn Asn Val Val Asn Ile Pro Ala Asn Gln Met Ala Val Phe
770                 775                 780

Asn Val Glu Thr Ala Gly Asn Thr Phe Gln Ile Gly Ile Phe Ala Asn
785                 790                 795                 800

Gly Tyr Ser Val Thr Asn Ala Ala Ile Gly Thr His Gln Leu Leu Asp
                805                 810                 815

Tyr Glu Thr Ser Phe Arg Phe Val Gly Leu Phe Pro Gln Ser Thr Ser
            820                 825                 830

Leu Gln Gly Pro Asn Gly Lys Arg Trp Thr Gly Pro Val Arg Phe Leu
            835                 840                 845

Glu

<210> SEQ ID NO 11
<211> LENGTH: 853
<212> TYPE: PRT
<213> ORGANISM: Houston/86 Sapovirus
<300> PUBLICATION INFORMATION:
<308> DATABASE ACCESSION NUMBER: GenBank/U95643
<309> DATABASE ENTRY DATE: 2005-07-12
<313> RELEVANT RESIDUES IN SEQ ID NO: (1)..(853)

<400> SEQUENCE: 11

Asp Ser Val Gln Met Gln Val Met Asn Asp Ser Leu Lys Gly Gly Val
1               5                   10                  15

Leu Tyr Cys Leu Asp Tyr Ser Lys Trp Asp Ser Thr Gln Asn Pro Ala
                20                  25                  30

```
Val Thr Ala Ala Ser Leu Ala Ile Leu Glu Arg Phe Ala Glu Pro His
        35                  40                  45

Pro Ile Val Ser Cys Ala Ile Glu Ala Leu Ser Ser Pro Ala Glu Gly
    50                  55                  60

Tyr Val Asn Asp Ile Lys Phe Val Thr Arg Gly Gly Leu Pro Ser Gly
65                  70                  75                  80

Met Pro Phe Thr Ser Val Val Asn Ser Ile Asn His Met Ile Tyr Val
                85                  90                  95

Ala Ala Ala Ile Leu Gln Ala Tyr Glu Ser His Asn Val Pro Tyr Thr
                100                 105                 110

Gly Asn Val Phe Gln Val Glu Thr Val His Thr Tyr Gly Asp Asp Cys
                115                 120                 125

Met Tyr Ser Val Cys Pro Ala Thr Ala Ser Ile Phe His Thr Val Leu
130                 135                 140

Ala Asn Leu Thr Ser Tyr Gly Leu Lys Pro Thr Ala Ala Asp Lys Ser
145                 150                 155                 160

Asp Ala Ile Lys Pro Thr Asn Thr Pro Val Phe Leu Lys Arg Thr Phe
                165                 170                 175

Thr Gln Thr Pro His Gly Val Arg Ala Leu Leu Asp Ile Thr Ser Ile
                180                 185                 190

Thr Arg Gln Phe Tyr Trp Leu Lys Ala Asn Arg Thr Ser Asp Pro Ser
                195                 200                 205

Ser Pro Pro Ala Phe Asp Arg Gln Ala Arg Ser Ala Glu Leu Glu Asn
210                 215                 220

Ala Leu Ala Tyr Ala Ser Gln His Gly Pro Ile Val Phe Asp Thr Val
225                 230                 235                 240

Arg Gln Ile Ala Ile Lys Ser Ala Gln Gly Glu Gly Leu Val Leu Val
                245                 250                 255

Asn Thr Asn Tyr Asp Gln Ala Leu Ala Thr Tyr Asn Ala Trp Phe Ile
                260                 265                 270

Gly Gly Thr Met Pro Asp Pro Val Gly His Thr Glu Gly Thr His Lys
                275                 280                 285

Ile Val Phe Glu Met Glu Gly Asn Gly Ser Asn Pro Glu Pro Lys Gln
                290                 295                 300

Ser Asn Asn Pro Met Val Val Asp Pro Pro Gly Thr Thr Gly Pro Thr
305                 310                 315                 320

Thr Ser His Ala Val Val Ala Asn Pro Glu Gln Pro Tyr Gly Ala Ala
                325                 330                 335

Gln Pro Leu Glu Leu Ala Val Ala Thr Gly Ala Ile Gln Ser Asn Val
                340                 345                 350

Pro Glu Ala Ile Arg Asn Cys Phe Ala Val Phe Arg Thr Phe Ala Trp
                355                 360                 365

Asn Asp Arg Met Pro Thr Gly Thr Phe Leu Gly Ser Ile Ser Leu His
370                 375                 380

Pro Asn Ile Asn Pro Tyr Thr Ser His Leu Ser Gly Met Trp Ala Gly
385                 390                 395                 400

Trp Gly Gly Thr Phe Glu Val Arg Leu Ser Ile Ser Gly Ser Gly Val
                405                 410                 415

Phe Ala Gly Arg Ile Ile Ala Ser Val Ile Pro Pro Gly Val Asp Pro
                420                 425                 430

Ser Ser Ile Arg Asp Pro Gly Val Leu Pro His Ala Phe Val Asp Ala
            435                 440                 445

Arg Ile Thr Glu Pro Val Ser Phe Met Ile Pro Ser Val Arg Ala Val
450                 455                 460
```

```
Asp Tyr His Arg Met Asp Gly Ala Glu Pro Thr Cys Ser Leu Gly Phe
465                 470                 475                 480

Trp Val Tyr Gln Pro Leu Leu Asn Pro Phe Ser Thr Thr Ala Val Ser
            485                 490                 495

Thr Cys Trp Val Ser Val Glu Thr Lys Pro Gly Gly Asp Phe Asp Phe
                500                 505                 510

Cys Leu Leu Ser Thr Pro Gly Gln His Met Glu Asn Gly Val Ser Pro
            515                 520                 525

Glu Gly Leu Leu Pro Arg Arg Phe Gly Tyr Ser Arg Gly Asn Arg Val
        530                 535                 540

Gly Gly Leu Val Val Gly Met Ile Leu Val Ala Glu His Arg Gln Val
545                 550                 555                 560

Asn Arg His Phe Asn Ser Asn Ser Val Thr Phe Gly Trp Ser Thr Ala
                565                 570                 575

Pro Val Asn Pro Met Ala Ala Glu Ile Val Thr Asn Gln Ala His Ser
            580                 585                 590

Thr Ser Arg His Ala Trp Leu Ser Ile Gly Ala Gln Asn Lys Gly Pro
        595                 600                 605

Leu Phe Pro Gly Ile Pro Asn His Phe Pro Ala Ser Cys Ala Ser Thr
610                 615                 620

Val Val Gly Ala Met Asp Thr Ser Leu Gly Gly Arg Pro Ser Thr Gly
625                 630                 635                 640

Val Cys Gly Pro Ala Ile Ser Phe Gln Asn Asn Gly Asp Val Tyr Glu
                645                 650                 655

Asn Asp Thr Pro Ser Val Met Phe Ala Thr Tyr Asp Pro Leu Thr Ser
            660                 665                 670

Gly Thr Gly Val Ala Leu Thr Asn Ser Ile Asn Pro Ala Ser Leu Ala
        675                 680                 685

Leu Val Arg Ile Ser Asn Asn Asp Phe Asp Thr Ser Gly Phe Ala Asn
690                 695                 700

Asp Lys Asn Val Val Gln Met Ser Trp Glu Met Tyr Thr Gly Thr
705                 710                 715                 720

Asn Gln Ile Arg Gly Gln Val Thr Pro Met Ser Gly Thr Asn Tyr Thr
                725                 730                 735

Phe Thr Ser Thr Gly Ala Asn Thr Leu Val Leu Trp Gln Glu Arg Met
            740                 745                 750

Leu Ser Tyr Asp Gly His Gln Ala Ile Leu Tyr Ser Ser Gln Leu Glu
        755                 760                 765

Arg Thr Ala Glu Tyr Phe Gln Asn Asp Ile Val Asn Ile Pro Glu Asn
770                 775                 780

Ser Met Ala Val Phe Asn Val Glu Thr Asn Ser Ala Ser Phe Gln Ile
785                 790                 795                 800

Gly Ile Arg Pro Asp Gly Tyr Met Val Thr Gly Gly Ser Ile Gly Val
                805                 810                 815

Asn Val Pro Leu Glu Pro Glu Thr Arg Phe Gln Tyr Val Gly Ile Leu
            820                 825                 830

Pro Leu Ser Ala Ala Leu Ser Gly Pro Ser Gly Asn Met Gly Arg Ala
        835                 840                 845

Arg Arg Val Phe Gln
    850

<210> SEQ ID NO 12
<211> LENGTH: 856
<212> TYPE: PRT
```

<213> ORGANISM: Parkville virus
<300> PUBLICATION INFORMATION:
<308> DATABASE ACCESSION NUMBER: GenBank/AF294739
<309> DATABASE ENTRY DATE: 2000-08-20
<313> RELEVANT RESIDUES IN SEQ ID NO: (1)..(856)

<400> SEQUENCE: 12

```
Met Asn Asp Ser Leu Arg Gly Gly Val Leu Tyr Cys Leu Asp Tyr Ser
1               5                   10                  15

Lys Trp Asp Ser Thr Gln Asn Pro Ala Val Thr Ala Ala Ser Leu Ser
            20                  25                  30

Ile Leu Glu Arg Phe Met Glu Ser Ser Pro Leu Val Ser Cys Ala Ile
        35                  40                  45

Glu Ser Leu Ser Ser Pro Ala Ile Gly Tyr Leu Asn Asp Ile Lys Phe
    50                  55                  60

Val Thr Lys Gly Gly Leu Pro Ser Gly Met Pro Phe Thr Ser Val Ile
65                  70                  75                  80

Asn Ser Val Asn His Met Ile Tyr Phe Ala Ala Gly Val Leu Lys Ala
                85                  90                  95

Tyr Glu Asp His His Val Pro Tyr Thr Gly Asn Val Phe Gln Ile Glu
            100                 105                 110

Thr Val His Thr Tyr Gly Asp Asp Cys Ile Tyr Ser Val Cys Pro Ala
        115                 120                 125

Thr Ala Ser Ile Phe Gly Ser Val Leu Ala Asn Leu Ser Ser Phe Gly
    130                 135                 140

Leu Lys Pro Thr Ala Ala Asp Lys Thr Ala Glu Ile Lys Pro Thr Gln
145                 150                 155                 160

Thr Pro Val Phe Leu Lys Arg Thr Phe Thr Gln Thr Pro His Gly Val
                165                 170                 175

Arg Ala Leu Leu Asp Ile Asn Ser Ile Ile Arg Gln Phe Tyr Trp Val
            180                 185                 190

Lys Ala Asn Arg Thr Ser Asp Pro Ser Ser Pro Pro Ala Phe Asp Arg
        195                 200                 205

Thr Ala Arg Ser Ala Gln Leu Glu Ala Ala Leu Ala Tyr Ala Ser Gln
    210                 215                 220

His Gly Pro Leu Val Phe Asp Lys Val Arg Asp Ile Ala Ile Lys Thr
225                 230                 235                 240

Ala Glu Gly Glu Gly Val Val Leu Val Asn Thr Asn Phe Asp Leu Ala
                245                 250                 255

Leu Ala Thr Tyr Asn Ala Trp Phe Ile Gly Gly Thr Ala Pro Asp Pro
            260                 265                 270

Glu Arg Pro Thr Glu Gly Ala Pro Lys Leu Val Phe Glu Met Glu Gly
        275                 280                 285

Asn Gly Ser Lys Leu Pro Thr Asn Gln Ser Gly Gly His Val Gly Gln
    290                 295                 300

Asp Val Asp Pro Pro Gly Ala Thr Gly Pro Thr Thr Ser His Val Val
305                 310                 315                 320

Val Ser Asn Pro Glu Gln Pro Asn Gly Pro Ala Gln Arg Leu Glu Met
                325                 330                 335

Ala Val Ala Thr Gly Ser Ile Gln Ser Asn Val Pro Glu Ala Ile Arg
            340                 345                 350

Asn Cys Phe Ala Val Cys Arg Thr Phe Ala Trp Asn Asp Arg Met Pro
        355                 360                 365

Thr Gly Thr Phe Leu Gly Ser Leu Ser Leu His Pro Asn Ile Asn Pro
    370                 375                 380
```

-continued

```
Tyr Thr Ser His Leu Ser Gly Met Trp Ala Gly Trp Gly Gly Ser Phe
385                 390                 395                 400

Glu Ala Arg Ile Ser Ile Ser Gly Ser Gly Met Phe Ala Gly Arg Ile
            405                 410                 415

Ile Ala Ser Val Ile Pro Pro Gly Val Asp Pro Thr Ser Ile Arg Asp
        420                 425                 430

Pro Gly Val Leu Pro His Ala Phe Val Asp Ala Arg Ile Thr Asp Pro
    435                 440                 445

Val Ser Phe Met Ile Pro Asp Val Arg Asn Ile Asp Tyr His Arg Met
450                 455                 460

Asp Ser Thr Asp Pro Thr Cys Ser Leu Gly Phe Trp Val Tyr Gln Pro
465                 470                 475                 480

Leu Leu Asn Pro Phe Ser Thr Thr Ala Val Thr Thr Cys Trp Val Ser
                485                 490                 495

Ile Glu Thr Lys Pro Gly Gly Asp Phe Asp Phe Cys Leu Leu Arg Pro
            500                 505                 510

Pro Gly Gln Gln Met Glu Asn Gly Val Ser Pro Glu Gly Leu Leu Pro
        515                 520                 525

Arg Arg Leu Gly Tyr Thr Arg Gly Asn Arg Val Gly Gly Leu Ile Val
    530                 535                 540

Gly Met Val Leu Val Ala Asp His Arg Gln Val Asn Arg His Phe Asn
545                 550                 555                 560

Ala Arg Ser Ile Thr Tyr Gly Trp Ser Thr Ala Pro Val Asn Pro Met
                565                 570                 575

Ala Ala Ala Ile Gln Thr Asn His Asn His Thr Gly Thr Thr Asn Ala
            580                 585                 590

Asn Lys Arg Asn Ala Trp Leu Leu Leu Ser Ala Glu Asn Lys Gly Pro
        595                 600                 605

Leu Phe Pro Gly Ile Pro Asn His Phe Pro Asp Ser Cys Ala Ser Thr
    610                 615                 620

Val Met Gly Gly Met Asp Thr Asp Arg His Met Pro Ser Thr Gly Val
625                 630                 635                 640

Cys Gly Pro Ala Ile Gly Phe Gln Asn Asn Gly Asp Val Tyr Glu Asn
                645                 650                 655

Glu Thr Pro Ala Val Met Phe Ala Thr Leu Asn Pro Leu Thr Gly Gly
            660                 665                 670

Thr Asn Glu Asn Pro Val Ala Leu Phe Gly Ser Ile Asn Met Ala Ser
        675                 680                 685

Leu Ala Val Val Arg Thr Gln Gln Asp Ala Asp Phe Pro Thr Ala Gly
    690                 695                 700

Phe Arg Asn Asp Met Asn Val Val Val Glu Met Ser Trp Glu Met Tyr
705                 710                 715                 720

Ser Gly Ser Gln Gln Ile Gln Gly Arg Val Thr Pro Met Asp Gly Thr
                725                 730                 735

Asn Phe Val Phe Thr Ser Ser Gly Ala Asn Thr Leu Ala Leu Trp Glu
            740                 745                 750

Glu Arg Leu Leu Ser Tyr Asp Gly His Gln Ala Ile Leu Tyr Ser Ser
        755                 760                 765

Gln Leu Glu Arg Thr Ala Glu Tyr Phe Gln Asn Asp Asn Val Asn Ile
    770                 775                 780

Pro Pro Gly Ser Met Ala Val Phe Asn Val Glu Thr Asn Ser Ala Ser
785                 790                 795                 800

Phe Gln Ile Gly Ile Arg Glu Asp Gly Tyr Met Val Thr Gly Gly Thr
                805                 810                 815
```

```
Val Gly Thr His Val Ala Leu Asp Ala Glu Thr Arg Phe Gln Phe Val
            820                 825                 830
Gly Ile Leu Pro Leu Thr Ala Thr Leu Ala Gly Pro Asn Gly Asn Ser
        835                 840                 845
Gly Arg Ala Arg Arg Leu Phe Gln
    850                 855

<210> SEQ ID NO 13
<211> LENGTH: 7556
<212> TYPE: DNA
<213> ORGANISM: Norovirus MD145-12
<300> PUBLICATION INFORMATION:
<308> DATABASE ACCESSION NUMBER: GenBank/AY032605
<309> DATABASE ENTRY DATE: 2002-01-29
<313> RELEVANT RESIDUES IN SEQ ID NO: (1)..(7556)

<400> SEQUENCE: 13
gtgaatgaag atggcgtcta acgacgcttc cgctgccgct gttgccaaca gcaacaacga 60
caccgcaaaa tcttcaagtg acggagtgct ttctagcatg gctatcactt ttaaacgagc 120
cctcggggcg cggcctaaac agcctccccc gagggaaata ctacaaagac ccccacgacc 180
acctacccca gaactggtca aaaagatccc ccctcccccg cccaacgggg aggatgaact 240
agtggtttct tatagtgtca aagatggcgt ttccggtctg cctgagcttt ccactgtcag 300
gcaaccggat gaagccaata cggccttcag tgttccccca ctcaatcaga gggagaatag 360
ggatgccaag gagccactaa ctggaacaat tctggaaatg tgggatggag agatctacca 420
ttacggccta tatgtggagc gaggtcttgt acttggtgtg cacaaaccac cagctgccat 480
cagcctcgcc aaggtcgaac taacaccact ctccttgttc tggagacctg tatacactcc 540
ccagtatctc atctccccag acactctcaa gagattgcac ggagaatcgt tcccctatac 600
agccttcgac aacaattgct atgccttctg ttgctgggtc ttagacctaa acgactcgtg 660
gctgagtagg agaacgatcc agagaacaac tggtttcttt agaccctatc aagactggaa 720
taggaaaccc ctccctactg tggatgactc caaattaaag aaggtagcta acttattcct 780
gtgtgctcta tcttcactat tcaccaggcc catcaaagac ataataggga aactaagacc 840
tctcaacatc ctcaacatct tggcctcatg tgattggact ttcgcaggca tagtggaatc 900
cttgatactc atggcagagc tctttggagt tttctggacg cccccagatg tgtctgcgat 960
gattgccccc ttgctaggtg attacgagtt acaagggcct gaggaccttg cagtggaact 1020
cgttcctata gtgatggggg gaattggttt ggtgctagga tttaccaaag agaagattgg 1080
gaagatgttg tcatctgctg catccacctt aagagcttgt aaagatcttg gtgcatacgg 1140
gctggaaatc ctaaaattag tcatgaagtg gttcttccca aagaaagagg aagcaaatga 1200
gctggctatg gtgagatcca tcgaggatgc ggtgctggac ctcgaggcaa ttgaaaacaa 1260
ccatatgacc agcctgctca aagacaaaga cagtctggca acctacatga gaacccttga 1320
ccttgaggag gagaaagcca ggaagctctc aaccaagtct gcttcacctg atatcgtggg 1380
tacaatcaac gcccttctgg caagaatcgc tgctgcacgt tccctggtgc atcgagcgaa 1440
ggaggagctt tccagcagac caagacccgt tgtcgtgatg atatcaggca gaccagggat 1500
agggaagacc caccttgcca gggaactggc caagagaatc gcagcctccc tcacaggaga 1560
ccagcgtgta ggtctcatcc cacgcaatgg cgtcgaccac tgggacgcat acaagggggga 1620
gagggtcgtc ctatgggacg actatggaat gagtaatccc atccatgatg ccctcaggtt 1680
acaagaactc gctgacactt gcccccctcac tctaaactgt gacaggattg agaacaaagg 1740
```

```
aaaggtctttt gacagtgatg ccataatcat caccactaat ctggccaacc cagcaccact      1800
ggactacgtc aactttgagg catgctcgag gcgcatcgat ttcctcgtgt atgcagatgc      1860
ccctgaagtc gagaaggcga acgtgatttt ccaggccaa cctgacatgt ggaagaacgc       1920
tttcagtcct gatttctcgc acataaaact aacgctggct ccacagggtg gcttcgacaa      1980
gaatggaaac accccacatg ggaagggcgt catgaagact ctcaccactg gctccctcat      2040
tgcccgggca tcagggctac tccatgagag gttagatgag tatgagctac agggcccaac      2100
tctcaccact ttcaactttg atcgcaacaa ggtgcttgct tttaggcagc ttgctgctga      2160
aaacaaatac gggctgatgg acacaatgaa agttggaaga cagctcaagg atgtcagaac      2220
catgccagag cttaaacaag cactcaagaa tatctcaatc aagaggtgcc agatagtgta      2280
cagtggttgc acctatacac ttgagtctga tggcaagggc agtgtgaaag ttgacagagt      2340
tcagagcgcc accgtgcaga ccaataacga gctggccggc gccctacacc atctaaggtg      2400
cgccagaatt aggtactatg tcaagtgtgt ccaggaggcc ctatattcca tcatccaaat      2460
tgctggagct gcatttgtca ccacgcgcat cgtcaagcgc atgaacatac aagacctctg      2520
gtccaagcca caagtggaag acacagagga gactatcaac aaggacgggt gcccaaaacc      2580
caaagatgat gaggagttcg tcgtctcatc tgacgacatc aaaactgagg caagaaagg      2640 gaagaacaag actggccgtg gcaagaagca cacagccttc tcaagcaaag gtctcagtga      2700
tgaagagtac gatgagtaca agagaatcag agaagaaaga aacggcaagt actccataga      2760
agagtacctt caggacaggg acaagtacta tgaggaggtg gccattgcca gggcgaccga      2820
agaggacttc tgtgaagagg aggaggccaa gattcggcag aggattttca ggccaacaag      2880
gaaacaacgc aaggaggaga gggcctctct cggtttagtc acaggctctg aaatcaggaa      2940
gaggaaccca gatgatttca gcccaagggg aaaactgtgg gctgatgatg acaggagtgt      3000
agactacaat gagagactca gttttgaggc cccaccaagc atctggtcga ggatagtcaa      3060 cttttggttca ggttggggct tctgggtttc tcccagcctg ttcataacat caactcatgt      3120 catacccag ggcgcacagg agttctttgg agtccccatc aagcaaattc agatacacaa      3180
atcgggcgaa ttctgtcgct tgaggttccc aaaaccaatc aggactgatg tgacgggcat      3240
gatcttagaa gaaggtgcgc ccgaaggtac cgtggccacc ctactcatca agaggcctac      3300
tggagaactt atgcccttag cagccagaat ggggacccat gcaaccatga aaattcaagg      3360
gcgcactgtt ggaggtcaaa tgggcatgct tctgacagga tccaacgcca aaagcatggt      3420
tctaggcacc acaccaggtg actgcggctg cccctacatc tacaagaggg agaatgacta      3480
cgtggttatt ggagtccaca cggctgccgc tcgtgggggg aacactgtca tatgtgccac      3540
ccaggggagt gagggagagg ctacacttga aggcggtgac agtaagggaa cctactgtgg      3600
tgcaccaatc ctaggcccag gaagtgcccc aaaactcagc accaagacta aattctggag      3660
atcatctaca acaccactcc cacctggcac ctatgaacca gcctaccttg gtggtaagga      3720
ccccagagtc aagggtggcc cttcattgca acaagtcatg agggatcagc tgaaaccatt      3780
tacagagccc aggggcaaac caccaaagcc aagtgtgttg gaggctgcca agaaaaccat      3840
catcaatgtc cttgaacaaa caattgatcc acctcagaag tggtcattca cgcaagcttg      3900
cgcgtccctc gacaagacta cttccagtgg ccatccgcac cacatacgga aaacgactg      3960 ctggaacggg gaatccttca caggcaagtt ggcagaccag gcttccaagg ccaacctgat      4020
gttcgaagag gggaagaaca tgaccccggt ctacacaggt gcgcttaagg atgagttggt      4080
caaaactgac aaaatttatg gtaagatcaa gaagaggctt ctctggggct cggacttagc      4140
```

```
gaccatgatc cggtgcgctc gggcattcgg aggcctaatg gatgaactca aagcacactg    4200
tgttacactt cctgtcagag ttggtatgaa tatgaatgag gatggcccca tcatcttcga    4260
gaggcattcc aggtataaat atcactatga tgctgattac tctcggtggg attcaacgca    4320
acagagagcc gtattagcag cagccctaga aatcatggtt aaattctccc cagaaccaca    4380
tctggcccag atagttgcag aagaccttct ctctcctagt gtgatggatg tgggtgactt    4440
caaaatatca atcaatgagg gtctcccctc tggggtgccc tgcacctccc aatggaattc    4500
catcgcccac tggctcctca ctctctgtgc actctctgaa gtcacaaacc tgtcccctga    4560
tatcatacag gctaattccc tcttctcctt ttatggcgat gatgaaattg tcagtacaga    4620
tataaagttg gacccagaga aattgacagc aaaactcaag gaatacgggt tgaaaccaac    4680
ccgccctgac aaaactgaag gaccccttac tatctctgaa gacttgaatg gtctgacctt    4740
cctgcggaga actgtgaccc gcgacccagc tggctggttt ggaaaattgg aacagagttc    4800
aatacttagg caaatgtact ggactagggg ccccaaccat gaagacccat ctgaaacaat    4860
gataccacac tcccaaagac ccatacaatt aatgtcccta ctgggcgagg ccgcactcca    4920
cggcccagca ttctacagca aaattagcaa gctagtcatt gcagagctga aggaaggtgg    4980
catggatttt tacgtgccca gacaagagcc aatgttcaga tggatgagat tctcagatct    5040
gagcacgtgg gagggcgatc gcaatctggc tcccagtttt gtgaatgaag atggcgtcga    5100
gtgacgccaa cccatctgat gggtccgcag ccaacctcgt cccagaggtc aacaatgagg    5160
ttatggctct ggagcccgtt gttggtgccg ctattgcggc acctgtagcg ggccaacaaa    5220
atataattga cccctggatt agaaataatt ttgtacaagc ccctggtgga gagtttacag    5280
tgtcccctag aaacgctcca ggtgagatac tatggagcgc gcccttgggc cctgatttga    5340
accccctatct ttctcatttg tccagaatgt acaatggtta tgcaggcggt ttcgaagtgc    5400
aagtaatcct cgcggggaac gcgttcaccg ccgggaaagt tatatttgca gcagttccac    5460
caaactttcc aactgaaggc ttaagcccca gccaggttac tatgttcccc catataattg    5520
tagatgttag gcaattggaa cctgtgttga tcccccctacc tgatgttagg aataaatttct    5580
atcattacaa tcaatcacat gattctaccc ttaagttgat agcaatgttg tatacaccac    5640
tcagggctaa taatgccggg gacgatgtct tcacagtctc ttgtcgagtt ctcacgaggc    5700
catcccccga ttttgatttc atattcttgg tgccacccac agttgaatca agaactaaac    5760
cattcaccgt cccaatctta actgttgagg aaatgtccaa ttcaagattc cccattcctt    5820
tggaaaagtt gtacacgggt cctagcagtg cttttgttgt ccaaccacaa aatggcagat    5880
gcacgactga tggcgtgctc ttaggtacta cccagctgtc agctgtcaac atctgtaact    5940
ttaggggggga tgtcacccat attgtgggca gccatgatta tacaatgaat ctggcttccc    6000
aaaattggag caattatgac ccaacagaag aaatcccagc cccctggga acaccagatt    6060
ttgtggggaa gatccaaggc ctgctcaccc agacacaag agcggatggc tcgacccgtg    6120
cccacaaagc tacagtgagc actgggagtg tccacttcac tccaaagctg gtagtgttc    6180
aattcaccac tgacacaaac aatgatttcc aaactgccca aaacacgaaa ttcacccag    6240
ttggcgtcat ccaggacggt gatcaccatc agaatgagcc ccaacaatgg gtactcccaa    6300
attactcagg tagaactggt cataatgtgc acctggcccc tgccgttgcc cccacttttc    6360
cgggtgagca actccttttc tttagatcca ctatgcccgg atgtagcggg tatcccaaca    6420
tgaatttgga ttgcctactc ccccaggaat gggtgctgca cttctaccag gaagcagctc    6480
cagcacaatc cgatgtggct ctgctgagat ttgtgaatcc agacacaggt agggttctgt    6540
```

-continued

```
ttgagtgcaa gctccataaa tcaggctata tcacagtggc tcacaccggc ccgtatgact      6600
tggttatccc ccccaatggt tattttagat ttgattcctg ggtcaaccag ttctacacac      6660
ttgcccccat gggaaatgga acggggcgca ggcgtgcatt ataatggctg atctttctt       6720 tgctggattg gcatctgatg tcctcggctc tggacttggt tctctaatca atgctggagc      6780
tggggccatc aaccaaaaag ttgaatttga aaataacaga aaattgcaac aagcttcctt      6840
ccaatttagt agcaatctac aacaggcttc cttccaacat gataaagaga tgctccaagc      6900
acaaattgag gctactcaaa aattgcaaca ggatctgatg aaggttaaac aggcagtgct      6960
cctagagggt ggattttcca acagatgc agcccgtggg gcaatcaacg cccccatgac        7020
aaaggctctg gactggagcg gaacaaggta ctgggcccct gatgccagga ccacaacata     7080
caatgcaggc cgcttttcca cccttcagcc ttcgggggca ctgccaggaa gaactaatcc      7140
taggattacc gtccccgctc ggggcccccc cagcacactt tctaatgctt ctactgctac      7200
ttctgtgtat tcaaatcaaa ctgtttcaac gagactaggt tcttcagctg gttctggtac      7260
cggtgtctcg agtctcccgt caactgcaag gactaggaac tgggttgagg accaaaacag      7320
gaatttgtca cctttcatga gggggctct caacacatca ttcgtcaccc ctccatctag        7380
tagatcctct aaccaaggca cagtctcaac cgtgcctaaa gaaattttgg actcctggac     7440
tggcgctttc aacacgcgca ggcagcctct cttcgctcac attcgcaaac gaggggagtc     7500
acgggtgtaa tgtgaaaaga caaaattgat tttctttctc ttctttagtg tctttt           7556
```

<210> SEQ ID NO 14
<211> LENGTH: 1699
<212> TYPE: PRT
<213> ORGANISM: Norovirus MD145-12
<300> PUBLICATION INFORMATION:
<308> DATABASE ACCESSION NUMBER: GenBank/AAK50354
<309> DATABASE ENTRY DATE: 2002-01-29
<313> RELEVANT RESIDUES IN SEQ ID NO: (1)..(1699)

<400> SEQUENCE: 14

```
Met Lys Met Ala Ser Asn Asp Ala Ser Ala Ala Val Ala Asn Ser
1               5                   10                  15

Asn Asn Asp Thr Ala Lys Ser Ser Ser Asp Gly Val Leu Ser Ser Met
                20                  25                  30

Ala Ile Thr Phe Lys Arg Ala Leu Gly Ala Arg Pro Lys Gln Pro Pro
            35                  40                  45

Pro Arg Glu Ile Leu Gln Arg Pro Arg Pro Pro Thr Pro Glu Leu
    50                  55                  60

Val Lys Lys Ile Pro Pro Pro Pro Asn Gly Glu Asp Glu Leu Val
65              70                  75                      80

Val Ser Tyr Ser Val Lys Asp Gly Val Ser Gly Leu Pro Glu Leu Ser
                85                  90                  95

Thr Val Arg Gln Pro Asp Glu Ala Asn Thr Ala Phe Ser Val Pro Pro
            100                 105                 110

Leu Asn Gln Arg Glu Asn Arg Asp Ala Lys Glu Pro Leu Thr Gly Thr
        115                 120                 125

Ile Leu Glu Met Trp Asp Gly Glu Ile Tyr His Tyr Gly Leu Tyr Val
    130                 135                 140

Glu Arg Gly Leu Val Leu Gly Val His Lys Pro Ala Ala Ile Ser
145                 150                 155                 160

Leu Ala Lys Val Glu Leu Thr Pro Leu Ser Leu Phe Trp Arg Pro Val
                165                 170                 175

Tyr Thr Pro Gln Tyr Leu Ile Ser Pro Asp Thr Leu Lys Arg Leu His
```

```
              180                 185                 190
Gly Glu Ser Phe Pro Tyr Thr Ala Phe Asp Asn Asn Cys Tyr Ala Phe
            195                 200                 205

Cys Cys Trp Val Leu Asp Leu Asn Asp Ser Trp Leu Ser Arg Arg Thr
        210                 215                 220

Ile Gln Arg Thr Thr Gly Phe Phe Arg Pro Tyr Gln Asp Trp Asn Arg
225                 230                 235                 240

Lys Pro Leu Pro Thr Val Asp Asp Ser Lys Leu Lys Lys Val Ala Asn
                245                 250                 255

Leu Phe Leu Cys Ala Leu Ser Ser Leu Phe Thr Arg Pro Ile Lys Asp
            260                 265                 270

Ile Ile Gly Lys Leu Arg Pro Leu Asn Ile Leu Asn Ile Leu Ala Ser
        275                 280                 285

Cys Asp Trp Thr Phe Ala Gly Ile Val Glu Ser Leu Ile Leu Met Ala
        290                 295                 300

Glu Leu Phe Gly Val Phe Trp Thr Pro Pro Asp Val Ser Ala Met Ile
305                 310                 315                 320

Ala Pro Leu Leu Gly Asp Tyr Glu Leu Gln Gly Pro Glu Asp Leu Ala
                325                 330                 335

Val Glu Leu Val Pro Ile Val Met Gly Gly Ile Gly Leu Val Leu Gly
                340                 345                 350

Phe Thr Lys Glu Lys Ile Gly Lys Met Leu Ser Ser Ala Ala Ser Thr
            355                 360                 365

Leu Arg Ala Cys Lys Asp Leu Gly Ala Tyr Gly Leu Glu Ile Leu Lys
        370                 375                 380

Leu Val Met Lys Trp Phe Phe Pro Lys Lys Glu Glu Ala Asn Glu Leu
385                 390                 395                 400

Ala Met Val Arg Ser Ile Glu Asp Ala Val Leu Asp Leu Glu Ala Ile
                405                 410                 415

Glu Asn Asn His Met Thr Ser Leu Leu Lys Asp Lys Asp Ser Leu Ala
                420                 425                 430

Thr Tyr Met Arg Thr Leu Asp Leu Glu Glu Glu Lys Ala Arg Lys Leu
            435                 440                 445

Ser Thr Lys Ser Ala Ser Pro Asp Ile Val Gly Thr Ile Asn Ala Leu
450                 455                 460

Leu Ala Arg Ile Ala Ala Arg Ser Leu Val His Arg Ala Lys Glu
465                 470                 475                 480

Glu Leu Ser Ser Arg Pro Arg Pro Val Val Met Ile Ser Gly Arg
                485                 490                 495

Pro Gly Ile Gly Lys Thr His Leu Ala Arg Glu Leu Ala Lys Arg Ile
            500                 505                 510

Ala Ala Ser Leu Thr Gly Asp Gln Arg Val Gly Leu Ile Pro Arg Asn
        515                 520                 525

Gly Val Asp His Trp Asp Ala Tyr Lys Gly Glu Arg Val Val Leu Trp
        530                 535                 540

Asp Asp Tyr Gly Met Ser Asn Pro Ile His Asp Ala Leu Arg Leu Gln
545                 550                 555                 560

Glu Leu Ala Asp Thr Cys Pro Leu Thr Leu Asn Cys Asp Arg Ile Glu
                565                 570                 575

Asn Lys Gly Lys Val Phe Asp Ser Asp Ala Ile Ile Ile Thr Thr Asn
                580                 585                 590

Leu Ala Asn Pro Ala Pro Leu Asp Tyr Val Asn Phe Glu Ala Cys Ser
            595                 600                 605
```

-continued

```
Arg Arg Ile Asp Phe Leu Val Tyr Ala Asp Ala Pro Glu Val Glu Lys
610             615                 620

Ala Lys Arg Asp Phe Pro Gly Gln Pro Asp Met Trp Lys Asn Ala Phe
625             630                 635                 640

Ser Pro Asp Phe Ser His Ile Lys Leu Thr Leu Ala Pro Gln Gly Gly
                645                 650                 655

Phe Asp Lys Asn Gly Asn Thr Pro His Gly Lys Gly Val Met Lys Thr
            660                 665                 670

Leu Thr Thr Gly Ser Leu Ile Ala Arg Ala Ser Gly Leu Leu His Glu
        675                 680                 685

Arg Leu Asp Glu Tyr Glu Leu Gln Gly Pro Thr Leu Thr Thr Phe Asn
690                 695                 700

Phe Asp Arg Asn Lys Val Leu Ala Phe Arg Gln Leu Ala Ala Glu Asn
705                 710                 715                 720

Lys Tyr Gly Leu Met Asp Thr Met Lys Val Gly Arg Gln Leu Lys Asp
                725                 730                 735

Val Arg Thr Met Pro Glu Leu Lys Gln Ala Leu Lys Asn Ile Ser Ile
            740                 745                 750

Lys Arg Cys Gln Ile Val Tyr Ser Gly Cys Thr Tyr Thr Leu Glu Ser
        755                 760                 765

Asp Gly Lys Gly Ser Val Lys Val Asp Arg Val Gln Ser Ala Thr Val
770                 775                 780

Gln Thr Asn Asn Glu Leu Ala Gly Ala Leu His His Leu Arg Cys Ala
785                 790                 795                 800

Arg Ile Arg Tyr Tyr Val Lys Cys Val Gln Glu Ala Leu Tyr Ser Ile
                805                 810                 815

Ile Gln Ile Ala Gly Ala Ala Phe Val Thr Thr Arg Ile Val Lys Arg
            820                 825                 830

Met Asn Ile Gln Asp Leu Trp Ser Lys Pro Gln Val Glu Asp Thr Glu
        835                 840                 845

Glu Thr Ile Asn Lys Asp Gly Cys Pro Lys Pro Lys Asp Asp Glu Glu
850                 855                 860

Phe Val Val Ser Ser Asp Asp Ile Lys Thr Glu Gly Lys Lys Gly Lys
865                 870                 875                 880

Asn Lys Thr Gly Arg Gly Lys Lys His Thr Ala Phe Ser Ser Lys Gly
                885                 890                 895

Leu Ser Asp Glu Glu Tyr Asp Glu Tyr Lys Arg Ile Arg Glu Glu Arg
            900                 905                 910

Asn Gly Lys Tyr Ser Ile Glu Glu Tyr Leu Gln Asp Arg Asp Lys Tyr
        915                 920                 925

Tyr Glu Glu Val Ala Ile Ala Arg Ala Thr Glu Glu Asp Phe Cys Glu
930                 935                 940

Glu Glu Glu Ala Lys Ile Arg Gln Arg Ile Phe Arg Pro Thr Arg Lys
945                 950                 955                 960

Gln Arg Lys Glu Glu Arg Ala Ser Leu Gly Leu Val Thr Gly Ser Glu
                965                 970                 975

Ile Arg Lys Arg Asn Pro Asp Asp Phe Lys Pro Lys Gly Lys Leu Trp
            980                 985                 990

Ala Asp Asp Asp Arg Ser Val Asp Tyr Asn Glu Arg Leu Ser Phe Glu
        995                 1000                1005

Ala Pro Pro Ser Ile Trp Ser Arg Ile Val Asn Phe Gly Ser Gly
    1010            1015                1020

Trp Gly Phe Trp Val Ser Pro Ser Leu Phe Ile Thr Ser Thr His
    1025            1030                1035
```

```
Val Ile Pro Gln Gly Ala Gln Glu Phe Phe Gly Val Pro Ile Lys
    1040            1045                1050

Gln Ile Gln Ile His Lys Ser Gly Glu Phe Cys Arg Leu Arg Phe
    1055            1060                1065

Pro Lys Pro Ile Arg Thr Asp Val Thr Gly Met Ile Leu Glu Glu
    1070            1075                1080

Gly Ala Pro Glu Gly Thr Val Ala Thr Leu Leu Ile Lys Arg Pro
    1085            1090                1095

Thr Gly Glu Leu Met Pro Leu Ala Ala Arg Met Gly Thr His Ala
    1100            1105                1110

Thr Met Lys Ile Gln Gly Arg Thr Val Gly Gly Gln Met Gly Met
    1115            1120                1125

Leu Leu Thr Gly Ser Asn Ala Lys Ser Met Val Leu Gly Thr Thr
    1130            1135                1140

Pro Gly Asp Cys Gly Cys Pro Tyr Ile Tyr Lys Arg Glu Asn Asp
    1145            1150                1155

Tyr Val Val Ile Gly Val His Thr Ala Ala Ala Arg Gly Gly Asn
    1160            1165                1170

Thr Val Ile Cys Ala Thr Gln Gly Ser Glu Gly Glu Ala Thr Leu
    1175            1180                1185

Glu Gly Gly Asp Ser Lys Gly Thr Tyr Cys Gly Ala Pro Ile Leu
    1190            1195                1200

Gly Pro Gly Ser Ala Pro Lys Leu Ser Thr Lys Thr Lys Phe Trp
    1205            1210                1215

Arg Ser Ser Thr Thr Pro Leu Pro Pro Gly Thr Tyr Glu Pro Ala
    1220            1225                1230

Tyr Leu Gly Gly Lys Asp Pro Arg Val Lys Gly Gly Pro Ser Leu
    1235            1240                1245

Gln Gln Val Met Arg Asp Gln Leu Lys Pro Phe Thr Glu Pro Arg
    1250            1255                1260

Gly Lys Pro Pro Lys Pro Ser Val Leu Glu Ala Ala Lys Lys Thr
    1265            1270                1275

Ile Ile Asn Val Leu Glu Gln Thr Ile Asp Pro Pro Gln Lys Trp
    1280            1285                1290

Ser Phe Thr Gln Ala Cys Ala Ser Leu Asp Lys Thr Thr Ser Ser
    1295            1300                1305

Gly His Pro His His Ile Arg Lys Asn Asp Cys Trp Asn Gly Glu
    1310            1315                1320

Ser Phe Thr Gly Lys Leu Ala Asp Gln Ala Ser Lys Ala Asn Leu
    1325            1330                1335

Met Phe Glu Glu Gly Lys Asn Met Thr Pro Val Tyr Thr Gly Ala
    1340            1345                1350

Leu Lys Asp Glu Leu Val Lys Thr Asp Lys Ile Tyr Gly Lys Ile
    1355            1360                1365

Lys Lys Arg Leu Leu Trp Gly Ser Asp Leu Ala Thr Met Ile Arg
    1370            1375                1380

Cys Ala Arg Ala Phe Gly Gly Leu Met Asp Glu Leu Lys Ala His
    1385            1390                1395

Cys Val Thr Leu Pro Val Arg Val Gly Met Asn Met Asn Glu Asp
    1400            1405                1410

Gly Pro Ile Ile Phe Glu Arg His Ser Arg Tyr Lys Tyr His Tyr
    1415            1420                1425

Asp Ala Asp Tyr Ser Arg Trp Asp Ser Thr Gln Gln Arg Ala Val
```

-continued

```
            1430                1435                1440

Leu Ala Ala Ala Leu Glu Ile Met Val Lys Phe Ser Pro Glu Pro
    1445                1450                1455

His Leu Ala Gln Ile Val Ala Glu Asp Leu Leu Ser Pro Ser Val
    1460                1465                1470

Met Asp Val Gly Asp Phe Lys Ile Ser Ile Asn Glu Gly Leu Pro
    1475                1480                1485

Ser Gly Val Pro Cys Thr Ser Gln Trp Asn Ser Ile Ala His Trp
    1490                1495                1500

Leu Leu Thr Leu Cys Ala Leu Ser Glu Val Thr Asn Leu Ser Pro
    1505                1510                1515

Asp Ile Ile Gln Ala Asn Ser Leu Phe Ser Phe Tyr Gly Asp Asp
    1520                1525                1530

Glu Ile Val Ser Thr Asp Ile Lys Leu Asp Pro Glu Lys Leu Thr
    1535                1540                1545

Ala Lys Leu Lys Glu Tyr Gly Leu Lys Pro Thr Arg Pro Asp Lys
    1550                1555                1560

Thr Glu Gly Pro Leu Thr Ile Ser Glu Asp Leu Asn Gly Leu Thr
    1565                1570                1575

Phe Leu Arg Arg Thr Val Thr Arg Asp Pro Ala Gly Trp Phe Gly
    1580                1585                1590

Lys Leu Glu Gln Ser Ser Ile Leu Arg Gln Met Tyr Trp Thr Arg
    1595                1600                1605

Gly Pro Asn His Glu Asp Pro Ser Glu Thr Met Ile Pro His Ser
    1610                1615                1620

Gln Arg Pro Ile Gln Leu Met Ser Leu Leu Gly Glu Ala Ala Leu
    1625                1630                1635

His Gly Pro Ala Phe Tyr Ser Lys Ile Ser Lys Leu Val Ile Ala
    1640                1645                1650

Glu Leu Lys Glu Gly Gly Met Asp Phe Tyr Val Pro Arg Gln Glu
    1655                1660                1665

Pro Met Phe Arg Trp Met Arg Phe Ser Asp Leu Ser Thr Trp Glu
    1670                1675                1680

Gly Asp Arg Asn Leu Ala Pro Ser Phe Val Asn Glu Asp Gly Val
    1685                1690                1695

Glu
```

<210> SEQ ID NO 15
<211> LENGTH: 1789
<212> TYPE: PRT
<213> ORGANISM: Norwalk virus
<300> PUBLICATION INFORMATION:
<308> DATABASE ACCESSION NUMBER: GenBank/M87661
<309> DATABASE ENTRY DATE: 1997-03-26
<313> RELEVANT RESIDUES IN SEQ ID NO: (1)..(1789)

<400> SEQUENCE: 15

```
Met Met Met Ala Ser Lys Asp Val Val Pro Thr Ala Ala Ser Ser Glu
1               5                   10                  15

Asn Ala Asn Asn Asn Ser Ser Ile Lys Ser Arg Leu Leu Ala Arg Leu
                20                  25                  30

Lys Gly Ser Gly Gly Ala Thr Ser Pro Pro Asn Ser Ile Lys Ile Thr
            35                  40                  45

Asn Gln Asp Met Ala Leu Gly Leu Ile Gly Gln Val Pro Ala Pro Lys
        50                  55                  60

Ala Thr Ser Val Asp Val Pro Lys Gln Gln Arg Asp Arg Pro Pro Arg
```

```
                65                  70                  75                  80
Thr Val Ala Glu Val Gln Gln Asn Leu Arg Trp Thr Glu Arg Pro Gln
                    85                  90                  95
Asp Gln Asn Val Lys Thr Trp Asp Glu Leu Asp His Thr Thr Lys Gln
                    100                 105                 110
Gln Ile Leu Asp Glu His Ala Glu Trp Phe Asp Ala Gly Gly Leu Gly
                    115                 120                 125
Pro Ser Thr Leu Pro Thr Ser His Glu Arg Tyr Thr His Glu Asn Asp
                    130                 135                 140
Glu Gly His Gln Val Lys Trp Ser Ala Arg Glu Gly Val Asp Leu Gly
145                 150                 155                 160
Ile Ser Gly Leu Thr Thr Val Ser Gly Pro Glu Trp Asn Met Cys Pro
                    165                 170                 175
Leu Pro Pro Val Asp Gln Arg Ser Thr Thr Pro Ala Thr Glu Pro Thr
                    180                 185                 190
Ile Gly Asp Met Ile Glu Phe Tyr Glu Gly His Ile Tyr His Tyr Ala
                    195                 200                 205
Ile Tyr Ile Gly Gln Gly Lys Thr Val Gly Val His Ser Pro Gln Ala
                    210                 215                 220
Ala Phe Ser Ile Thr Arg Ile Thr Ile Gln Pro Ile Ser Ala Trp Trp
225                 230                 235                 240
Arg Val Cys Tyr Val Pro Gln Pro Lys Gln Arg Leu Thr Tyr Asp Gln
                    245                 250                 255
Leu Lys Glu Leu Glu Asn Glu Pro Trp Pro Tyr Ala Ala Val Thr Asn
                    260                 265                 270
Asn Cys Phe Glu Phe Cys Cys Gln Val Met Cys Leu Glu Asp Thr Trp
                    275                 280                 285
Leu Gln Arg Lys Leu Ile Ser Ser Gly Arg Phe Tyr His Pro Thr Gln
                    290                 295                 300
Asp Trp Ser Arg Asp Thr Pro Glu Phe Gln Gln Asp Ser Lys Leu Glu
305                 310                 315                 320
Met Val Arg Asp Ala Val Leu Ala Ala Ile Asn Gly Leu Val Ser Arg
                    325                 330                 335
Pro Phe Lys Asp Leu Leu Gly Lys Leu Lys Pro Leu Asn Val Leu Asn
                    340                 345                 350
Leu Leu Ser Asn Cys Asp Trp Thr Phe Met Gly Val Val Glu Met Val
                    355                 360                 365
Val Leu Leu Leu Glu Leu Phe Gly Ile Phe Trp Asn Pro Pro Asp Val
                    370                 375                 380
Ser Asn Phe Ile Ala Ser Leu Leu Pro Asp Phe His Leu Gln Gly Pro
385                 390                 395                 400
Glu Asp Leu Ala Arg Asp Leu Val Pro Ile Val Leu Gly Gly Ile Gly
                    405                 410                 415
Leu Ala Ile Gly Phe Thr Arg Asp Lys Val Ser Lys Met Met Lys Asn
                    420                 425                 430
Ala Val Asp Gly Leu Arg Ala Ala Thr Gln Leu Gly Gln Tyr Gly Leu
                    435                 440                 445
Glu Ile Phe Ser Leu Leu Lys Lys Tyr Phe Phe Gly Gly Asp Gln Thr
                    450                 455                 460
Glu Lys Thr Leu Lys Asp Ile Glu Ser Ala Val Ile Asp Met Glu Val
465                 470                 475                 480
Leu Ser Ser Thr Ser Val Thr Gln Leu Val Arg Asp Lys Gln Ser Ala
                    485                 490                 495
```

```
Arg Ala Tyr Met Ala Ile Leu Asp Asn Glu Glu Lys Ala Arg Lys
            500                 505                 510

Leu Ser Val Arg Asn Ala Asp Pro His Val Val Ser Thr Asn Ala
        515                 520                 525

Leu Ile Ser Arg Ile Ser Met Ala Arg Ala Ala Leu Ala Lys Ala Gln
530                 535                 540

Ala Glu Met Thr Ser Arg Met Arg Pro Val Val Ile Met Met Cys Gly
545                 550                 555                 560

Pro Pro Gly Ile Gly Lys Thr Lys Ala Ala Glu His Leu Ala Lys Arg
            565                 570                 575

Leu Ala Asn Glu Ile Arg Pro Gly Gly Lys Val Gly Leu Val Pro Arg
        580                 585                 590

Glu Ala Val Asp His Trp Asp Gly Tyr His Gly Glu Glu Val Met Leu
    595                 600                 605

Trp Asp Asp Tyr Gly Met Thr Lys Ile Gln Glu Asp Cys Asn Lys Leu
610                 615                 620

Gln Ala Ile Ala Asp Ser Ala Pro Leu Thr Leu Asn Cys Asp Arg Ile
625                 630                 635                 640

Glu Asn Lys Gly Met Gln Phe Val Ser Asp Ala Ile Val Ile Thr Thr
            645                 650                 655

Asn Ala Pro Gly Pro Ala Pro Val Asp Phe Val Asn Leu Gly Pro Val
        660                 665                 670

Cys Arg Arg Val Asp Phe Leu Val Tyr Cys Thr Ala Pro Glu Val Glu
    675                 680                 685

His Thr Arg Lys Val Ser Pro Gly Asp Thr Thr Ala Leu Lys Asp Cys
690                 695                 700

Phe Lys Pro Asp Phe Ser His Leu Lys Met Glu Leu Ala Pro Gln Gly
705                 710                 715                 720

Gly Phe Asp Asn Gln Gly Asn Thr Pro Phe Gly Lys Gly Val Met Lys
            725                 730                 735

Pro Thr Thr Ile Asn Arg Leu Leu Ile Gln Ala Val Ala Leu Thr Met
        740                 745                 750

Glu Arg Gln Asp Glu Phe Gln Leu Gln Gly Pro Thr Tyr Asp Phe Asp
    755                 760                 765

Thr Asp Arg Val Ala Ala Phe Thr Arg Met Ala Arg Ala Asn Gly Leu
770                 775                 780

Gly Leu Ile Ser Met Ala Ser Leu Gly Lys Lys Leu Arg Ser Val Thr
785                 790                 795                 800

Thr Ile Glu Gly Leu Lys Asn Ala Leu Ser Gly Tyr Lys Ile Ser Lys
            805                 810                 815

Cys Ser Ile Gln Trp Gln Ser Arg Val Tyr Ile Ile Glu Ser Asp Gly
        820                 825                 830

Ala Ser Val Gln Ile Lys Glu Asp Lys Gln Ala Leu Thr Pro Leu Gln
    835                 840                 845

Gln Thr Ile Asn Thr Ala Ser Leu Ala Ile Thr Arg Leu Lys Ala Ala
850                 855                 860

Arg Ala Val Ala Tyr Ala Ser Cys Phe Gln Ser Ala Ile Thr Thr Ile
865                 870                 875                 880

Leu Gln Met Ala Gly Ser Ala Leu Val Ile Asn Arg Ala Val Lys Arg
            885                 890                 895

Met Phe Gly Thr Arg Thr Ala Ala Met Ala Leu Glu Gly Pro Gly Lys
        900                 905                 910

Glu His Asn Cys Arg Val His Lys Ala Lys Glu Ala Gly Lys Gly Pro
    915                 920                 925
```

-continued

```
Ile Gly His Asp Asp Met Val Glu Arg Phe Gly Leu Cys Glu Thr Glu
            930                 935                 940
Glu Glu Glu Ser Glu Asp Gln Ile Gln Met Val Pro Ser Asp Ala Val
945                 950                 955                 960
Pro Glu Gly Lys Asn Lys Gly Lys Thr Lys Gly Arg Gly Arg Lys
                965                 970                 975
Asn Asn Tyr Asn Ala Phe Ser Arg Arg Gly Leu Ser Asp Glu Tyr
            980                 985                 990
Glu Glu Tyr Lys Lys Ile Arg Glu Glu Lys Asn Gly Asn Tyr Ser Ile
            995                 1000                1005
Gln Glu Tyr Leu Glu Asp Arg Gln Arg Tyr Glu Glu Glu Leu Ala
        1010                1015                1020
Glu Val Gln Ala Gly Gly Asp Gly Gly Ile Gly Glu Thr Glu Met
        1025                1030                1035
Glu Ile Arg His Arg Val Phe Tyr Lys Ser Lys Ser Lys Lys His
        1040                1045                1050
Gln Gln Glu Gln Arg Arg Gln Leu Gly Leu Val Thr Gly Ser Asp
        1055                1060                1065
Ile Arg Lys Arg Lys Pro Ile Asp Trp Thr Pro Pro Lys Asn Glu
        1070                1075                1080
Trp Ala Asp Asp Arg Glu Val Asp Tyr Asn Glu Lys Ile Asn
        1085                1090                1095
Phe Glu Ala Pro Pro Thr Leu Trp Ser Arg Val Thr Lys Phe Gly
        1100                1105                1110
Ser Gly Trp Gly Phe Trp Val Ser Pro Thr Val Phe Ile Thr Thr
        1115                1120                1125
Thr His Val Val Pro Thr Gly Val Lys Glu Phe Phe Gly Glu Pro
        1130                1135                1140
Leu Ser Ser Ile Ala Ile His Gln Ala Gly Glu Phe Thr Gln Phe
        1145                1150                1155
Arg Phe Ser Lys Lys Met Arg Pro Asp Leu Thr Gly Met Val Leu
        1160                1165                1170
Glu Glu Gly Cys Pro Glu Gly Thr Val Cys Ser Val Leu Ile Lys
        1175                1180                1185
Arg Asp Ser Gly Glu Leu Leu Pro Leu Ala Val Arg Met Gly Ala
        1190                1195                1200
Ile Ala Ser Met Arg Ile Gln Gly Arg Leu Val His Gly Gln Ser
        1205                1210                1215
Gly Met Leu Leu Thr Gly Ala Asn Ala Lys Gly Met Asp Leu Gly
        1220                1225                1230
Thr Ile Pro Gly Asp Cys Gly Ala Pro Tyr Val His Lys Arg Gly
        1235                1240                1245
Asn Asp Trp Val Val Cys Gly Val His Ala Ala Ala Thr Lys Ser
        1250                1255                1260
Gly Asn Thr Val Val Cys Ala Val Gln Ala Gly Glu Gly Glu Thr
        1265                1270                1275
Ala Leu Glu Gly Gly Asp Lys Gly His Tyr Ala Gly His Glu Ile
        1280                1285                1290
Val Arg Tyr Gly Ser Gly Pro Ala Leu Ser Thr Lys Thr Lys Phe
        1295                1300                1305
Trp Arg Ser Ser Pro Glu Pro Leu Pro Pro Gly Val Tyr Glu Pro
        1310                1315                1320
Ala Tyr Leu Gly Gly Lys Asp Pro Arg Val Gln Asn Gly Pro Ser
```

-continued

```
            1325                1330                1335

Leu Gln Gln Val Leu Arg Asp Gln Leu Lys Pro Phe Ala Asp Pro
    1340                1345                1350

Arg Gly Arg Met Pro Glu Pro Gly Leu Leu Glu Ala Ala Val Glu
    1355                1360                1365

Thr Val Thr Ser Met Leu Glu Gln Thr Met Asp Thr Pro Ser Pro
    1370                1375                1380

Trp Ser Tyr Ala Asp Ala Cys Gln Ser Leu Asp Lys Thr Thr Ser
    1385                1390                1395

Ser Gly Tyr Pro His His Lys Arg Lys Asn Asp Asp Trp Asn Gly
    1400                1405                1410

Thr Thr Phe Val Gly Glu Leu Gly Glu Gln Ala Ala His Ala Asn
    1415                1420                1425

Asn Met Tyr Glu Asn Ala Lys His Met Lys Pro Ile Tyr Thr Ala
    1430                1435                1440

Ala Leu Lys Asp Glu Leu Val Lys Pro Glu Lys Ile Tyr Gln Lys
    1445                1450                1455

Val Lys Lys Arg Leu Leu Trp Gly Ala Asp Leu Gly Thr Val Val
    1460                1465                1470

Arg Ala Ala Arg Ala Phe Gly Pro Phe Cys Asp Ala Ile Lys Ser
    1475                1480                1485

His Val Ile Lys Leu Pro Ile Lys Val Gly Met Asn Thr Ile Glu
    1490                1495                1500

Asp Gly Pro Leu Ile Tyr Ala Glu His Ala Lys Tyr Lys Asn His
    1505                1510                1515

Phe Asp Ala Asp Tyr Thr Ala Trp Asp Ser Thr Gln Asn Arg Gln
    1520                1525                1530

Ile Met Thr Glu Ser Phe Ser Ile Met Ser Arg Leu Thr Ala Ser
    1535                1540                1545

Pro Glu Leu Ala Glu Val Val Ala Gln Asp Leu Leu Ala Pro Ser
    1550                1555                1560

Glu Met Asp Val Gly Asp Tyr Val Ile Arg Val Lys Glu Gly Leu
    1565                1570                1575

Pro Ser Gly Phe Pro Cys Thr Ser Gln Val Asn Ser Ile Asn His
    1580                1585                1590

Trp Ile Ile Thr Leu Cys Ala Leu Ser Glu Ala Thr Gly Leu Ser
    1595                1600                1605

Pro Asp Val Val Gln Ser Met Ser Tyr Phe Ser Phe Tyr Gly Asp
    1610                1615                1620

Asp Glu Ile Val Ser Thr Asp Ile Asp Phe Asp Pro Ala Arg Leu
    1625                1630                1635

Thr Gln Ile Leu Lys Glu Tyr Gly Leu Lys Pro Thr Arg Pro Asp
    1640                1645                1650

Lys Thr Glu Gly Pro Ile Gln Val Arg Lys Asn Val Asp Gly Leu
    1655                1660                1665

Val Phe Leu Arg Arg Thr Ile Ser Arg Asp Ala Ala Gly Phe Gln
    1670                1675                1680

Gly Arg Leu Asp Arg Ala Ser Ile Glu Arg Gln Ile Phe Trp Thr
    1685                1690                1695

Arg Gly Pro Asn His Ser Asp Pro Ser Glu Thr Leu Val Pro His
    1700                1705                1710

Thr Gln Arg Lys Ile Gln Leu Ile Ser Leu Leu Gly Glu Ala Ser
    1715                1720                1725
```

```
Leu His Gly Glu Lys Phe Tyr Arg Lys Ile Ser Ser Lys Val Ile
    1730                1735                1740

His Glu Ile Lys Thr Gly Gly Leu Glu Met Tyr Val Pro Gly Trp
    1745                1750                1755

Gln Ala Met Phe Arg Trp Met Arg Phe His Asp Leu Gly Leu Trp
    1760                1765                1770

Thr Gly Asp Arg Asp Leu Leu Pro Glu Phe Val Asn Asp Asp Gly
    1775                1780                1785

Val

<210> SEQ ID NO 16
<211> LENGTH: 1699
<212> TYPE: PRT
<213> ORGANISM: Snow Mountain virus
<300> PUBLICATION INFORMATION:
<308> DATABASE ACCESSION NUMBER: GenBank/AY134748
<309> DATABASE ENTRY DATE: 2004-07-01
<313> RELEVANT RESIDUES IN SEQ ID NO: (1)..(1699)

<400> SEQUENCE: 16

Met Lys Met Ala Ser Asn Asp Ala Ser Ala Ala Ala Val Asn Ser
1               5                   10                  15

Asn Asn Asp Asn Ala Lys Ser Ser Ser Asp Gly Val Leu Ser Ser Met
                20                  25                  30

Ala Val Thr Phe Lys Arg Ala Leu Gly Ala Arg Pro Lys Gln Pro Pro
                35                  40                  45

Pro Arg Glu Ile Pro Gln Arg Pro Arg Pro Pro Thr Pro Glu Leu
    50                  55                  60

Val Lys Lys Ile Pro Pro Pro Pro Asn Gly Glu Asp Glu Pro Val
65                  70                  75                  80

Val His Tyr Ser Ala Lys Asp Gly Ile Thr Gly Leu Pro Glu Leu Thr
                85                  90                  95

Thr Val Arg Gln Pro Glu Glu Ala Ala Thr Ala Phe Ser Val Pro Pro
                100                 105                 110

Leu Asp Gln Arg Glu Asn Arg Asp Ala Lys Glu Pro Leu Thr Gly Thr
                115                 120                 125

Ile Leu Glu Met Trp Asp Gly Glu Ile Tyr His Tyr Gly Leu Tyr Val
                130                 135                 140

Glu Arg Gly Leu Val Leu Gly Val His Lys Pro Pro Ala Ala Ile Ser
145                 150                 155                 160

Leu Ala Lys Val Glu Leu Thr Pro Leu Ser Leu Tyr Trp Arg Pro Val
                165                 170                 175

Tyr Thr Pro Gln Tyr Leu Ile Ala Pro Asp Thr Leu Arg Lys Leu His
                180                 185                 190

Gly Glu Leu Phe Pro Tyr Thr Ala Phe Asp Asn Asn Cys Tyr Ala Phe
                195                 200                 205

Cys Cys Trp Val Leu Asp Leu Asn Asp Ser Trp Leu Ser Arg Arg Met
                210                 215                 220

Ile Gln Arg Thr Thr Gly Phe Phe Arg Pro Tyr Gln Asp Trp Asn Arg
225                 230                 235                 240

Lys Pro Leu Pro Thr Met Asp Asp Ser Lys Leu Lys Lys Val Ala Asn
                245                 250                 255

Ile Leu Leu Cys Ala Leu Ser Ser Leu Phe Thr Arg Pro Ile Lys Asp
                260                 265                 270

Ile Ile Gly Lys Leu Arg Pro Leu Asn Ile Leu Asn Ile Leu Ala Ser
                275                 280                 285
```

```
Cys Asp Trp Thr Phe Ala Gly Ile Val Glu Ser Leu Ile Leu Leu Ala
290                 295                 300
Glu Leu Phe Gly Val Phe Trp Thr Pro Pro Asp Val Ser Ala Met Ile
305                 310                 315                 320
Ala Pro Leu Leu Gly Asp Tyr Glu Leu Gln Gly Pro Glu Asp Leu Ala
                325                 330                 335
Val Glu Leu Val Pro Ile Val Met Gly Ile Gly Leu Val Leu Gly
            340                 345                 350
Phe Thr Lys Glu Lys Ile Gly Lys Met Leu Ser Ser Ala Ala Ser Thr
        355                 360                 365
Leu Arg Thr Cys Lys Asp Leu Gly Ala Tyr Gly Leu Glu Ile Leu Lys
    370                 375                 380
Leu Val Met Lys Trp Phe Phe Pro Lys Lys Glu Glu Ala Asn Glu Leu
385                 390                 395                 400
Ala Met Val Arg Ala Ile Glu Asp Ala Val Leu Asp Leu Glu Ala Ile
                405                 410                 415
Glu Asn Asn His Met Thr Ala Leu Leu Lys Asp Lys Asp Ser Leu Ala
                420                 425                 430
Thr Tyr Met Arg Thr Leu Asp Leu Glu Glu Lys Ala Arg Lys Leu
        435                 440                 445
Ser Thr Lys Ser Ala Ser Pro Asp Ile Val Gly Thr Ile Asn Ala Leu
    450                 455                 460
Leu Ala Arg Ile Ala Ala Ala Arg Ser Leu Val His Arg Ala Lys Glu
465                 470                 475                 480
Glu Leu Ser Ser Arg Leu Arg Pro Val Val Met Ile Ser Gly Lys
                485                 490                 495
Pro Gly Ile Gly Lys Thr His Leu Ala Arg Glu Leu Ala Lys Lys Ile
            500                 505                 510
Ala Ile Thr Leu Ser Gly Asp Gln Arg Val Gly Leu Ile Pro Arg Asn
        515                 520                 525
Gly Val Asp His Trp Asp Ala Tyr Lys Gly Glu Arg Val Val Leu Trp
    530                 535                 540
Asp Asp Tyr Gly Met Ser Asn Pro Val His Asp Ala Leu Arg Leu Gln
545                 550                 555                 560
Glu Leu Ala Asp Thr Cys Pro Leu Thr Leu Asn Cys Asp Arg Ile Glu
                565                 570                 575
Asn Lys Gly Lys Val Phe Asp Ser Asp Ala Ile Ile Ile Thr Thr Asn
                580                 585                 590
Leu Ala Asn Pro Ala Pro Leu Asp Tyr Val Asn Phe Glu Ala Cys Ser
        595                 600                 605
Arg Arg Ile Asp Phe Leu Val Tyr Ala Asp Ala Pro Asp Val Glu Lys
    610                 615                 620
Ala Lys Arg Asp Phe Pro Gly Gln Pro Asp Met Trp Lys Ser Ala Tyr
625                 630                 635                 640
Ser Pro Asp Phe Ser His Ile Lys Leu Met Leu Ala Pro Gln Gly Gly
                645                 650                 655
Phe Asp Lys Asn Gly Asn Thr Pro His Gly Lys Gly Val Met Lys Thr
                660                 665                 670
Leu Thr Thr Gly Ser Leu Ile Ala Arg Ala Ser Gly Leu Leu His Glu
        675                 680                 685
Arg Leu Asp Glu Phe Glu Leu Gln Gly Pro Asn Leu Thr Thr Phe Asn
    690                 695                 700
Phe Asp Arg Asn Lys Ile Gln Ala Phe Arg Gln Leu Ala Ala Glu Asn
705                 710                 715                 720
```

```
Lys Tyr Gly Leu Val Asp Thr Met Arg Val Gly Gly Gln Leu Lys Gly
                725                 730                 735

Val Arg Thr Ile Pro Glu Leu Lys Gln Ala Leu Lys Asn Ile Leu Ile
            740                 745                 750

Lys Arg Cys Gln Ile Val Tyr Gly Gly Ser Thr Tyr Thr Leu Glu Ser
            755                 760                 765

Asp Gly Lys Gly Asn Val Lys Val Glu Lys Val Gln Asn Thr Asn Ile
        770                 775                 780

Gln Ile Asn Asn Glu Leu Ala Gly Ala Leu His His Leu Arg Cys Ala
785                 790                 795                 800

Arg Ile Arg Tyr Tyr Val Lys Cys Val Gln Glu Ala Leu Tyr Ser Ile
                805                 810                 815

Ile Gln Ile Ala Gly Ala Ala Phe Val Thr Thr Arg Ile Val Lys Arg
                820                 825                 830

Met Asn Ile Gln Asn Leu Trp Ser Arg Pro Pro Val Gly Asp Ala Glu
                835                 840                 845

Glu Val Thr Ser Gln Asp Gly Cys Pro Lys Pro Lys Asp Asp Glu Glu
            850                 855                 860

Phe Val Ile Ser Ser Ser Asp Ile Thr Pro Glu Gly Lys Lys Gly Lys
865                 870                 875                 880

Asn Lys Thr Gly Arg Gly Lys Lys His Thr Ala Phe Ser Ser Lys Gly
                    885                 890                 895

Leu Ser Asp Glu Glu Tyr Asp Glu Tyr Lys Arg Ile Arg Glu Glu Arg
                900                 905                 910

Asn Gly Lys Tyr Ser Ile Glu Glu Tyr Leu Gln Asp Arg Asp Lys Tyr
                915                 920                 925

Tyr Glu Glu Val Ala Ile Ala Arg Ala Thr Glu Glu Asp Phe Cys Glu
            930                 935                 940

Glu Glu Glu Ala Lys Ile Arg Gln Arg Ile Phe Arg Pro Thr Arg Lys
945                 950                 955                 960

Gln Arg Lys Glu Glu Arg Ala Ser Leu Gly Leu Val Thr Gly Ser Glu
                965                 970                 975

Ile Arg Lys Arg Asn Pro Asp Asp Phe Lys Pro Lys Gly Lys Leu Trp
                980                 985                 990

Ala Asp Asp Glu Arg Val Val Asp Tyr Asn Glu Lys Leu Ser Phe Glu
            995                 1000                1005

Ala Pro Pro Ser Ile Trp Ser Arg Ile Val Asn Phe Gly Ser Gly
        1010                1015                1020

Trp Gly Phe Trp Val Ser Pro Ser Leu Phe Ile Thr Ser Thr His
        1025                1030                1035

Val Ile Pro Gln Gly Thr Gln Glu Phe Phe Gly Val Pro Ile Lys
        1040                1045                1050

Gln Ile Gln Ile His Lys Ser Gly Glu Phe Cys Arg Leu Arg Phe
        1055                1060                1065

Pro Lys Ser Ile Arg Thr Ala Val Thr Gly Met Ile Leu Glu Glu
        1070                1075                1080

Gly Ala Pro Glu Gly Thr Val Val Ser Leu Leu Ile Lys Arg Pro
        1085                1090                1095

Thr Gly Glu Leu Met Pro Leu Ala Ala Arg Met Gly Thr His Ala
        1100                1105                1110

Thr Met Lys Ile Gln Gly Arg Thr Val Gly Gly Gln Met Gly Met
        1115                1120                1125

Leu Leu Thr Gly Ser Asn Ala Lys Ser Met Asp Leu Gly Thr Thr
```

-continued

```
            1130                1135                1140
Pro Gly Asp Cys Gly Cys Pro Tyr Ile Tyr Lys Arg Gly Asn Asp
    1145                1150                1155
Tyr Val Val Ile Gly Val His Thr Ala Ala Arg Gly Gly Asn
    1160                1165                1170
Thr Val Ile Cys Ala Thr Gln Ser Glu Gly Glu Ala Thr Leu
    1175                1180                1185
Glu Gly Gly Asp Asn Lys Gly Thr Tyr Cys Gly Ala Pro Ile Leu
    1190                1195                1200
Gly Pro Gly Asn Ala Pro Lys Leu Ser Thr Lys Thr Lys Phe Trp
    1205                1210                1215
Arg Ser Ser Thr Val Pro Leu Pro Pro Gly Thr Tyr Glu Pro Ala
    1220                1225                1230
Tyr Leu Gly Gly Lys Asp Pro Arg Val Lys Gly Gly Pro Ser Leu
    1235                1240                1245
Gln Gln Val Met Arg Asp Gln Leu Lys Pro Phe Thr Glu Pro Arg
    1250                1255                1260
Gly Lys Pro Pro Lys Pro Ser Val Leu Glu Ala Ala Lys Lys Thr
    1265                1270                1275
Ile Ile Asn Val Leu Glu Gln Thr Ile Asp Pro Pro Gln Lys Trp
    1280                1285                1290
Ser Phe Ser Gln Ala Cys Ala Ser Leu Asp Lys Thr Thr Ser Ser
    1295                1300                1305
Gly His Pro His His Ile Arg Lys Asn Asp Cys Trp Asn Gly Glu
    1310                1315                1320
Ser Phe Thr Gly Lys Leu Ala Asp Gln Ala Ser Lys Ala Asn Leu
    1325                1330                1335
Met Tyr Glu Glu Gly Lys Asn Met Thr Pro Val Tyr Thr Gly Ala
    1340                1345                1350
Leu Lys Asp Glu Leu Val Lys Thr Asp Lys Ile Tyr Gly Gln Ile
    1355                1360                1365
Lys Lys Arg Leu Leu Trp Gly Ser Asp Leu Ala Thr Met Ile Arg
    1370                1375                1380
Cys Ala Arg Ala Phe Gly Gly Leu Met Asp Glu Leu Lys Ala His
    1385                1390                1395
Cys Val Thr Leu Pro Val Arg Val Gly Met Asn Met Asn Glu Asp
    1400                1405                1410
Gly Pro Ile Ile Phe Glu Lys His Ser Arg Phe Ser Tyr His Tyr
    1415                1420                1425
Asp Ala Asp Tyr Ser Arg Trp Asp Ser Thr Gln Gln Arg Ala Val
    1430                1435                1440
Leu Ala Ala Ala Leu Glu Ile Met Val Lys Phe Ser Pro Glu Pro
    1445                1450                1455
His Leu Ala Gln Ile Val Ala Glu Asp Leu Leu Ala Pro Ser Val
    1460                1465                1470
Met Asp Val Gly Asp Phe Lys Ile Thr Ile Asn Glu Gly Leu Pro
    1475                1480                1485
Ser Gly Val Pro Cys Thr Ser Gln Trp Asn Ser Ile Ala His Trp
    1490                1495                1500
Leu Leu Thr Leu Cys Ala Leu Ser Glu Val Thr Asn Leu Ala Pro
    1505                1510                1515
Asp Ile Ile Gln Ala Asn Ser Leu Phe Ser Phe Tyr Gly Asp Asp
    1520                1525                1530
```

-continued

```
Glu Ile Val Ser Thr Asp Ile Lys Leu Asp Pro Glu Lys Leu Thr
    1535                1540                1545

Ala Lys Leu Lys Glu Tyr Gly Leu Lys Pro Thr Arg Pro Asp Lys
    1550                1555                1560

Thr Glu Gly Pro Leu Ile Ile Ser Glu Asp Leu Asn Gly Leu Thr
    1565                1570                1575

Phe Leu Arg Arg Thr Val Thr Arg Asp Pro Ala Gly Trp Phe Gly
    1580                1585                1590

Lys Leu Asp Gln Ser Ser Ile Leu Arg Gln Ile Tyr Trp Thr Arg
    1595                1600                1605

Gly Pro Asn His Glu Asp Pro Ser Glu Thr Met Ile Pro His Ser
    1610                1615                1620

Gln Arg Pro Ile Gln Leu Met Ser Leu Leu Gly Glu Ala Ala Leu
    1625                1630                1635

His Gly Pro Thr Phe Tyr Thr Lys Ile Ser Lys Leu Val Ile Thr
    1640                1645                1650

Glu Leu Lys Glu Gly Gly Met Asp Phe Tyr Val Pro Arg Gln Glu
    1655                1660                1665

Pro Met Phe Arg Trp Met Arg Phe Ser Asp Leu Ser Thr Trp Glu
    1670                1675                1680

Gly Asp Arg Asn Leu Ala Pro Ser Phe Val Asn Glu Asp Gly Val
    1685                1690                1695

Glu

<210> SEQ ID NO 17
<211> LENGTH: 1699
<212> TYPE: PRT
<213> ORGANISM: Hawaii virus
<300> PUBLICATION INFORMATION:
<308> DATABASE ACCESSION NUMBER: GenBank/U07611
<309> DATABASE ENTRY DATE: 2000-09-05
<313> RELEVANT RESIDUES IN SEQ ID NO: (1)..(1699)

<400> SEQUENCE: 17

Met Lys Met Ala Ser Asn Asp Ala Ser Ala Ala Ala Ala Asn Ser
1               5                   10                  15

Asn Asn Asp Thr Val Lys Ser Ser Ser Asp Gly Val Leu Ser Ser Met
                20                  25                  30

Ala Val Thr Phe Lys Arg Ala Leu Gly Ala Arg Pro Lys Gln Pro Pro
            35                  40                  45

Pro Arg Glu Ile Pro Gln Arg Pro Pro Arg Pro Thr Pro Glu Leu
    50                  55                  60

Ile Lys Lys Val Pro Pro Pro Pro Asn Gly Glu Asp Glu Pro Val
65                  70                  75                  80

Val Ser Tyr Ser Val Lys Asp Gly Val Ser Gly Leu Pro Asp Leu Ser
                85                  90                  95

Thr Val Arg Gln Pro Pro Glu Asn Asn Thr Ala Phe Ser Val Pro Pro
                100                 105                 110

Leu Asn Gln Arg Glu Asn Arg Asp Ala Lys Glu Pro Leu Thr Gly Thr
            115                 120                 125

Ile Leu Glu Met Trp Asp Gly Glu Ile Tyr His Tyr Gly Leu Tyr Val
        130                 135                 140

Glu Gln Gly Leu Val Leu Gly Val His Lys Pro Ala Ala Ile Ser
145                 150                 155                 160

Leu Ala Lys Val Glu Leu Thr Pro Leu Ser Leu Tyr Trp Arg Pro Val
                165                 170                 175
```

-continued

```
Tyr Thr Pro Gln Tyr Leu Ile Ser Pro Asp Thr Leu Arg Arg Leu His
            180                 185                 190

Gly Glu Ser Phe Pro Tyr Thr Ala Phe Asp Asn Asn Cys Tyr Ala Phe
            195                 200                 205

Cys Cys Trp Val Leu Asp Leu Asn Asp Ser Trp Leu Ser Arg Arg Met
210                 215                 220

Ile His Arg Thr Thr Gly Phe Phe Arg Pro Tyr Gln Asp Trp Asn Arg
225                 230                 235                 240

Lys Pro Leu Pro Thr Met Asp Asp Ser Lys Leu Lys Lys Val Ala Asn
            245                 250                 255

Ile Phe Leu Cys Ala Leu Ser Ser Leu Phe Thr Arg Pro Ile Lys Asp
            260                 265                 270

Ile Ile Gly Lys Leu Arg Pro Leu Asn Ile Leu Asn Ile Leu Ala Ser
            275                 280                 285

Cys Asp Trp Thr Phe Ala Gly Ile Val Glu Ser Leu Ile Leu Leu Ala
            290                 295                 300

Glu Leu Phe Gly Val Phe Trp Thr Pro Pro Asp Val Ser Ala Met Ile
305                 310                 315                 320

Ala Pro Leu Leu Gly Asp Tyr Glu Leu Gln Gly Pro Glu Asp Leu Ala
            325                 330                 335

Val Glu Leu Val Pro Val Val Met Gly Gly Ile Gly Leu Val Leu Gly
            340                 345                 350

Phe Thr Lys Glu Lys Ile Gly Lys Met Leu Ser Ser Ala Ala Ser Thr
            355                 360                 365

Leu Arg Ala Cys Lys Asp Leu Gly Ala Tyr Gly Leu Glu Ile Leu Lys
            370                 375                 380

Leu Val Met Lys Trp Phe Phe Pro Lys Lys Glu Glu Ala Ser Glu Leu
385                 390                 395                 400

Ala Met Val Arg Ser Ile Glu Asp Ala Val Leu Asp Leu Glu Ala Ile
            405                 410                 415

Glu Asn Asn His Met Thr Ala Leu Leu Lys Asp Lys Asp Ser Leu Ala
            420                 425                 430

Ala Tyr Met Arg Thr Leu Asp Leu Glu Glu Lys Ala Arg Lys Leu
            435                 440                 445

Ser Thr Lys Ser Ala Ser Pro Asp Ile Val Gly Thr Ile Asn Ala Leu
450                 455                 460

Leu Ala Arg Ile Ala Ala Ala Arg Ser Leu Val His Arg Ala Lys Glu
465                 470                 475                 480

Glu Leu Ser Ser Arg Pro Arg Pro Val Val Met Ile Ser Gly Lys
            485                 490                 495

Pro Gly Ile Gly Lys Thr His Leu Ala Arg Glu Leu Ala Lys Lys Ile
            500                 505                 510

Ala Ala Thr Leu Thr Gly Asp Gln Arg Val Gly Leu Ile Pro Arg Asn
            515                 520                 525

Gly Val Asp His Trp Asp Ala Tyr Lys Gly Glu Arg Val Val Leu Trp
            530                 535                 540

Asp Asp Tyr Gly Met Ser Asn Pro Ile His Asp Ala Leu Arg Ile Gln
545                 550                 555                 560

Glu Leu Ala Asp Thr Cys Pro Leu Thr Leu Asn Cys Asp Arg Ile Glu
            565                 570                 575

Asn Lys Gly Lys Val Phe Asp Ser Asp Ala Ile Ile Ile Thr Thr Asn
            580                 585                 590

Leu Ala Asn Pro Ala Pro Leu Asp Tyr Val Asn Phe Glu Ala Cys Ser
            595                 600                 605
```

```
Arg Arg Ile Asp Phe Leu Val Tyr Ala Asp Ala Pro Asp Val Glu Lys
    610                 615                 620
Ala Lys Arg Asp Phe Pro Gly Gln Pro Asp Met Trp Lys Asn Ala Phe
625                 630                 635                 640
Ser Pro Asp Phe Ser His Ile Lys Leu Met Leu Ala Pro Gln Gly Gly
                645                 650                 655
Phe Asp Lys Asn Gly Asn Thr Pro His Gly Lys Gly Val Met Lys Thr
            660                 665                 670
Leu Thr Val Gly Ser Leu Ile Ala Arg Ala Ser Gly Leu Leu His Glu
        675                 680                 685
Arg Leu Asp Glu Tyr Glu Leu Gln Gly Pro Ala Leu Thr Thr Tyr Asn
    690                 695                 700
Phe Asp Arg Asn Lys Val Leu Ala Phe Arg Gln Leu Ala Ala Glu Asn
705                 710                 715                 720
Lys Tyr Gly Leu Met Asp Thr Met Arg Val Gly Gly Gln Leu Lys Gly
                725                 730                 735
Val Arg Thr Met Ser Glu Leu Lys Gln Ala Leu Lys Asn Ile Ser Val
            740                 745                 750
Lys Arg Cys Gln Ile Val Tyr Ser Gly Cys Thr Tyr Thr Leu Glu Ser
        755                 760                 765
Asp Gly Lys Gly Ser Val Arg Val Asp Arg Val Gln Asn Thr Thr Val
    770                 775                 780
Gln Thr Asn Asn Glu Leu Ala Gly Ala Leu His His Leu Arg Cys Ala
785                 790                 795                 800
Arg Ile Arg Tyr Tyr Val Lys Cys Val Gln Glu Ala Leu Tyr Ser Ile
                805                 810                 815
Ile Gln Ile Ala Gly Ala Ala Phe Val Thr Thr Arg Ile Ala Lys Arg
            820                 825                 830
Met Asn Ile Gln Asp Leu Trp Ser Lys Pro Gln Leu Glu Asp Thr Gly
        835                 840                 845
Glu Ala Val Ser Lys Glu Gly Cys Pro Lys Pro Lys Asp Asp Glu Glu
    850                 855                 860
Phe Val Val Ser Ser Asp Asp Ile Lys Val Glu Gly Lys Lys Gly Lys
865                 870                 875                 880
Asn Lys Thr Gly Arg Gly Lys Lys His Thr Ala Phe Ser Ser Lys Gly
                885                 890                 895
Leu Ser Asp Glu Glu Tyr Asp Glu Tyr Lys Arg Ile Arg Glu Glu Arg
            900                 905                 910
Asn Gly Lys Tyr Ser Ile Glu Glu Tyr Leu Gln Asp Arg Asp Lys Tyr
        915                 920                 925
Tyr Glu Glu Val Ala Ile Ala Arg Ala Thr Glu Glu Asp Phe Cys Glu
    930                 935                 940
Glu Glu Glu Ala Lys Ile Arg Gln Arg Ile Phe Arg Pro Thr Arg Lys
945                 950                 955                 960
Gln Arg Lys Glu Glu Arg Ala Ser Leu Gly Leu Val Thr Gly Ser Glu
                965                 970                 975
Ile Arg Lys Arg Asn Pro Asp Asp Phe Lys Pro Lys Gly Lys Leu Trp
            980                 985                 990
Ala Asp Asp Asp Arg Ser Val Asp Tyr Asn Glu Lys Leu Ser Phe Glu
        995                 1000                1005
Ala Pro Pro Ser Ile Trp Ser Arg Ile Val Asn Phe Gly Ser Gly
    1010                1015                1020
Trp Gly Phe Trp Val Ser Pro Ser Leu Phe Ile Thr Ser Thr His
```

1025                1030                1035

Val Ile Pro Gln Gly Thr Gln Glu Phe Phe Gly Val Ser Ile Lys
            1040                1045                1050

Gln Ile Gln Ile His Lys Ser Gly Glu Phe Cys Arg Leu Arg Phe
            1055                1060                1065

Pro Lys Pro Ile Arg Thr Asp Val Thr Gly Met Ile Leu Glu Glu
            1070                1075                1080

Gly Ala Pro Glu Gly Thr Val Ala Thr Leu Leu Ile Lys Arg Pro
            1085                1090                1095

Thr Gly Glu Leu Met Pro Leu Ala Ala Arg Met Gly Thr His Ala
            1100                1105                1110

Thr Met Lys Ile Gln Gly Arg Thr Val Gly Gly Gln Met Gly Met
            1115                1120                1125

Leu Leu Thr Gly Ser Asn Ala Lys Ser Met Asp Leu Gly Thr Thr
            1130                1135                1140

Pro Gly Asp Cys Gly Cys Pro Tyr Ile Tyr Lys Arg Gly Asn Asp
            1145                1150                1155

Tyr Val Val Ile Gly Val His Thr Ala Ala Arg Gly Gly Asn
            1160                1165                1170

Thr Val Ile Cys Ala Thr Gln Gly Asn Glu Gly Glu Ala Ile Leu
            1175                1180                1185

Glu Gly Gly Asp Asp Lys Gly Thr Tyr Cys Gly Ala Pro Ile Leu
            1190                1195                1200

Gly Pro Gly Ser Ala Pro Lys Leu Ser Thr Lys Thr Lys Phe Trp
            1205                1210                1215

Arg Ser Ser Thr Thr Pro Leu Pro Pro Gly Thr Tyr Glu Pro Ala
            1220                1225                1230

Tyr Leu Gly Gly Lys Asp Pro Arg Val Lys Ser Gly Pro Ser Leu
            1235                1240                1245

Gln Gln Val Met Arg Asp Gln Leu Lys Pro Phe Thr Glu Pro Arg
            1250                1255                1260

Gly Lys Gln Pro Lys Pro Ser Val Leu Glu Ala Ala Lys Lys Thr
            1265                1270                1275

Ile Ile Asn Val Leu Glu Gln Thr Ile Asp Pro Pro Gln Lys Trp
            1280                1285                1290

Ser Phe Ala Gln Ala Cys Ala Ser Leu Asp Lys Thr Thr Ser Ser
            1295                1300                1305

Gly His Pro His His Ile Arg Lys Asn Asp Cys Trp Asn Gly Asp
            1310                1315                1320

Ser Phe Thr Gly Lys Leu Ala Asp Gln Ala Ser Lys Ala Asn Leu
            1325                1330                1335

Met Phe Glu Glu Gly Lys Asn Met Thr Pro Val Tyr Thr Gly Ala
            1340                1345                1350

Leu Lys Asp Glu Leu Val Lys Thr Asp Lys Ile Tyr Gly Lys Ile
            1355                1360                1365

Lys Lys Arg Leu Leu Trp Gly Ser Asp Leu Ala Thr Met Ile Arg
            1370                1375                1380

Cys Ala Arg Ala Phe Gly Gly Leu Met Asp Glu Leu Lys Ala His
            1385                1390                1395

Cys Val Thr Leu Pro Val Arg Val Gly Met Asn Met Asn Glu Asp
            1400                1405                1410

Gly Pro Ile Ile Phe Glu Lys His Ser Arg Tyr Lys Tyr His Tyr
            1415                1420                1425

-continued

| Asp Ala Asp Tyr Ser Arg Trp Asp Ser Thr Gln Gln Arg Ala Val |
| 1430 1435 1440 |

Leu Ala Ala Ala Leu Glu Ile Met Val Lys Phe Ser Pro Glu Pro
1445         1450             1455

His Leu Ala Gln Val Val Ala Glu Asp Leu Leu Ser Pro Ser Val
1460         1465             1470

Met Asp Val Gly Asp Phe Lys Ile Ser Ile Asn Glu Gly Leu Pro
1475         1480             1485

Ser Gly Val Pro Cys Thr Ser Gln Trp Asn Ser Ile Thr His Trp
1490         1495             1500

Leu Leu Thr Leu Cys Ala Leu Ser Glu Val Thr Asp Leu Ser Pro
1505         1510             1515

Asp Ile Ile Gln Ala Asn Ser Leu Phe Ser Phe Tyr Gly Asp Asp
1520         1525             1530

Glu Ile Val Ser Thr Asp Ile Lys Leu Asp Pro Glu Lys Leu Thr
1535         1540             1545

Ala Lys Leu Lys Glu Tyr Gly Leu Lys Pro Thr Arg Pro Asp Lys
1550         1555             1560

Thr Glu Gly Pro Leu Ile Ile Ser Glu Asp Leu Asp Gly Leu Thr
1565         1570             1575

Phe Leu Arg Arg Thr Val Thr Arg Asp Pro Ala Gly Trp Phe Gly
1580         1585             1590

Lys Leu Glu Gln Ser Ser Ile Leu Arg Gln Met Tyr Trp Thr Arg
1595         1600             1605

Gly Pro Asn His Glu Asp Pro Ser Glu Thr Met Ile Pro His Ser
1610         1615             1620

Gln Arg Pro Ile Gln Leu Met Ser Leu Leu Gly Glu Ala Ala Leu
1625         1630             1635

His Gly Pro Ala Phe Tyr Ser Lys Ile Ser Lys Leu Val Ile Ala
1640         1645             1650

Glu Leu Lys Glu Gly Gly Met Asp Phe Tyr Val Pro Arg Gln Glu
1655         1660             1665

Pro Met Phe Arg Trp Met Arg Phe Ser Asp Leu Ser Thr Trp Glu
1670         1675             1680

Gly Asp Arg Asn Leu Ala Pro Ser Phe Val Asn Glu Asp Gly Val
1685         1690             1695

Glu

<210> SEQ ID NO 18
<211> LENGTH: 7458
<212> TYPE: DNA
<213> ORGANISM: Sapovirus Mc10
<300> PUBLICATION INFORMATION:
<308> DATABASE ACCESSION NUMBER: GenBank/AY237420
<309> DATABASE ENTRY DATE: 2005-06-06
<313> RELEVANT RESIDUES IN SEQ ID NO: (1)..(7458)

<400> SEQUENCE: 18
gtgattggtt agtatggctt ccaagccatt ctacccaata gagttcaacc cgagtgttga   60
gcttcaagtg ctccgatcgg cccaccctcag ggtgggtggt cgtgagcaaa tgtttgaaac  120
cattaatgac ctcaatgatc atgtcagggg tgtggtggcc aaactgtggt gcaagcattt  180
gcaccgtagt ttggctgccg cccccacatt cacggaggag ggcttgttag actcttttcct 240 ttcaaaacca ccggttgaca tcaatcctga cacaacgttc cgtgagctgt ttggtattaa  300
tccccacgag cagttcccgc tgtccattca tgatttggca aaattacagg gtgagcttgt  360

-continued

```
ggatgcggca cgcaacccag gccatgtgtt gcggcgtcat tattccaccg attcgctcac    420
cgccctaatt aacaaaatca cgaaatttgt ccctgtgcat gccacacttc aagaaatgca    480
agcacgccgt gctttcgagc gagagcgcgc ggagctgttt agggaactgc cacatgctga    540
tttgatgta agtcgccaac aaaagtcgta cttttatgcc atgtggcgtc aggtggttaa     600
gaagagcaaa gagttttca tccccctggt caaatgtaca tcttggcgga agaagtttac     660
agagcctgcg gaaattgtta dacaggttct ggtccacttt tgtgaaggga tgaggtcgca    720
gttttccacc aatgcaaatt acatcaattt gtccctcatt gccaaactcc ggccaacagt    780
cctcacaatg attctccagc aacacaagaa cacctacaga gggtggttgg caacagtcac    840
tgctttggtt gaagtgtact ccaacctgtt tcaagacatg cgggacaccg ctgtctcagc    900
agtgtcagcc attacactgg tgtttgaaac cattaaggac tttgtagtca atgtgataga    960
ccttgttaag agcacgttcc agtcacaagg cccaacatct tgcggctggg ctgctatcat   1020
tgctggtgca ctgctcatct taatgaaatt gtcagggtgc tccaacacca caagttattg   1080
gcaccgactc ctcaaggtgt gtgggggtgt cactaccatt gctgcggcgg cccgtgctgt   1140
cgtgtgggtg cgagacatca tagcagaagc tgatggcaag gctagactga aaaagtacat   1200
ggcccgcaca gcagctctac ttgagcttgc agcatctcga gacgtgacgg cactgatga   1260
actcaagcgc ctattagatt gtttcacaca gctcatcgag gagggtactg agttgataca   1320
ggaatttggt acatcaccac ttgctggtct gactaggtca tatgtgagtg agcttgagtc   1380
aactgcaaac agtatcagga gcaccatcct cctagacaca ccccgaaaga ctccagttgc   1440
aatcatcctc actggtcctc ctggtatagg caaaacaagg cttgcacagc accttgctgc   1500
aggttttggc aaagtgtcaa acttttccgt cacgttggac caccacgact cttacaccgg   1560
aaatgaagtc gcaatttggg atgagtttga cgttgacaca cagggtaaat ttgtggagac   1620
catgattggt gtagttaata ccgcccccta cccactcaat tgcgaccgag tggagaacaa   1680
aggcaaagtg ttcacatctg attatatcat atgcaccagc aattacccaa cctctgtgtt   1740
acctgacaac ccacgagcgg gggctttcta tcgccgagtc acaacgatag atgtgtcatc   1800
tcctaccatt gaagattgga agaagaagaa cccagggaag aaaccccac ccgacttgta    1860
caagaacgat ttcacacacc ttcgcctatc tgttagaccg ttcttggggt acaaccccga   1920
ggggggacacc ttgatggtg tccgagtgaa acctgtgctc actagtgtgg atggtctgtc   1980
acgcttgatg gaaaccaagt ttaaggagca gggcaatgaa catcggaacc tgtggataac   2040
atgcccgcgt gacctggtgg cccccgccgc atctggttta aaagcataca tggccgccaa   2100
ccgagcgctc gcacaagtgt tccaggaacc atcttcacag gacattggtg aaacctgcac   2160
gtcccgtgtg tacgtgtcat gtaacaatcc acctcccaca tacagtggac gggtggtgaa   2220
aatcacagcc atcaatccat gggatgcatc actcgccaat tccatgttat caatgtttga   2280
aaccaccagt cacatccctg cctcgattca gcgtgaaatc atgtatagag tttgggaccc   2340
actggttcac ctgcagacac gtgagccaaa tacgcagatg ctcccctaca tcaacagagt   2400
ggtcccggtg tcttctgcat ttgacttcat ccgaggcctc aggcaccatc ttggtctgtg   2460
ttcagtcaaa ggcatgtgga gagcttatca gggttggaac agttccagct cgatcttgga   2520
attcctgtca aagcacatgg ctgatgttgc tttcccacac aaccccgagt gcaccgtttt   2580
ccgggccccg gacggtgatg tgatctttta cacgttcggg tcatatgctt gctttgtgtc   2640
cccagcccgt gtcccatttg ttggagagcc cccgaagaac gtgcattcaa atataacacg   2700
caacatgacg tgggctgaga cactccgcct gttggcagaa actataactg aaagtctggt   2760
```

```
gcactttggc cccttcctac tcatgatgca caatgttttca tacctcgcca cccggtctgg    2820
tcggaggag gaggccaaag gaaagaccaa gcatggccgt ggtgccaaac acgctaggag      2880
gggaggtgtc agcttgtctg atgatgagta tgatgagtgg cgtgacctgg tacgggactg    2940
gcggcaagac atgactgttg gggagtttgt ggagcttcgt gagcgatacg cgctcggaat    3000
ggactctgag gatgtgcaac gttatcgtgc ttggcttgag ctacgagcga tgcgcatggg    3060
tgcaggtgcc taccaacatg ccaccattat tggtagggga ggagtacaag acaccatcat    3120
ccgcacccaa ccaatgcgtg ctccacgtgc gccccgtaat caaggttatg atgaagaagc    3180
tcccacacca attgttacat tcacatctgg gggtgatcac attgggtatg ttgtcacat     3240
gggtaatggg gtggttgtca cagttacaca cgtggcctct gcgtctgacc aagtagaagg    3300
gcaggacttc gcaatcagga agaccgaggg tgaaaccacc tgggtgaaca ccaaccttgg    3360
tcacttgccc cactaccaga tcggtgatgg cgccccctgtc tactactcgg cgcgcctaca   3420
ccctgtcacc acgcttgcgg aggggacgta tgagacaccc aatatcacgg tccagggggta  3480
tcacctgcgc atcataaatg gatacccaac aaagcgtggg gactgtggca cccctatt     3540
tgactcatgc cgtcgtttgg tcggactgca cgcagccaca tcaacaaatg gagaaaccaa   3600
gcttgctcag cgagtgacta aaacatccaa ggtggagaat gcttttgctt ggaagggtct   3660
accagtggtt cgaggcccg actgtggcgg catgcccacg gggactcgtt accaccgctc    3720
acctgcatgg cccaacccctg tggaaggaga acacacgcc cctgcgccgt ttggttccgg   3780
tgatgagcgg tacaaatttt cccaggtgga gatgttggtc aacggcttaa agccttactc   3840
agagcccacc cctggcatac cccccgcttt gttacaacgt gcagccacac acacacgcac   3900
gtatctggaa acaataattg gcacccaccg atcaccaaat ttgtcattca gtgaggcatg   3960
ttcactcttg gaaaaatcaa catcgtgtgg tccgttcgtg gctggccaaa aggggggacta  4020
ctggacgag gacaaacagt gttacacagg tgtgttggca gaacatcttg ccaaagcatg    4080
ggatgcagcc aacaggggcg ttgcacccca aaacgcctac aaattggctt tgaaagatga   4140
actgagacca attgaaaaga atgcacaagg aaaaagacgc ctcctgtggg gttgtgatgc   4200
gggtgccaca ttggtggcta ctgcggcctt caagggtgtt gccacccgcc tccaagcagt   4260
tgctccaatg acaccagtta gcgttggcat aaacatggac agttaccagg ttgaggtgct   4320
gaatgagtca ctcaagggtg gggtgcttta ctgtctcgat tatagcaagt gggattcaac   4380
acagcaccct gccgtcacgg ccgcctcact tgggattttg agagattgt ctgaagccac    4440
tcccattaca acgtcagctg tcgagttgct atcctcccct gctagaggcc atttaaacga   4500
cattgtattt atcacaaaat ctggtctccc atctggcatg ccgtttacca gtgtcatcaa   4560
ctcactcaac cacatgactt actttgcagc tgcagtgctt aaggcgtatg aacaacacgg   4620
agcaccatac acaggtaacg tgtttcaggt tgaaactgtt cacacctacg gggatgactg   4680
tttatactca gtgtgccctg caacagcctc cattttccag acagttctag ccaacttgac   4740
ctcgttcggt ctcaaaccaa cagctgcaga taagagtgag acgatagccc cgacccacac   4800
tcctgtcttc cttaagagaa ctctaacatg cacaccacgt ggtgtgcgtg cctattaga   4860
catcacatcc ataaagaggc aattcttgtg gatcaaggct aacaggacag ttgacatcaa   4920
ttcaccacca gcatacgatc gcgacgcgcg tggcatccag ttagaaaacg ccctcgcgta    4980
cgcatcgcag catggccatg cagtttttga ggaagttgct gaattggctc gacacacagc   5040
caaggctgag ggactggtgc taaccaatgt caactatgac caggctctcg ccacctcga    5100
atcttggttc ataggtggta caggcctggt acaaggtagc cccagtgaag agaccaccaa   5160
```

```
attagtgttt gaaatggagg gcctaggcca accacagcca cagggtggcg aaaagaccag   5220
cccacagcct gtgacaccac aggacaccat tggccctaca gcggccctct tacttccaac   5280
tcagattgaa acaccaaacg caagtgcaca gcgcttggag ttggccatgg ccacaggggc   5340
agtcacgagt aatgtaccaa actgtattcg tgagtgtttt gcctctgtta ccacaatccc   5400
ctggacaact cgacaggccg ctaacacttt ccttggggct atccaccttg gcccacgcat   5460
caacccatac accgctcacc tgagcgcaat gtttgctggg tggggtggtg gttttcaagt   5520
gagagtgact atatctggtt ctggcctgtt tgctggtcgg gcggtaactg ccatcttgcc   5580
acccggagtg aaccccgcga gtgtccaaaa ccctgggggtt ttccctcatg ccttcattga   5640
tgcacgtacc actgagccaa tcttgattaa tctgccagac attcgtcctg ttgacttcca   5700
ccgtgtagac ggagacgatg ccacggcatc tgttggactg tgggtagctc aaccectcat   5760 caacccattt cagacaggcc ctgtgtccac ttgttggttg agttttgaaa caagacccgg   5820
ccctgacttt gacttttgtc tgttgaaggc cccagagcag cagatggaca atggaatttc   5880
gcccgcctct tgttgccccc gtaggctcgg acgttcccga ggcaacagaa tgggtgggcg   5940
aattgtggga ctggttgtgg tggcggctgc ggaacaggtg aaccatcact ttgatgcccg   6000
gtcaacaaca ttagggtggt ccacattgcc tgttgaacct attgcagggg atatatcctg   6060
gtatggtgat gctgggaaca agtcaatccg agggcttgtt agtgctcagg caaaggtat    6120 aatatttcca aacatagtca accactggac tgacgttgca ctgtcctcca agacatctaa   6180
caccacaacc ataccaactg acacatctac tcttggcaat ttaccaggtg cctctggacc   6240
acttgtcact tttgctgaca atggggatgt taatgagagt tccgcccaaa atgccatatt   6300
gacagctgca aatcagaact tcacatcatt ctctccaact tttgatgcgg cagggatatg   6360
ggtgtggatg ccttgggcca cggatcgtcc aggtgcgtca gacagcaaca tctacattag   6420
ccccacctgg gtaaatggca atccctccca cccaatccat gaaaaatgca ctaacatgat   6480
tggcacaaac tttcagtttg gagggaccgg caccaacaac atcatgttgt ggcaggaaca   6540
gcacttcaca tcctggcccg gtgcagcaga ggtgtactgc tcgcaactgg aaagcactgc   6600
cgagattttc cagaacaaca ttgttaacat cccaatgaac caaatggcag tgtttaatgt   6660
tgagactgca ggtaattcat tccaaatagc catcttgccc aatggttatt gtgtcaccaa   6720
cgcaccagtg gaacacacc  aacttcttga ctatgagact agcttcaaat ttgtaggact   6780
cttcccccaa agcacttcac ttcaggggcc ccatgggaac agtggccggg ccgttaggtt   6840
cttagaataa tgtcttggtt tactggagca tctctggctg ccggttcact cgtgacatg    6900 gcaggcacca tttcatcaat tgtggcacaa caaagacaaa ttgatctgat ggcagaagca   6960
aatagaatcc aggcagattg ggtgcgccgt caagaggcac tacaaatccg tggccaggac   7020
atctcacggg atcttgctgt taacggcact gcccagcgtg ttgagtcttt agtcaatgca   7080
ggcttcacac ccgtggacgc acgtcggctg gccggcggaa cggaaacggt gagttacggc   7140
ctactggatc gccctatcct acaacggggc atcctttctg gcatcactga gacacgacac   7200
ctccaggcca tgcagggcgc tctaagtgca ttcaaaaatg gtgcctctta cggagccccg   7260
ccagccccat caggctttgt gaatccaaat tatcaacctt cacctccgag attgaaacta   7320
ggccctaggc ccctagcac caatgtttga aatcctatct cttatacaaa ttttctatct    7380
tttcttttct ttctacacgg tacctcacgc gttcgggtgg tcaaatgcaa ttaagcgatt   7440
gcagccgtgc tttcttgg                                                 7458
```

<210> SEQ ID NO 19

```
<211> LENGTH: 2278
<212> TYPE: PRT
<213> ORGANISM: Sapovirus Mc10
<300> PUBLICATION INFORMATION:
<308> DATABASE ACCESSION NUMBER: GenBank/AY237420
<309> DATABASE ENTRY DATE: 2005-06-06
<313> RELEVANT RESIDUES IN SEQ ID NO: (1)..(2278)

<400> SEQUENCE: 19
```

Met Ala Ser Lys Pro Phe Tyr Pro Ile Glu Phe Asn Pro Ser Val Glu
1               5                   10                  15

Leu Gln Val Leu Arg Ser Ala His Leu Arg Val Gly Gly Arg Glu Gln
            20                  25                  30

Met Phe Glu Thr Ile Asn Asp Leu Asn Asp His Val Arg Gly Val Val
        35                  40                  45

Ala Lys Leu Trp Cys Lys His Leu His Arg Ser Leu Ala Ala Ala Pro
    50                  55                  60

Thr Phe Thr Glu Glu Gly Leu Leu Asp Ser Phe Leu Ser Lys Pro Pro
65                  70                  75                  80

Val Asp Ile Asn Pro Asp Thr Thr Phe Arg Glu Leu Phe Gly Ile Asn
                85                  90                  95

Pro His Glu Gln Phe Pro Leu Ser Ile His Asp Leu Ala Lys Leu Gln
            100                 105                 110

Gly Glu Leu Val Asp Ala Ala Arg Asn Pro Gly His Val Leu Arg Arg
        115                 120                 125

His Tyr Ser Thr Asp Ser Leu Thr Ala Leu Ile Asn Lys Ile Thr Lys
    130                 135                 140

Phe Val Pro Val His Ala Thr Leu Gln Glu Met Gln Ala Arg Arg Ala
145                 150                 155                 160

Phe Glu Arg Glu Arg Ala Glu Leu Phe Arg Glu Leu Pro His Ala Asp
                165                 170                 175

Leu Asp Val Ser Arg Gln Gln Lys Ser Tyr Phe Tyr Ala Met Trp Arg
            180                 185                 190

Gln Val Val Lys Lys Ser Lys Glu Phe Phe Ile Pro Leu Val Lys Cys
        195                 200                 205

Thr Ser Trp Arg Lys Lys Phe Thr Glu Pro Ala Glu Ile Val Arg Gln
    210                 215                 220

Val Leu Val His Phe Cys Glu Gly Met Arg Ser Gln Phe Ser Thr Asn
225                 230                 235                 240

Ala Asn Tyr Ile Asn Leu Ser Leu Ile Ala Lys Leu Arg Pro Thr Val
                245                 250                 255

Leu Thr Met Ile Leu Gln Gln His Lys Asn Thr Tyr Arg Gly Trp Leu
            260                 265                 270

Ala Thr Val Thr Ala Leu Val Glu Val Tyr Ser Asn Leu Phe Gln Asp
        275                 280                 285

Met Arg Asp Thr Ala Val Ser Ala Val Ser Ala Ile Thr Leu Val Phe
    290                 295                 300

Glu Thr Ile Lys Asp Phe Val Val Asn Val Ile Asp Leu Val Lys Ser
305                 310                 315                 320

Thr Phe Gln Ser Gln Gly Pro Thr Ser Cys Gly Trp Ala Ala Ile Ile
                325                 330                 335

Ala Gly Ala Leu Leu Ile Leu Met Lys Leu Ser Gly Cys Ser Asn Thr
            340                 345                 350

Thr Ser Tyr Trp His Arg Leu Leu Lys Val Cys Gly Gly Val Thr Thr
        355                 360                 365

Ile Ala Ala Ala Ala Arg Ala Val Val Trp Val Arg Asp Ile Ile Ala

-continued

```
            370                 375                 380
Glu Ala Asp Gly Lys Ala Arg Leu Lys Lys Tyr Met Ala Arg Thr Ala
385                 390                 395                 400

Ala Leu Leu Glu Leu Ala Ala Ser Arg Asp Val Thr Gly Thr Asp Glu
                405                 410                 415

Leu Lys Arg Leu Leu Asp Cys Phe Thr Gln Leu Ile Glu Glu Gly Thr
                420                 425                 430

Glu Leu Ile Gln Glu Phe Gly Thr Ser Pro Leu Ala Gly Leu Thr Arg
                435                 440                 445

Ser Tyr Val Ser Glu Leu Glu Ser Thr Ala Asn Ser Ile Arg Ser Thr
        450                 455                 460

Ile Leu Leu Asp Thr Pro Arg Lys Thr Pro Val Ala Ile Ile Leu Thr
465                 470                 475                 480

Gly Pro Pro Gly Ile Gly Lys Thr Arg Leu Ala Gln His Leu Ala Ala
                485                 490                 495

Gly Phe Gly Lys Val Ser Asn Phe Ser Val Thr Leu Asp His His Asp
                500                 505                 510

Ser Tyr Thr Gly Asn Glu Val Ala Ile Trp Asp Glu Phe Asp Val Asp
        515                 520                 525

Thr Gln Gly Lys Phe Val Glu Thr Met Ile Gly Val Val Asn Thr Ala
530                 535                 540

Pro Tyr Pro Leu Asn Cys Asp Arg Val Glu Asn Lys Gly Lys Val Phe
545                 550                 555                 560

Thr Ser Asp Tyr Ile Ile Cys Thr Ser Asn Tyr Pro Thr Ser Val Leu
                565                 570                 575

Pro Asp Asn Pro Arg Ala Gly Ala Phe Tyr Arg Arg Val Thr Thr Ile
                580                 585                 590

Asp Val Ser Ser Pro Thr Ile Glu Asp Trp Lys Lys Asn Pro Gly
        595                 600                 605

Lys Lys Pro Pro Pro Asp Leu Tyr Lys Asn Asp Phe Thr His Leu Arg
610                 615                 620

Leu Ser Val Arg Pro Phe Leu Gly Tyr Asn Pro Glu Gly Asp Thr Leu
625                 630                 635                 640

Asp Gly Val Arg Val Lys Pro Val Leu Thr Ser Val Asp Gly Leu Ser
                645                 650                 655

Arg Leu Met Glu Thr Lys Phe Lys Glu Gln Gly Asn Glu His Arg Asn
                660                 665                 670

Leu Trp Ile Thr Cys Pro Arg Asp Leu Val Ala Pro Ala Ala Ser Gly
        675                 680                 685

Leu Lys Ala Tyr Met Ala Ala Asn Arg Ala Leu Ala Gln Val Phe Gln
        690                 695                 700

Glu Pro Ser Ser Gln Asp Ile Gly Glu Thr Cys Thr Ser Arg Val Tyr
705                 710                 715                 720

Val Ser Cys Asn Asn Pro Pro Thr Tyr Ser Gly Arg Val Val Lys
                725                 730                 735

Ile Thr Ala Ile Asn Pro Trp Asp Ala Ser Leu Ala Asn Ser Met Leu
                740                 745                 750

Ser Met Phe Glu Thr Thr Ser His Ile Pro Ala Ser Ile Gln Arg Glu
        755                 760                 765

Ile Met Tyr Arg Val Trp Asp Pro Leu Val His Leu Gln Thr Arg Glu
        770                 775                 780

Pro Asn Thr Gln Met Leu Pro Tyr Ile Asn Arg Val Val Pro Val Ser
785                 790                 795                 800
```

-continued

```
Ser Ala Phe Asp Phe Ile Arg Gly Leu Arg His His Leu Gly Leu Cys
            805                 810                 815

Ser Val Lys Gly Met Trp Arg Ala Tyr Gln Gly Trp Asn Ser Ser Ser
            820                 825                 830

Ser Ile Leu Glu Phe Leu Ser Lys His Met Ala Asp Val Ala Phe Pro
            835                 840                 845

His Asn Pro Glu Cys Thr Val Phe Arg Ala Pro Asp Gly Asp Val Ile
        850                 855                 860

Phe Tyr Thr Phe Gly Ser Tyr Ala Cys Phe Val Ser Pro Ala Arg Val
865                 870                 875                 880

Pro Phe Val Gly Glu Pro Pro Lys Asn Val His Ser Asn Ile Thr Arg
                885                 890                 895

Asn Met Thr Trp Ala Glu Thr Leu Arg Leu Leu Ala Glu Thr Ile Thr
                900                 905                 910

Glu Ser Leu Val His Phe Gly Pro Phe Leu Leu Met Met His Asn Val
                915                 920                 925

Ser Tyr Leu Ala Thr Arg Ser Gly Arg Glu Glu Ala Lys Gly Lys
            930                 935                 940

Thr Lys His Gly Arg Gly Ala Lys His Ala Arg Arg Gly Gly Val Ser
945                 950                 955                 960

Leu Ser Asp Asp Glu Tyr Asp Glu Trp Arg Asp Leu Val Arg Asp Trp
                965                 970                 975

Arg Gln Asp Met Thr Val Gly Glu Phe Val Glu Leu Arg Glu Arg Tyr
            980                 985                 990

Ala Leu Gly Met Asp Ser Glu Asp Val Gln Arg Tyr Arg Ala Trp Leu
            995                1000                1005

Glu Leu Arg Ala Met Arg Met Gly Ala Gly Ala Tyr Gln His Ala
    1010                1015                1020

Thr Ile Ile Gly Arg Gly Gly Val Gln Asp Thr Ile Ile Arg Thr
    1025                1030                1035

Gln Pro Met Arg Ala Pro Arg Ala Pro Arg Asn Gln Gly Tyr Asp
    1040                1045                1050

Glu Glu Ala Pro Thr Pro Ile Val Thr Phe Thr Ser Gly Gly Asp
    1055                1060                1065

His Ile Gly Tyr Gly Cys His Met Gly Asn Gly Val Val Val Thr
    1070                1075                1080

Val Thr His Val Ala Ser Ala Ser Asp Gln Val Glu Gly Gln Asp
    1085                1090                1095

Phe Ala Ile Arg Lys Thr Glu Gly Glu Thr Thr Trp Val Asn Thr
    1100                1105                1110

Asn Leu Gly His Leu Pro His Tyr Gln Ile Gly Asp Gly Ala Pro
    1115                1120                1125

Val Tyr Tyr Ser Ala Arg Leu His Pro Val Thr Thr Leu Ala Glu
    1130                1135                1140

Gly Thr Tyr Glu Thr Pro Asn Ile Thr Val Gln Gly Tyr His Leu
    1145                1150                1155

Arg Ile Ile Asn Gly Tyr Pro Thr Lys Arg Gly Asp Cys Gly Thr
    1160                1165                1170

Pro Tyr Phe Asp Ser Cys Arg Arg Leu Val Gly Leu His Ala Ala
    1175                1180                1185

Thr Ser Thr Asn Gly Glu Thr Lys Leu Ala Gln Arg Val Thr Lys
    1190                1195                1200

Thr Ser Lys Val Glu Asn Ala Phe Ala Trp Lys Gly Leu Pro Val
    1205                1210                1215
```

```
Val Arg Gly Pro Asp Cys Gly Gly Met Pro Thr Gly Thr Arg Tyr
    1220            1225                1230

His Arg Ser Pro Ala Trp Pro Asn Pro Val Glu Gly Glu Thr His
    1235            1240                1245

Ala Pro Ala Pro Phe Gly Ser Gly Asp Glu Arg Tyr Lys Phe Ser
    1250            1255                1260

Gln Val Glu Met Leu Val Asn Gly Leu Lys Pro Tyr Ser Glu Pro
    1265            1270                1275

Thr Pro Gly Ile Pro Pro Ala Leu Leu Gln Arg Ala Ala Thr His
    1280            1285                1290

Thr Arg Thr Tyr Leu Glu Thr Ile Ile Gly Thr His Arg Ser Pro
    1295            1300                1305

Asn Leu Ser Phe Ser Glu Ala Cys Ser Leu Leu Glu Lys Ser Thr
    1310            1315                1320

Ser Cys Gly Pro Phe Val Ala Gly Gln Lys Gly Asp Tyr Trp Asp
    1325            1330                1335

Glu Asp Lys Gln Cys Tyr Thr Gly Val Leu Ala Glu His Leu Ala
    1340            1345                1350

Lys Ala Trp Asp Ala Ala Asn Arg Gly Val Ala Pro Gln Asn Ala
    1355            1360                1365

Tyr Lys Leu Ala Leu Lys Asp Glu Leu Arg Pro Ile Glu Lys Asn
    1370            1375                1380

Ala Gln Gly Lys Arg Arg Leu Leu Trp Gly Cys Asp Ala Gly Ala
    1385            1390                1395

Thr Leu Val Ala Thr Ala Ala Phe Lys Gly Val Ala Thr Arg Leu
    1400            1405                1410

Gln Ala Val Ala Pro Met Thr Pro Val Ser Val Gly Ile Asn Met
    1415            1420                1425

Asp Ser Tyr Gln Val Glu Val Leu Asn Glu Ser Leu Lys Gly Gly
    1430            1435                1440

Val Leu Tyr Cys Leu Asp Tyr Ser Lys Trp Asp Ser Thr Gln His
    1445            1450                1455

Pro Ala Val Thr Ala Ala Ser Leu Gly Ile Leu Glu Arg Leu Ser
    1460            1465                1470

Glu Ala Thr Pro Ile Thr Thr Ser Ala Val Glu Leu Leu Ser Ser
    1475            1480                1485

Pro Ala Arg Gly His Leu Asn Asp Ile Val Phe Ile Thr Lys Ser
    1490            1495                1500

Gly Leu Pro Ser Gly Met Pro Phe Thr Ser Val Ile Asn Ser Leu
    1505            1510                1515

Asn His Met Thr Tyr Phe Ala Ala Ala Val Leu Lys Ala Tyr Glu
    1520            1525                1530

Gln His Gly Ala Pro Tyr Thr Gly Asn Val Phe Gln Val Glu Thr
    1535            1540                1545

Val His Thr Tyr Gly Asp Asp Cys Leu Tyr Ser Val Cys Pro Ala
    1550            1555                1560

Thr Ala Ser Ile Phe Gln Thr Val Leu Ala Asn Leu Thr Ser Phe
    1565            1570                1575

Gly Leu Lys Pro Thr Ala Ala Asp Lys Ser Glu Thr Ile Ala Pro
    1580            1585                1590

Thr His Thr Pro Val Phe Leu Lys Arg Thr Leu Thr Cys Thr Pro
    1595            1600                1605

Arg Gly Val Arg Gly Leu Leu Asp Ile Thr Ser Ile Lys Arg Gln
```

-continued

```
           1610                1615                1620

Phe Leu Trp Ile Lys Ala Asn Arg Thr Val Asp Ile Asn Ser Pro
    1625                1630                1635

Pro Ala Tyr Asp Arg Asp Ala Arg Gly Ile Gln Leu Glu Asn Ala
    1640                1645                1650

Leu Ala Tyr Ala Ser Gln His Gly His Ala Val Phe Glu Glu Val
    1655                1660                1665

Ala Glu Leu Ala Arg His Thr Ala Lys Ala Glu Gly Leu Val Leu
    1670                1675                1680

Thr Asn Val Asn Tyr Asp Gln Ala Leu Ala Thr Tyr Glu Ser Trp
    1685                1690                1695

Phe Ile Gly Gly Thr Gly Leu Val Gln Gly Ser Pro Ser Glu Glu
    1700                1705                1710

Thr Thr Lys Leu Val Phe Glu Met Glu Gly Leu Gly Gln Pro Gln
    1715                1720                1725

Pro Gln Gly Gly Glu Lys Thr Ser Pro Gln Pro Val Thr Pro Gln
    1730                1735                1740

Asp Thr Ile Gly Pro Thr Ala Ala Leu Leu Leu Pro Thr Gln Ile
    1745                1750                1755

Glu Thr Pro Asn Ala Ser Ala Gln Arg Leu Glu Leu Ala Met Ala
    1760                1765                1770

Thr Gly Ala Val Thr Ser Asn Val Pro Asn Cys Ile Arg Glu Cys
    1775                1780                1785

Phe Ala Ser Val Thr Thr Ile Pro Trp Thr Thr Arg Gln Ala Ala
    1790                1795                1800

Asn Thr Phe Leu Gly Ala Ile His Leu Gly Pro Arg Ile Asn Pro
    1805                1810                1815

Tyr Thr Ala His Leu Ser Ala Met Phe Ala Gly Trp Gly Gly Gly
    1820                1825                1830

Phe Gln Val Arg Val Thr Ile Ser Gly Ser Gly Leu Phe Ala Gly
    1835                1840                1845

Arg Ala Val Thr Ala Ile Leu Pro Pro Gly Val Asn Pro Ala Ser
    1850                1855                1860

Val Gln Asn Pro Gly Val Phe Pro His Ala Phe Ile Asp Ala Arg
    1865                1870                1875

Thr Thr Glu Pro Ile Leu Ile Asn Leu Pro Asp Ile Arg Pro Val
    1880                1885                1890

Asp Phe His Arg Val Asp Gly Asp Asp Ala Thr Ala Ser Val Gly
    1895                1900                1905

Leu Trp Val Ala Gln Pro Leu Ile Asn Pro Phe Gln Thr Gly Pro
    1910                1915                1920

Val Ser Thr Cys Trp Leu Ser Phe Glu Thr Arg Pro Gly Pro Asp
    1925                1930                1935

Phe Asp Phe Cys Leu Leu Lys Ala Pro Glu Gln Gln Met Asp Asn
    1940                1945                1950

Gly Ile Ser Pro Ala Ser Leu Leu Pro Arg Arg Leu Gly Arg Ser
    1955                1960                1965

Arg Gly Asn Arg Met Gly Gly Arg Ile Val Gly Leu Val Val Val
    1970                1975                1980

Ala Ala Ala Glu Gln Val Asn His His Phe Asp Ala Arg Ser Thr
    1985                1990                1995

Thr Leu Gly Trp Ser Thr Leu Pro Val Glu Pro Ile Ala Gly Asp
    2000                2005                2010
```

```
Ile Ser Trp Tyr Gly Asp Ala Gly Asn Lys Ser Ile Arg Gly Leu
    2015            2020                2025

Val Ser Ala Gln Gly Lys Gly Ile Ile Phe Pro Asn Ile Val Asn
    2030            2035                2040

His Trp Thr Asp Val Ala Leu Ser Ser Lys Thr Ser Asn Thr Thr
    2045            2050                2055

Thr Ile Pro Thr Asp Thr Ser Thr Leu Gly Asn Leu Pro Gly Ala
    2060            2065                2070

Ser Gly Pro Leu Val Thr Phe Ala Asp Asn Gly Asp Val Asn Glu
    2075            2080                2085

Ser Ser Ala Gln Asn Ala Ile Leu Thr Ala Ala Asn Gln Asn Phe
    2090            2095                2100

Thr Ser Phe Ser Pro Thr Phe Asp Ala Ala Gly Ile Trp Val Trp
    2105            2110                2115

Met Pro Trp Ala Thr Asp Arg Pro Gly Ala Ser Asp Ser Asn Ile
    2120            2125                2130

Tyr Ile Ser Pro Thr Trp Val Asn Gly Asn Pro Ser His Pro Ile
    2135            2140                2145

His Glu Lys Cys Thr Asn Met Ile Gly Thr Asn Phe Gln Phe Gly
    2150            2155                2160

Gly Thr Gly Thr Asn Asn Ile Met Leu Trp Gln Glu Gln His Phe
    2165            2170                2175

Thr Ser Trp Pro Gly Ala Ala Glu Val Tyr Cys Ser Gln Leu Glu
    2180            2185                2190

Ser Thr Ala Glu Ile Phe Gln Asn Asn Ile Val Asn Ile Pro Met
    2195            2200                2205

Asn Gln Met Ala Val Phe Asn Val Glu Thr Ala Gly Asn Ser Phe
    2210            2215                2220

Gln Ile Ala Ile Leu Pro Asn Gly Tyr Cys Val Thr Asn Ala Pro
    2225            2230                2235

Val Gly Thr His Gln Leu Leu Asp Tyr Glu Thr Ser Phe Lys Phe
    2240            2245                2250

Val Gly Leu Phe Pro Gln Ser Thr Ser Leu Gln Gly Pro His Gly
    2255            2260                2265

Asn Ser Gly Arg Ala Val Arg Phe Leu Glu
    2270            2275

<210> SEQ ID NO 20
<211> LENGTH: 2294
<212> TYPE: DNA
<213> ORGANISM: Norwalk Virus

<400> SEQUENCE: 20
atgatggcgt ctaaggacgc tacatcaagc gtggatggcg ctagtggcgc tggtcagttg      60
gtaccggagg ttaatgcttc tgaccctctt gcaatggatc ctgtagcagg ttcttcgaca     120
gcagtcgcga ctgctggaca agttaatcct attgatccct ggataattaa taattttgtg     180
caagcccccc aaggtgaatt tactatttcc ccaaataata cccccggtga tgttttgttt     240
gatttgagtt tgggtcccca tcttaatcct ttcttgctcc atctatcaca aatgtataat     300
ggttgggttg gtaacatgag agtcaggatt atgctagctg gtaatgcctt tactgcgggg     360
aagataatag tttcctgcat accccctggt tttggttcac ataatcttac tatagcacaa     420
gcaactctct ttccacatgt gattgctgat gttaggactc tagacccat tgaggtgcct     480 ttggaagatg ttaggaatgt tctctttcat aataatgata gaaatcaaca aaccatgcgc     540
```

```
cttgtgtgca tgctgtacac ccccctccgc actggtggtg gtactggtga ttctttgta      600
gttgcagggc gagttatgac ttgccccagt cctgatttta atttcttgtt tttagtccct      660
cctacggtgg agcagaaaac caggcccttc acactcccaa atctgccatt gagttctctg      720
tctaactcac gtgcccctct cccaatcagt agtatcggca tttccccaga caatgtccag      780
agtgtgcagt tccaaaatgg tcggtgtact ctggatggcc gcctggttgg caccacccca      840
gtttcattgt cacatgttgc caagataaga gggacctcca atggcactgt aatcaacctt      900
actgaattgg atggcacacc ctttcaccct tttgagggcc ctgcccccat tgggtttcca      960
gacctcggtg gttgtgattg gcatatcaat atgacacagt ttggccattc tagccagacc     1020
cagtatgatg tagacaccac ccctgacact tttgtccccc atcttggttc aattcaggca     1080
aatggcattg gcagtggtaa ttatgttggt gttcttagct ggatttcccc cccatcacac     1140
ccgtctggct cccaagttga cctttggaag atccccaatt atgggtcaag tattacggag     1200
gcaacacatc tagccccttc tgtataccccc cctggtttcg gagaggtatt ggtcttttc      1260
atgtcaaaaa tgccaggtcc tggtgcttat aatttgccct gtctattacc acaagagtac     1320
atttcacatc ttgctagtga acaagcccct actgtaggtg aggctgccct gctccactat     1380
gttgaccctg ataccggtcg gaatcttggg gaattcaaag cataccctga tggtttcctc     1440
acttgtgtcc ccaatggggc tagctcgggt ccacaacagc tgccgatcaa tggggtcttt     1500
gtctttgttt catgggtgtc cagattttat caattaaagc ctgtgggaac tgccagctcg     1560
gcaagaggta ggcttggtct cgccgataa tggcccaagc cataattggt gcaattgctg      1620
cttccacagc aggtagtgct ctgggagcgg gcatacaggt tggtggcgaa gcggccctcc     1680
aaagccaaag gtatcaacaa atttgcaac tgcaagaaaa ttcttttaaa catgacaggg      1740
aaatgattgg gtatcaggtt gaagcttcaa atcaattatt ggctaaaaat ttggcaacta     1800
gatattcact cctccgtgct gggggtttga ccagtgctga tgcagcaaga tctgtggcag     1860
gagctccagt cacccgcatt gtagattgga atggcgtgag agtgtctgct cccgagtcct     1920
ctgctaccac attgagatcc ggtggcttca tgtcagttcc cataccattt gcctctaagc     1980
aaaaacaggt tcaatcatct ggtattagta atccaaatta ttccccttca tccatttctc     2040
gaaccactag ttgggtcgag tcacaaaact catcgagatt tggaaatctt tctccatacc     2100
acgcggaggc tctcaataca gtgtggttga ctccacccgg ttcaacagcc tcttctacac     2160
tgtcttctgt gccacgtggt tatttcaata cagacaggtt gccattattc gcaaataata     2220
ggcgatgatg ttgtaatatg aaatgtgggc atcatattca tttaattagg tttaattagg     2280
tttaatttga tgtt                                                       2294
```

<210> SEQ ID NO 21
<211> LENGTH: 539
<212> TYPE: PRT
<213> ORGANISM: Norovirus

<400> SEQUENCE: 21

```
Met Lys Met Ala Ser Ser Asp Ala Asn Pro Ser Asp Gly Ser Ala Ala
1               5                   10                  15

Asn Leu Val Pro Glu Val Asn Asn Glu Val Met Ala Leu Glu Pro Val
            20                  25                  30

Val Gly Ala Ala Ile Ala Ala Pro Val Ala Gly Gln Gln Asn Ile Ile
        35                  40                  45

Asp Pro Trp Ile Arg Asn Asn Phe Val Gln Ala Pro Gly Gly Glu Phe
    50                  55                  60
```

```
Thr Val Ser Pro Arg Asn Ala Pro Gly Glu Ile Leu Trp Ser Ala Pro
 65                  70                  75                  80

Leu Gly Pro Asp Leu Asn Pro Tyr Leu Ser His Leu Ser Arg Met Tyr
                 85                  90                  95

Asn Gly Tyr Ala Gly Gly Phe Glu Val Gln Val Ile Leu Ala Gly Asn
            100                 105                 110

Ala Phe Thr Ala Gly Lys Val Ile Phe Ala Ala Val Pro Pro Asn Phe
        115                 120                 125

Pro Thr Glu Gly Leu Ser Pro Ser Gln Val Thr Met Phe Pro His Ile
    130                 135                 140

Ile Val Asp Val Arg Gln Leu Glu Pro Val Leu Ile Pro Leu Pro Asp
145                 150                 155                 160

Val Arg Asn Asn Phe Tyr His Tyr Asn Gln Ser His Asp Ser Thr Leu
                165                 170                 175

Lys Leu Ile Ala Met Leu Tyr Thr Pro Leu Arg Ala Asn Asn Ala Gly
            180                 185                 190

Asp Asp Val Phe Thr Val Ser Cys Arg Val Leu Thr Arg Pro Ser Pro
        195                 200                 205

Asp Phe Asp Phe Ile Phe Leu Val Pro Pro Thr Val Glu Ser Arg Thr
    210                 215                 220

Lys Pro Phe Thr Val Pro Ile Leu Thr Val Glu Glu Met Ser Asn Ser
225                 230                 235                 240

Arg Phe Pro Ile Pro Leu Glu Lys Leu Tyr Thr Gly Pro Ser Ser Ala
                245                 250                 255

Phe Val Val Gln Pro Gln Asn Gly Arg Cys Thr Thr Asp Gly Val Leu
            260                 265                 270

Leu Gly Thr Thr Gln Leu Ser Ala Val Asn Ile Cys Asn Phe Arg Gly
        275                 280                 285

Asp Val Thr His Ile Val Gly Ser His Asp Tyr Thr Met Asn Leu Ala
    290                 295                 300

Ser Gln Asn Trp Ser Asn Tyr Asp Pro Thr Glu Glu Ile Pro Ala Pro
305                 310                 315                 320

Leu Gly Thr Pro Asp Phe Val Gly Lys Ile Gln Gly Leu Leu Thr Gln
                325                 330                 335

Thr Thr Arg Ala Asp Gly Ser Thr Arg Ala His Lys Ala Thr Val Ser
            340                 345                 350

Thr Gly Ser Val His Phe Thr Pro Lys Leu Gly Ser Val Gln Phe Thr
        355                 360                 365

Thr Asp Thr Asn Asn Asp Phe Gln Thr Gly Gln Asn Thr Lys Phe Thr
    370                 375                 380

Pro Val Gly Val Ile Gln Asp Gly Asp His His Gln Asn Glu Pro Gln
385                 390                 395                 400

Gln Trp Val Leu Pro Asn Tyr Ser Gly Arg Thr Gly His Asn Val His
                405                 410                 415

Leu Ala Pro Ala Val Ala Pro Thr Phe Pro Gly Glu Gln Leu Leu Phe
            420                 425                 430

Phe Arg Ser Thr Met Pro Gly Cys Ser Gly Tyr Pro Asn Met Asn Leu
        435                 440                 445

Asp Cys Leu Leu Pro Gln Glu Trp Val Leu His Phe Tyr Gln Glu Ala
    450                 455                 460

Ala Pro Ala Gln Ser Asp Val Ala Leu Leu Arg Phe Val Asn Pro Asp
465                 470                 475                 480

Thr Gly Arg Val Leu Phe Glu Cys Lys Leu His Lys Ser Gly Tyr Ile
                485                 490                 495
```

```
Thr Val Ala His Thr Gly Pro Tyr Asp Leu Val Ile Pro Pro Asn Gly
            500                 505                 510

Tyr Phe Arg Phe Asp Ser Trp Val Asn Gln Phe Tyr Thr Leu Ala Pro
            515                 520                 525

Met Gly Asn Gly Thr Gly Arg Arg Ala Leu
    530                 535

<210> SEQ ID NO 22
<211> LENGTH: 268
<212> TYPE: PRT
<213> ORGANISM: Norovirus

<400> SEQUENCE: 22

Met Ala Gly Ser Phe Phe Ala Gly Leu Ala Ser Asp Val Leu Gly Ser
1               5                   10                  15

Gly Leu Gly Ser Leu Ile Asn Ala Gly Ala Gly Ala Ile Asn Gln Lys
            20                  25                  30

Val Glu Phe Glu Asn Asn Arg Lys Leu Gln Gln Ala Ser Phe Gln Phe
        35                  40                  45

Ser Ser Asn Leu Gln Gln Ala Ser Phe Gln His Asp Lys Glu Met Leu
    50                  55                  60

Gln Ala Gln Ile Glu Ala Thr Gln Lys Leu Gln Gln Asp Leu Met Lys
65                  70                  75                  80

Val Lys Gln Ala Val Leu Leu Glu Gly Gly Phe Ser Thr Thr Asp Ala
                85                  90                  95

Ala Arg Gly Ala Ile Asn Ala Pro Met Thr Lys Ala Leu Asp Trp Ser
            100                 105                 110

Gly Thr Arg Tyr Trp Ala Pro Asp Ala Arg Thr Thr Thr Tyr Asn Ala
        115                 120                 125

Gly Arg Phe Ser Thr Leu Gln Pro Ser Gly Ala Leu Pro Gly Arg Thr
    130                 135                 140

Asn Pro Arg Ile Thr Val Pro Ala Arg Gly Pro Pro Ser Thr Leu Ser
145                 150                 155                 160

Asn Ala Ser Thr Ala Thr Ser Val Tyr Ser Gln Thr Val Ser Thr
                165                 170                 175

Arg Leu Gly Ser Ser Ala Gly Ser Gly Thr Gly Val Ser Ser Leu Pro
            180                 185                 190

Ser Thr Ala Arg Thr Arg Asn Trp Val Glu Asp Gln Asn Arg Asn Leu
        195                 200                 205

Ser Pro Phe Met Arg Gly Ala Leu Asn Thr Ser Phe Val Thr Pro Pro
    210                 215                 220

Ser Ser Arg Ser Ser Asn Gln Gly Thr Val Ser Thr Val Pro Lys Glu
225                 230                 235                 240

Ile Leu Asp Ser Trp Thr Gly Ala Phe Asn Thr Arg Arg Gln Pro Leu
                245                 250                 255

Phe Ala His Ile Arg Lys Arg Gly Glu Ser Arg Val
            260                 265

<210> SEQ ID NO 23
<211> LENGTH: 8
<212> TYPE: PRT
<213> ORGANISM: Artificial Sequence
<220> FEATURE:
<223> OTHER INFORMATION: Synthetic peptide

<400> SEQUENCE: 23

Trp Thr Arg Gly Ser His Asn Leu
```

-continued

```
<210> SEQ ID NO 24
<211> LENGTH: 8
<212> TYPE: PRT
<213> ORGANISM: Artificial Sequence
<220> FEATURE:
<223> OTHER INFORMATION: Synthetic peptide

<400> SEQUENCE: 24

Trp Thr Arg Gly Gly His Gly Leu
1               5

<210> SEQ ID NO 25
<211> LENGTH: 8
<212> TYPE: PRT
<213> ORGANISM: Artificial Sequence
<220> FEATURE:
<223> OTHER INFORMATION: Synthetic peptide

<400> SEQUENCE: 25

Trp Thr Arg Gly Gln His Gln Leu
1               5

<210> SEQ ID NO 26
<211> LENGTH: 9
<212> TYPE: PRT
<213> ORGANISM: Artificial Sequence
<220> FEATURE:
<223> OTHER INFORMATION: Synthetic peptide

<400> SEQUENCE: 26

Trp Leu Pro Ala Pro Ile Asp Lys Leu
1               5

<210> SEQ ID NO 27
<211> LENGTH: 10
<212> TYPE: DNA
<213> ORGANISM: Artificial Sequence
<220> FEATURE:
<223> OTHER INFORMATION: Synthetic oligonucleotide

<400> SEQUENCE: 27
acaaaacaaa                                                        10
```